United States Patent
Tsumuki et al.

(10) Patent No.: US 6,222,035 B1
(45) Date of Patent: Apr. 24, 2001

(54) [1,2,4] TRIAZOLO [1,5-C] PYRIMIDINE DERIVATIVES

(75) Inventors: Hiroshi Tsumuki, Osaka; Junichi Shimada; Hironori Imma, both of Shizuoka; Akiko Nakamura, Niigata; Hiromi Nonaka, Shizuoka; Shizuo Shiozaki, Shizuoka; Shunji Ichikawa, Shizuoka; Tomoyuki Kanda, Shizuoka; Yoshihisa Kuwana, Shizuoka; Michio Ichimura, Shizuoka; Fumio Suzuki, Shizuoka, all of (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/401,984

(22) Filed: Sep. 23, 1999

Related U.S. Application Data

(63) Continuation-in-part of application No. PCT/JP98/01266, filed on Mar. 24, 1998.

(30) Foreign Application Priority Data

Mar. 24, 1997 (JP) .......................................... 9-69566

(51) Int. Cl.$^7$ ........................ C07D 487/00; A61K 31/505
(52) U.S. Cl. ............................................ 544/263; 544/262
(58) Field of Search ..................................... 544/263, 262

(56) References Cited

U.S. PATENT DOCUMENTS

| 4,477,450 | 10/1984 | Wade | .................. | 424/246 |
| 4,483,987 | 11/1984 | Wagner | ................. | 544/263 |
| 4,572,910 | 2/1986 | Wade | .................. | 514/222 |
| 4,831,013 | 5/1989 | Francis | .................. | 514/23 |
| 5,217,973 | 6/1993 | Bru-Magntez et al. | ............. | 514/258 |
| 5,358,950 | 10/1994 | Bru-Magntez et al. | ............. | 514/258 |
| 5,565,460 | 10/1996 | Suzuki et al. | ......... | 514/259 |

FOREIGN PATENT DOCUMENTS

| 0263071 | * 6/1988 | (CH) . |
| 0 132 851 | 2/1985 | (EP) . |
| 0 459 702 | 12/1991 | (EP) . |
| 59-167592 | 9/1984 | (JP) . |
| 60-013792 | 1/1985 | (JP) . |
| 1-500996 | 4/1989 | (JP) . |
| 60-56983 | 3/1994 | (JP) . |
| 6-122685 | 5/1994 | (JP) . |
| 95/03806 | 2/1995 | (WO) . |

OTHER PUBLICATIONS

Brown et al., Aust. J. Chem. 33(5) pp. 1147–52 91980); Bis–s–triazolo(1,5–a:1',5'–c)pyrimidine . . . derivats, Jan. 30, 1980.*
Medicinal Chemistry, vol. 35, No. 3 (1992), pp. 407–422.
J. Med. Chem. vol. 31 (1988), pp. 1014–1020.
European Journal of Pharmacology, 168 (1989), pp. 285–290.

* cited by examiner

*Primary Examiner*—Mukund J. Shah
*Assistant Examiner*—Sudhaker B. Patel
(74) *Attorney, Agent, or Firm*—Fitzpatrick, Cella, Harper & Scinto

(57) ABSTRACT

[1,2,4]Triazolo[1,5-c]pyrimidine derivatives represented by formula (I) or pharmaceutically acceptable salts thereof are provided, which have adenosine $A_{2A}$ receptor antagonism and are useful for the treatment or prevention of various diseases induced by hyperactivity of adenosine $A_{2A}$ receptors (for example, Parkinson's disease or senile dementia):

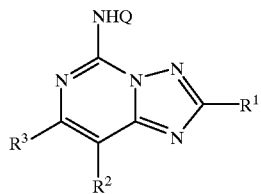

I wherein $R^1$ represents substituted or unsubstituted aryl, or the like; $R^2$ represents hydrogen, halogen, lower alkyl, substituted or unsubstituted aryl, or the like; $R^3$ represents hydrogen, halogen, $XR^{10}$ (wherein X represents O or S; and $R^{10}$ represents substituted or unsubstituted aryl, a substituted or unsubstituted aromatic heterocyclic ring, substituted or unsubstituted aralkyl, lower alkyl, or hydroxy lower alkyl), or the like; and Q represents hydrogen or 3,4-dimethoxybenzyl.

36 Claims, 1 Drawing Sheet

[1,2,4] TRIAZOLO [1,5-C] PYRIMIDINE DERIVATIVES

This application is a CIP of PCT/JP98/01266 filed Mar. 24, 1998.

TECHNICAL FIELD

The present invention relates to novel [1,2,4]triazolo[1,5-c]pyrimidine derivatives and pharmaceutically acceptable salts thereof which show adenosine $A_{2A}$ receptor antagonism and are useful for treating or preventing various diseases induced by hyperactivity of adenosine $A_{2A}$ receptors (for example, Parkinson's disease, senile dementia, or depression).

BACKGROUND ART

It is known that adenosine shows attenuation of the activity of neurotransmitters via an $A_{2A}$ receptor [*European Journal of Pharmacology*, 168: 285 (1989)]. Consequently, adenosine $A_{2A}$ receptor antagonists are expected as remedies or preventives for various diseases induced by hyperactivity of adenosine $A_{2A}$ receptors, such as a remedy for Parkinson's disease, an anti-dementia drug, a remedy for depression, and the like. Furthermore, the above antagonists are expected to show therapeutic and symptom-improving effects upon Alzheimer's disease, progressive supranuclear palsy, AIDS encephalopathy, propagative cavernous encephalopathy, multiple sclerosis, amyotrophic lateral sclerosis, Huntington's disease, multiple system atrophy, cerebral ischemia, somnipathy, ischemic heart disease, intermittent claudication, or the like.

On the other hand, [1,2,4]triazolo[1,5-c]-pyrimidine derivatives are disclosed as compounds having diuresis activity in Japanese Published Unexamined Patent Application No. 13792/85, as compounds having antiasthma activity in Japanese Published Unexamined Patent Application No. 56983/85, and as compounds having bronchodilation activity in Japanese Published Unexamined Patent Application No. 167592/84.

However, adenosine receptor antagonism of [1,2,4]triazolo[1,5-c]pyrimidine derivatives and their activity on the central nervous system are not known.

DISCLOSURE OF THE INVENTION

An object of the present invention is to provide [1,2,4]triazolo[1,5-c]pyrimidine derivatives which have adenosine $A_{2A}$ receptor antagonism and are useful for treating or preventing various diseases induced by hyperactivity of an adenosine $A_{2A}$ receptor (for example, Parkinson's disease, dementia, depression, or the like).

The present invention can provide [1,2,4]triazolo[1,5-c]pyrimidine derivatives represented by formula (I):

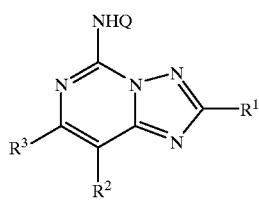

{wherein $R^1$ represents substituted or unsubstituted aryl, or a substituted or unsubstituted aromatic heterocyclic ring;

$R^2$ represents hydrogen, halogen, lower alkyl, lower alkanoyl, aroyl, substituted or unsubstituted aryl, a substituted or unsubstituted aromatic heterocyclic ring, $CHR^{4A}R^{4B}$ (wherein $R^{4A}$ represents hydrogen, hydroxy, or aryl; and $R^{4B}$ represents hydroxy, substituted or unsubstituted aryloxy, lower alkyl, lower alkoxy, formyl, lower alkanoyl, halogen, lower alkylthio, formula ($A^1$):

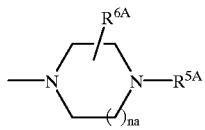

(wherein na represents an integer of 0 to 3; $R^{5A}$ represents hydrogen, substituted or unsubstituted lower alkyl, substituted or unsubstituted aryl, a substituted or unsubstituted aromatic heterocyclic ring, lower alkoxycarbonyl, formyl, lower alkanoyl, aroyl, or substituted or unsubstituted aralkyl; and $R^{6A}$ represents hydrogen, lower alkyl, halogen, or hydroxy), formula ($B^1$):

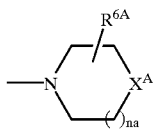

(wherein na and $R^{6A}$ have the same meanings as defined above; and $X^A$ represents methylene, oxygen, sulfur, sulfinyl, or sulfonyl), or $NR^{7A}R^{8A}$ (wherein $R^{7A}$ and $R^{8A}$ are the same or different, and each represents hydrogen, lower alkyl, lower cycloalkyl, substituted or unsubstituted aryl, a substituted or unsubstituted aromatic heterocyclic ring, substituted or unsubstituted aralkyl, aroyl, formyl, or lower alkanoyl)), formyl, carboxyl, lower alkoxycarbonyl, $CONR^{9A}R^{9B}$ (wherein $R^{9A}$ represents hydrogen or lower alkyl; and $R^{9B}$ represents hydrogen, substituted or unsubstituted aryl, a substituted or unsubstituted aromatic heterocyclic ring, substituted or unsubstituted aralkyl, lower cycloalkyl, lower alkoxy, or lower alkyl), $COA^3$ ($A^3$ represents formula ($A^3$):

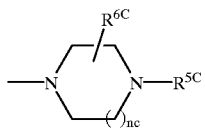

(wherein nc, $R^{5C}$, and $R^{6C}$ have the same meanings as the above-described na, $R^{5A}$, and $R^{6A}$, respectively)), or $COB^3$ ($B^3$ represents formula ($B^3$):

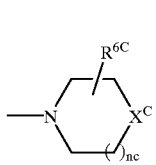

(wherein nc, $R^{6C}$, and $X^C$ have the same meanings as the above-described na, $R^{5A}$, and $X^A$, respectively));

$R^3$ represents hydrogen, halogen, $XR^{10}$ (wherein X represents O or S; and $R^{10}$ represents substituted or unsubstituted aryl, a substituted or unsubstituted aromatic heterocyclic ring, substituted or unsubstituted aralkyl, lower alkyl, or hydroxy-substituted lower alkyl), formula ($A^2$):

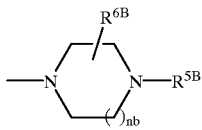

(wherein nb, $R^{5B}$, and $R^{6B}$ have the same meanings as the above-described na, $R^{5A}$, and $R^{6A}$, respectively), formula ($B^2$):

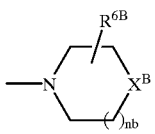

(wherein nb, $R^{6B}$, and $X^B$ have the same meanings as the above-described na, $R^{5A}$, and $X^A$, respectively), or $NR^{7B}R^{8B}$ (wherein $R^{7B}$ and $R^{8B}$ have the same meanings as the above-described $R^{7A}$ and $R^{8A}$, respectively), and Q represents hydrogen or 3,4-dimethoxybenzyl}, or pharmaceutically acceptable salts thereof.

In the definition of each group in formula (I), examples of the lower alkyl and the lower alkyl moiety of the lower alkoxy, lower alkanoyl, lower alkylthio, lower cloalkyl-substituted lower alkyl, hydrosxy-substituted lower alkyl, lower alkoxy-substituted lower alkyl, substituted or unsubstituted aromatic heterocyclic ring-substituted lower alkyl and lower alkoxycarbonyl include straight-or branched-chain groups having 1 to 6 carbon atoms, such as methyl, ethyl, propyl, isopropyl, butyl, isobutyl, sec-butyl, tert-butyl, pentyl, neopentyl, hexyl and the like. Examples of the lower cycloalkyl include those having 3 to 8 carbon atoms, such as cyclopropyl, cyclopentyl, cyclohexyl and the like. Examples of the halogen include fluorine, chlorine, bromine and iodine atoms. Examples of the aryl moiety of the substituted or unsubstituted aryl, substituted or unsubstituted aryloxy and aroyl include phenyl, naphthyl, indenyl, anthryl and the like. Examples of the aromatic heterocyclic ring moiety of the substituted or unsubstituted aromatic heterocyclic ring include furyl, thienyl, pyrrolyl, pyridyl, oxazolyl, thiazolyl, imidazolyl, pyrimidyl, triazinyl, indolyl, quinolyl, purinyl, benzoxazolyl, benzothiazolyl, benzimidazolyl and the like. Examples of the aralkyl moiety of the substituted or unsubstituted aralkyl include those having 7 to 15 carbon atoms, such as benzyl, 1-phenylethyl, 2-phenylethyl, 3-phenylpropyl, 2-phenylpropyl, diphenylmethyl, 1-naphthylmethyl, 2-naphthylmethyl and the like.

Examples of the substituent in the substituted lower alkyl include 1 to 3 substituents which are the same or different, such as hydroxy, carboxyl, lower cycloalkyl, lower alkoxy, lower alkoxycarbonyl, aryl, aryloxy, aralkyloxy, an aromatic heterocyclic group, a lower alkyl-substituted aromatic heterocyclic group, hydroxy-substituted lower alkoxy, lower alkoxy-substituted lower alkoxy, lower alkanoyl, aryl-substituted lower alkanoyl, aroyl, formyl, halogen, trifluoromethyl, vinyl, styryl, phenylethynyl and the like. Also, the lower cycloalkyl, the lower alkoxy, the lower alkoxy of the lower alkoxycarbonyl, the aryl, the aryl of the aryloxy, the aralkyl of the aralkyloxy, the aromatic heterocyclic group, the lower alkyl of the lower alkanoyl, the aryl of the aroyl and the halogen have the same meanings as defined above.

Examples of the substituent of the aryl, aromatic heterocyclic ring and aralkyl include 1 to 3 substituents which are the same or different, such as lower alkyl, hydroxy, hydroxy-substituted lower alkyl, halogeno lower alkyl, lower alkoxy, lower alkoxycarbonyl, lower alkylthio, lower alkylsulfinyl, lower alkylsulfonyl, aryl, aryloxy, aralkyl, aralkyloxy, an aromatic heterocyclic ring, halogenoaryloxy, halogenoaralkyloxy, carboxy, carbamoyl, formyl, lower alkanoyl, aroyl, halogen, nitro, amino, cyano, trifluoromethyl, trifluoromethoxy, methylenedioxy, ethylenedioxy and the like. The lower alkyl and the lower alkyl moiety of the hydroxy lower alkyl, halogeno lower alkyl, lower alkoxy, lower alkoxycarbonyl, lower alkylthio, lower alkylsulfinyl, lower alkylsulfonyl and lower alkanoyl have the same meaning as the above-described lower alkyl. The aryl and the aryl moiety of the aryloxy, halogenoaryloxy and aroyl have the same meaning as the above-described aryl. The aralkyl and the aralkyl moiety of the aralkyloxy and halogenoaralkyloxy have the same meaning as the above-described aralkyl. The aromatic heterocyclic ring has the same meaning as defined above. The halogen and the halogen moiety of the halogeno lower alkyl, halogenoaryloxy and halogenoaralkyloxy have the same meaning as the above-described halogen.

Hereinafter, the compound represented by formula (I) is referred to as Compound (I). Compounds of other formula numbers are also called similarly. Among Compounds (I), a compound in which Q is 3,4-dimethoxybenzyl is hereinafter referred to Compound (IQ) which has excellent adenosine $A_{2A}$ receptor antagonism and is also useful as a synthetic intermediate for a compound in which Q is hydrogen in formula (I). A compound in which Q is hydrogen in formula (I) is sometimes referred to as Compound (IH).

Compounds (IH) wherein Q in formula (I) is hydrogen are preferred compounds in the present invention. Preferred examples of Compound (IH) are shown below. Among the examples, compounds wherein $R^2$ is hydrogen, lower alkanoyl, aroyl, $CONR^{9A}R^{9B}$ (wherein $R^{9A}$ and $R^{9B}$ have the same meanings as defined above), or $CH_2R^{4B}$ (wherein $R^{4B}$ has the same meaning as defined above) are preferred. Compounds wherein $R^1$ is a substituted or unsubstituted aromatic heterocyclic ring, particularly furyl, are also preferred. Also, compounds wherein $R^3$ is hydrogen or $A^2$ ($A^2$ has the same meaning as defined above) are preferred, and nb is preferably 1 in the latter case.

Next, more preferred compounds can be shown by the combination of $R^1$, $R^2$ and $R^3$. Such compounds wherein $R^1$ is a substituted or unsubstituted aromatic heterocyclic ring, $R^2$ is hydrogen, and $R^3$ is $A^2$ ($A^2$ has the same meaning as defined above) are preferred, and among these, compounds wherein nb is 1 in $A^2$ are particularly preferred. Furthermore, among these, compounds wherein $R^1$ is furyl, $R^2$ is hydrogen, nb in $A^2$ is 1, $R^{6B}$ is hydrogen and $R^{5B}$ is hydroxy-substituted lower alkyl, lower alkoxy-substituted lower alkyl, a substituted or unsubstituted aromatic heterocyclic ring, or substituted or unsubstituted aralkyl are most preferred. Compounds wherein $R^1$ is a substituted or unsubstituted aromatic heterocyclic ring, $R^3$ is hydrogen and $R^2$ is lower alkanoyl, aroyl, $CONR^{9A}R^{9B}$ (wherein $R^{9A}$ and $R^{9B}$ have the same meanings as defined above) or COA³ (A³ has the same meaning as defined above) are also preferred, and among these, compounds wherein R¹ is furyl are more preferred.

Examples of the pharmaceutically acceptable salts of Compound (I) include pharmaceutically acceptable metal salts, ammonium salts, organic amine addition salts, amino acid addition salts, acid addition salts and the like. The pharmaceutically acceptable metal salts of Compound (I) include alkali metal salts, such as sodium salt, potassium salt and the like, alkaline earth metal salts, such as magnesium salt, calcium salt and the like, aluminum salt and the like. The ammonium salts include salts of ammonium, tetramethylammonium and the like. The pharmaceutically acceptable organic amine addition salts include addition salts of morpholine, piperidine and the like. The pharmaceutically acceptable amino acid addition salts include addition salts of lysine, glycine, phenylalanine and the like. The pharmaceutically acceptable acid addition salts include inorganic acid salts, such as hydrochloride, sulfate, phosphate and the like, and organic acid salts, such as acetate, maleate, fumarate, tartrate, citrate and the like.

Next, production methods of Compounds (I) are explained.

Production Method 1

Compound (IH) can be produced via Compound (IQ) by the following reaction steps.

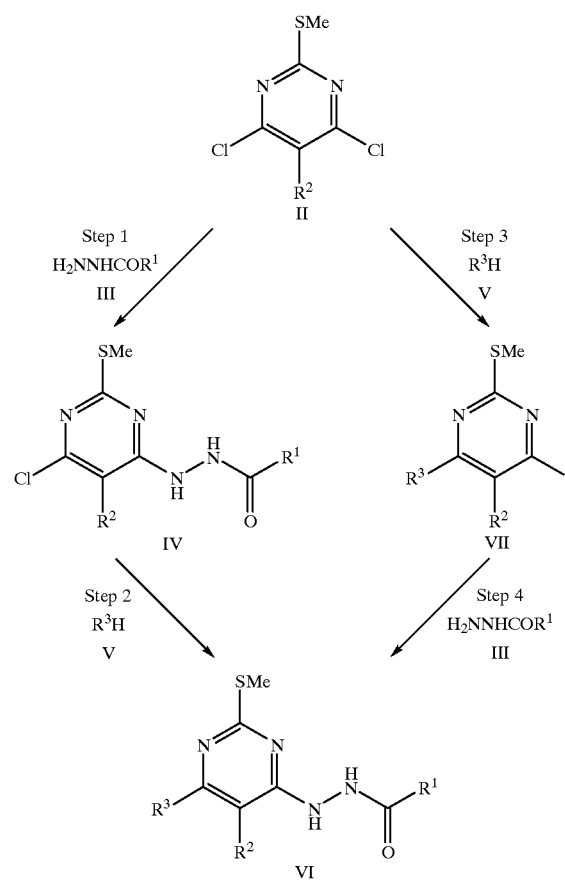

(In the above formula, R¹, R² and R³ have the same meanings as defined above; and Me is methyl and has the same meaning in the following formulae.)

Step 1

Starting Compound (II) is commercially available (manufactured by Aldrich) or can be synthesized in accordance with a known method [*Journal of Chemical Society*, p. 383 (1943)] or a method similar thereto. Also, Compound (III) is commercially available (manufactured by Aldrich) or can be synthesized in accordance with a known method [*New Experimental Chemistry Course*, Vol. 14, Syntheses and Reactions of Organic Compounds (II), p. 1221 (Maruzen) (1977)] or a method similar thereto.

Compound (IV) can be obtained by allowing Compound (II) to react with 1 to 5 equivalents, preferably 1 to 2 equivalents, of Compound (III) in an inert solvent to the reaction in the presence of 1 to 3 equivalents, preferably 2 equivalents, of an appropriate base, generally at room temperature to 200° C., preferably at room temperature, for 10 minutes to 48 hours. Examples of the inert solvent include methylene chloride, chloroform, methanol, ethanol, propanol, butanol, tetrahydrofuran (hereinafter referred to as "THF"), dioxane, diethylene glycol, N,N-dimethylformamide (hereinafter referred to as "DMF"), dimethylacetamide, dimethyl sulfoxide (hereinafter referred to as "DMSO"), benzene, toluene, xylene, acetonitrile, ethyl acetate, pyridine, tetralin and the like, which may be used alone or as a mixture thereof. Among these, THF and DMF are preferred. Examples of the appropriate base include triethylamine, diisopropylethylamine, 1,8-diazabicyclo-[5.4.0]undec-7-ene (hereinafter referred to as "DBU"), pyridine, N-methylmorpholine, potassium carbonate, sodium hydride, calcium hydride and the like. Among these, DBU is preferred.

Step 2

Compound (VI) can be obtained by allowing Compound (IV) to react with one equivalent to a large excess of Compound (V) without a solvent or in an inert solvent to the reaction in the presence of 0.1 to 3 equivalents, preferably 1.2 equivalents, of an appropriate base, generally at room temperature to 200° C., preferably at 100 to 150° C., for 10 minutes to 48 hours. Examples of the inert solvent include methylene chloride, chloroform, THF, dioxane, diethylene glycol, DMF, dimethylacetamide, DMSO, benzene, toluene, xylene, acetonitrile, ethyl acetate, pyridine, tetralin and the like, which may be used alone or as a mixture thereof. Among these, DMF and THF are preferred. Examples of the appropriate base include triethylamine, diisopropylethylamine, DBU, pyridine, N-methylmorpholine, potassium carbonate, sodium hydride, calcium hydride and the like. Among these, DBU is preferred.

Step 3

Compound (VII) can be obtained by allowing Compound (II) to react with 1 to 3 equivalents, preferably 1.2 equivalents, of Compound (V) without a solvent or in an inert solvent to the reaction in the presence of 1 to 3 equivalents, preferably 1.2 equivalents, of an appropriate base, generally at 10 to 200° C., preferably at 10 to 40° C., for 10 minutes to 48 hours. Examples of the inert solvent include methylene chloride, chloroform, THF, dioxane, diethylene glycol, DMF, dimethylacetamide, DMSO, benzene, toluene, xylene, acetonitrile, ethyl acetate, pyridine, tetralin and the like, which may be used alone or as a mixture thereof. Among these, DMF and THF are preferred. Examples of the appropriate base include triethylamine, diisopropylethylamine, DBU, pyridine, N-methylmorpholine, potassium carbonate, sodium hydride, calcium hydride and the like. Among these, DBU and sodium hydride are preferred.

Step 4

Compound (VI) can be obtained by allowing Compound (VII) to react with 1 to 3 equivalents, preferably 1.2 equivalents, of Compound (III) in an inert solvent to the reaction in the presence of 1 to 3 equivalents, preferably 1.2 equivalents, of an appropriate base, generally at 10 to 200° C., preferably at 90 to 100° C., for 10 minutes to 48 hours. Examples of the inert solvent include methylene chloride, chloroform, methanol, ethanol, propanol, butanol, THF, dioxane, diethylene glycol, DMF, dimethylacetamide, DMSO, benzene, toluene, xylene, acetonitrile, ethyl acetate, pyridine, tetralin and the like, which may be used alone or as a mixture thereof. Among these, DMF is preferred. Examples of the appropriate base include triethylamine, diisopropylethylamine, DBU, pyridine, N-methylmorpholine, potassium carbonate, sodium hydride, calcium hydride and the like. Among these, DBU is preferred.

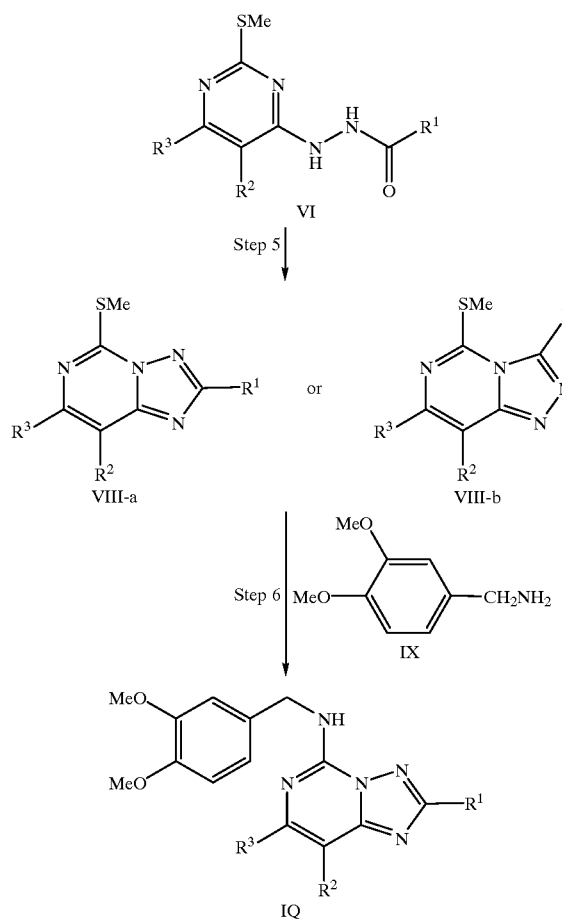

(In the above formula, $R^1$, $R^2$ and $R^3$ have the same meanings as defined above.)

Step 5

Compound (VIII-a) or Compound (VIII-b) can be obtained by allowing Compound (VI) to react with 2 to 100 equivalents of a dehydrating-condensing agent, such as polyphosphoric acid, ethyl polyphosphate, trimethylsilyl polyphosphate or the like, without a solvent or in an inert solvent to the reaction, generally at 10 to 200° C., preferably at 130 to 150° C., for 1 to 48 hours, preferably for 4 to 7 hours. Production of Compound (VIII-a) in this reaction is known as Dimroth rearrangement [for example, see *Journal of Medicinal Chemistry*, 33: 1231 (1990)]. Examples of the inert solvent include methylene chloride, chloroform, hexane, benzene, toluene, xylene, tetralin, phenyl ether and the like, which may be used alone or as a mixture thereof. Among these, xylene is preferred.

Step 6

Compound (IQ) can be obtained by allowing Compound (VIII-a) or Compound (VIII-b) to react with 1 to 6 equivalents, preferably 3 equivalents, of veratrylamine (IX) without a solvent or in an inert solvent to the reaction, generally at 10 to 200° C., preferably at 130 to 150° C., for 10 minutes to 24 hours. This reaction also accompanies the Dimroth rearrangement described in Step 5. Examples of the inert solvent include methylene chloride, chloroform, methanol, ethanol, propanol, butanol, THF, dioxane, diethylene glycol, DMF, dimethylacetamide, DMSO, benzene, toluene, xylene, acetonitrile, ethyl acetate, pyridine, tetralin and the like, which may be used alone or as a mixture thereof. Among these, DMSO is preferred.

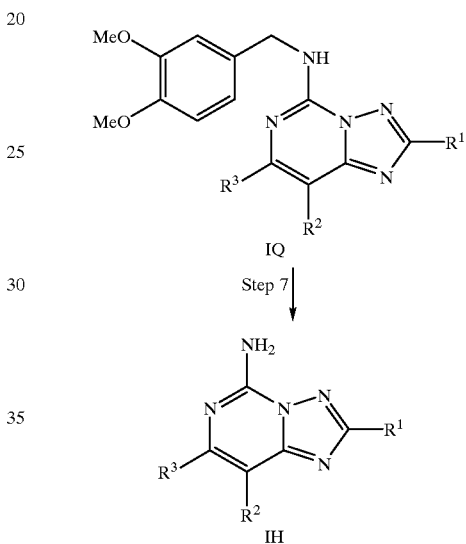

(In the above formula, $R^1$, $R^2$ and $R^3$ have the same meanings as defined above.)

Step 7

Compound (IH) can be obtained by allowing Compound (IQ) to react in an acidic solvent, such as hydrochloric acid, acetic acid, dichloroacetic acid, trifluoroacetic acid, trifluoromethanesulfonic acid or the like, preferably in trifluoroacetic acid or a mixed solvent of trifluoroacetic acid and trifluoromethanesulfonic acid, generally at 10 to 100° C. for 10 minutes to 24 hours, or by treating Compound (IQ) with 1 to 50 equivalents, preferably 3 to 5 equivalents, of trifluoromethanesulfonic acid or sulfuric acid in an acidic solvent, such as hydrochloric acid, acetic acid, dichloroacetic acid, trifluoroacetic acid or the like, preferably in trifluoroacetic acid, in the presence of 1 to 10 equivalents, preferably 4 equivalents of anisole, dimethoxybenzene or trimethoxybenzene, preferably anisole, generally at −20 to 80° C., preferably at 10 to 40° C., for 10 minutes to 18 hours.

Production Method 2

Among Compounds (IH), Compound (IH-b) wherein $R^{5B}$ is hydrogen and Compound (IH-c) wherein $R^{5B}$ is not hydrogen can also be produced from Compound (IH-a) wherein $R^3$ is represented by formula ($A^2$):

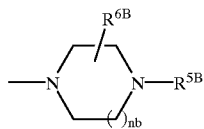

(wherein nb, $R^{5B}$ and $R^{6B}$ have the same meanings as defined above) and $R^{5B}$ is benzyl, by the following steps.

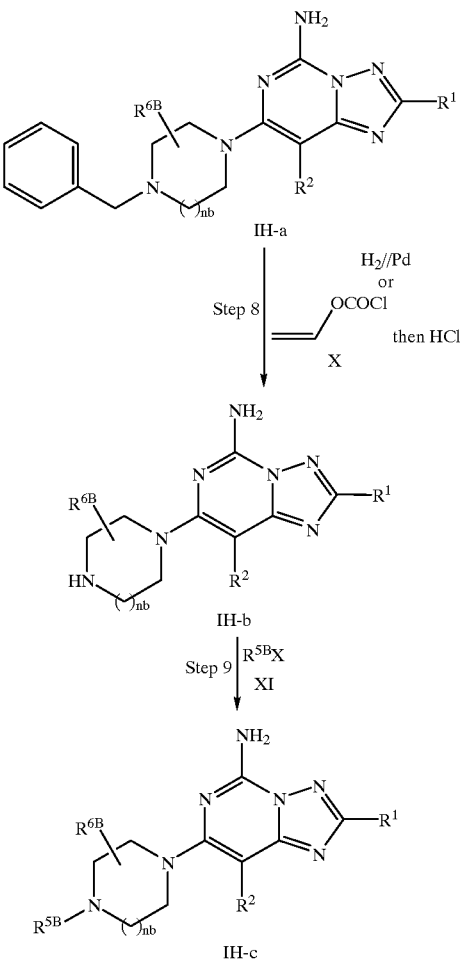

(In the above formula, nb, $R^1$, $R^2$, $R^{5B}$ and $R^{6B}$ have the same meanings as defined above.)

Step 8

Compound (IH-b) can be obtained by allowing Compound (IH-a) which is Compound (I) obtained in Step 7 wherein $R^3$ is represented by formula ($A^2$) to react with 1 to 5 equivalents, preferably 1.2 equivalents, of vinyl chlorocarbonate (X) in an inert solvent to the reaction, generally at 0 to 100° C., at preferably at 10 to 40° C., for 10 minutes to 24 hours, and then treating the reaction product in an inert solvent to the reaction containing 1 to 4 mol/l of hydrogen chloride, generally at 0 to 100° C., preferably at 10 to 40° C., for 10 minutes to 24 hours. Examples of the solvent in the reaction with vinyl chlorocarbonate (X) include dichloromethane, chloroform, carbon tetrachloride, benzene, toluene, THF, DMF, diethyl ether and the like, which may be used alone or as a mixture thereof. Among these, chloroform is preferred. Examples of the solvent in the treatment with hydrogen chloride include methanol, ethanol, propanol, isopropanol, ethyl acetate, dioxane and the like, which may be used alone or as a mixture thereof. Among these, methanol is preferred. Also, Compound (IH-b) can be obtained from Compound (IH-a) by treating it under usual catalytic reduction conditions.

Step 9

Compound (IH-c) can be obtained by allowing Compound (IH-b) to react with 1 to 10 equivalents, preferably 1 to 2 equivalents, of Compound (XI) in an inert solvent to the reaction, optionally in the presence of 1 to 3 equivalents of an appropriate base, generally at 0 to 150° C., preferably at 10 to 40° C., for 10 minutes to 48 hours. Examples of the inert solvent to the reaction include ethyl acetate, hexane, acetonitrile, pyridine, DMF, dimethylacetamide, THF, dioxane, diethyl ether, dichloromethane, chloroform, carbon tetrachloride, benzene, toluene, xylene, methanol, ethanol and the like, which may be used alone or as a mixture thereof. Among these, pyridine and DMF are preferred. Examples of the appropriate base include triethylamine, diisopropylethylamine, DBU, N-methylmorpholine, potassium carbonate, sodium hydride and the like. Among these, triethylamine is preferred.

Production Method 3

Among Compounds (I), Compound (IQ-a) and Compound (IH-d) wherein $R^3$ is hydrogen can also be produced by the following steps.

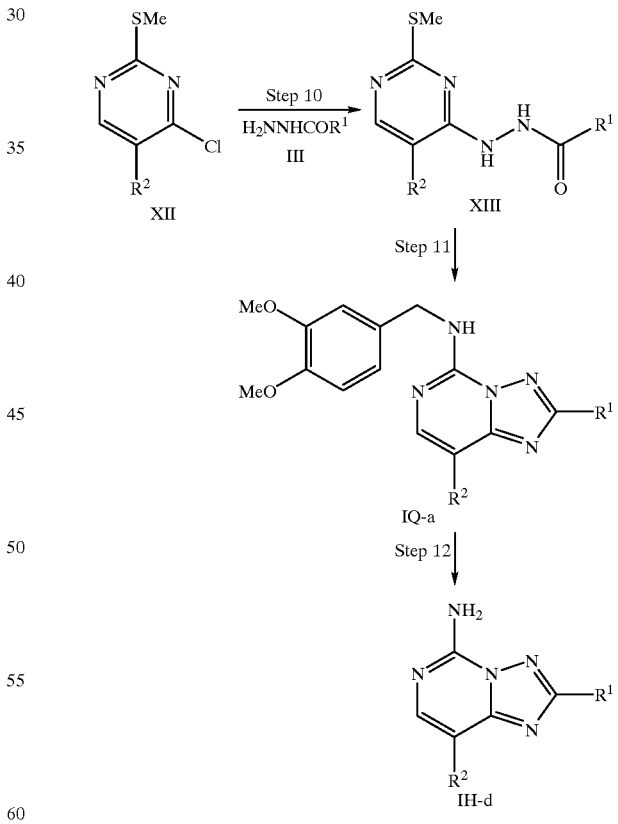

(In the above formula, $R^1$ and $R^2$ have the same meanings as defined above.)

Step 10

Compound (XIII) can be obtained by allowing Compound (XII) (manufactured by Aldrich) to react with 1 to 5 equivalents, preferably 1 to 2 equivalents, of Compound (III) in an inert solvent to the reaction in the presence of 1 to 3 equivalents, preferably 1.2 equivalents, of an appropriate base, generally at 10 to 200° C. for 10 minutes to 48 hours. Examples of the inert solvent include methylene chloride, chloroform, methanol, ethanol, propanol, butanol, THF, dioxane, diethylene glycol, DMF, dimethylacetamide, DMSO, benzene, toluene, xylene, acetonitrile, ethyl acetate, pyridine, tetralin and the like, which may be used alone or as a mixture thereof. Among these, DMF and THF are preferred. Examples of the appropriate base include triethylamine, diisopropylethylamine, DBU, pyridine, N-methylmorpholine, potassium carbonate, sodium hydride, calcium hydride and the like. Among these, DBU is preferred.

Step 11

Compound (IQ-a) can be obtained from Compound (XIII) by steps similar to continuous Steps 5 and 6 of Production Method 1.

Step 12

Compound (IH-d) can be obtained from Compound (IQ-a) by the step similar to Step 7 of Production Method 1.

Production Method 4

Among Compounds (I) wherein $R^2$ is represented by $CH_2R^{4B}$, Compound (IQ-c) and Compound (IH-e) wherein $R^{4B}$ is hydroxy can be produced by the following steps.

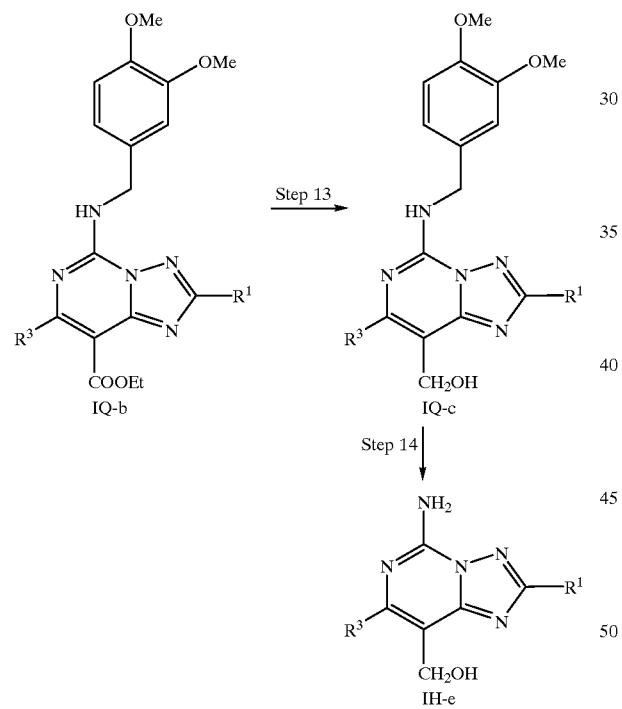

(In the above formula, $R^1$ and $R^3$ have the same meanings as defined above; and Et represents ethyl and has the same meaning in the following formulae.)

Step 13

Compound (IQ-c) can be obtained by treating Compound (IQ-b) which is the compound obtained in Step 6 of Production Method 1 wherein $R^2$ is ethoxycarbonyl with 2 to 4 equivalents of a reducing agent, such as lithium aluminum hydride, sodium borohydride, diisobutylaluminum hydride or the like, preferably diisobutylaluminum hydride, in an inert solvent to the reaction, generally at −78 to 40° C. for 10 minutes to 24 hours, preferably from 1 to 3 hours. Examples of the inert solvent include benzene, toluene, xylene, dichloromethane, chloroform, methanol, ethanol, tetralin, ether, THF and the like, which may be used alone or as a mixture thereof. Among these, dichloromethane is preferred.

Step 14

Compound (IH-e) can be obtained using Compound (IQ-c) by the step similar to Step 7 of Production Method 1.

Production Method 5

Compound (IQ-d) and Compound (IH-f) wherein $R^{4B}$ is lower alkoxy or substituted or unsubstituted aryloxy can also be produced by the following steps.

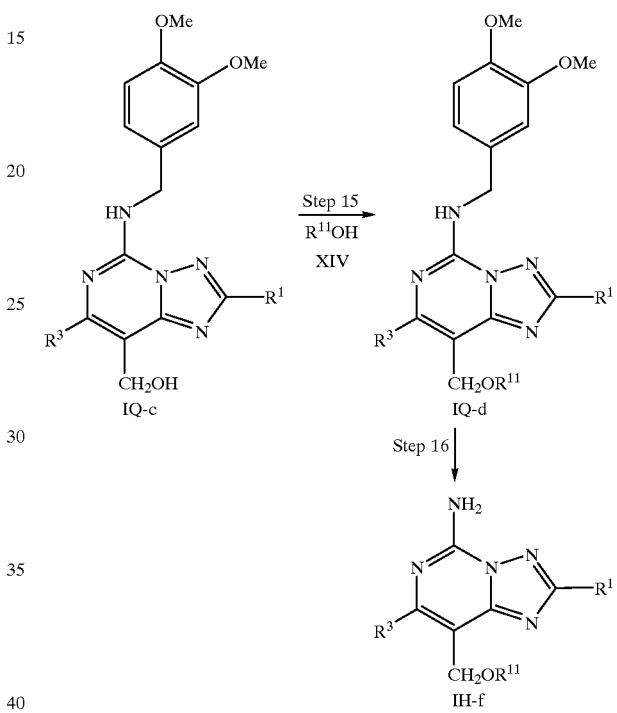

(In the above formula, $R^1$ and $R^3$ have the same meanings as defined above; and $R^{11}$ represents lower alkyl or substituted or unsubstituted aryl.)

Step 15

Compound (IQ-d) can be obtained by allowing Compound (IQ-c) to react with one equivalent of Compound (XIV) without a solvent or in an inert solvent to the reaction in the presence of 1 to 1.5 equivalents of triphenylphosphine and 1 to 1.5 equivalents of diethyl azodicarboxylate or diisopropyl azodicarboxylate, generally at 0 to 40° C., preferably at 10 to 30° C., for 1 to 48 hours. Examples of the inert solvent include THF, dioxane, DMF, dimethylacetamide, DMSO, benzene, toluene, xylene, acetonitrile, ethyl acetate, pyridine, tetralin, N-methylmorpholine, triethylamine and the like, which may be used alone or as a mixture thereof. Among these, THF and N-methylmorpholine are preferred.

Step 16

Compound (IH-f) can be obtained using Compound (IQ-d) by the step similar to Step 7 of Production Method 1.

Production Method 6

Among Compounds (I), Compound (IQ-e) and Compound (IH-g) wherein $R^2$ is formyl can also be produced by the following steps.

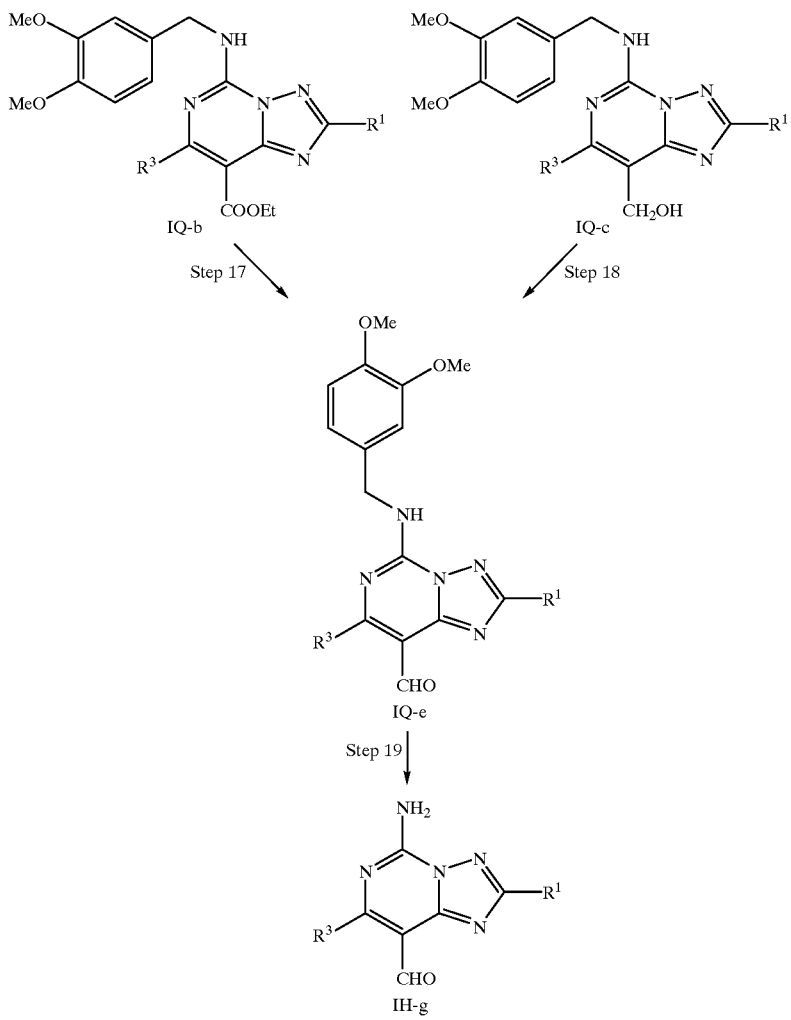

(In the above formula, $R^1$ and $R^3$ have the same meanings as defined above.)

Step 17

Compound (IQ-e) can be obtained by treating Compound (IQ-b) with 2 to 5 equivalents of a reducing agent, such as lithium aluminum hydride, sodium borohydride, diisobutylaluminum hydride or the like, preferably 2.5 equivalents of diisobutylaluminum hydride, in an inert solvent to the reaction, generally at −78 to 0° C. for 10 minutes to 24 hours. Examples of the inert solvent used together with the reducing agent include benzene, toluene, xylene, dichloromethane, chloroform, dichloroethane, methanol, ethanol, tetralin, ether, THF and the like, which may be used alone or as a mixture thereof. Among these, dichloromethane is preferred.

Step 18

Compound (IQ-e) can be obtained by treating Compound (IQ-c) with one equivalent to a large excess of an oxidizing agent, such as manganese dioxide, chromic acid, pyridinium chlorochromate, pyridinium chromate or the like, preferably 5 to 10 equivalents of manganese dioxide, in an inert solvent to the reaction, for 10 minutes to 24 hours, preferably for 3 to 6 hours. Examples of the inert solvent used together with the oxidizing agent include water, benzene, toluene, xylene, dichloromethane, chloroform, dichloroethane, acetic acid, and propionic acid, which may be used alone or as a mixture thereof. Among these, dichloromethane is preferred.

Step 19

Compound (IH-g) can be obtained using Compound (IQ-e) by the step similar to Step 7 of Production Method 1.

Production Method 7

Among Compounds (IH), Compound (IH-ha) or Compound (IH-hb) wherein $R^2$ is represented by $CH_2NR^{7A}R^{8A}$ or $CH_2A^1$ can also be produced by the following steps.

(wherein na, $R^{5A}$ and $R^{6A}$ have the same meanings as defined above)

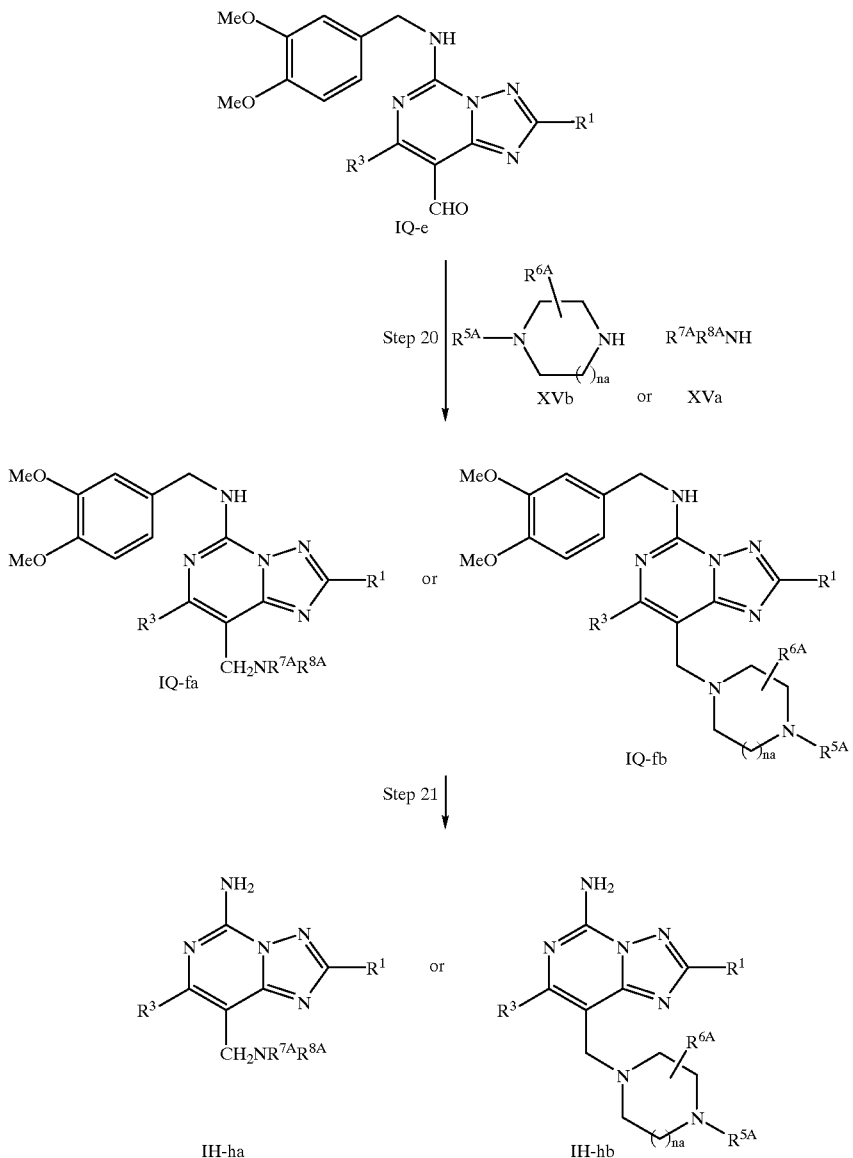

(In the above formula, $R^1$, $R^3$, na, $R^{5A}$, $R^{6A}$, $R^{7A}$ and $R^{8A}$ have the same meanings as defined above.)

Step 20

Compound (IQ-fa) or Compound (IQ-fb) can be obtained by allowing Compound (IQ-e) to react with 1 to 3 equivalents, preferably 1 to 2 equivalents, of Compound (XVa) or Compound (XVb) together with 1 to 10 equivalents, preferably 1 to 3 equivalents, of a reducing agent, such as sodium borohydride, sodium triacetoxyborohydride, sodium cyanoborohydride or the like, preferably sodium triacetoxyborohydride, in an inert solvent to the reaction, generally at −78 to 100° C. for 10 minutes to 24 hours. Optionally, 0.5 to 3 equivalents, preferably 1.1 equivalents, of acetic acid may be added. Examples of the inert solvent include dichloromethane, chloroform, dichloroethane, dioxane, ethyl acetate, hexane, acetonitrile, DMF, benzene, toluene, xylene, ether, THF and the like, which may be used alone or as a mixture thereof. Among these, dichloroethane is preferred.

Step 21

Compound (IH-ha) or Compound (IH-hb) can be obtained using Compound (IQ-fa) or Compound (IQ-fb) by the step similar to Step 7 of Production Method 1.

Production Method 8

As an alternative method, Compound (IH) can also be produced by the following steps.

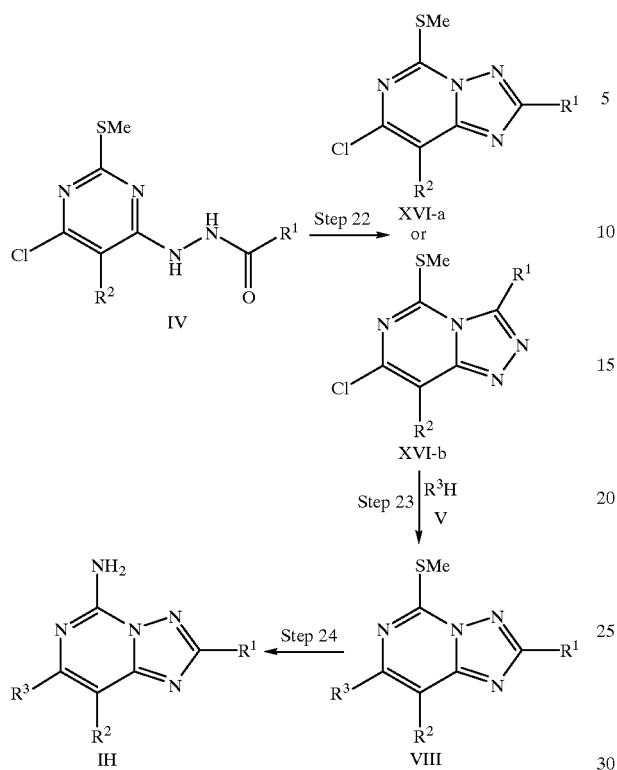

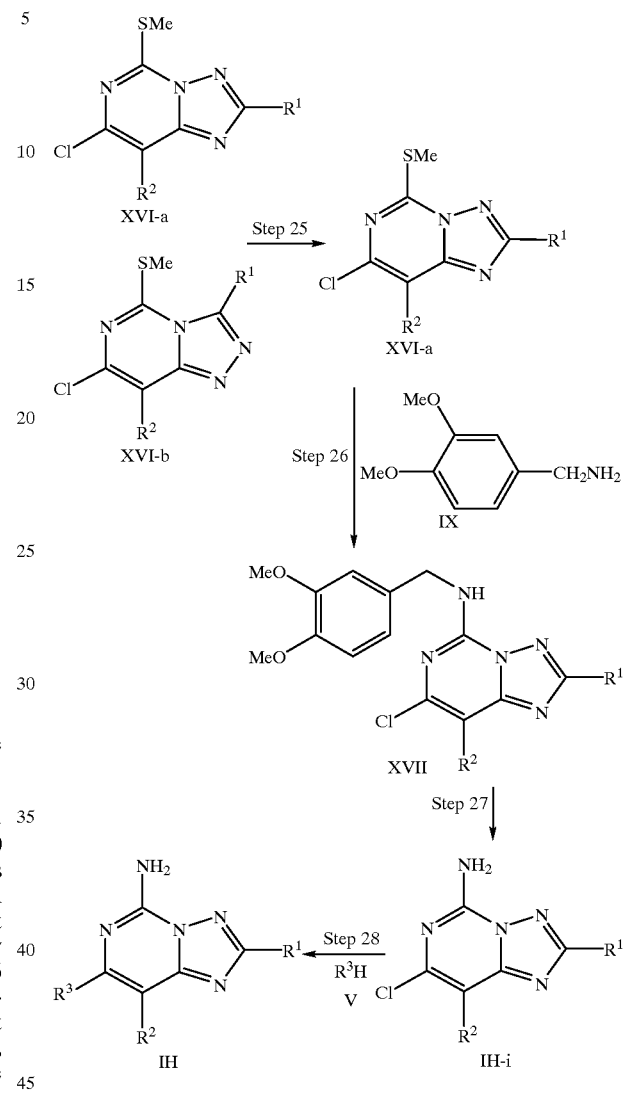

(In the above formula, $R^1$, $R^2$ and $R^3$ have the same meanings as defined above.)

Step 22

Compound (XVI-a) or Compound (XVI-b) can be obtained by allowing Compound (IV) to react with 2 to 100 equivalents of a dehydrating-condensing agent, such as polyphosphoric acid, ethyl polyphosphate, trimethylsilyl polyphosphate or the like, without a solvent or in an inert solvent to the reaction, generally at 10 to 200° C., preferably at 130 to 150° C., for 1 to 12 hours, preferably for 3 to 6 hours. This reaction also accompanies the Dimroth rearrangement described in Step 5. Examples of the inert solvent include methylene chloride, chloroform, toluene, xylene, tetralin, phenyl ether and the like, which may be used alone or as a mixture thereof. Among these, xylene is preferred.

Step 23

Compound (VIII) can be obtained by allowing Compound (XVI-a) or Compound (XVI-b) to react with 1 to 5 equivalents, preferably 1.2 equivalents, of Compound (V) in an inert solvent to the reaction in the presence of 1 to 5 equivalents, preferably 1.5 equivalents, of an appropriate base, generally at 10 to 200° C., preferably at 50 to 70° C., for 10 minutes to 48 hours. This reaction also accompanies the Dimroth rearrangement described in Step 5. Examples of the inert solvent include THF, dioxane, diethylene glycol, DMF, dimethylacetamide, DMSO, benzene, toluene, xylene, acetonitrile, ethyl acetate, pyridine, tetralin and the like, which may be used alone or as a mixture thereof. Among these, DMF and THF are preferred. Examples of the appropriate base include triethylamine, diisopropylethylamine, DBU, pyridine, N-methylmorpholine, potassium carbonate, sodium hydride, calcium hydride and the like. Among these, DBU is preferred.

Step 24

Compound (IH) can be obtained from Compound (VIII) by the step similar to continuous Steps 6 and 7 of Production Method 1.

Production Method 9

Also, as another method, Compound (IH) can be produced by the following steps.

(In the above formula, $R^1$, $R^2$ and $R^3$ have the same meanings as defined above.)

Step 25

Only Compound (XVI-a) can be obtained via the Dimroth rearrangement described in Step 5 by treating a mixture of Compound (XVI-a) and Compound (XVI-b) or Compound (XVI-b) alone in an inert solvent to the reaction in the presence of 0.5 to 3 equivalents, preferably one equivalent, of an appropriate base, generally at 0 to 100° C., preferably at 10 to 40° C., for 5 minutes to 10 hours. Examples of the inert solvent to the reaction include methylene chloride, chloroform, methanol, ethanol, propanol, butanol, THF, dioxane, diethylene glycol, DMF, dimethylacetamide, DMSO, benzene, toluene, xylene, acetonitrile, ethyl acetate, pyridine, tetralin and the like, which may be used alone or as a mixture thereof. Among these, DMF and THF are preferred. Examples of the appropriate base include triethylamine, diisopropylethylamine, DBU, pyridine, N-methylmorpholine, potassium carbonate, sodium hydride, calcium hydride and the like. Among these, DBU is preferred.

Step 26

Compound (XVII) can be obtained by allowing Compound (XVI-a) to react with 1 to 6 equivalents, preferably 3 equivalents, of veratrylamine without a solvent or in an inert solvent to the reaction, generally at 0 to 200° C., preferably at 40 to 60° C., for 10 minutes to 24 hours. Examples of the inert solvent include methylene chloride, chloroform, methanol, ethanol, propanol, butanol, THF, dioxane, diethylene glycol, DMF, dimethylacetamide, DMSO, benzene, toluene, xylene, acetonitrile, ethyl acetate, pyridine, tetralin and the like, which may be used alone or as a mixture thereof. Among these, DMSO is preferred.

Step 27

Compound (IH-i) can be obtained by allowing Compound (XVII) to react for 10 minutes to 24 hours in an acidic solvent, such as hydrochloric acid, acetic acid, dichloroacetic acid, trifluoroacetic acid, trifluoromethanesulfonic acid or the like, preferably in trifluoroacetic acid or a mixed solvent of trifluoroacetic acid and trifluoromethanesulfonic acid, or by treating Compound (XVII) with 1 to 10 equivalents, preferably 5 equivalents, of trifluoromethanesulfonic acid in an acidic solvent, such as hydrochloric acid, acetic acid, dichloroacetic acid, trifluoroacetic acid or the like, preferably in trifluoroacetic acid, in the presence of 1 to 10 equivalents, preferably 4 equivalents of anisole, dimethoxybenzene or trimethoxybenzene, preferably anisole, generally at −20 to 100° C., preferably at 10 to 40° C., for 10 minutes to 18 hours.

Step 28

Compound (IH) can be obtained by allowing Compound (IH-i) to react with 1 to 50 equivalents, preferably 1 to 3 equivalents, of Compound (V) without a solvent or in an inert solvent to the reaction, optionally in the presence of 1 to 5 equivalents, preferably 1.5 equivalents, of an appropriate base, generally at 10 to 200° C. for 10 minutes to 48 hours. Examples of the inert solvent include methylene chloride, chloroform, THF, dioxane, diethylene glycol, DMF, dimethylacetamide, DMSO, benzene, toluene, xylene, acetonitrile, ethyl acetate, pyridine, tetralin and the like, which may be used alone or as a mixture thereof. Among these, DMSO is preferred. Examples of the appropriate base include triethylamine, diisopropylethylamine, DBU, pyridine, N-methylmorpholine, potassium carbonate, sodium hydride, calcium hydride and the like. Among these, DBU is preferred.

Production Method 10

Among Compounds (I), Compound (IH-ca) wherein $R^{5B}$ is a substituent shown below can also be obtained from Compound (IH-b) by the following step.

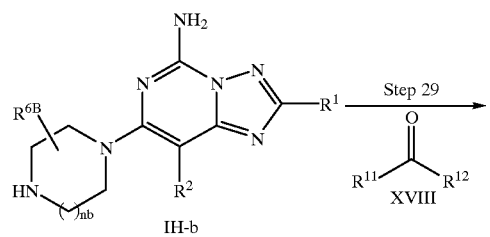

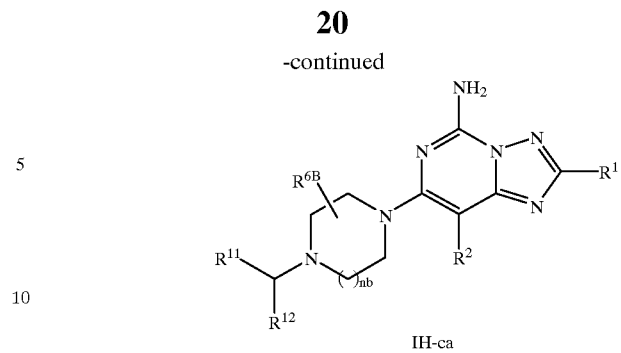

(In the above formula, $R^1$, $R^2$, nb and $R^{6B}$ have the same meanings as defined above; and $R^{11}$ and $R^{12}$ are the same or different, and each represents hydrogen, lower alkyl, lower cycloalkyl, hydroxy lower alkyl, lower alkoxy-substituted lower alkyl, substituted or unsubstituted aryl-substituted lower alkyl, substituted or unsubstituted aromatic group-substituted lower alkyl, substituted or unsubstituted aryl, or a substituted or unsubstituted aromatic heterocyclic ring.)

Step 29

Compound (IH-ca) can be obtained by allowing Compound (IH-b) to react with one equivalent to a large excess, preferably 1 to 10 equivalents, of Compound (XVIII) without a solvent or in an inert solvent to the reaction in the presence of one equivalent to a large excess, preferably 1 to 3 equivalents, of an appropriate reducing agent, generally at −78 to 100° C., preferably at 0 to 50° C., for 10 minutes to 24 hours. Examples of the inert solvent to the reaction include dichloromethane, chloroform, carbon tetrachloride, dichloroethane, benzene, toluene, xylene, ether, tetrahydrofuran, dioxane, dimethylformamide, dimethylacetamide, acetonitrile, hexane and the like, which may be used alone or as a mixture thereof. Among these, dichloroethane and dichloromethane are preferred. Examples of the appropriate reducing agent include sodium borohydride, sodium triacetoxyborohydride, sodium cyanoborohydride and the like. Among these, sodium triacetoxyborohydride is preferred. In this case, an appropriate acid may optionally be added in an amount of a catalytically effective amount to a large excess, preferably 0.5 to 5 equivalents. Examples of the appropriate acid include formic acid, acetic acid, trifluoroacetic acid, propionic acid, hydrochloric acid and the like. Among these, acetic acid is preferred.

Production Method 11

Among Compounds (I), Compound (IH-cc) in which $R^{5B}$ is a hydroxy-substituted alkyl can also be produced by the following step.

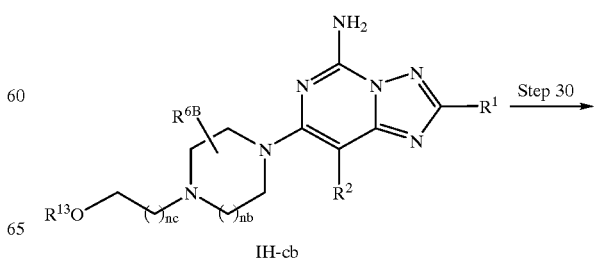

-continued

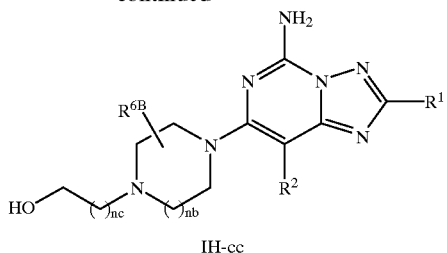

IH-cc (In the above formula, $R^1$, $R^2$, nb and $R^{6B}$ have the same meanings as defined above; nc has the same meaning as na and nb; and $R^{13}$ represents a substituted or unsubstituted benzyl group.)

Step 30

Compound (IH-cc) can be obtained by allowing Compound (IH-cb) to react with one equivalent to a large excess, preferably a large excess, of an appropriate sulfur compound without a solvent or in an inert solvent to the reaction in the presence of a catalytically effective amount to a large excess, preferably 5 to 15 equivalents, of an appropriate Lewis acid, generally at −78 to 100° C. for 10 minutes to 72 hours. Examples of the inert solvent to the reaction include dichloromethane, chloroform, carbon tetrachloride, dichloroethane, benzene, toluene, xylene, ether, tetrahydrofuran, dioxane, dimethylformamide, dimethylacetamide, ethyl acetate, hexane, acetonitrile and the like, which may be used alone or as a mixture thereof. Among these, dichloromethane is preferred. Examples of the appropriate sulfur compound include ethanethiol, dimethyl sulfide, benzenethiol and the like. Examples of the appropriate Lewis acid include a boron trifluoride diethyl ether complex, aluminum trichloride, titanium tetrachloride, tin tetrachloride and the like. Among these, a boron trifluoride diethyl ether complex is preferred.

Production Method 12

Among Compounds (I), Compound (I-b) in which $R^3$ has a structure shown below can also be produced by the following step from Compound (I-a) wherein $R^3$ is a chlorine atom.

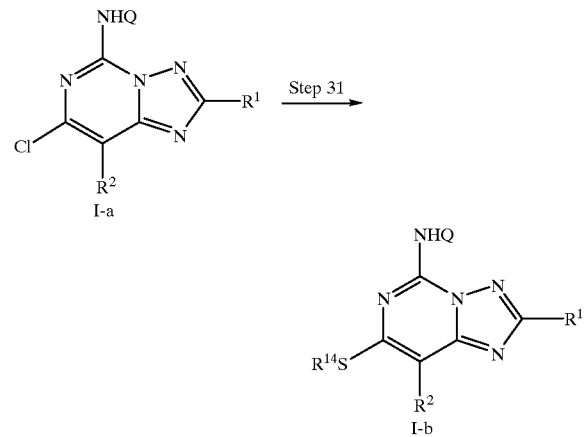

(In the above formula, $R^1$, $R^2$ and Q have the same meanings as defined above; and $R^{14}$ has the same meaning as $R^{10}$.)

Step 31

Compound (I-b) can be obtained by allowing Compound (I-a) to react in an inert solvent to the reaction in the presence of 1 to 20 equivalents, preferably 3 to 10 equivalents, of an appropriate alkali metal sulfide, generally at room temperature to 160° C. for 10 minutes to 12 hours, followed by addition of water, and then the mixture is allowed to react with one equivalent to a large excess of an appropriate alkyl halide or aralkyl halide. Examples of the inert solvent to the reaction include methylene chloride, chloroform, dichloroethane, acetonitrile, pyridine, ethyl acetate, water, dimethylformamide, dimethylacetamide, dimethyl sulfoxide, dioxane, tetrahydrofuran, diethyl ether, benzene, toluene, xylene and the like. Among these, dimethylformamide is preferred. Examples of the appropriate alkali metal sulfide include sodium hydrosulfide, sodium sulfide and the like. Among these, sodium hydrosulfide is preferred.

Production Method 13

Among Compounds (I), Compound (I-d) wherein $R^3$ has a structure shown below can also be produced by the following step.

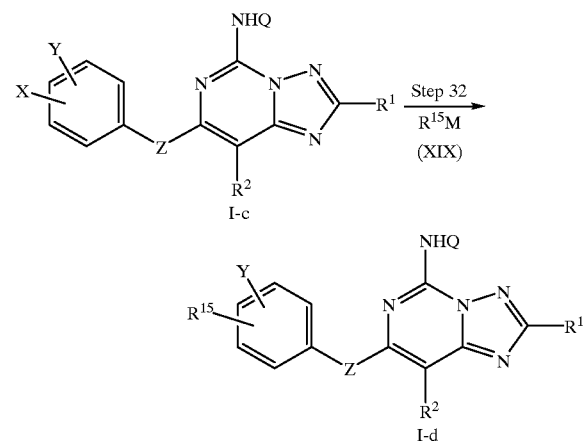

(In the above formula, $R^1$, $R^3$ and Q have the same meanings as defined above; $R^{15}$ represents lower alkyl, aryl, or an aromatic heterocyclic group; X represents iodine, bromine, or a trifluoromethanesulfonyloxy group; Y represents hydrogen, lower alkyl, lower alkoxy, cyano, amino, fluorine, chlorine, hydroxy, hydroxy lower alkyl, lower alkoxycarbonyl, lower alkylthio, aryl, aryloxy, aralkyl, aralkyloxy, carboxy, carbamoyl, lower alkanoyl, aroyl, nitro, trifluoromethyl, methylenedioxy, or the like; M represents tributyltin, trimethyltin, triphenyltin, or dihydroxyboron; and Z represents O or S.)

Step 32

Compound (I-d) can be obtained by allowing Compound (I-c) to react with 1 to 10 equivalents of Compound (XIX) without a solvent or in an inert solvent to the reaction in the presence of a catalytically effective amount of a palladium compound, generally at room temperature to 140° C. for 10 minutes to 48 hours. In this case, the reaction can also be carried out by adding 0.2 to 5 equivalents, preferably one equivalent, of an inorganic salt, such as lithium chloride, potassium chloride, silver oxide, copper oxide, silver nitrate, silver acetate or the like, preferably silver oxide. Examples of the inert solvent to the reaction include ether, tetrahydrofuran, dioxane, N,N-dimethylformamide, N,N-dimethylacetamide, dimethyl sulfoxide, benzene, toluene, xylene, dichloromethane, chloroform, carbon tetrachloride, 1,2-dichloroethane, acetonitrile, ethyl acetate, methyl acetate, methyl ethyl ketone, methanol, ethanol, propanol, isopropanol, butanol, hexane and the like. Among these, tetrahydrofuran and N,N-dimethylformamide are preferred.

Examples of the palladium compound include bis(triphenylphosphine)palladium (II) chloride, tetrakis(triphenylphosphine)palladium (0), [1,2-bis(diphenylphosphino)ethane]palladium (II) chloride, (1,1'-bis(diphenylphosphino)ferrocene)palladium (II) chloride and the like. Among these, bis(triphenylphosphine)palladium (II) chloride and terakis(triphenylphosphine)palladium (0) are preferred.

Production Method 14

Among Compounds (I), Compound (I-f), Compound (I-g), Compound (I-h) and Compound (I-i) wherein $R^2$ has a structure shown below can also be produced by the following steps.

Examples of the appropriate solvent include water, methanol, ethanol, propanol, isopropanol, tetrahydrofuran, dioxane, ethylene glycol, diethylene glycol, acetonitrile, pyridine, triethylamine and the like, which may be used alone or as a mixture thereof, and a mixed solvent of ethanol-water is preferred. Examples of the appropriate alkali metal salt include lithium hydroxide, sodium hydroxide, potassium hydroxide, potassium carbonate, sodium carbonate, cesium carbonate, sodium bicarbonate and the like. Among these, lithium hydroxide is preferred.

Step 34

Compound (I-g) can be obtained by allowing Compound (I-f) to react with 1 to 20 equivalents of a halogenating agent

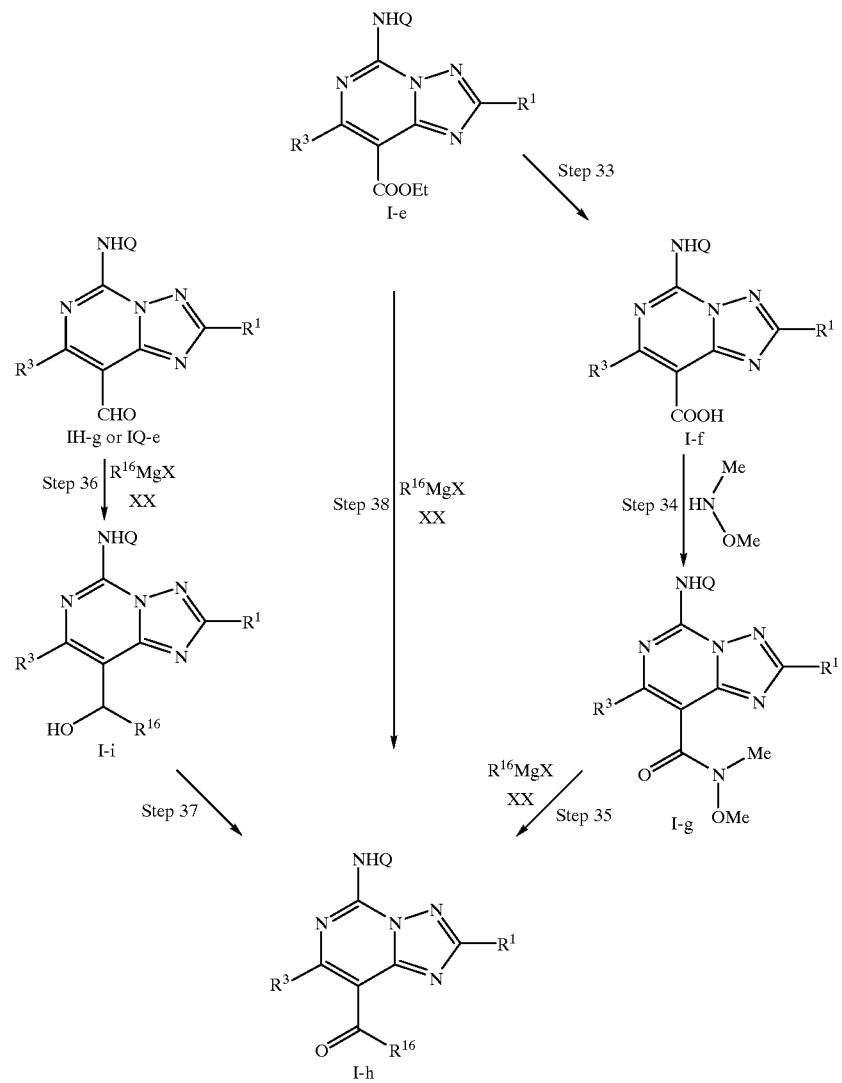

(In the above formula, $R^1$, $R^3$ and Q have the same meanings as defined above; and $R^{16}$ represents hydrogen, lower alkyl, lower cycloalkyl, aryl, aralkyl, or a substituted or unsubstituted aromatic heterocyclic group.)

Step 33

Compound (I-f) can be obtained by allowing Compound (I-e) to react together with one equivalent to a large excess of an appropriate alkali metal salt in an appropriate solvent, generally at 0 to 150° C. for 10 minutes to 24 hours.

and 1 to 10 equivalents of N,O-dimethoxyhydroxylamine hydrochloride in an appropriate basic solvent, generally at −10 to 100° C., preferably at room temperature, for 10 minutes to 24 hours. As the appropriate solvent, pyridine, triethylamine, diisopropylethylamine, DBU, N-methylmorpholine and the like are used alone or as a mixture thereof; or methylene chloride, chloroform, ethyl acetate, tetrahydrofuran, dioxane, dimethylformamide, dimethylacetamide, acetonitrile, benzene, toluene, xylene or the like may be used by mixing it with pyridine, triethylamine, diisopropylethylamine, DBU, N-methylmorpholine or the like. Among these, pyridine is preferred. Examples of the halogenating agent include thionyl chloride, oxalyl chloride, phosphorus oxychloride and the like. Among these, thionyl chloride is preferred. Alternatively, Compound (I-g) can be obtained using a technique usually used in the peptide chemistry, for example, by allowing Compound (I-f) to react with 1 to 10 equivalents of N,O-dimethoxyhydroxylamine hydrochloride together with 0.5 to 10 equivalents of an appropriate condensing agent in an inert solvent to the reaction, generally at 0 to 50° C. for 10 minutes to 70 hours. Examples of the inert solvent to the reaction include diethyl ether, tetrahydrofuran, dioxane, dimethylformamide, dimethylacetamide, dimethyl sulfoxide, benzene, toluene, xylene, acetonitrile, ethyl acetate, pyridine, methylene chloride, chloroform, carbon tetrachloride and the like. Among these, dimethylformamide and methylene chloride are preferred. Examples of the appropriate condensing agent include 1,3-dicyclohexylcarbodiimide, 1-ethyl-3-(3-dimethylaminopropyl)carbodilmide hydrochloride and the like. In this case, an additive, such as 1-hydroxysuccinimide, 3,4-dihydro-3-hydroxy-4-oxo-1,2,3-benzotriazine, 1-hydroxybenzotriazole or the like, preferably 1-hydroxybenzotriazole, may be used.

Step 35

Compound (I-h) can be obtained by allowing Compound (I-g) to react with 1 to 20 equivalents of a Grignard reagent (XX) in an inert solvent to the reaction, generally at −10 to 100° C., preferably at room temperature, for 10 minutes to 24 hours. Examples of the inert solvent to the reaction include dichloromethane, chloroform, carbon tetrachloride, benzene, toluene, xylene, diethyl ether, tetrahydrofuran, dioxane, dimethylformamide, dimethylacetamide and the like, which may be used alone or as a mixture thereof. Among these, tetrahydrofuran and diethyl ether are preferred.

Step 36

Compound (I-i) can be obtained by allowing Compound (IH-g) or Compound (IQ-e) to react with 1 to 20 equivalents of a Grignard reagent (XX) in an inert solvent to the reaction, generally at −10 to 100° C., preferably at room temperature, for 10 minutes to 24 hours. Examples of the inert solvent to the reaction include dichloromethane, chloroform, carbon tetrachloride, benzene, toluene, xylene, diethyl ether, tetrahydrofuran, dioxane, dimethylformamide, dimethylacetamide and the like, which may be used alone or as a mixture thereof. Among these, tetrahydrofuran and diethyl ether are preferred.

Step 37

Compound (I-h) can be obtained by allowing Compound (I-i) to react with one equivalent to a large excess of an appropriate oxidizing agent in an inert solvent to the reaction, generally at 0 to 100° C., preferably at room temperature, for 10 minutes to 24 hours. Examples of the inert solvent to the reaction include methylene chloride, chloroform, carbon tetrachloride, dichloroethane, benzene, toluene, xylene, ethyl acetate, acetic acid, propionic acid, butyric acid, trifluoroacetic acid, water, pyridine and the like, which may be used alone or as a mixture thereof. Among these, methylene chloride is preferred. Examples of the appropriate oxidizing agent include manganese dioxide, chromic acid, pyridinium chlorochromate, pyridinium dichromate, potassium permanganate, sulfur trioxidepyridine, oxone and the like. Among these, manganese dioxide and pyridinium chlorochromate are preferred.

Step 38

Compound (I-h) can be obtained by allowing Compound (I-e) to react with 1 to 20 equivalents of a Grignard reagent (XX) in an inert solvent to the reaction, generally at −10 to 100° C., preferably at room temperature, for 10 minutes to 24 hours. Examples of the inert solvent to the reaction include dichloromethane, chloroform, carbon tetrachloride, benzene, toluene, xylene, diethyl ether, tetrahydrofuran, dioxane, dimethylformamide, dimethylacetamide and the like, which may be used alone or as a mixture thereof. Among these, tetrahydrofuran and diethyl ether are preferred.

Production Method 15

Among Compounds (I), Compound (I-j) wherein $R^2$ has a structure shown below can also be produced by the following steps.

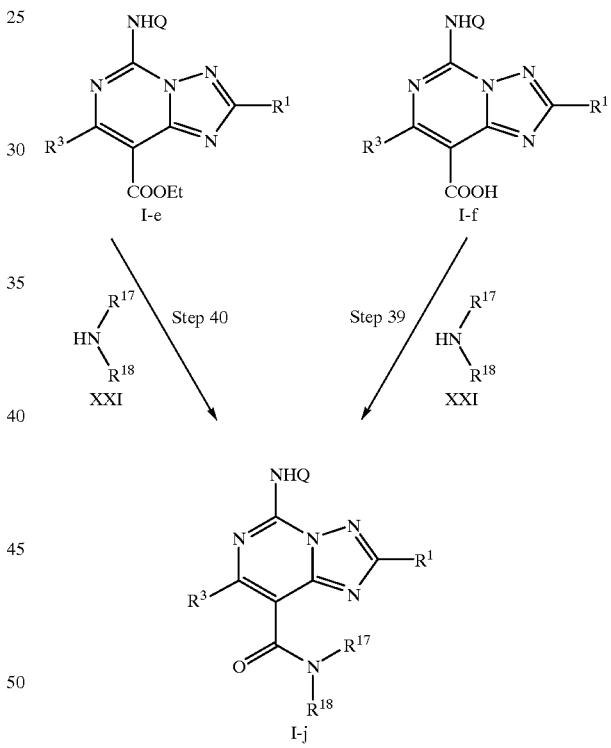

(In the above formula, $R^1$, $R^3$, Q have the same meanings as defined above; $R^{17}$ represents hydrogen or lower alkyl; $R^{18}$ represents hydrogen, susbtituted or unsubstituted aryl, a substituted or unsubstituted aromatic heterocyclic ring, substituted or sunsubstituted aralkyl, lower cycloalkyl, lower alkoxy, or lower alkyl; or $R^{17}$ and $R^{18}$ are combined together with an adjacent nitrogen atom to represent a group represented by $(A^3)$ having the same meaning as defined above or a group represented by $(B^3)$ having the same meaning as defined above.)

Step 39

Compound (I-j) can be obtained by allowing Compound (I-f) to react with 1 to 20 equivalents of a halogenating agent and 1 to 10 equivalents of Compound (XXI) in an appropriate basic solvent, generally at −10 to 100° C., preferably at room temperature, for 10 minutes to 24 hours. As the appropriate solvent, pyridine, triethylamine, diisopropylethylamine, DBU, N-methylmorpholine and the like may be used alone or as a mixture thereof; or methylene chloride, chloroform, ethyl acetate, tetrahydrofuran, dioxane, dimethylformamide, dimethylacetamide, acetonitrile, benzene, toluene, xylene or the like may be used by mixing it with pyridine, triethylamine, diisopropylethylamine, DBU, N-methylmorpholine or the like. Among these, pyridine is preferred. Examples of the halogenating agent include thionyl chloride, oxalyl chloride, phosphorus oxychloride and the like. Among these, thionyl chloride is preferred. Alternatively, Compound (I-j) can be obtained using a technique usually used in the peptide chemistry, for example, by allowing Compound (I-f) to react with 1 to 10 equivalents of Compound (XXI) together with 0.5 to 10 equivalents of an appropriate condensing agent in an inert solvent to the reaction, generally at 0 to 50° C. for 10 minutes to 70 hours. Examples of the inert solvent to the reaction include diethyl ether, tetrahydrofuran, dioxane, dimethylformamide, dimethylacetamide, dimethyl sulfoxide, benzene, toluene, xylene, acetonitrile, ethyl acetate, pyridine, methylene chloride, chloroform, carbon tetrachloride and the like. Among these, dimethylformamide and methylene chloride are preferred. Examples of the appropriate condensing agent include 1,3-dicyclohexylcarbodiimide, 1-ethyl-3-(3-dimethylaminopropyl)carbodiimide hydrochloride and the like. In this case, an additive, such as 1-hydroxysuccinimide, 3,4-dihydro-3-hydroxy-4-oxo-1,2,3-benzotriazine, 1-hydroxybenzotriazole or the like, preferably 1-hydroxybenzotriazole, may be used.

Step 40

Compound (I-j) can be obtained by allowing Compound (I-f) to react with one equivalent to a large excess of Compound (XXI) in the presence of one equivalent to a large excess of an appropriate Grignard reagent in an inert solvent to the reaction, generally at −78° C. to room temperature for 10 minutes to 48 hours. Examples of the inert solvent to the reaction include dichloromethane, chloroform, carbon tetrachloride, benzene, toluene, xylene, diethyl ether, tetrahydrofuran, dioxane, dimethylformamide, dimethylacetamide and the like, which may be used alone or as a mixture thereof. Among these, tetrahydrofuran and diethyl ether are preferred. Examples of the appropriate Grignard reagent include methylmagnesium bromide, ethylmagnesium bromide, ethylmagnesium chloride, propylmagnesium bromide, isopropylmagnesium bromide, isopropylmagnesium chloride, butylmagnesium bromide, tert-butylmagnesium bromide, tert-butylmagnesium chloride, phenylmagnesium bromide and the like. Among these, isopropylmagnesium bromide, isopropylmagnesium chloride, tert-butylmagnesium bromide and tert-butylmagnesium chloride are preferred.

The intermediates and objective compounds obtained in the above-described production methods can be isolated and purified according to the separation and purification methods usually used in the synthetic organic chemistry, such as filtration, extraction, washing, drying, concentration, recrystallization, various kinds of chromatography and the like. In the case of the intermediates, they may be applied to the subsequent reactions without purification.

In the case where a salt of Compound (I) is desired, when Compound (I) is produced in the form of the salt, it can be purified as it is, but when it is produced in its free form, it can be dissolved or suspended in an appropriate solvent, converted into a salt by adding an acid or base and then isolated and purified. Additionally, Compound (I) or pharmaceutically acceptable salts thereof may exist in the form of their addition products with water or various solvents, and these addition products are also included in the present invention.

Examples of Compound (I) obtained by the present invention are shown in Table 1. In the table, Ph, Me, Et, Pr, Bz, Bzl, Ac and $^t$Bu represent phenyl, methyl, ethyl, propyl, benzoyl, benzyl, acetyl and tert-butyl, respectively.

TABLE 1

| Compound No. | Q | R¹ | R² | R³ |
|---|---|---|---|---|
| 1 | 3,4-dimethoxybenzyl | 2-furyl | H | phenyl |
| 2 | 3,4-dimethoxybenzyl | 2-furyl | H | 2,4-dimethoxyphenyl |
| 3 | 3,4-dimethoxybenzyl | 2-furyl | H | 2,6-dimethoxyphenyl |
| 4 | 3,4-dimethoxybenzyl | 2-furyl | H | 3,5-dimethoxyphenyl |

TABLE 1-continued
| Compound No. | Q | R¹ | R² | R³ |
|---|---|---|---|---|
| 5 | 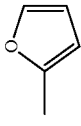 | 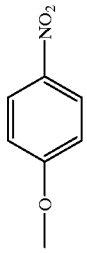 furan | H | 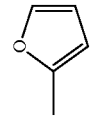 4-NO₂-C₆H₄-O- |
| 6 | 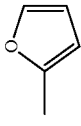 | 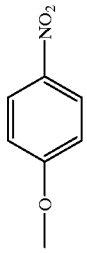 furan | H | 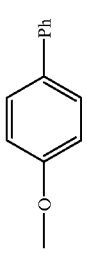 4-Cl-C₆H₄-O- |
| 7 | 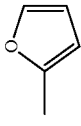 | 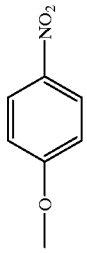 furan | H | 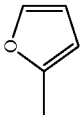 4-Ph-C₆H₄-O- |
| 8 | 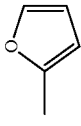 | 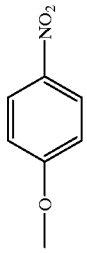 furan | 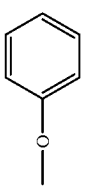 Ph | 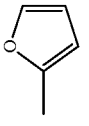 C₆H₅-O- |
| 9 | 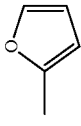 | 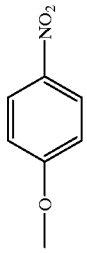 furan | OMe | 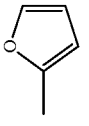 C₆H₅-O- |

TABLE 1-continued

| Compound No. | Q | R¹ | R² | R³ |
|---|---|---|---|---|
| 10 | 4-methoxy-3-methoxybenzyl (CH₂-C₆H₃(OMe)₂) | 2-furyl | H | phenylthio (PhS-) |
| 11 | 4-methoxy-3-methoxybenzyl | 2-furyl | phenyl | phenylthio |
| 12 | 4-methoxy-3-methoxybenzyl | phenyl | H | phenoxy (PhO-) |
| 13 | 4-methoxy-3-methoxybenzyl | 3-methoxyphenyl | H | phenoxy |
| 14 | 4-methoxy-3-methoxybenzyl | 3-pyridyl | H | phenoxy |

TABLE 1-continued

![structure: NHQ-substituted imidazo-fused pyrimidine with R1, R2, R3]

| Compound No. | Q | R¹ | R² | R³ |
|---|---|---|---|---|
| 15 | 4-methyl-2,3-dimethoxybenzyl (-CH₂-C₆H₃(OMe)₂) | 2-thienyl | H | phenoxy (-O-Ph) |
| 16 | 4-methyl-2,3-dimethoxybenzyl | 2-furyl | H | 1-piperidinyl |
| 17 | 4-methyl-2,3-dimethoxybenzyl | 2-furyl | H | 4-morpholinyl |
| 18 | 4-methyl-2,3-dimethoxybenzyl | 2-furyl | H | 4-methyl-1-piperazinyl |
| 19 | 4-methyl-2,3-dimethoxybenzyl | 2-furyl | H | 4-phenyl-1-piperazinyl |

TABLE 1-continued

| Compound No. | Q | R¹ | R² | R³ |
|---|---|---|---|---|
| 20 | 3,4-dimethoxybenzyl | 2-furyl | H | 4-benzylpiperazin-1-yl |
| 21 | 3,4-dimethoxybenzyl | 2-furyl | phenyl | morpholin-4-yl |
| 22 | 3,4-dimethoxybenzyl | 2-furyl | COOEt | H |
| 23 | 3,4-dimethoxybenzyl | 2-furyl | CH₂OH | H |
| 24 | 3,4-dimethoxybenzyl | 2-furyl | CHO | H |

TABLE 1-continued

| Compound No. | Q | R¹ | R² | R³ |
|---|---|---|---|---|
| 25 | 3,4-dimethoxybenzyl | 2-furyl | N-methylpiperazinyl-CH₂- | H |
| 26 | 3,4-dimethoxybenzyl | 2-furyl | N-phenylpiperazinyl-CH₂- | H |
| 27 | 3,4-dimethoxybenzyl | 2-furyl | 4-fluorophenyl-NH-CH₂- | H |
| 28 | 3,4-dimethoxybenzyl | 2-furyl | morpholinyl-CH₂- | H |
| 29 | 3,4-dimethoxybenzyl | 2-furyl | H | Cl |

TABLE 1-continued

| Compound No. | Q | R¹ | R² | R³ |
|---|---|---|---|---|
| 30 | H | 2-furyl | H | phenyl |
| 31 | H | 2-furyl | H | 2,4-dimethoxyphenyl |
| 32 | H | 2-furyl | H | 2,6-dimethoxyphenyl |
| 33 | H | 2-furyl | H | 3,5-dimethoxyphenyl |
| 34 | H | 2-furyl | H | 4-nitrophenyl |

TABLE 1-continued

| Compound No. | Q | R¹ | R² | R³ |
|---|---|---|---|---|
| 35 | H | 2-methylfuran | H | 4-chlorophenoxy (4-Cl-C₆H₄-O-) |
| 36 | H | 2-methylfuran | H | 4-phenylphenoxy (4-Ph-C₆H₄-O-) |
| 37 | H | 2-methylfuran | H | phenylthio (Ph-S-) |
| 38 | H | 2-methylfuran | H | piperidin-1-yl |
| 39 | H | 2-methylfuran | H | morpholin-4-yl |
| 40 | H | 2-methylfuran | H | 4-methylpiperazin-1-yl |
| 41 | H | 2-methylfuran | H | 4-phenylpiperazin-1-yl |

TABLE 1-continued

| Compound No. | Q | R¹ | R² | R³ |
|---|---|---|---|---|
| 42 | H | 2-furyl | H | 4-benzyl-piperazin-1-yl |
| 43 | H | 2-furyl | H | piperazin-1-yl |
| 44 | H | 2-furyl | H | 4-acetyl-piperazin-1-yl |
| 45 | H | 2-furyl | H | 4-benzoyl-piperazin-1-yl |
| 46 | H | 2-furyl | H | 4-(2-phenylethyl)-piperazin-1-yl |
| 47 | H | 2-furyl | H | phenoxy |
| 48 | H | 3-methoxyphenyl | H | phenoxy |

TABLE 1-continued

| Compound No. | Q | R¹ | R² | R³ |
|---|---|---|---|---|
| 49 | H | 3-methylpyridine | H | 4-methoxyphenyl |
| 50 | H | 2-methylthiophene | H | 4-methoxyphenyl |
| 51 | H | 2-methylfuran | phenyl | 4-methoxyphenyl |
| 52 | H | 2-methylfuran | phenyl | 4-(methylthio)phenyl |
| 53 | H | 2-methylfuran | phenyl | 4-methylmorpholine |
| 54 | H | 2-methylfuran | Me | 4-methoxyphenyl |
| 55 | H | 2-methylfuran | COOEt | H |

TABLE 1-continued
| Compound No. | Q | R¹ | R² | R³ |
|---|---|---|---|---|
| 56 | H | 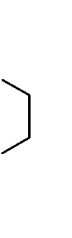 |  | H |
| 57 | H | 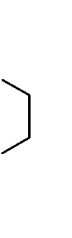 |  | H |
| 58 | H | 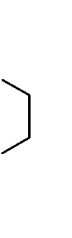 |  | H |
| 59 | H | 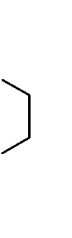 |  | H |
| 60 | H | 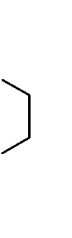 | H |  |
| 61 | H | 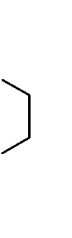 | H | Cl |
| 62 | H |  | H | 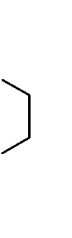 |

TABLE 1-continued

| Compound No. | Q | R¹ | R² | R³ |
|---|---|---|---|---|
| 63 | H | 2-furyl | H | 4-(3-phenylpropyl)piperazin-1-yl |
| 64 | H | 2-furyl | H | 4-(pyrimidin-2-yl)piperazin-1-yl |
| 65 | H | 2-furyl | H | 4-(4-methoxyphenyl)piperazin-1-yl |
| 66 | H | 2-furyl | H | 4-(1,3-benzodioxol-5-ylmethyl)piperazin-1-yl |
| 67 | H | 2-furyl | H | 4-(3,4-dimethoxybenzyl)piperazin-1-yl |
| 68 | H | 2-furyl | H | 4-(2-chlorobenzyl)piperazin-1-yl |

TABLE 1-continued

| Compound No. | Q | R¹ | R² | R³ |
|---|---|---|---|---|
| 69 | H | 5-methylfuran-2-yl | H | 4-methylpiperazin-1-yl-CH₂-(3-chlorophenyl) |
| 70 | H | 5-methylfuran-2-yl | H | 4-methylpiperazin-1-yl-CH₂-(pyridin-3-yl) |
| 71 | H | 5-methylfuran-2-yl | H | 4-methylpiperazin-1-yl-CH₂-(pyridin-4-yl) |
| 72 | H | 5-methylfuran-2-yl | H | 4-methylpiperazin-1-yl-CH₂-cyclohexyl |
| 73 | H | 5-methylfuran-2-yl | H | 4-methylpiperazin-1-yl-CH(Me)-phenyl |
| 74 | H | 5-methylfuran-2-yl | H | 4-methylpiperazin-1-yl-CH₂CH₂OMe |

TABLE 1-continued
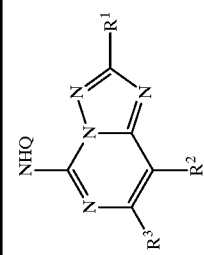
| Compound No. | Q | R¹ | R² | R³ |
|---|---|---|---|---|
| 75 | H | 2-furyl-CH₂- | H | 1-(2,5-dimethoxybenzyl)-4-methylpiperazine |
| 76 | H | 2-furyl-CH₂- | H | 1-(3,5-dimethoxybenzyl)-4-methylpiperazine |
| 77 | H | 2-furyl-CH₂- | H | 1-(3,4,5-trimethoxybenzyl)-4-methylpiperazine |
| 78 | H | 2-furyl-CH₂- | H | 1-(2-fluorobenzyl)-4-methylpiperazine |
| 79 | H | 2-furyl-CH₂- | H | 1-(4-chlorobenzyl)-4-methylpiperazine |

TABLE 1-continued

| Compound No. | Q | R¹ | R² | R³ |
|---|---|---|---|---|
| 80 | H | 2-methylfuran | H | 1-methyl-4-[(2,6-dichlorobenzyl)]piperazine |
| 81 | H | 2-methylfuran | H | 1-methyl-4-[(4-phenylbenzyl)]piperazine |
| 82 | H | 2-methylfuran | H | 1-methyl-4-(diphenylmethyl)piperazine |
| 83 | H | 2-methylfuran | H | 1-benzyl-4-methyl-1,4-diazepane |
| 84 | H | 2-methylfuran | H | 1-methyl-4-[(pyridin-2-yl)methyl]piperazine |
| 85 | H | 2-methylfuran | H | 1-methyl-4-[2-(3,4-dimethoxyphenyl)ethyl]piperazine |

TABLE 1-continued

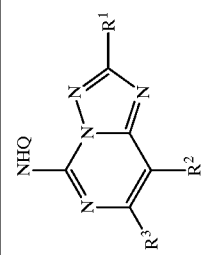

| Compound No. | Q | R¹ | R² | R³ |
|---|---|---|---|---|
| 86 | H | (5-methylfuran-2-yl) | H | 1-methylpiperidin-4-yl-N-CH₂CH₂CH₂-(3,4-dimethoxyphenyl) |
| 87 | H | (5-methylfuran-2-yl) | H | 1-methylpiperidin-4-yl-N-CH₂CH₂-(pyridin-3-yl) |
| 88 | H | (5-methylfuran-2-yl) | H | 1-methylpiperidin-4-yl-N-CH₂-CH=CH-phenyl |
| 89 | H | (5-methylfuran-2-yl) | H | 1-methylpiperidin-4-yl-N-CH₂-C≡C-phenyl |
| 90 | H | (5-methylfuran-2-yl) | H | 1-methylpiperidin-4-yl-N-CH₂CH₂OPh |
| 91 | H | (5-methylfuran-2-yl) | H | 1-methylpiperidin-4-yl-N-CH₂-CH(OH)-Ph |

TABLE 1-continued

| Compound No. | Q | R¹ | R² | R³ |
|---|---|---|---|---|
| 92 | H | 2-furyl | H | 4-methylpiperazinyl-N-CH₂CH₂CH₂CH₂Ph |
| 93 | H | 2-furyl | H | 4-methylpiperazinyl-N-(2-pyridyl) |
| 94 | H | 2-furyl | H | 4-methylpiperazinyl-N-(benzoxazol-2-yl) |
| 95 | H | 2-furyl | H | 4-methylpiperazinyl-N-(benzothiazol-2-yl) |
| 96 | H | 2-furyl | H | 4-methylpiperazinyl-N-CH₂CH₂OCH₂CH₃ |
| 97 | H | 2-furyl | H | 4-methylpiperazinyl-N-CH₂CH₂OCH₂Ph |
| 98 | H | 2-furyl | H | 4-methylpiperazinyl-N-CH₂CH₂OH |

TABLE 1-continued

| Compound No. | Q | R¹ | R² | R³ |
|---|---|---|---|---|
| 99 | H | 2-furyl | H | 4-(3-methoxypropyl)piperazin-1-yl |
| 100 | H | 2-furyl | H | 4-(3-ethoxypropyl)piperazin-1-yl |
| 101 | H | 2-furyl | H | 4-(3-isopropoxypropyl)piperazin-1-yl |
| 102 | H | 2-furyl | H | 4-(3-phenoxypropyl)piperazin-1-yl |
| 103 | H | 2-furyl | H | 4-[3-(2-hydroxyethoxy)propyl]piperazin-1-yl |
| 104 | H | 2-furyl | H | 4-[3-(2-methoxyethoxy)propyl]piperazin-1-yl |
| 105 | H | 2-furyl | H | 4-(2-hydroxypropyl)piperazin-1-yl |

TABLE 1-continued

| Compound No. | Q | R¹ | R² | R³ |
|---|---|---|---|---|
| 106 | H | 2-furyl | H | 4-methylpiperazin-1-yl, N-CH₂-CH(OMe)-CH₃ |
| 107 | H | 2-furyl | H | 4-methylpiperazin-1-yl, N-CH₂COOEt |
| 108 | H | 2-furyl | H | 4-methylpiperazin-1-yl, N-CH₂COOH |
| 109 | H | 2-furyl | H | 4-methylpiperazin-1-yl, N-CH(CH₃)-COOEt |
| 110 | H | 2-furyl | H | 4-methylpiperazin-1-yl, N-CH(CH₃)-COOH |
| 111 | H | 2-furyl | H | 4-methylpiperazin-1-yl, N-CH(CH₃)-CH₂OH |
| 112 | H | 2-furyl | H | 4-methylpiperazin-1-yl, N-COOtBu |

TABLE 1-continued

| Compound No. | Q | R¹ | R² | R³ |
|---|---|---|---|---|
| 113 | H | 2-methylfuran | H | 4-CHO-piperazin-1-yl, N-methyl |
| 114 | H | 2-methylfuran | H | (2R,6S)-2,6-dimethyl-4-NH-piperidine, N-methyl |
| 115 | H | 2-methylfuran | H | (2R,6S)-2,6-dimethyl-4-N-Me-piperidine, N-methyl |
| 116 | H | 2-methylfuran | H | (2R,6S)-2,6-dimethyl-4-N-Bzl-piperidine, N-methyl |

TABLE 1-continued
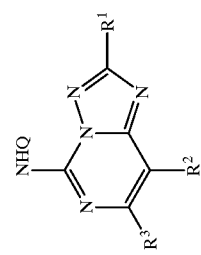
| Compound No. | Q | R¹ | R² | R³ |
|---|---|---|---|---|
| 117 | H | 2-furyl | H | 4-Me, 2,6-diMe piperidine N-CH₂CH₂OMe |
| 118 | H | 2-furyl | H | 4-Me, 2,6-diMe piperidine N-CH₂CH₂OCH₂Ph |
| 119 | H | 2-furyl | H | 4-Me, 2,6-diMe piperidine N-CH₂CH₂CH₂Ph |
| 120 | H | 2-furyl | H | 4-Me, 2,6-diMe piperidine N-CH₂CH₂OH |

TABLE 1-continued

| Compound No. | Q | R¹ | R² | R³ |
|---|---|---|---|---|
| 121 | H | 2-methylfuran | H | 4-methylthiomorpholine |
| 122 | H | 2-methylfuran | H | 1-methyl-4-hydroxypiperidine |
| 123 | H | 2-methylfuran | H | 1-methyl-4-(N-propyl)piperazine |
| 124 | H | 2-methylfuran | H | 1-methyl-4-(N-allyl)piperazine |
| 125 | H | 2-methylfuran | H | 1-methyl-4-(N-CH₂CH=CH₂)piperazine |
| 126 | H | 2-methylfuran | H | 1-methyl-4-(N-CH₂CH₂F)piperazine |
| 127 | H | 2-methylfuran | H | 1-methyl-4-(N-CH₂CH₂CH₂F)piperazine |

TABLE 1-continued

| Compound No. | Q | R¹ | R² | R³ |
|---|---|---|---|---|
| 128 | H | 2-methylfuran | H | 4-(CH₂CH₂CH₂F)-piperazin-1-yl |
| 129 | H | 2-methylfuran | H | 4-(CH₂CF₃)-piperazin-1-yl |
| 130 | H | 2-methylfuran | H | 4-(CH₂CH₂-cyclohexyl)-piperazin-1-yl |
| 131 | H | 2-methylfuran | H | 4-(CH₂COCH₃)-piperazin-1-yl |
| 132 | H | 2-methylfuran | H | 4-(CH₂CH₂COPh)-piperazin-1-yl |
| 133 | H | 2-methylfuran | H | 4-(CH₂CH₂-CH(OH)-Ph)-piperazin-1-yl |
| 134 | H | 2-methylfuran | H | 4-(COCH₂CH₂Ph)-piperazin-1-yl |

TABLE 1-continued

| Compound No. | Q | R¹ | R² | R³ |
|---|---|---|---|---|
| 135 | H | 2-furyl | H | 1-methyl-4-(n-butyl)piperazine |
| 136 | H | 2-furyl | H | 1-methyl-4-(isobutyl)piperazine |
| 137 | H | 2-furyl | H | 1-methyl-4-(cyclopropylmethyl)piperazine |
| 138 | H | 2-furyl | H | 1-methyl-4-(4-trifluoromethoxybenzyl)piperazine |
| 139 | H | 2-furyl | H | 1-methyl-4-(isopropyl)piperazine |
| 140 | H | 2-furyl | H | 1-methyl-4-(sec-butyl)piperazine |
| 141 | H | 2-furyl | H | 1-methyl-4-(1-methoxyprop-2-yl)piperazine |

TABLE 1-continued
| Compound No. | Q | R¹ | R² | R³ |
|---|---|---|---|---|
| 142 | H | 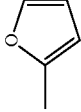 | H | 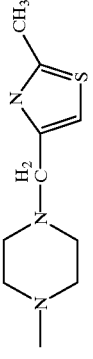 |
| 143 | H | 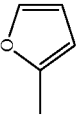 | H | 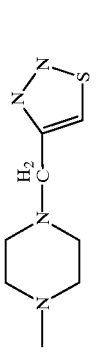 |
| 144 | H | 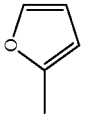 | H | 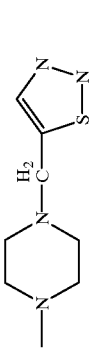 |
| 145 | H |  | H | 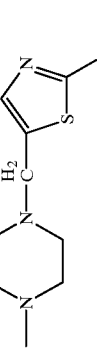 |
| 146 | H | 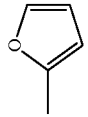 | H | 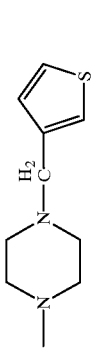 |
| 147 | H | 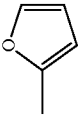 | H | 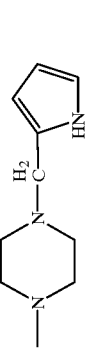 |

TABLE 1-continued

| Compound No. | Q | R¹ | R² | R³ |
|---|---|---|---|---|
| 148 | H | 2-furyl | H | 1-methyl-2-(N-methylimidazolyl)methyl-piperidine |
| 149 | H | 2-furyl | H | (1H-pyrazol-3-yl)methyl-N-methylpiperidine |
| 150 | H | 2-furyl | H | (thiazol-2-yl)methyl-N-methylpiperidine |
| 151 | 3,4-dimethoxybenzyl | 2-furyl | CH(CH₃)(CH(CH₃)OH) | H |
| 152 | 3,4-dimethoxybenzyl | 2-furyl | C(=O)CH(CH₃)₂ | H |
| 153 | H | 2-furyl | C(=O)CH(CH₃)₂ | H |

TABLE 1-continued

| Compound No. | Q | R¹ | R² | R³ |
|---|---|---|---|---|
| 154 | 3,4-dimethoxybenzyl | 2-furyl | CH(OH)Ph | H |
| 155 | 3,4-dimethoxybenzyl | 2-furyl | C(=O)Ph | H |
| 156 | H | | 2-furyl | C(=O)Ph | H |
| 157 | 3,4-dimethoxybenzyl | 2-furyl | C(=O)CH₂CH₃ | H |
| 158 | H | | 2-furyl | C(=O)CH₂CH₃ | H |
| 159 | 3,4-dimethoxybenzyl | 2-furyl | —COOH | H |

TABLE 1-continued

| Compound No. | Q | R¹ | R² | R³ |
|---|---|---|---|---|
| 160 | 3,4-diOMe-benzyl | 2-furyl | C(=O)N(Me)OMe | H |
| 161 | 3,4-diOMe-benzyl | 2-furyl | C(=O)CH₃ | H |
| 162 | H | 2-furyl | C(=O)CH₃ | H |
| 163 | H | 2-furyl | —CHO | H |
| 164 | 3,4-diOMe-benzyl | 2-furyl | C(=O)NH-CH(CH₃)₂ | H |
| 165 | H | 2-furyl | C(=O)NH-CH(CH₃)₂ | H |

TABLE 1-continued

| Compound No. | Q | R¹ | | R² | R³ |
|---|---|---|---|---|---|
| 166 | 3,4-di(OMe)benzyl | furan-2-yl | | C(O)NHCH₃ | H |
| 167 | H | furan-2-yl | | C(O)NHCH₃ | H |
| 168 | 3,4-di(OMe)benzyl | furan-2-yl | | C(O)NHCH₂CH₃ | H |
| 169 | H | furan-2-yl | | C(O)NHCH₂CH₃ | H |
| 170 | 3,4-di(OMe)benzyl | furan-2-yl | | C(O)NEt₂ | H |
| 171 | H | furan-2-yl | | C(O)NEt₂ | H |

TABLE 1-continued

| Compound No. | Q | R¹ | | R² | R³ |
|---|---|---|---|---|---|
| 172 | 3,4-di-OMe-benzyl | furan-2-yl | | C(=O)NMe₂ | H |
| 173 | H | furan-2-yl | | C(=O)NMe₂ | H |
| 174 | 3,4-di-OMe-benzyl | furan-2-yl | | C(=O)-piperidin-1-yl | H |
| 175 | H | furan-2-yl | | C(=O)-piperidin-1-yl | H |
| 176 | 3,4-di-OMe-benzyl | furan-2-yl | | C(=O)-morpholin-4-yl | H |
| 177 | H | furan-2-yl | | C(=O)-morpholin-4-yl | H |

TABLE 1-continued

| Compound No. | Q | R¹ | R² | R³ |
|---|---|---|---|---|
| 178 | H | furyl | H | -S-CH₂-C₆H₄-Br |
| 179 | H | furyl | H | -S-CH₂-C₆H₄-OMe |
| 180 | H | furyl | H | -S-CH₂-C₆H₄-OCF₃ |
| 181 | H | furyl | H | -S-CH₂-(4-pyridyl) |
| 182 | H | furyl | H | -S-CH₂-(2-pyridyl) |
| 183 | H | furyl | H | -S-CH₂-C₆H₅ |
| 184 | H | furyl | H | -S-CH₂-C₆H₄-CN |

TABLE 1-continued

| Compound No. | Q | R¹ | R² | R³ |
|---|---|---|---|---|
| 185 | H | 2-furyl-CH₂- | H | -S-CH₂-C₆H₄-4-NO₂ |
| 186 | H | 2-furyl-CH₂- | H | -S-CH₂-C₆H₄-4-CH₃ |
| 187 | H | 2-furyl-CH₂- | H | -S-CH₂-C₆H₄-4-tBu |
| 188 | H | 2-furyl-CH₂- | H | -S-CH₂-C₆H₄-2-CN |
| 189 | H | 2-furyl-CH₂- | H | -S-CH₂-C₆H₄-4-F |
| 190 | H | 2-furyl-CH₂- | H | -S-CH₂-C₆H₄-4-CO₂Me |

TABLE 1-continued
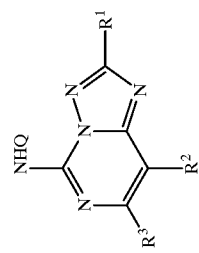
| Compound No. | Q | R¹ | R² | R³ |
|---|---|---|---|---|
| 191 | H | 2-furyl-CH₂- | H | -S-CH₂-(3-I-C₆H₄) |
| 192 | H | 2-furyl-CH₂- | H | -S-CH₂-(3-NO₂-C₆H₄) |
| 193 | H | 2-furyl-CH₂- | H | -S-CH₂-(3-CN-C₆H₄) |
| 194 | H | 2-furyl-CH₂- | H | -S-CH₂-(2-NO₂-C₆H₄) |
| 195 | H | 2-furyl-CH₂- | H | -S-CH₂-(2-Ph-C₆H₄) |

TABLE 1-continued

| Compound No. | Q | R¹ | R² | R³ |
|---|---|---|---|---|
| 196 | H | 2-furyl-CH₂- | H | -S-CH₂-(4-CO₂H, 3-NO₂-phenyl) |
| 197 | H | 2-furyl-CH₂- | H | -S-CH₂-(4-CO₂H-phenyl) |
| 198 | H | 2-furyl-CH₂- | H | -S-CH₂-(4-Cl-phenyl) |
| 199 | H | 2-furyl-CH₂- | H | -S-CH₂-(3-CF₃-phenyl) |
| 200 | H | 2-furyl-CH₂- | H | -S-CH₂-(2-Cl-phenyl) |
| 201 | H | 2-furyl-CH₂- | H | -S-CH₂-(2-F-phenyl) |

TABLE 1-continued
| Compound No. | Q | R¹ | R² | R³ |
|---|---|---|---|---|
| 202 | H | 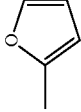 | H | 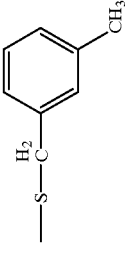 |
| 203 | H | 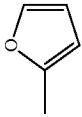 | H | 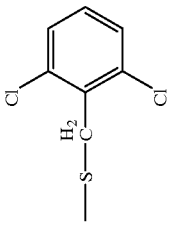 |
| 204 | H | 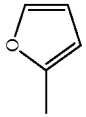 | H | 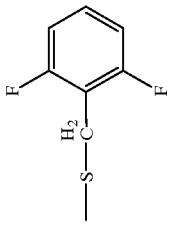 |
| 205 | H | 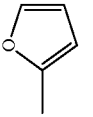 | H | 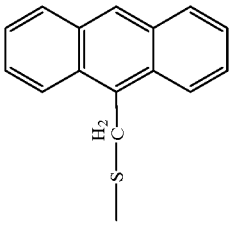 |

TABLE 1-continued

| Compound No. | Q | R¹ | R² | R³ |
|---|---|---|---|---|
| 206 | H | 2-furyl | H | -S-CH₂-(4-CF₃-phenyl) |
| 207 | H | 2-furyl | H | -S-CH₂-(4-(OCH₂Ph)-phenyl) |
| 208 | H | 2-furyl | H | -S-CH₂-(4-CH(CH₃)₂-phenyl) |
| 209 | H | 2-furyl | H | -S-CH₂-(4-CH₂CH₃-phenyl) |
| 210 | H | 2-furyl | H | -S-CH₂-(4-phenyl-phenyl) |
| 211 | H | 2-furyl | H | -S-CH₂-(4-CHO-phenyl) |

TABLE 1-continued

| Compound No. | Q | R¹ | R² | R³ |
|---|---|---|---|---|
| 212 | H | 2-furyl-methyl | H | 3-CHO-benzyl-S-CH₂- |
| 213 | H | 2-furyl-methyl | H | 2-CHO-benzyl-S-CH₂- |
| 214 | H | 2-furyl-methyl | H | phenyl-CH₂-S-CH₂- |
| 215 | H | 2-furyl-methyl | H | phenyl-CH(CH₃)-S- |
| 216 | 3,4-diOMe-benzyl | 2-furyl-methyl | Me | Cl |
| 217 | H | 2-furyl-methyl | Me | Cl |

TABLE 1-continued

| Compound No. | Q | R¹ | R² | R³ |
|---|---|---|---|---|
| 218 | H | 5-methylfuran-2-yl | Me | 4-methylpiperazin-1-yl (N'-Me) |
| 219 | H | 5-methylfuran-2-yl | Me | 4-phenylpiperazin-1-yl (N'-Ph) |
| 220 | H | 5-methylfuran-2-yl | Me | 4-benzylpiperazin-1-yl (N'-Bzl) |
| 221 | H | 5-methylfuran-2-yl | Me | 4-(tert-butoxycarbonyl)piperazin-1-yl (N'-COOtBu) |
| 222 | H | 5-methylfuran-2-yl | Me | 4-(2-hydroxyethyl)piperazin-1-yl (N'-CH₂CH₂OH) |

TABLE 1-continued

| Compound No. | Q | R¹ | R² | R³ |
|---|---|---|---|---|
| 223 | H | 2-methylfuran | Me | 4-(2-methoxyethyl)-1-methylpiperazine |
| 224 | H | 2-methylfuran | Me | 4-methylpiperazine (NH) |
| 225 | H | 2-methylfuran | H | —SCH$_2$CH$_2$CH$_3$ |
| 226 | 3,4-dimethoxybenzyl | 2-methylfuran | H | 4-bromophenoxy |
| 227 | 3,4-dimethoxybenzyl | 2-methylfuran | H | 4-iodophenoxy |
| 228 | H | 2-methylfuran | H | 4-bromophenoxy |

TABLE 1-continued

| Compound No. | Q | R¹ | R² | R³ |
|---|---|---|---|---|
| 229 | H | furan-2-yl | H | 4-methoxyphenyl (with I) |
| 230 | H | furan-2-yl | H | 4-(pyridin-2-yl)phenyl methoxy |
| 231 | H | furan-2-yl | H | 4-(thiazol-2-yl)phenyl methoxy |

Next, pharmacological activities of Compound (I) are described with test examples.

TEST EXAMPLE 1

Adenosine receptor binding activity (adenosine $A_{2A}$ receptor binding test)

This test was carried out by slightly modifying the method of Bruns et al. [*Molecular Pharmacology*, 29: 331 (1986)].

Corpus striatum of a rat was suspended in an ice-cooled 50 mM tris(hydroxymethyl)aminomethane hydrochloride (hereinafter referred to as "Tris-HCl") buffer (pH 7.7) using Polytron Homogenizer (manufactured by Kinematica Co.). The suspension was centrifuged (50,000×g, 10 minutes), and the obtained precipitate was re-suspended in the same amount of 50 mM Tris-HCl buffer. The suspension was centrifuged under the same conditions, and the final precipitate was suspended in 50 mM Tris-HCl [containing 10 mM magnesium chloride and 0.02 unit/mg tissue of adenosine deaminase (manufactured by Sigma Co.)] to give a tissue concentration of 5 mg (wet weight)/ml.

To 1 ml of the tissue suspension thus prepared were added 50 μl of tritium-labeled CGS 21680 {$^3$H-2-[p-(2-carboxyethyl)phenethylamino]- 5'-N-ethylcarboxamido) adenosine: 40 Ci/mmol; manufactured by New England Nuclear Co.[*The Journal of Pharmacology and Experimental Therapeutics*, 251: 888 (1989)]} (final concentration:4.0 nM) and 50 μl of a test compound. The resulting mixture was allowed to stand for 120 minutes at 25° C., and then rapidly filtered by suction through a glass fiber filter (GF/C, manufactured by Whatman Co.) The filter was immediately washed three times with 5 μl of an ice-cooled 50 mM Tris-HCl buffer, and transferred to a vial, a scintillator (EX-H , manufactured by Wako Pure Chemical Industries, Ltd.) was added thereto, and the radioactivity on the filter was determined with a liquid scintillation counter (manufactured by Packard Instrument Co.)

The inhibition ratio of the test compound against the $A_{2A}$ receptor binding ($^3$H-CGS 21680 binding) was calculated by the following equation:

Inhibition ratio (%)={1−(Amount of the binding in the presence of the test compound−Amount of the nonspecific binding)/ (Amount of the total binding−Amount of the nonspecific binding)}×100

(Note) Amount of the total binding means the amount of radioactivity of $^3$H-CGS 21680 bound in the absence of the test compound. Amount of the nonspecific binding means the amount of radioactivity of $^3$H-CGS 21680 bound in the presence of 100 μM cyclopentyladenosine (CPA, manufactured by Sigma Co.) Amount of the binding in the presence of the test compound means the amount of radioactivity of $^3$H-CGS 21680 bound in the presence of the test compound at various levels of concentrations.

The results are shown in Table 2.

TABLE 2

| Compound No. | $A_{2A}$ receptor inhibition ratio (%) | |
| --- | --- | --- |
| | $10^{-8}$M | $10^{-7}$M |
| 10 | 16 | 54 |
| 32 | 71 | 89 |
| 33 | 46 | 86 |
| 35 | 43 | 82 |
| 40 | 11 | 50 |

TABLE 2-continued

| Compound No. | $A_{2A}$ receptor inhibition ratio (%) | |
| --- | --- | --- |
| | $10^{-8}$M | $10^{-7}$M |
| 42 | 43 | 82 |
| 46 | 35 | 79 |
| 63 | 31 | 82 |
| 66 | 20 | 79 |
| 67 | 39 | 77 |
| 68 | 59 | 90 |
| 69 | 44 | 62 |
| 70 | 17 | 66 |
| 71 | 29 | 73 |
| 72 | 10 | 66 |
| 73 | 51 | 86 |
| 75 | N.T. | 84 |
| 76 | N.T. | 73 |
| 77 | N.T. | 77 |
| 78 | N.T. | 85 |
| 80 | N.T. | 93 |
| 84 | N.T. | 63 |
| 85 | N.T. | 80 |
| 86 | N.T. | 83 |
| 87 | N.T. | 77 |
| 88 | N.T. | 57 |
| 89 | N.T. | 52 |
| 90 | N.T. | 82 |
| 93 | N.T. | 36 |
| 94 | N.T. | 37 |
| 96 | N.T. | 58 |
| 97 | N.T. | 79 |
| 99 | N.T. | 59 |
| 100 | N.T. | 54 |
| 101 | N.T. | 46 |
| 102 | N.T. | 72 |
| 103 | N.T. | 53 |
| 105 | N.T. | 41 |
| 111 | N.T. | 52 |
| 115 | N.T. | 22 |
| 116 | N.T. | 38 |
| 117 | N.T. | 38 |
| 119 | N.T. | 51 |
| 120 | N.T. | 29 |
| 123 | N.T. | 42 |
| 124 | N.T. | 59 |
| 126 | N.T. | 60 |
| 127 | N.T. | 59 |
| 135 | N.T. | 49 |
| 142 | N.T. | 66 |
| 144 | N.T. | 58 |
| 153 | N.T. | 48 |
| 158 | N.T. | 92 |
| 165 | N.T. | 103 |
| 167 | N.T. | 90 |
| 169 | N.T. | 96 |
| 182 | N.T. | 82 |
| 183 | N.T. | 82 |
| 186 | N.T. | 52 |
| 188 | N.T. | 91 |
| 194 | N.T. | 75 |

Compounds (I) and pharmaceutically acceptable salts thereof show strong adenosine $A_{2A}$ receptor antagonism. Consequently, it was suggested that a drug which contains Compound (I) as the active ingredient would be useful for various diseases induced by hyperactivity of adenosine $A_{2A}$ receptors (for example, Parkinson's disease, senile dementia or depression).

TEST EXAMPLE 2

Activity on CGS 21680-induced Catalepsy

Parkinson's disease is motor deficit based on the degeneration and cell death of the nigrostriatal dopaminergic neuron. When CGS 21680 (adenosine $A_{2A}$ receptor agonist) is administered into the intracerebro-ventricle, it directly inhibits inhibitory synaptic transmission of GABA in medium sized spiny neuron in the striatum via the adenosine $A_{2A}$ receptor. [*Journal of Neuroscience*, 16: 605 (1996)]. Accordingly, it is considered that adenosine $A_{2A}$ receptor agonists positively regulate the output of the striopallidal GABAergic neurons and, as a result, catalepsy is induced by the administration of CGS 21680.

This test was carried out using 10 animals per group of male ddY mice of 5 week age (22 to 25 g in body weight, Japan SLC). CGS 21680 (manufactured by RBI) was dissolved in a physiological saline (manufactured by Otsuka Pharmaceutical), and 10 µg/20 µl of the solution was injected into mouse intracerebro-ventricle. Test compounds were used by suspending them in distilled water containing 0.3% of polyoxyethylene(20)sorbitan monooleate (hereinafter referred to as "Tween 80") (manufactured by Otsuka Pharmaceutical). The suspension containing each of the test compounds or a solution which does not contain the test compound (distilled water containing 0.3% Tween 80; control) was orally administered (0.1 ml per 10 g mouse body weight) 30 minutes before the injection of CGS 21680 into the intracerebro-ventricle. One hour after the administration of the test compound, only forelimbs or only hindlimbs of each animal were laid on a vertically arranged stand made of acryl, having a size of 4.5 cm in height and 1.0 cm in width, to measure catalepsy symptoms. All of the compounds were administered orally in a dose of 10 mg/kg.

The following shows judging criteria of catalepsy score.

TABLE 3

Judging criteria of catalepsy score

| Score | Duration of catalepsy |
|---|---|
| 0 | The cataleptic posture lasted less than 5 seconds for both forelimbs and hindlimbs. |
| 1 | (1) The cataleptic posture of forelimbs lasted not less than 5 seconds and less than 10 seconds, and that of hindlimbs lasted less than 5 seconds, or (2) The cataleptic posture of hindlimbs lasted not less than 5 seconds and less than 10 seconds, and that of forelimbs lasted less than 5 seconds. |
| 2 | The cataleptic posture of forelimbs lasted not less than 10 seconds and that of hindlimbs lasted less than 5 seconds. |
| 3 | (1) The cataleptic posture of both forelimbs and hindlimbs lasted not less than 5 seconds and less than 10 seconds, or (2) The cataleptic posture of forelims lasted less than 5 seconds but that of hindlimbs lasted not less than 10 seconds. |
| 4 | (1) The cataleptic posture of forelimbs lasted not less than 10 seconds and that of hindlimbs lasted not less than 5 seconds and less than 10 seconds, or (2) The cataleptic posture of forelimbs lasted not less than 5 seconds and less than 10 seconds, and that of hindlimbs lasted not less than 10 seconds. |
| 5 | The cataleptic posture of both forelimbs and hindlimbs lasted not less than 10 seconds. |

The effect was judged by total catalepsy scores of 10 animals in one group (the maximum is 50 points). When the total score was 40 points or less, the activity of drugs was judged positive. The number of animals showing remission of catalepsy was expressed by the number of cases in which the catalepsy score was 4 points or less in 10 cases. The catalepsy remission ratio was expressed as the percentage of the total score in the test compound-administered group to the total score in the control group.

The results are shown in Table 4.

TABLE 4

| Compound No. | Number of Animals used | Total score | Number of Animals showing remission | Remission ratio (%) |
|---|---|---|---|---|
| 0.3% Tween 80 (control) | 10 | 48 | 2 | 4 |
| 31 | 10 | 28 | 9 | 42 |
| 32 | 10 | 21 | 9 | 54 |
| 35 | 10 | 15 | 8 | 66 |
| 39 | 10 | 20 | 9 | 56 |
| 40 | 10 | 20 | 10 | 56 |
| 42 | 10 | 12 | 9 | 72 |
| 46 | 10 | 9 | 10 | 78 |
| 55 | 10 | 29 | 9 | 36 |
| 60 | 10 | 10 | 8 | 76 |
| 62 | 10 | 4 | 10 | 88 |
| 63 | 10 | 7 | 10 | 84 |
| 64 | 10 | 5 | 10 | 88 |
| 74 | 10 | 0 | 10 | 98 |
| 75 | 10 | 10 | 9 | 76 |
| 76 | 10 | 11 | 10 | 76 |
| 77 | 10 | 21 | 9 | 54 |
| 78 | 10 | 6 | 10 | 86 |
| 80 | 10 | 3 | 10 | 92 |
| 84 | 10 | 9 | 9 | 78 |
| 86 | 10 | 13 | 9 | 72 |
| 87 | 10 | 14 | 9 | 68 |
| 88 | 10 | 0 | 10 | 98 |
| 89 | 10 | 15 | 10 | 68 |
| 90 | 10 | 12 | 9 | 80 |
| 93 | 10 | 10 | 8 | 66 |
| 95 | 10 | 16 | 8 | 66 |
| 96 | 10 | 7 | 9 | 86 |
| 97 | 10 | 4 | 10 | 90 |
| 99 | 10 | 5 | 10 | 90 |
| 100 | 10 | 4 | 10 | 90 |
| 101 | 10 | 8 | 10 | 82 |
| 103 | 10 | 2 | 10 | 94 |
| 104 | 10 | 4 | 10 | 92 |
| 105 | 10 | 4 | 10 | 92 |
| 115 | 10 | 5 | 10 | 88 |
| 116 | 10 | 5 | 10 | 90 |
| 120 | 10 | 3 | 10 | 94 |
| 123 | 10 | 1 | 10 | 96 |
| 124 | 10 | 12 | 9 | 76 |
| 125 | 10 | 13 | 10 | 74 |
| 126 | 10 | 2 | 9 | 96 |
| 127 | 10 | 3 | 10 | 96 |
| 128 | 10 | 9 | 10 | 80 |
| 135 | 10 | 9 | 9 | 80 |
| 136 | 10 | 1 | 10 | 98 |
| 139 | 10 | 10 | 9 | 80 |
| 140 | 10 | 13 | 10 | 74 |
| 142 | 10 | 6 | 10 | 88 |
| 143 | 10 | 0 | 10 | 98 |
| 144 | 10 | 9 | 9 | 80 |
| 145 | 10 | 3 | 10 | 92 |
| 146 | 10 | 3 | 10 | 94 |
| 153 | 10 | 10 | 9 | 80 |
| 158 | 10 | 23 | 8 | 52 |
| 163 | 10 | 3 | 10 | 94 |
| 165 | 10 | 13 | 9 | 74 |
| 167 | 10 | 9 | 10 | 82 |
| 169 | 10 | 9 | 10 | 82 |
| 175 | 10 | 12 | 10 | 74 |
| 177 | 10 | 13 | 9 | 72 |
| 181 | 10 | 14 | 8 | 72 |
| 188 | 10 | 15 | 2 | 70 |
| 190 | 10 | 13 | 10 | 72 |
| 200 | 10 | 14 | 9 | 70 |
| 201 | 10 | 10 | 10 | 78 |
| 213 | 10 | 15 | 10 | 70 |
| 222 | 10 | 9 | 10 | 80 |
| 223 | 10 | 15 | 9 | 68 |
| 228 | 10 | 14 | 8 | 72 |

TEST EXAMPLE 3

Activity on haloperidol-induced Catalepsy

Parkinson's disease is a disease based on the degeneration and cell death of the nigrostriatal dopaminergic neuron. When haloperidol (dopamine D1/D2 antagonist) is administered, catalepsy is induced by the block of postsynaptic D2 receptor. This haloperidol-induced catalepsy is known as a classic model in which symptoms of Parkinson's disease are produced by drug administration [*European Journal of Pharmacology*, 182: 327 (1990) and U.S. Pat. No. 3,991,207].

This test was carried out using 10 animals per group of male ddY mice of 5 week age (22 to 24 g in body weight, Japan SLC). Haloperidol (manufactured by Janssen) was suspended in 0.3% CMC and administered intraperitoneally into mice at a dose of 1.0 mg/kg. Each test compound was used by mixing it with Tween 80 and then suspending it in distilled water for injection (manufactured by Otsuka Pharmaceutical). Also, L-DOPA (manufactured by Kyowa Hakko Kogyo Co., Ltd.) and benserazide HCl (manufactured by Kyowa Hakko Kogyo Co., Ltd.) were used by suspending them in 0.3% CMC. One hour after the intraperitoneal injection of haloperidol, the suspension containing each of the test compounds or a suspension which does not contain the test compound [distilled water for injection (manufactured by Otsuka Pharmaceutical) containing Tween 80; control] was orally administered (0.1 ml per 10 g mouse body weight) and, one hour after the administration of test compound, only forelimbs or only hindlimbs of each animal were laid on a stand having a size of 4.5 cm in height and 1.0 cm in width, to measure catalepsy symptoms. All of the test compounds were administered orally in a dose of 10 mg/kg, and 100 mg/kg of L-DOPA and 25 mg/kg of benserazide were used in combination as a control drug and administered by intraperitoneal injection. The catalepsy score was evaluated by the judging criteria shown in the above-described Table 3.

The effect was judged by total catalepsy scores of 10 animals in one group (the maximum is 50 points). When the total score was 40 points or less, the activity of drugs was judged positive. The number of animals showing remission of catalepsy was expressed by the number of cases in which the catalepsy score was 4 points or less in 10 cases. The catalepsy remission ratio was expressed as the percentage of the total score in the test compound-administered group to the total score in the control group.

The results are shown in Table 5.

TABLE 5

| Compound No. | Number of Animals used | Total score | Number of Animals showing Remission | Remission ratio (%) |
| --- | --- | --- | --- | --- |
| 0.3% Tween 80 (control) | 10 | 50 | 0 | 0 |
| 31 | 10 | 15 | 10 | 70 |
| 32 | 10 | 37 | 5 | 26 |
| 40 | 10 | 18 | 7 | 64 |
| 42 | 10 | 1 | 10 | 98 |
| 46 | 10 | 13 | 10 | 74 |
| 55 | 10 | 35 | 5 | 30 |

TEST EXAMPLE 4

Activity on Clonidine-induced Aggressive Behavior

Effect of test compounds to increase aggressive behavior induced by the intraperitoneal injection of clonidine [*European Journal of Pharmacology*, 29: 374 (1968)] was examined.

This test was carried out using 2 animals per group of male ddY mice of 20 to 25 g in body weight (Japan SLC). Each test compound was used by mixing it with Tween 80 and then suspending it in distilled water for injection (manufactured by Otsuka Pharmaceutical), and clonidine hydrochloride (manufactured by Sigma Co.) was used by dissolving it in physiological saline (manufactured by Otsuka Pharmaceutical). The suspension containing each of the test compounds or a suspension which does not contain the test compound (control) was orally administered (0.1 ml per 10 g mouse body weight) and, 60 minutes after the administration of the test compound, clonidine was administered by intraperitoneal injection in a dose of 20 mg/kg. The number of aggressive behavior of each mouse was measured for 30 minutes immediately after the administration of clonidine. The effect was judged by comparing values of the number of aggressive behavior in the control and those in test compound-administered groups (significance test: Student t-test).

The results are shown in Table 6.

TABLE 6

| Test compound | Dose (mg/kg po) | Number of attacks (count; average ± S.E.M.) Control group (Number of animals used) | Number of attacks (count; average ± S.E.M.) Test compound group (Number of animals used) | Number of attacks in test compound group/number of attacks in control group |
| --- | --- | --- | --- | --- |
| 31 | 10 | 4.20 ± 2.38 (10) | 38.1 ± 13.06* (10) | 9.1 |
| 39 | 10 | 1.20 ± 1.00 (10) | 9.70 ± 3.42* (10) | 8.1 |
| 40 | 10 | 2.90 ± 1.95 (10) | 22.00 ± 6.44* (10) | 7.6 |

*: $p < 0.05$

It was confirmed by Test Examples 2 to 4 that Test Compounds (I) have anti-Parkinson's disease activity and anti-depressant activity.

TEST EXAMPLE 5

Activity in a Parkinson's Disease Model [common marmoset treated with 1-methyl-4-phenyl-1,2,3,6-tetrahydropyridine (MPTP)]

Parkinson's disease is a disease based on the degeneration and cell death of the nigrostriatal dopaminergic neuron. In the primates, treatment with a dopamine neurotoxin 1-methyl-4-phenyl-1,2,3,6-tetrahydropyridine (hereinafter referred to as "MPTP") causes selective degeneration and dropout of the nigrostriatal dopaminergic neuron and shows akinesia, rigidity of muscle or the like. These MPTP-treated primates are known as a model of Parkinson's disease [*Proceedings of the National Academy of Science USA*, 80: 4546 (1983)]. Common marmoset belongs to Anthropoidae, and it is known that it shows symptoms of Parkinson's disease caused by MPTP as in the case of other animals of Anthropoidae [*Neuroscience Letter*, 57: 37 (1985)].

This test was carried out using 4 animals per group of female and male common marmosets of 2 to 3 year age (300 to 375 g in body weight, CLEA Japan). MPTP (manufactured by RBI) was dissolved in a physiological saline for injection (manufactured by Otsuka Pharmaceutical) and administered to common marmoset once a day for 5 days by subcutaneous injection in a dose of 2.0 mg/kg. Six weeks or more after the administration, animals showing chronic symptoms of Parkinson's disease were used in the test of test compounds. Each test compound was used by suspending it in 0.3% Tween 80 and 10% sucrose solution. The same solution containing no test compound was used as a control. One hour before the administration of the test compound, the animals to be tested were put into an observation cage (equipped with a spontaneous locomotor count measuring apparatus) to adapt them to the environment. Symptoms of Parkinson's disease were observed from a one way see-through window at 30 minutes' interval for 8 hours to score their motor disability. The spontaneous locomotor count was measured at 30 minutes' interval for 12 hours by a computer-controlled automatic measuring apparatus. Symptoms of Parkinson's disease were judged based on the judging criteria of each item shown in the following, and the total of the points was used as the score of each animal.

Relationship between observation items and scores is shown in Table 7 below.

Tween 80 solution alone was orally administered. Measurement of immobility time was carried out in accordance with the method of Porsolt [*Arch. int Pharmacodyn.*, 229: 327–336 (1977)]. That is, a cylindrical transparent acrylic water tank (10 cm in diameter and 25 cm in height) was filled with 9 cm in depth of water having a temperature of 23±1° C., and mice were forced to swim for 6 minutes. When mice are put into water, they immediately start to swim trying to escape from the tank, but the motion gradually decreases 1 to 2 minutes thereafter. Measurement of immobility time was carried out by leaving them for 2 minutes as such and thereafter measuring the period of time during which they did not show the escaping action (immobility time: behavioral despair) for 4 minutes (240 seconds) at one second's interval. In order to reduce effects of daily rhythm, the test was carried out by using 5 of the 10 animals per group in the morning, and the remaining 5

TABLE 7

Judging criteria of the symptoms of Parkinson's disease

| Items observed | Score | 0 | 1 | 2 | 3 | 4 |
|---|---|---|---|---|---|---|
| Attention | | normal | decrease | sleeping tendency | | |
| Observation | | | yes | decrease | no | |
| Blinking | | | normal | abnormal | | |
| Posture | | normal | abnormality in trunk, tail or limbs.(1 point for each) | | | all abnormal |
| Balance | | normal | asymmetry | cannot stand | drop out | |
| Reaction | | normal | decrease | slow | no | |
| Utterance | | normal | decrease | no | | |
| Total | 0–17 points | | | | | |

The effect was judged by comparing average scores of the symptoms of Parkinson's disease in 4 animals per group in the test compound-administered and solvent-administered groups (significance test: Sign-Wilcoxon test). Also with respective to the spontaneous locomotor count, the effect was judged by comparing the test compound-administered and solvent-administered groups.

The results are shown in FIGS. 1 and 2 (the score of symptoms of Parkinson's disease was expressed as the total score of respective observation items, and the spontaneous locomotor count was expressed as the total locomotor count due to its continuous measurement).

It was confirmed that Compound 63 is effective in the common marmoset MPTP-treated Parkinson's disease model.

TEST EXAMPLE 6

Forced Swimming Method (measurement of immobility time)

Ten animals per group of ddY male mice (21 to 26 g in body weight, Japan SLC) were used as the experimental animal. During the preliminary feeding period, they were allowed to have feed and water freely in an animal room of a room temperature of 23±1° C. and a humidity of 55±5%. Animals which showed abnormal reactions in terms of spontaneous activity, myotonia, eyesight or the like were excluded. The drugs to be tested were suspended in a 0.3% Tween 80 solution and orally administered one hour before the test. In the negative control group, 10 ml/kg of the 0.3% animals in the afternoon. Further, measurement of immobility time was carried out by observing 2 animals at the same time and by not telling the observers distinctions about the solvent-administered group and doses of administered test drugs. Statistical analysis of the results was carried out by a multiple comparison test of the solvent-administered control group and each of the test drug-administered groups by Steel-test.

Significant immobility time-shortening activity was observed by 10 mg/kg oral administration of Compounds 45, 62, 66, 67, 69, 70, 71, 72, 74, 78, 80, 84, 88, 89, 90, 96, 99, 100, 103, 104, 115, 126, 127, 165 and 167. Since each of these compounds having such activity showed strong antagonism for the $A_{2A}$ receptor (inhibition ratio of 50% or more at $10^{-7}$ M), a general correlation was found between $A_{2A}$ antagonism and anti-depression activity.

TEST EXAMPLE 7

Activity in Learned Helplessness (LH) Model
1) Animals Used

As experimental animals, 10 to 15 animals per group of SD male rats (220 to 320 g in body weight, 7 week age, Charles River Japan, Atsugi) were used. During the preliminary feeding period, they were allowed to have feed (CRF-1, Oriental Yeast, Tokyo) and water (tap water) freely in an animal room at a room temperature of 22 to 24° C. and a humidity of 50 to 60%. The test compound was orally administered in a dose of 2 ml/kg and 1 hour before FR 1 (fixed ratio schedule 1: repetition of fixed trial conditions) on the second day of the test.

2) Preparation of Learned Helplessness Model

A shuttle box apparatus (TK-401S; manufactured by UNICOM, Chiba) was used as the learning test apparatus. On the first day, a partition wall was set at the center of the shuttle box to arrange two rooms, and one rat was put into each of the rooms. Each of the two rooms (22×20×26 cm) has a stainless steel floor grid to which an electric shock (1.3 mA, scramble stimulus) can be applied. Each animal was put into the shuttle box for 50 minutes of which 25 minutes were used as a period for charging inescapable electric shock (IES) by random continued times (10 to 90 seconds) and random on-off, off-on (10 to 90 seconds) effected by computer control.

On the second day, a shuttle box test was carried out by slightly modifying the method of Maier et al. [*J. Comp. Physiol. Psychol.*, 85: 581–592 (1973)] and the method of Geoffroy & Christensen [*Drug Dev. Res.*, 29: 48–55 (1993)]. The partition wall in the center was removed and replaced by a hurdle of 2 cm in height to arrange two rooms. In the shuttle box test, FR 1 (buzzer 10 sec, 0.6 mA foot shock; 5 sec, interval time; 10 sec/trial, 15 escape trials) was carried, followed continuously by FR 2 (0.6 mA foot shock; 10 sec, interval time; 0.5 sec, 0.6 mA foot shock; 10 sec, interval time; 15 sec/trial, 15 trials). The escape reaction was judged success when both of the two escape times in FR 2 were less than 10 seconds, and the escape response was calculated by the following formula: "the number of trials of successful escape/15×100=escape response (%)" Further, migration in the box other than the escape reaction observed during a period between trials (resting time) was used as an index of psychomotor stimulant action by calculating "total number of migration in the box/15×100=intertrial response (%)"

3) Statistical Treatment

The results were statistically analyzed by treating the difference between normal control and IES-loaded control with Student-t and carrying out a multiple comparison test for the escape responses and intertrial responses between the IES-loaded control group and the test drug-administered group by the Steel method, and the results were treated as significant when the level of significance was less than 5%. In this case, an SAS statistical analysis software was used in the statistical analysis.

TABLE 8

| Test compound | Electric shock (IES) | Dose (mg/kg, po) | Escape response | Intertrial response |
|---|---|---|---|---|
| | | | (Average % ± SE) | |
| Normal control | − | | 76.7 ± 9.1 | 7.3 ± 4.8 |
| Loaded control | + | | 9.3 ± 9.3### | 0.7 ± 0.7 |
| Compound 45 | + | 5.0 | 64 ± 9.8** | 6.7 ± 3.8 |

: $p < 0.001$ comparison with normal control group;
**: $p < 0.01$ comparison with loaded control group According to the test results, it was shown that Compound 45 can significantly reverse a reduced escape response induced by the IES loading and therefore has an antidepressant activity, and that its psychomotor stimulant activity is weak because of no difference in the intertrial responses between the test compound-administered group and electric shock loaded control group.

The anti-depressant activity (activity to inhibit reduction of escape response) was markedly attenuated when a small amount of an adenosine $A_{2A}$ agonist CGS 21680 (20 μg/2 μl) was injected into the nucleus accumbens 30 minutes before FR 1 on the second day. Consequently, it was suggested that the pharmacological activity of this compound is mediated by the $A_{2A}$ receptor.

Compound (I) or a pharmaceutically acceptable salt thereof can be administered as it is, but it is generally preferred to provide it as various pharmaceutical preparations. Further, such pharmaceutical preparations are used in animals and human.

The pharmaceutical preparations of the present invention can contain Compound (I) or a pharmaceutically acceptable salt thereof as the active ingredient alone or together with other optional active ingredients for the treatment of different diseases. Further, these pharmaceutical preparations are produced by optional methods well known in the technical field of pharmaceutics, by mixing the active ingredient with one or more pharmaceutically acceptable carriers.

It is preferred to select the route of administration which is most effective in the treatment. Examples include oral administration and parenteral administrations, such as intraoral, intratracheal, rectal, subcutaneous, intramuscular, intravenous and the like.

Examples of the dosage form include sprays, capsules, tablets, granules, syrups, emulsions, suppositories, injections, ointments, tapes and the like.

Liquid preparations, such as emulsions, syrups and the like, suitable for oral administration can be produced using, for example, water, sugars, such as fructose, sucrose, sorbitol and the like, glycols, such as polyethylene glycol, propylene glycol and the like, oils, such as sesame oil, olive oil, soybean oil and the like, antiseptics, such as p-hydroxybenzoic acid esters and the like, and flavors, such as strawberry flavor, peppermint and the like. Further, capsules, tablets, powders, granules and the like can be produced using, for example, excipients, such as lactose, glucose, sucrose, mannitol and the like, disintegrators, such as starch, sodium alginate and the like, lubricants, such as magnesium stearate, talc and the like, binders, such as polyvinyl alcohol, hydroxypropylcellulose, gelatin and the like, surfactant, such as fatty acid esters and the like, and plasticizers, such as glycerol and the like.

Preparations suitable for parenteral administration are preferably sterile aqueous preparations which contain an active compound that becomes isotonic in the blood of acceptors. For example, in the case of injections, a solution for injection is prepared using a carrier comprising a salt solution, a glucose solution or a mixture of salt water with a glucose solution. In that case, the injections are prepared in the form of a solution, suspension or dispersion in the usual way using an appropriate auxiliary agent. Preparations for rectal administration are prepared using a carrier, such as cacao butter, hydrogenated fat, hydrogenated carboxylic acid or the like, and provided as suppositories. Further, sprays are prepared using an active compound and a carrier which does not stimulate the oral cavity and airway mucous membrane of the acceptors and can facilitate absorption of the active compound by dispersing it in fine particles. Specific examples include lactose, glycerol and the like. Preparations, such as aerosols, dry powders and the like, can be produced depending on the properties of the active compound and the carriers to be used.

Additionally, these parenteral preparations can also be mixed with one or more auxiliary agents selected from the diluents, flavors, antiseptics, excipients, disintegrators, lubricants, binders, surfactants, plasticizers and the like exemplified in relation to the oral preparations.

The effective amount of Compound (I) or a pharmaceutically acceptable salt thereof and the frequency of its administration vary depending on the administration mode, the age and body weight of each patient and properties and seriousness of the symptoms to be treated, but it is generally preferred to administer it in a dose of from 1 to 50 mg/kg per day, by dividing the daily dose into 3 or 4 doses per day. However, these doses may vary depending on the above-described various conditions.

BEST MODE FOR CARRYING OUT THE INVENTION

Figure 1:
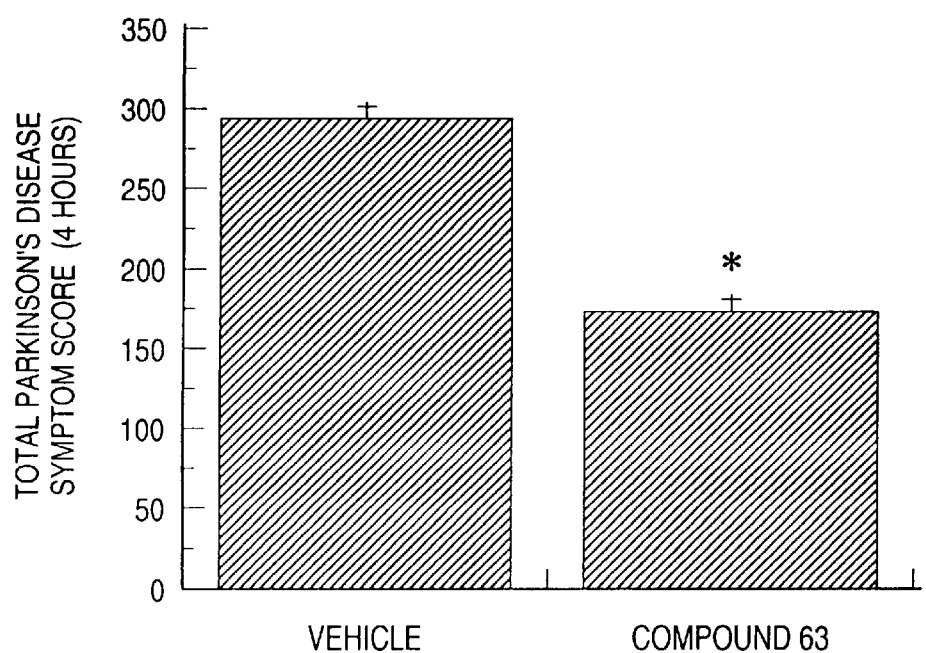
FIG. 1 is a graph showing the total Parkinson's disease symptom score of Compound 63 in a Parkinson's disease model [common marmoset treated with 1-methyl-4-phenyl-1,2,3,6-tetrahydropyridine (MPTP)]. The vehicle means an administered solution which contains no test compound.
Figure 2:
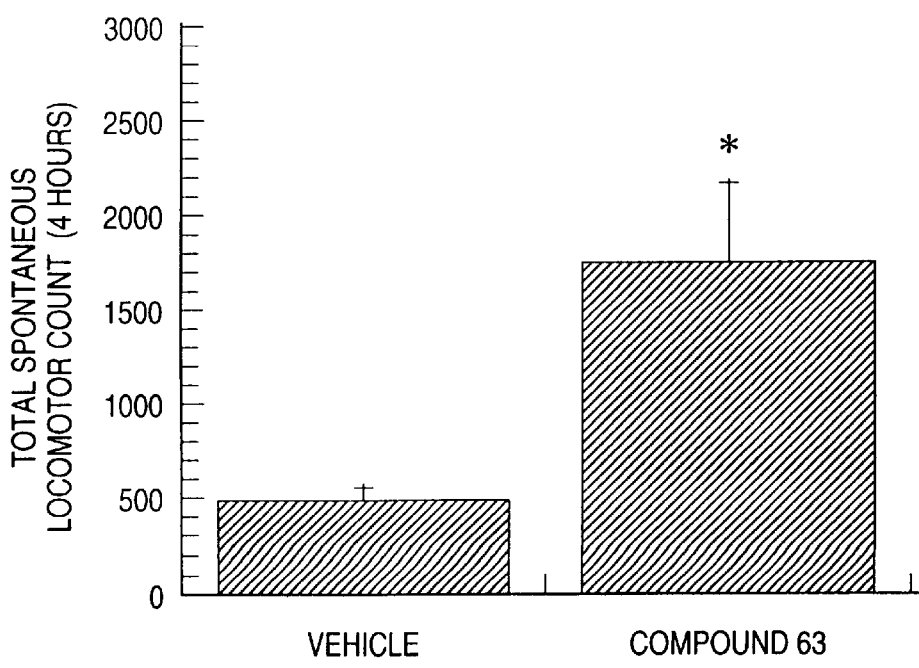
FIG. 2 is a graph showing increase in the total spontaneous motor count by Compound 63 in a Parkinson's disease model [common marmoset treated with 1-methyl-4-phenyl-1,2,3,6-tetrahydropyridine (MPTP)]. The vehicle means an administered solution which does not contain the test compound.

Reference Examples, Examples and Formulation Examples are shown below. In $^1$H NMR data, a symbol "br" which is present before the symbol showing multiplicity means that broad signals were measured. For example, "brs" means a broad singlet.

REFERENCE EXAMPLE 1

6-Chloro-2-methylthio-4-phenoxypyrimidine (Compound a)

In 100 ml of THF, 7.23 g (76.9 mmol) of phenol was dissolved, 3.69 g (60%, 153.8 mmol) of sodium hydride was added thereto at 0° C., and 15.0 g (76.9 mmol) of 4,6-dichloro-2-methylthiopyrimidine was further added thereto, followed by stirring at room temperature for 4 hours. The reaction mixture was extracted by adding water and ethyl acetate. The organic phase was washed with a saturated brine and dried over anhydrous magnesium sulfate, and then the solvent was evaporated under reduced pressure to give 19.8 g (yield: quantitative) of Compound a.

$^1$H NMR (δ ppm, CDCl$_3$): 7.43 (t, J=7.4 Hz, 2H), 7.28 (dt, J=7.4 Hz, 1.5 Hz, 1H), 7.13 (dd, J=8.4 Hz, 1.5 Hz, 2H), 6.47 (s, 1H), 2.38 (s, 3H); Mass (m/z): 254, 252 (M$^+$).

Reference Examples 2 to 9 were carried out below using corresponding dichloropyrimidine derivatives and phenol derivatives in the same manner as in Reference Example 1 to give Compounds b to i.

REFERENCE EXAMPLE 2

6-Chloro-4-(3, 4-dimethoxyphenoxy)-2-methylthiopyrimidine (Compound b)

Yield: quantitative; $^1$H NMR (δ ppm, CDCl$_3$): 6.88 (d, J=9.4 Hz, 1H), 6.72–6.66 (m, 3H), 6.43 (s, 1H), 3.91 (s, 3H), 3.86 (s, 3H), 2.42 (s, 3H); Mass (m/z): 314, 312 (M$^+$).

REFERENCE EXAMPLE 3

6-Chloro-4-(2,6-dimethoxyphenoxy)-2-methylthiopyrimidine (Compound c)

Yield: 92%; $^1$H NMR (δppm, CDCl$_3$): 7.81 (t, J=8.4 Hz, 1H), 6.64 (dd, J=8.4 Hz, 4.5 Hz, 2H), 6.50 (s, 1H), 3.78 (s, 6H), 2.33 (s, 3H); Mass (m/z): 314, 312 (M$^+$).

REFERENCE EXAMPLE 4

6-Chloro-4-(3,5-dimethoxyphenoxy)-2-methylthiopyrimidine (Compound d)

Yield: 83%; $^1$H NMR (δ ppm, CDCl$_3$): 6.44 (s, 1H), 6.39–6.38 (m, 1H), 6.31–6.30 (m, 2H), 3.79 (s, 6H), 2.45 (s, 3H); Mass (m/z): 314, 312 (M$^+$).

REFERENCE EXAMPLE 5

6-Chloro-2-methylthio-4-(4-nitrophenoxy)pyrimidine (Compound e)

Yield: 74%; $^1$H NMR (δppm, CDCl$_3$): 8.31 (dd, J=6.9 Hz, 2.0 Hz, 2H), 7.33 (dd, J=6.9 Hz, 2.0 Hz, 2H), 6.67 (s, 1H), 2.37 (s, 3H); Mass (m/z): 299, 297 (M$^+$).

REFERENCE EXAMPLE 6

6-Chloro-4-(4-chlorophenoxy)-2-methylthiopyrimidine (Compound f)

Yield: 98%; $^1$H NMR (δ ppm, CDCl$_3$): 7.39 (d, J=8.9 Hz, 2H), 7.09 (d, J=8.9 Hz, 2H), 6.53 (s, 1H), 2.38 (s, 3H); Mass (m/z): 288 ($^{35}$Cl$^{37}$Cl compound), 286 ($^{35}$Cl$_2$ compound) (M$^+$).

REFERENCE EXAMPLE 7

6-Chloro-2-methylthio-4-(4-phenylphenoxy)pyrimidine (Compound g)

Yield: quantitative; $^1$H NMR (δ ppm, CDCl$_3$): 7.65–7.58 (m, 4H), 7.48–7.33 (m, 3H), 7.25–7.18 (m, 2H), 6.52 (s, 1H), 2.41 (s, 3H); Mass (m/z): 328, 326 (M$^+$).

REFERENCE EXAMPLE 8

6-Chloro-2-methylthio-4-phenoxy-5-phenylpyrimidine (Compound h)

Yield: quantitative; $^1$H NMR (δ ppm, CDCl$_3$): 7.50–7.31 (m, 5H), 7.24–7.05 (m, 5H), 2.28 (s, 3H); Mass (m/z): 330, 328 (M$^+$).

REFERENCE EXAMPLE 9

6-Chloro-5-methyl-2-methylthio-4-phenoxypyrimidine (Compound i)

Yield: quantitative; $^1$H NMR (δ ppm, CDCl$_3$): 7.40 (t, J=7.4 Hz, 2H), 7.24 (t, J=7.4 Hz, 1H), 7.13 (dd, J=7.4 Hz, 1.0 Hz, 2H), 2.33 (s, 3H), 2.45 (s, 3H); Mass (m/z): 268, 266 (M$^+$).

REFERENCE EXAMPLE 10

N-(2-Furoyl)-N'-($^2$-methylthio-4-phenoxypyrimidin-6-yl)hydrazine (Compound j)

To 30 ml of dioxane and 10 ml of water, 4.0 g (15.8 mmol) of Compound a obtained in Reference Example 1 and 3.99 g (31.7 mmol) of 2-furoic hydrazide were added, and 2.37 ml (15.84 mmol) of DBU was added thereto, followed by refluxing for 5 hours. The reaction mixture was cooled to room temperature, the solvent was evaporated under reduced pressure, and the residue was extracted by adding chloroform and water. The organic phase was dried over anhydrous magnesium sulfate, the solvent was evaporated under reduced pressure, and the residue was purified by silica gel column chromatography [chloroform-methanol (99:1)] to g ive 3.51 g (yield: 65%) of Compound j.

$^1$H NMR (δ ppm, CDCl$_3$): 8.38 (brs, 1H), 7.51 (t, J=1.0 Hz, 1H), 7.39–7.09 (m, 7H), 6.55 (dd, J=3.5 Hz, 2.0 Hz, 1H), 5.76 (s, 1H), 2.32 (s, 3H); Mass (m/z): 342 (M$^+$).

REFERENCE EXAMPLE 11

N-[4-(3, 4-Dimethoxyphenoxy)-2-methylthiopyrimidin-6-yl]-N'-(2-furoyl)hydrazine (Compound k)

In 50 ml of DMF, 8.0 g (25.6 mmol) of Compound b obtained in Reference Example 2 and 3.88 g (30.8 mmol) of 2-furoic hydrazide were dissolved, and 4.61 ml (30.8 mmol) of DBU was added thereto, followed by stirring at 100° C. for 5 hours. The reaction mixture was cooled to room temperature and extracted by adding chloroform and water. The organic phase was dried over anhydrous magnesium sulfate, the solvent was evaporated under reduced pressure, and the residue was purified by silica gel column chromatography [chloroform-methanol (98:2)] to give 4.97 g (yield: 48%) of Compound k.

$^1$H NMR (δ ppm, DMSO-d$_6$): 7.91 (s, 1H), 7.24–7.22 (m, 1H), 6.97–6.92 (m, 1H), 6.82–6.79 (m, 1H), 6.70–6.66 (m, 1H), 5.52 (s, 1H), 3.74 (s, 3H), 3.71 (s, 3H), 2.32 (s, 3H); Mass (m/z): 402 (M$^+$)

Reference Examples 12 to 18 were carried out below using Compounds c to i obtained in Reference Examples 3 to 9 in the same manner as in Reference Example 11 to give Compounds L to r.

REFERENCE EXAMPLE 12

N-[4-(2,6-Dimethoxyphenoxy)-2-methylthiopyrimidin-6-yl]-N'-(2-furoyl)hydrazine (Compound L)

Yield: 35%; $^1$H NMR (δ ppm, CDCl$_3$): 8.27 (brs, 1H), 7.51 (t, J=1.0 Hz, 1H), 7.26–6.95 (m, 4H), 6.62–6.54 (m, 3H), 5.88 (s, 1H), 3.76 (s, 6H), 2.25 (s, 3H); Mass (m/z): 402 (M$^+$).

REFERENCE EXAMPLE 13

N-[4-(3,5-Dimethoxyphenoxy)-2-methylthiopyrimidin-6-yl]-N'-(2-furoyl)hydrazine (Compound m)

Yield: 21%; $^1$H NMR (δ ppm, CDCl$_3$): 8.21 (brs, 1H), 7.52 (dd, J=1.7 Hz, 0.7 Hz, 1H), 7.24 (dd, J=3.6 Hz, 0.7 Hz, 1H), 6.91 (d(br), J=2.0 Hz, 1H), 6.57 (dd, J=3.6 Hz, 2.0 Hz, 1H), 6.32–6.30 (m, 3H), 5.76 (s, 1H), 3.75 (s, 6H), 2.40 (s, 3H); Mass (m/z): 402 (M$^+$).

REFERENCE EXAMPLE 14

N-[2-Methylthio-4-(4-nitrophenoxypyrimidin-6-yl)]-N'-(2-furoyl)hydrazine (Compound n)

Yield: 52%; $^1$H NMR (δ ppm, CDCl$_3$): 8.25 (dd, J=6.9 Hz, 2.5 Hz, 2H), 8.20 (brs, 1H), 7.54 (d, J=1.0 Hz, 1H), 7.30–7.20 (m, 3H), 7.04 (brs, 1H), 6.59 (dd, J=4.0 Hz, 2.0 Hz, 1H), 5.95 (s, 1H), 2.32 (s, 3H); Mass (m/z): 387 (M$^+$).

REFERENCE EXAMPLE 15

N-[4-(4-Chlorophenoxy)-2-methylthiopyrimidin-6-yl]-N'-(2-furoyl)hydrazine (Compound o)

Yield: 33%; $^1$H NMR (δ ppm, CDCl$_3$): 8.22 (brs, 1H), 7.54 (dd, J=1.7 Hz, 0.7 Hz, 1H), 7.34–7.25 (m, 3H), 7.09–6.60 (m, 3H), 6.58 (dd, J=3.6 Hz, 1.7 Hz, 1H), 5.81 (s, 1H), 2.33 (s, 3H); Mass (m/z): 378, 376 (M$^+$).

REFERENCE EXAMPLE 16

N-[2-Methylthio-4-(4-phenylphenoxy)pyrimidin-6-yl]-N'-(2-furoyl)hydrazine (Compound p)

Yield: 53%; $^1$H NMR (δ ppm, CDCl$_3$): 7.58–7.16 (m, 11H), 6.54–6.52 (m, 1H), 5.81 (s, 1H), 2.35 (s, 3H); Mass (m/z): 418 (M$^+$).

REFERENCE EXAMPLE 17

N-(2-Methylthio-4-phenoxy-5-phenylpyrimidin-6-yl)-N'-(2-furoyl)hydrazine (Compound q)

Yield: 24%; Mass (m/z): 418 (M$^+$).

REFERENCE EXAMPLE 18

N-(5-Methyl-2-methylthio-4-phenoxypyrimidin-6-yl)-N'-(2-furoyl)hydrazine (Compound r)

Yield: 35%; $^1$H NMR (δ ppm, CDCl$_3$): 9.24 (brs, 1H), 7.51–7.09 (m, 8H), 6.52 (dd, J=3.5 Hz, 2.0 Hz, 1H), 2.18 (s, 3H), 2.15 (s, 3H); Mass (m/z): 356 (M$^+$).

REFERENCE EXAMPLE 19

N-( 4-chloro-2-methylthiopyrimidin-6-yl)-N'-(2-furoyl)hydrazine (Compound s)

In 100 ml of THF, 15 g (76.9 mmol) of 4,6-dichloro-2-methylthiopyrimidine and 14.3 g (113 mmol) of 2-furoic hydrazide were dissolved, and 16.7 ml (121.5 mmol) of DBU was added thereto, followed by stirring at room temperature for 5 hours. The reaction mixture was extracted by adding chloroform and water. The organic phase was dried over anhydrous magnesium sulfate, the solvent was evaporated under reduced pressure, and the residue was purified by silica gel column chromatography [chloroform-methanol (96:4)] to give 16.0 g (yield: 73%) of Compound s.

$^1$H NMR (δ ppm, CDCl$_3$): 8.22 (brs, 1H), 7.54 (s, 1H), 7.28–7.27 (m, 1H), 7.18 (brs, 1H), 6.60–6.58 (m, 1H), 6.36 (s, 1H), 2.50 (s, 3H); Mass (m/z): 286, 284 (M$^+$).

REFERENCE EXAMPLE 20

N-(4-Chloro-2-methylthio-5-phenylpyrimidin-6-yl)-N'-(2-furoyl)hydrazine (Compound t)

In 180 ml of THF, 25 g (92.2 mmol) of 4,6-dichloro-2-methylthio-5-phenylpyrimidine and 12.8 g (101.1 mmol) of 2-furoic hydrazide were dissolved, and 15.2 ml (110.6 mmol) of DBU was added thereto, followed by stirring at room temperature overnight. The reaction mixture was extracted by adding chloroform and water. The organic phase was dried over anhydrous magnesium sulfate, the solvent was evaporated under reduced pressure, and the residue was purified by silica gel column chromatography [chloroform-methanol (99:1)] to give 24.4 g (yield: 73%) of Compound t.

¹H NMR (δ ppm, CDCl₃): 8.63 (brs, 1H), 7.56–7.37 (m, 6H), 7.17 (d, J=3.0 Hz, 1H), 6.96 (brs, 1H), 6.54 (dd, J=3.5 Hz, 1.5 Hz, 1H), 2.48 (s, 3H); Mass (m/z): 362, 360 (M⁺).

Reference Examples 21 to 24 were carried out below using some hydrazide derivatives and Compound a obtained in Reference Example 1 in the same manner as in Reference Example 11 to give Compounds u to x.

REFERENCE EXAMPLE 21

N-(2-Methylthio-4-phenoxypyrimidin-6-yl)-N'-benzoylhydrazine (Compound u)

Yield: 32%; ¹H NMR (δ ppm, CDCl₃): 8.40 (brs, 1H), 7.82–7.78 (m, 2H), 7.59–7.08 (m, 9H), 5.73 (s, 1H), 2.33 (s, 3H); Mass (m/z): 352 (M⁺).

REFERENCE EXAMPLE 22

N-(2-Methylthio-4-phenoxypyrimidin-6-yl)-N'-(3-anisoyl)hydrazine (Compound v)

Yield: 42%; ¹H NMR (δ ppm, CDCl₃): 8.60 (brs, 1H), 7.55 (s, 1H), 7.40–7.05 (m, 8H), 5.78 (s, 1H), 3.83 (s, 3H), 2.31 (s, 3H); Mass (m/z): 381 (M⁺).

REFERENCE EXAMPLE 23

N-(2-Methylthio-4-phenoxypyrimidin-6-yl)-N'-nicotinoylhydrazine (Compound w)

Yield: 50%; ¹H NMR (δ ppm, DMSO-d₆): 10.71 (brs, 1H), 9.45 (s, 1H), 9.02 (d, J=1.5 Hz, 1H), 8.77 (dd, J=4.7 Hz, 2.0 Hz, 1H), 8.21 (dd, J=7.9 Hz, 2.0 Hz, 1H), 7.58–7.53 (m, 1H), 7.43 (t, J=7.9 Hz, 2H), 7.25 (t, J=7.4 Hz, 1H), 7.17 (d, J=7.9 Hz, 2H), 5.69 (s, 1H), 2.29 (s, 3H); Mass (m/z): 353 (M⁺).

REFERENCE EXAMPLE 24

N-(2-Methylthio-4-phenoxypyrimidin-6-yl)-N'-(2-thenoyl)hydrazine (Compound x)

Yield: 71%; ¹H NMR (δ ppm, CDCl₃): 10.54 (brs, 1H), 9.39 (s, 1H), 7.87–7.84 (m, 2H), 7.45–7.39 (m, 2H), 7.24–7.14 (m, 4H), 5.62 (s, 1H), 2.28 (s, 3H); Mass (m/z): 358 (M⁺).

REFERENCE EXAMPLE 25

N-(2-Methylthio-4-piperidinopyrimidin-6-yl)-N'-(2-furoyl)hydrazine (Compound y)

To 6.4 g (22 5 mmol) of Compound s obtained in Reference Example 19, 30 ml of piperidine and 5 mg of dimethylaminopyridine were added, followed by refluxing overnight. The reaction mixture was cooled to room temperature, concentrated under reduced pressure, and then extracted by adding chloroform and water. The organic phase was dried over anhydrous magnesium sulfate, the solvent was evaporated under reduced pressure, and the residue was purified by silica gel column chromatography [chloroform-methanol (99:1)] to give 4.8 g (yield: 64%) of Compound y.

¹H NMR (δ ppm, DMSO-d₆): 10.24 (brs, 1H), 8.60 (s, 1H), 7.90 (s, 1H), 7.25 (d, J=3.46 Hz, 1H), 6.66 (dd, J=3.5 Hz, 1.5 Hz, 1H), 5.42 (s, 1H), 3.48–3.37 (m, 4H), 2.36 (s, 3H), 1.59–1.47 (m, 6H); Mass (m/z): 333 (M⁺).

Reference Examples 26 and 27 were carried out below using Compound s obtained in Reference Example 19 and a corresponding reagent (morpholine or 1-methylpiperazine) in the same manner as in Reference Example 25 to give Compound z and Compound aa.

REFERENCE EXAMPLE 26

N-(2-Methylthio-4-morpholinopyrimidin-6-yl)-N'-(2-furoyl)hydrazine (Compound z)

Yield: 30%; ¹H NMR (δ ppm, DMSO-d₆): 10.27 (brs, 1H), 8.73 (brs, 1H), 7.90 (s, 1H), 7.25 (d, J=3.0 Hz, 1H), 6.66 (dd, J=3.0 Hz, 1.5 Hz, 1H), 5.44 (s, 1H), 3.62–3.51 (m, 4H), 3.44–3.38 (m, 4H), 2.37 (s, 3H); Mass (m/z): 335 (M⁺).

REFERENCE EXAMPLE 27

N-[4-(4-Methylpiperazinyl)-2-methylthiopyrimidin-6-yl]-N'-(2-furoyl)hydrazine (Compound aa)

Yield: 84%; ¹H NMR (δ ppm, DMSO-d₆): 10.20 (brs, 1H), 8.67 (brs, 1H), 7.88 (d, J=1.5 Hz, 1H), 7.22 (d, J=3.5 Hz, 1H), 6.65 (dd, J=3.5 Hz, 1.5 Hz, 1H), 5.44 (s, 1H), 3.45–3.37 (m, 4H), 2.36 (s, 3H), 2.34–2.23 (m, 4H), 2.18 (s, 3H); Mass (m/z): 348 (M⁺).

REFERENCE EXAMPLE 28

N-[2-Methylthio-4-(4-phenylpiperazinyl)pyrimidin-6-yl]-N'-(2-furoyl)hydrazine (Compound bb)

To 6.0 g (21.1 mmol) of Compound s obtained in Reference Example 19, 12 ml of DMSO and 8.06 ml (52.75 mmol) of 1-phenylpiperazine were added, followed by stirring at 130° C. overnight. The reaction mixture was cooled to room temperature and extracted by adding chloroform and water. The organic phase was dried over anhydrous magnesium sulfate, chloroform and then hexane were added to the residue, and then the precipitated solid was collected by filtration. The solid was washed with hexane and then dried under reduced pressure to give 4.9 g (yield: 57%) of Compound bb.

¹H NMR (δ ppm, DMSO-d₆): 10.29 (brs, 1H), 8.73 (brs, 1H), 7.91 (d, J=1.0 Hz, 1H), 7.32–7.19 (m, 3H), 6.95 (d, J=7.9 Hz, 2H), 6.80 (t, J=7.4 Hz, 1H), 6.68 (dd, J=3.5 Hz, 1.5 Hz, 1H), 5.50 (s, 1H), 3.63–3.41 (m, 4H), 3.26–3.11 (m, 4H), 2.39 (s, 3H); Mass (m/z): 410 (M⁺).

REFERENCE EXAMPLE 29

N-[4-(4-Benzylpiperazinyl)-2-methylthiopyrimidin-6-yl]-N'-(2-furoyl)hydrazine (Compound cc)

Compound cc was obtained using Compound s obtained in Reference Example 19 and benzylpiperazine in the same manner as in Reference Example 28.

Yield: 87%; ¹H NMR (δ ppm, DMSO-d₆): 10.28 (brs, 1H), 8.71 (brs, 1H), 7.90 (dd, J=1.7 Hz, 0.7 Hz, 1H), 7.27–7.32 (m, 5H), 7.25 (dd, J=3.3 Hz, 0.7 Hz, 1H), 6.66 (dd, J=3.3 Hz, 1.7 Hz, 1H), 5.44 (s, 1H), 3.48 (t, J=5.0 Hz, 4H), 3.36 (s, 2H), 2.38 (t, J=5.0 Hz, 4H), 2.35 (s, 3H); Mass (m/z): 424 (M⁺).

REFERENCE EXAMPLE 30

N-(2-Methylthio-4-morpholino-5-phenylpyrimidin-6-yl)-N'-(2-furoyl)hydrazine (Compound dd)

Compound dd was obtained using Compound t obtained in Reference Example 20 in the same manner as in Reference Example 25.

Yield: 94%; $^1$H NMR (δ ppm, CDCl$_3$): 8.86 (brs, 1H), 7.50–7.31 (m, 6H), 7.12 (d, J=3.5 Hz, 1H), 6.95 (brs, 1H), 6.51 (t, J=3.5 Hz, 1.5 Hz, 1H), 3.50 (t, J=4.5 Hz, 4H), 3.21 (t, J=4.9 Hz, 4H), 2.46 (s, 3H); Mass (m/z): 411 (M$^+$).

REFERENCE EXAMPLE 31

N-(5-Ethoxycarbonyl-2-methylthiopyrimidin-6-yl]-N'-(2-furoyl)hydrazine (Compound ee)

Compound ee was obtained using 5-ethoxycarbonyl-4-chloro-2-methylthiopyrimidine and 2-furoic hydrazide in the same manner as in Reference Example 19.

Yield: 63%; $^1$H NMR (δ ppm, CDCl$_3$): 10.09 (brs, 1H), 9.06 (brs, 1H), 8.01 (s, 1H), 7.53 (t, J=1.0 Hz, 1H), 7.24 (d, J=3.5 Hz, 1H), 6.56 (dd, J=3.5 Hz, 2.0 Hz, 1H), 4.38 (q, J=6.9 Hz, 2H), 2.44 (s, 3H), 1.40 (t, J=7.4 Hz, 3H); Mass (m/z): 322 (M$^+$).

EXAMPLE 1

5-(3,4-Dimethoxybenzylamino)-2-(2-furyl)-7-phenoxy-[1,2,4]triazolo[1,5-c]pyrimidine (Compound 1)

In 80 ml of xylene, 4.80 g (16.9 mmol) of diphosphorus pentaoxide was suspended, and 7.18 ml (33.8 mmol) of hexamethyldisiloxane was added thereto, followed by stirring at 90° C. for 2 hours. Next, 3.85 g (11.2 mmol) of Compound j obtained in Reference Example 10 was added thereto, followed by refluxing for 5 hours. The reaction mixture was cooled to room temperature and extracted by adding ethyl acetate and water. The organic phase was washed with a saturated brine and dried over anhydrous magnesium sulfate. The solvent was evaporated under reduced pressure, and the residue was purified by silica gel column chromatography [chloroform-hexane (9:1)] to give 2.83 g of a main product.

In 25 ml of DMSO, 2.8 g of the obtained main product was dissolved, and 6.98 ml (46.3 mmol) of veratrylamine was added thereto, followed by stirring at 140° C. for 2 hours. The reaction mixture was cooled to room temperature and extracted by adding chloroform and water. The organic phase was dried over anhydrous magnesium sulfate, the solvent was evaporated under reduced pressure, and the residue was purified by silica gel column chromatography [hexane-ethyl acetate (3:1)] to give 3.02 g (yield: 62%) of Compound 1 as a white solid.

$^1$H NMR (δ ppm, CDCl$_3$): 7.58–7.57 (m, 1H), 7.48–7.39 (m, 3H), 7.28–7.14 (m, 4H), 6.87–6.82 (m, 3H), 6.59–6.42 (m, 2H), 6.16 (s, 1H), 4.63 (d, J=5.4 Hz, 2H), 3.88 (s, 3H), 3.86 (s, 3H); Mass (m/z): 443 (M$^+$); IR (KBr, cm$^{-1}$): 1616, 1589, 1513, 1207; Melting point: 133.4–134.0° C.

Examples 2 to 9 were carried out below using Compounds k to r obtained in Reference Examples 11 to 18 in the same manner as in Example 1 to give Compounds 2 to 9.

EXAMPLE 2

5-(3,4-Dimethoxybenzylamino)-7-(3,4-dimethoxyphenoxy)-2-(2-furyl)[1,2,4]triazolo[1,5-c]pyrimidine (Compound 2)

Yield: 53% (amorphous); $^1$H NMR (δ ppm, CDCl$_3$): 7.58–7.57 (m, 1H), 7.15 (d, J=3.5 Hz, 1H), 6.91–6.74 (m, 5H), 6.57–6.51 (m, 2H), 6.14 (s, 1H), 4.66 (d, J=5.5 Hz, 2H), 3.91 (s, 3H), 3.89 (s, 3H), 3.88 (s, 3H), 3.84 (s, 3H); Mass (m/z): 503 (M$^+$); IR (KBr, cm$^{-1}$): 1639, 1596, 1267, 1202.

EXAMPLE 3

5-(3,4-Dimethoxybenzylamino)-7-(2,6-dimethoxyphenoxy)-2-(2-furyl)[1,2,4]triazolo[1,5-c]pyrimidine (Compound 3)

Yield: 18% (yellow solid); $^1$H NMR (δ ppm, CDCl$_3$): 7.56 (d, J=1.0 Hz, 1H), 7.19 (t, J=8.4 Hz, 1H), 7.13 (d, J=3.5 Hz, 1H), 6.92 (s, 1H), 6.84–6.82 (m, 2H), 6.67 (d, J=8.4 Hz, 2H), 6.54 (dd, J=3.5 Hz, 2.0 Hz, 1H), 6.45 (t, J=5.9 Hz, 1H), 6.11 (s, 1H), 4.65 (d, J=5.9 Hz, 2H), 3.88 (s, 6H), 3.79 (s, 6H); Mass (m/z): 503 (M$^+$); IR (KBr, cm$^{-1}$): 1629, 1594, 1577, 1479, 1224; Melting point: 60.5–60.9° C.

EXAMPLE 4

5-(3,4-Dimethoxybenzylamino)-7-(3,5-dimethoxyphenoxy)-2-(2-furyl)[1,2,4]triazolo[1,5-c]pyrimidine (Compound 4)

Yield: 45% (white solid); $^1$H NMR (δ ppm, CDCl$_3$): 7.58 (dd, J=2.0 Hz, 0.7 Hz, 1H), 7.16 (dd, J=3.3 Hz, 0.7 Hz, 1H), 6.89–6.84 (m, 3H), 6.57–6.53 (m, 2H), 6.38–6.36 (m, 3H), 6.22 (s, 1H), 4.66 (d, J=5.9 Hz, 2H), 3.88 (d, J=3.5 Hz, 6H), 3.78 (s, 6H); Mass (m/z): 503 (M$^+$); IR (KBr, cm$^{-1}$): 3244, 2920, 2820, 1637, 1601, 1417, 1213; Melting point: 85.6–89.5° C.

EXAMPLE 5

5-(3,4-Dimethoxybenzylamino)-2-(furyl)-7-(4-nitrophenoxy)[1,2,4]triazolo[1,5-c]pyrimidine (Compound 5)

Yield: 14% (yellow solid); $^1$H NMR (δ ppm, CDCl$_3$): 7.59–6.25 (m, 12H), 4.65 (d, J=5.6 Hz, 2H), 3.88 (s, 3H), 3.86 (s, 3H); Mass (m/z): 488 (M$^+$); IR (KBr, cm$^{-1}$): 1600, 1587, 1321, 1234; Melting point: 51.5–52.0° C.

EXAMPLE 6

7-(4-Chlorophenoxy)-5-(3,4-dimethoxybenzylamino)-2-(2-furyl)[1,2,4]triazolor[1,5-c]pyrimidine (Compound 6)

Yield: 67% (pale yellow solid); $^1$H NMR (δ ppm, CDCl$_3$): 7.59 (dd, J=1.7 Hz, 0.7 Hz, 1H), 7.38 (d, J=8.9 Hz, 2H), 7.17 (dd, J=3.3 Hz, 0.7 Hz, 1H), 7.11 (d, J=8.9 Hz, 2H), 6.87–6.82 (m, 3H), 6.59–6.55 (m, 2H), 6.24 (s, 1H), 4.59 (d, J=5.9 Hz, 2H), 3.88 (d, J=7.6 Hz, 6H); Mass (m/z): 479, 477 (M$^+$); IR (KBr, cm$^{-1}$): 3419, 3120, 2925, 2820, 1637, 1417, 1213; Melting point: 82.5–94.5° C.

EXAMPLE 7

5-(3,4-Dimethoxybenzylamino)-2-(2-furyl)-7-(4-phenylphenoxy)[1,2,4]triazolo[1,5-c]pyrimidine (Compound 7)

Yield: 42% (white solid); $^1$H NMR (δ ppm, CDCl$_3$): 7.65–7.57 (m, 5H), 7.49–7.33 (m, 3H), 7.27–7.23 (m, 2H), 7.17–7.15 (m, 1H), 6.88–6.78 (m, 3H), 6.57–6.54 (m, 1H), 6.24 (s, 1H), 4.64 (d, J=5.9 Hz, 2H), 3.86 (s, 3H), 3.84 (s, 3H); Mass (m/z): 519 (M$^+$); IR (KBr, cm$^{-1}$): 1635, 1592, 1415, 1226; Melting point: 75.8–76.8° C.

EXAMPLE 8

5-(3,4-Dimethoxybenzylamino)-2-(2-furyl)-7-phenoxy-8-phenyl[1,2,4]triazolo[1,5-c]pyrimidine (Compound 8)

Yield: 65% (white solid); $^1$H NMR (δ ppm, CDCl$_3$): 7.92 (dd, J=7.2 Hz, 1.7 Hz, 2H), 7.57 (d, J=1.0 Hz, 1H), 7.48–7.13 (m, 9H), 6.77–6.73 (m, 2H), 6.66 (dd, J=8.2 Hz, 2.0 Hz, 1H), 6.56–6.53 (m, 2H), 4.42 (d, J=5.9 Hz, 2H), 3.87 (s, 3H), 3.81 (s, 3H); Mass (m/z): 519 (M$^+$); IR (KBr, cm$^{-1}$): 1635, 1591, 1583; Melting point: 83.5–90.5° C.

EXAMPLE 9

5-(3,4-Dimethoxybenzylamino)-2-(2-furyl)-8-methyl-7-phenoxy[1,2,4]triazolo[1,5-c]pyrimidine (Compound 9)

Yield: 53% (yellow solid); $^1$H NMR (δ ppm, CDCl$_3$): 7.59 (t, J=1.0 Hz, 1H), 7.37 (t, J=7.4 Hz, 2H), 7.22–7.09 (m, 4H), 6.76–6.65 (m, 3H), 6.56 (dd, J=3.5 Hz, 2.0 Hz, 1H), 6.35 (t, J=5.9 Hz, 1H), 4.40 (d, J=5.9 Hz, 2H), 3.86 (s, 3H), 3.79 (s, 3H), 2.44 (s, 3H); Mass (m/z): 457 (M$^+$); IR (KBr, cm$^{-1}$): 1517, 1511, 1490, 1465, 1361; Melting point: 160.2–163.5° C.

EXAMPLE 10

5-(3,4-Dimethoxybenzylamino)-2-(2-furyl)-7-phenylthio[1,2,4]triazolo[1,5-c]pyrimidine (Compound 10)

In 110 ml of xylene, 28.8 g (101 mmol) of diphosphorus pentaoxide was suspended, and 42.8 ml (201 mmol) of hexamethyldisiloxane was added thereto, followed by stirring at 90° C. for 2 hours. Next, 19.2 g (67.3 mmol) of Compound s obtained in Reference Example 19 was added thereto, followed by refluxing for 5 hours. The reaction mixture was cooled to room temperature and extracted by adding ethyl acetate and water. The organic phase was washed with a saturated brine and dried over anhydrous magnesium sulfate. The solvent was evaporated under reduced pressure, and the residue was purified by silica gel column chromatography [chloroform-methanol (99:1)] to give 10.7 g of a main product.

In 5 ml of THF, 1.0 g of the obtained main product was dissolved, and 462 μl (4.5 mmol) of thiophenol and 841 μl (5.63 mmol) of DBU were added thereto, followed by refluxing for 3 hours. The reaction mixture was cooled to room temperature and extracted by adding chloroform and water. The organic phase was dried over anhydrous magnesium sulfate, the solvent was evaporated under reduced pressure, and the residue was purified by silica gel column chromatography [ethyl acetate-hexane (1:4)] to give 0.92 g (yield: 43%) of 2-(2-furyl)-5-methylthio-7-phenylthio[1,2,4]triazolo[1,5-c]pyrimidine.

$^1$H NMR (δ ppm, CDCl$_3$): 7.67–7.59 (m, 3H), 7.50–7.46 (m, 3H), 7.18 (d, J=3.5 Hz, 1H), 6.70 (s, 1H), 6.55 (dd, J=4.0 Hz, 1.5 Hz, 1H), 2.64 (s, 3H); Mass (m/z): 340 (M$^+$);

In 10 ml of DMSO, 1.43 g (4.21 mmol) of the obtained 2-(2-furyl)-5-methylthio-7-phenylthio[1,2,4]triazolo[1,5-c]pyrimidine was dissolved, and 1.90 ml (12.6 mmol) of veratrylamine was added thereto, followed by stirring at 140° C. for 2 hours. The reaction mixture was cooled to room temperature and extracted by adding chloroform and water. The organic phase was dried over anhydrous magnesium sulfate, the solvent was evaporated under reduced pressure, and the residue was purified by silica gel column chromatography [chloroform-methanol (99:1)] to give 1.08 g (yield: 93%) of Compound 10 as a yellow solid.

$^1$H NMR (δ ppm, CDCl$_3$): 7.67–6.30 (m, 13H), 4.70 (d, J=6.0 Hz, 2H), 3.91 (s, 3H), 3.89 (s, 3H); Mass (m/z): 459 (M$^+$); IR (KBr, cm$^{-1}$): 1621, 1610, 1575, 1508; Melting point: 62.5–63.0° C.

EXAMPLE 11

5-(3,4-Dimethoxybenzylamino)-2-(2-furyl)-8-phenyl-7-phenylthio[1,2,4]triazolo[1,5-c]pyrimidine (Compound 11)

Compound 11 was obtained using Compound t obtained in Reference Example 20 in the same manner as in Example 10.

Yield: 23% (white solid); $^1$H NMR (δ ppm, CDCl$_3$): 7.68 (dd, J=8.4 Hz, 1.5 Hz, 2H), 7.59–7.31 (m, 9H), 7.14 (dd, J=3.5 Hz, 1.0 Hz, 1H), 6.76 (d, J=7.9 Hz, 1H), 6.69 (d, J=2.0 Hz, 1H), 6.60 (dd, J=8.4 Hz, 2.0 Hz, 1H), 6.51 (dd, J=3.5 Hz, 1.5 Hz, 1H), 6.35 (t, J=5.9 Hz, 1H), 4.30 (d, J=5.9 Hz, 2H), 3.87 (s, 3H), 3.85 (s, 3H); Mass (m/z): 535 (M$^+$); IR (KBr, cm$^{-1}$): 1621, 1612, 1567, 1265; Melting point: 210.5–211.5° C.

EXAMPLE 12

5-(3,4-Dimethoxybenzylamino)-7-phenoxy-2-phenyl[1,2,4]triazolo[1,5-c]pyrimidine (Compound 12)

Compound 12 was obtained using Compound u obtained in Reference Example 21 in the same manner as in Example 1.

Yield: 28% (white solid); $^1$H NMR (δ ppm, CDCl$_3$): 8.21–8.17 (m, 2H), 7.47–7.40 (m, 4H), 7.28–7.18 (m, 3H), 6.92–6.86 (m, 3H), 6.50–6.47 (m, 1H), 6.18 (s, 1H), 4.69 (d, J=5.9 Hz, 2H), 3.89 (s, 3H), 3.88 (s, 3H); Mass (m/z): 453 (M$^+$); IR (KBr, cm$^{-1}$): 1592, 1589, 1459, 1396, 1205; Melting point: 45.5–46.0° C.

Examples 13–15 were carried out below using Compounds v, w and x obtained in Reference Examples 22–24 to give Compounds 13–15.

EXAMPLE 13

2-(3-Anisyl)-5-(3,4-dimethoxybenzylamino)-7-phenoxy[1,2,4]triazolo[1,5-c]pyrimidine (Compound 13)

Yield: 59% (white solid); $^1$H NMR (δ ppm, CDCl$_3$): 7.79 (d, J=7.9 Hz, 1H), 7.73 (t, J=3.0 Hz, 1H), 7.49–7.18 (m, 6H), 7.03–6.83 (m, 4H), 6.50 (t, J=5.4 Hz, 1H), 4.69 (d, J=5.4 Hz, 2H), 3.89 (s, 3H), 3.88 (s, 6H); Mass (m/z): 483 (M$^+$); IR (KBr, cm$^{-1}$): 1637, 1592, 1589, 1575, 1394; Melting point: 135.5–136.0° C.

EXAMPLE 14

5-(3,4-Dimethoxybenzylamino)-7-phenoxy-2-(3-pyridyl)[1,2,4]triazolo[1,5-c]pyrimidine (Compound 14)

Yield: 31% (yellow solid); $^1$H NMR (δ ppm, CDCl$_3$): 9.41 (d, J=2.0 Hz, 1H), 8.68 (dd, J=4.5 Hz, 2.0 Hz, 1H), 8.45 (dt, J=7.9 Hz, 2.0 Hz, 1H), 7.47–7.37 (m, 3H), 7.29–7.18 (m, 3H), 6.92–6.82 (m, 4H), 6.55 (t, J=5.4 Hz, 1H), 6.21 (s, 1H), 4.65 (d, J=5.4 Hz, 2H), 3.88 (s, 3H), 3.86 (s, 3H) Mass (m/z): 454 (M$^+$); IR (KBr, cm$^{-1}$): 1639, 1618, 1600, 1519, 1490, 1232; Melting point: 159.5–160.0° C.

EXAMPLE 15

5-(3,4-Dimethoxybenzylamino)-7-phenoxy-2-(2-thienyl)[1,2,4]triazolo[1,5-c]pyrimidine (Compound 15)

Yield: 47% (yellow solid); $^1$H NMR (δ ppm, CDCl$_3$): 7.81 (dd, J=3.5 Hz, 0.99 Hz, 1H), 7.45–7.38 (m, 3H), 7.26–7.11 (m, 4H), 6.90–6.83 (m, 3H), 6.50 (t, J=5.9 Hz, 1H), 6.15 (s, 1H), 4.65 (d, J=5.9 Hz, 2H), 3.88 (s, 3H), 3.86 (s, 3H); Mass (m/z): 459 (M$^+$); IR (KBr, cm$^{-1}$): 1631, 1604, 1585, 1390, 1213; Melting point: 110.5–111.0° C.

Examples 16 to 21 were carried out below using Compounds y to dd obtained in Reference Examples 25 to 30, respectively, in the same manner as in Example 1 to give Compounds 16 to 21.

EXAMPLE 16

5-(3,4-Dimethoxybenzylamino)-2-(2-furyl)-7-piperidino[1,2,4]triazolo[1,5-c]pyrimidine (Compound 16)

Yield: 58% (amorphous); $^1$H NMR (δ ppm, CDCl$_3$): 7.55 (t, J=1.0 Hz, 1H), 7.20 (d, J=3.5 Hz, 1H), 6.95–6.79 (m, 3H), 6.54–6.52 (m, 1H), 6.30 (t, J=5.4 Hz, 1H), 5.97 (s, 1H), 4.67 (d, J=5.4 Hz, 2H), 3.88 (s, 3H), 3.87 (s, 3H), 3.63–3.57 (m, 4H), 1.77–1.63 (m, 6H); Mass (m/z): 434 (M$^+$); IR (KBr, cm$^{-1}$): 1637, 1594, 1456, 1265.

EXAMPLE 17

5-(3,4-Dimethoxybenzylamino)-2-(2-furyl)-7-morpholino[1,2,4]triazolo[1,5-c]pyrimidine (Compound 17)

Yield: 30% (orange solid); $^1$H NMR (δ ppm, CDCl$_3$): 7.56 (d, J=1.0 Hz, 1H), 7.14 (d, J=3.5 Hz, 1H), 6.95–6.91 (m, 1H), 6.84 (d, J=7.9 Hz, 2H), 6.55 (dd, J=3.5 Hz, 2.0 Hz, 1H), 6.32 (t, J=5.5 Hz, 1H), 5.98 (s, 1H), 4.68 (d, J=5.5 Hz, 2H), 3.89 (s, 3H), 3.88 (s, 3H), 3.82 (t, J=5.4 Hz, 4H), 3.58 (t, J=5.4 Hz, 4H); Mass (m/z): 436 (M$^+$); IR (KBr, cm$^{-1}$): 1635, 1614, 1577, 1511, 1423; Melting point: 61.5–62.5° C.

EXAMPLE 18

5-(3,4-Dimethoxybenzylamino)-2-(2-furyl)-7-(4-methylpiperazinyl)[1,2,4]triazolo[1,5-c]pyrimidine (Compound 18)

Yield: 24% (white solid); $^1$H NMR (δ ppm, CDCl$_3$): 7.55 (d, J=1.0 Hz, 1H), 7.13 (d, J=3.5 Hz, 1H), 6.99–6.82 (m, 3H), 6.54 (dd, J=3.0 Hz, 1.5 Hz, 1H), 6.35–6.32 (m, 1H), 5.99 (s, 1H), 4.67 (d, J=5.4 Hz, 2H), 3.88 (s, 3H), 3.87 (s, 3H), 3.62 (t, J=4.5 Hz, 4H), 2.51 (t, J=5.0 Hz, 4H), 2.36 (s, 3H); Mass (m/z): 449 (M$^+$); IR (KBr, c$^{-1}$): 1672, 1610, 1459, 1288; Melting point: 161.5–162.7° C.

EXAMPLE 19

5-(3 4-Dimethoxybenzylamino)-2-(2-furyl)-7-(4-phenylpiperazinyl)[1,2,4]triazolo[1,5-c]pyrimidine (Compound 19)

Yield: 20% (white solid); $^1$H NMR (δ ppm, CDCl$_3$): 7.56 (t, J=1.0 Hz, 1H), 7.33–7.24 (m, 2H), 7.13 (d, J=3.5 Hz, 1H), 7.00–6.83 (m, 7H), 6.54 (dd, J=3.5 Hz, 1.5 Hz, 1H), 6.04 (s, 1H), 4.70 (d, J=5.9 Hz, 2H), 3.89 (s, 3H), 3.88 (s, 3H), 3.78–3.73 (m, 4H), 3.34–3.28 (m, 4H); Mass (m/z): 511 (M$^+$); IR (KBr, cm$^{-1}$): 1596, 1496, 1423, 1228; Melting point: 80.5–81.0° C.

EXAMPLE 20

7-(4-Benzylpiperazinyl)-5-(3,4-dimethoxybenzylamino)-2-(2-furyl)[1,2,4]triazolo[1, 5-c]pyrimidine (Compound 20)

Yield: 62% (white solid); $^1$H NMR (δ ppm, CDCl$_3$): 7.56 (dd, J=1.7 Hz, 0.7 Hz, 1H), 7.27–7.36 (m, 5H), 7.13 (dd, J=3.3 Hz, 0.66 Hz, 1H), 6.82–6.95 (m, 3H), 6.54 (dd, J=3.3 Hz, 1.65 Hz, 1H), 6.34 (t, J=5.6 Hz, 1H), 5.97 (s, 1H), 4.66 (d, J=5.6 Hz, 2H), 3.88 (s, 3H), 3.87 (s, 3H), 3.60 (t, J=5.0 Hz, 4H), 3.57 (s, 2H), 2.55 (t, J=5.0 Hz, 4H); Mass (m/z): 525 (M$^+$); IR (KBr, cm$^{-1}$): 1637, 1618, 1593, 1516, 1464, 1458, 1442, 1425, 1265, 1223; Melting point: 62–68° C.

EXAMPLE 21

5-(3,4-Dimethoxybenzylamino)-2-(2-furyl)-7-morpholino-8-phenyl[1,2,4]triazolo[1,5-c]pyrimidine (Compound 21)

Yield: 49% (pale yellow solid); $^1$H NMR (δ ppm, CDCl$_3$): 7.73 (d, J=8.4 Hz, 2H), 7.54 (s, 1H), 7.43 (t, J=7.4 Hz, 2H), 7.28 (t, J=7.4 Hz, 1H), 7.13 (d, J=3.5 Hz, 1H), 7.00–6.84 (m, 3H), 6.51 (dd, J=3.5 Hz, 1.98 Hz, 1H), 6.41 (t, J=5.9 Hz, 1H), 4.72 (d, J=5.9 Hz, 2H), 3.90 (s, 6H), 3.62 (t, J=4.0 Hz, 4H), 3.26 (t, J=4.9 Hz, 4H); Mass (m/z): 512 (M$^+$); IR (KBr, cm$^{-1}$): 1646, 1591, 1515, 1236; Melting point: 170.5–171.2° C.

EXAMPLE 22

8-Ethoxycarbonyl-5-(3,4-dimethoxybenzylamino)-2-(2-furyl)[1,2,4]triazolo[1,5-c]pyrimidine (Compound 22)

Compound 22 was obtained using Compound ee obtained in Reference Example 31 in the same manner as in Example 1.

Yield: 34% (white solid); $^1$H NMR (δ ppm, CDCl$_3$): 8.74 (s, 1H), 7.59 (d, J=1.5 Hz, 1H), 7.36 (d, J=3.5 Hz, 1H), 6.99–6.83 (m, 4H), 6.58 (dd, J=3.5 Hz, 1.5 Hz, 1H), 4.83 (d, J=5.9 Hz, 2H), 4.48 (q, J=7.4 Hz, 2H), 3.88 (s, 6H), 1.45 (t, J=7.4 Hz, 3H); Mass (m/z): 423 (M$^+$); IR (KBr, cm$^{-1}$): 1714, 1604, 1581, 1519, 1259; Melting point: 145.5–151.5° C.

EXAMPLE 23

5-(3,4-Dimethoxybenzylamino)-2-(2-furyl)-8-hydroxymethyl[1,2,4]triazolo[1,5-c]pyrimidine (Compound 23)

In 70 ml of dichloromethane, 5.0 g (11.8 mmol) of Compound 22 obtained in Example 22 was dissolved, and 30 ml of a toluene solution of diisobutylaluminum hydride (1 M) was added dropwise thereto while stirring at −78° C. One hour after, the reaction mixture was slowly heated to 0°

C. and further stirred for 2 hours. Next, the reaction was terminated by adding a saturated aqueous sodium sulfate solution, solid materials in the reaction mixture were removed by filtration, and the filtrate was concentrated under reduced pressure. Ethyl acetate was added to the residue, and the obtained solid was collected by filtration and washed with ethyl acetate to give 2.5 g (yield: 62%) of Compound 23 as a white solid.

$^1$H NMR (δ ppm, DMSO-d$_6$): 8.67 (t, J=6.4 Hz, 1H), 7.94 (d, J=1.0 Hz, 1H), 7.87 (s, 1H), 7.22 (d, J=3.5 Hz, 1H), 7.07 (d, J=1.5 Hz, 1H), 6.93–6.83 (m, 2H), 6.72 (dd, J=3.5 Hz, 2.0 Hz, 1H), 5.16 (t, J=5.4 Hz, 1H), 4.65–4.62 (m, 4H), 3.73 (s, 3H), 3.70 (s, 3H); Mass (m/z): 381 (M$^+$); IR (KBr, cm$^{-1}$): 1629, 1587, 1523, 1267; Melting point: 190.5–191.0° C.

EXAMPLE 24

5-(3,4-Dimethoxybenzylamino)-8-formyl-2-(2-furyl)[1,2,4]triazolo[1,5-c]pyrimidine (Compound 24)

In 20 ml of dichloromethane, 500 mg (1.31 mmol) of Compound 23 obtained in Example 23 was suspended, and 1.14 g (13.1 mmol) of manganese dioxide was added thereto. After stirring at room temperature for 2 hours, solid materials were removed by filtration through celite, and the filtrate was concentrated under reduced pressure. The residue was purified by silica gel column chromatography to give 420 mg (yield: 85%) of Compound 24 as a white solid.

$^1$H NMR (δ ppm, CDCl$_3$): 10.31 (s, 1H), 8.60 (s, 1H), 7.62 (d, J=1.0 Hz, 1H), 7.34 (d, J=3.5 Hz, 1H), 7.00–6.85 (m, 4H), 6.60 (dd, J=3.5 Hz, 2.0 Hz, 1H), 4.87 (d, J=5.4 Hz, 2H), 3.89 (s, 6H); Mass (m/z): 379 (M$^+$); IR (KBr, cm$^{-1}$): 1626, 1585, 1321, 1240; Melting point: 184.5–185.0° C.

EXAMPLE 25

5-(3,4-Dimethoxybenzylamino)-2-(2-furyl)-8-(4-methylpiperazinylmethyl)[1,2,4]triazolo[1,5-c]pyrimidine (Compound 25)

In 20 ml of 1,2-dichloroethane, 200 mg (0.53 mmol) of Compound 24 obtained in Example 24 was dissolved, and 62 μl (0.55 mmol) of N-methylpiperazine was added thereto, followed by stirring at room temperature for 5 minutes. Next, 168 mg (0.79 mmol) of sodium triacetoxyborohydride was added thereto at 0° C., followed by stirring at room temperature overnight. The reaction mixture was extracted by adding an aqueous sodium bicarbonate solution. The organic phase was dried over anhydrous magnesium sulfate, the solvent was evaporated, and the residue was recrystallized from ethanol to give 173 mg (yield: 71%) of Compound 25 as a white solid.

$^1$H NMR (δ ppm, CDCl$_3$): 7.93 (s, 1H), 7.60 (t, J=1.0 Hz, 1H), 7.21 (d, J=3.5 Hz, 1H), 6.99–6.83 (m, 3H), 6.56 (dd, J=3.5 Hz, 2.0 Hz, 1H), 6.40 (t, J=5.4 Hz, 1H), 4.75 (d, J=5.9 Hz, 4H), 3.88 (s, 6H), 2.78–2.31 (m, 8H), 2.89 (s, 3H); Mass (m/z): 463 (M$^+$); IR (KBr, cm$^{-1}$): 1618, 1589, 1511, 1432, 1278; Melting point: 147.5–148.0° C.

EXAMPLE 26

5-(3,4-Dimethoxybenzylamino)-2-(2-furyl)-8-(4-phenylpiperazinylmethyl)[1,2,4]triazolo[1,5-c]pyrimidine (Compound 26)

Example 26 was carried out using Compound 24 obtained in Example 24 and N-phenylpiperadine in the same manner as in Example 25 to give Compound 26.

Yield: 53% (white solid); $^1$H NMR (δ ppm, CDCl$_3$): 7.96 (s, 1H), 7.60–7.54 (m, 1H), 7.28–7.22 (m, 3H), 6.98–6.81 (m, 6H), 6.56 (dd, J=3.3 Hz, 1.7 Hz, 1H), 6.50 (t, J=5.6 Hz, 1H), 4.78 (d, J=5.6 Hz, 2H), 3.90 (s, 2H), 3.87 (s, 6H), 3.22 (t, J=5.0 Hz, 4H), 2.76 (t, J=5.6 Hz, 4H); Mass (m/z): 525 (M$^+$); IR (KBr, cm$^{-1}$): 3128, 2816, 1579, 1260, 1235; Melting point: 192.0–194.0° C.

EXAMPLE 27

5-(3,4-Dimethoxybenzylamino)-8-(4-fluoroanilinomethyl)-2-(2-furyl)[1,2,4]triazolo[1,5-c]pyrimidine (Compound 27)

In 60 ml of 1,2-dichloroethane, 800 mg (2.11 mmol) of Compound 24 obtained in Example 24 was dissolved, and 0.21 ml (2.22 mmol) of 4-fluoroaniline was added thereto, followed by stirring at room temperature for 5 minutes. Next, 0.13 ml (2.22 mmol) of acetic acid and 671 mg (3.17 mmol) of sodium triacetoxyborohydride were added thereto at 0° C., followed by stirring at room temperature for 3.5 hours. The reaction mixture was mixed with an aqueous sodium bicarbonate solution and extracted with chloroform. The organic phase was dried over anhydrous magnesium sulfate, the solvent was evaporated under reduced pressure, and the residue was purified by silica gel column chromatography (chloroform) and recrystallized from ethanol to give 800 mg (yield: 80%) of Compound 27 as a white solid.

$^1$H NMR (δ ppm, CDCl$_3$): 7.90 (s, 1H), 7.62 (dd, J=1.7 Hz, 0.7 Hz, 1H), 7.46 (dd, J=3.3 Hz, 0.7 Hz, 1H), 6.92–6.83 (m, 5H), 6.68–6.58 (m, 3H), 6.40 (t, J=5.6 Hz, 1H), 4.73 (d, J=5.6 Hz, 2H), 4.55 (d, J=5.3 Hz, 2H), 3.88 (t, J=3.3 Hz, 6H); Mass (m/z): 474 (M$^+$); IR (KBr, cm$^{-1}$): 3373, 3230, 1618, 1583, 1512; Melting point: 154.0–154.2° C.

EXAMPLE 28

5-(3,4-Dimethoxybenzylamino)-2-(2-furyl)-8-morpholinomethyl[1,2,4]triazolo[1,5-c]pyrimidine (Compound 28)

Example 28 was carried out using Compound 24 obtained in Example 24 and morpholine in the same manner as in Example 27 to give Compound 28.

Yield: 89% (white solid); $^1$H NMR (δ ppm, CDCl$_3$): 7.94 (s, 1H), 7.61 (s, 1H), 7.22 (d, J=3.3 Hz, 1H), 6.99–6.95 (m, 2H), 6.86 (d, J=7.9 Hz, 1H), 6.57 (dd, J=3.3 Hz, 1.7 Hz, 1H), 6.43 (t, J=5.6 Hz, 1H), 4.76 (d, J=5.9 Hz, 2H), 3.89 (s, 6H), 3.82 (s, 2H), 3.74 (t, J=4.6 Hz, 4H), 2.60 (t, J=4.6 Hz, 4H); Mass (m/z): 423 (M$^+$); IR (KBr, cm$^1$): 3327, 2821, 1628, 1587; Melting point: 148.0–149.0° C.

EXAMPLE 29

7-Chloro-5-(3,4-dimethoxybenzylamino)-2-(2-furyl)[1,2,4]triazolo[1,5-c]pyrimidine (Compound 29)

In an argon atmosphere, 50.0 g (350 mmol) of diphosphorus pentaoxide was suspended in 70 ml of xylene, and 75 ml (350 mmol) of hexamethyldisiloxane was added thereto, followed by heating at 90° C. for about 1.5 hours. After the contents were almost dissolved, 20.0 g (70 mmol) of Compound s obtained in Reference Example 19 was added thereto, followed by heating at 160° C. for another 2 hours. After completion of the reaction, chloroform and water were added to the reaction solution, the water layer was alkalified by adding aqueous ammonia under ice-cooling, and the mixture was extracted with chloroform. The organic layer was dried over magnesium sulfate, the solvent was evaporated, and the residue was purified by silica gel column chromatography [hexane-ethyl acetate (1:1)] to give 12.1 g of a main product.

In 120 ml of THF, 12.1 g of the obtained main product was dissolved, and 10.5 ml (70 mmol) of DBU was added thereto under ice-cooling, followed by stirring at room temperature for about 1 hour. During this period, solid materials were precipitated from the reaction solution. Next, 21.0 ml (140 mmol) of veratrylamine was added thereto, followed by stirring at 50° C. for about 3 hours. After completion of the reaction, the reaction solution was diluted with chloroform and washed with water, and the organic layer was dried over magnesium sulfate. The solvent was evaporated, and the residue was washed with ethyl acetate to give 14.0 g (yield: 80%) of Compound 29 as a white solid.

$^1$H NMR (δ ppm, CDCl$_3$): 7.60 (dd, J=1.7 Hz, 0.7 Hz, 1H), 7.20 (dd, J=3.3 Hz, 0.7 Hz, 1H), 6.94–6.98 (m, 3H), 6.85 (d, J=7.9 Hz, 1H), 6.61 (brs, 1H), 6.58 (dd, J=3.3 Hz, 1.7 Hz, 1H), 4.74 (d, J=5.6 Hz, 2H), 3.90 (s, 3H), 3.89 (s, 3H); Mass (m/z): 387, 385 (M$^+$); IR (KBr, cm$^{-1}$): 2359, 1630, 1616, 1585, 1515; Melting point: 193° C.

EXAMPLE 30

5-Amino-2-(2-furyl)-7-phenoxy[1,2,4]triazolo[1,5-c]pyrimidine (Compound 30)

In 5 ml of trifluoroacetic acid, 500 mg (1.12 mmol) of Compound 1 obtained in Example 1 was dissolved, and 400 μl (4.5 mmol) of anisole and 490 μl (4.5 mmol) of trifluoromethanesulfonic acid were added thereto, followed by stirring at 0° C. to room temperature for 4 hours. The reaction mixture was extracted by adding chloroform and water, and the organic phase was dried over anhydrous magnesium sulfate. After evaporation of the solvent under reduced pressure, the residue was purified by silica gel column chromatography (chloroform) and recrystallized from ethanol to give 218 mg (yield: 66%) of Compound 30 as a white solid.

$^1$H NMR (δ ppm, DMSO-d$_6$): 8.17 (brs, 2H), 7.92 (d, J=0.7 Hz, 1H), 7.45 (t, J=7.6 Hz, 2H), 7.26–7.15 (m, 4H), 6.72–6.70 (m, 1H), 6.23 (s, 1H); Mass (m/z): 293 (M$^+$); IR (KBr, cm$^{-1}$): 1662, 1619, 1568, 1405, 1245; Melting point: 167.5–171.5° C.; Elemental analysis: C$_{15}$H$_{11}$N$_5$O$_2$; Found (%): C, 61.41, H, 3.81, N, 23.99; Calcd.(%): C, 61.43, H, 3.78, N, 23.88.

Examples 31 to 36 were carried out below using Compounds 2 to 7 obtained in Examples 2 to 7 in the same manner as in Example 30 to give Compounds 31 to 36.

EXAMPLE 31

5-Amino-7-(3,4-dimethoxyphenoxy)-2-(2-furyl)[1,2,4]triazolo[1,5-c]pyrimidine (Compound 31)

Yield: 81% (yellow solid); $^1$H NMR (δ ppm, DMSO-d$_6$): 8.14 (brs, 2H), 7.91 (d, J=1.0 Hz, 1H), 7.13 (d, J=3.7 Hz, 1H), 6.98 (d, J=8.4 Hz, 1H), 6.86 (d, J=2.5 Hz, 1H), 6.73–6.68 (m, 1H), 6.04 (s, 1H), 3.77 (s, 3H), 3.74 (s, 3H); Mass (m/z): 353 (M$^+$); IR (KBr, cm$^{-1}$): 1673, 1656, 1614, 1511, 1402; Melting point: 197.2–198.5° C. Elemental analysis: C$_{17}$H$_{15}$N$_5$O$_4$ 0.2H$_2$O; Found (%): C, 57.23, H, 4.31, N, 19.44; Calcd.(%): C, 57.20, H, 4.35, N, 19.62.

EXAMPLE 32

5-Anino-7-(2,6-dimethoxyphenoxy)-2-(2-furyl)[1,2,4]triazolo[1,5-c]pyrimidine (Compound 32)

Yield: 73% (white solid); $^1$H NMR (δ ppm, CDCl$_3$): 7.59 (d, J=1.0 Hz, 1H), 7.25–7.16 (m, 3H), 6.66 (d, J=8.4 Hz, 2H), 6.56 (dd, J=3.5 Hz, 2.0 Hz, 1H), 6.19 (s, 1H), 5.86 (brs, 2H), 3.79 (s, 6H); Mass (m/z): 353 (M$^+$); IR (KBr, cm$^{-1}$): 1604, 1481, 1405, 1222; Melting point: 268.5–269.5° C.; Elemental analysis: C$_{17}$H$_{15}$N$_5$O$_4$; Found (%): C, 57.50, H, 4.23, N, 19.20; Calcd.(%): C, 57.79, H, 4.28, N, 19.82.

EXAMPLE 33

5-Amino-7-(3,5-dimethoxyphenoxy)-2-(2-furyl)[1,2,4]triazolo[1,5-c]pyrimidine (Compound 33)

Yield: 92% (pale dark brown solid); $^1$H NMR (δ ppm, DMSO-d$_6$): 8.19 (brs, 2H), 7.91 (dd, J=2.0 Hz, 0.7 Hz, 1H), 7.15 (dd, J=3.6 Hz, 0.7 Hz, 1H), 6.70 (dd, J=3.6 Hz, 2.0 Hz, 1H), 6.37 (s, 3H), 6.24 (s, 1H), 3.73 (s, 6H); Mass (m/z): 353 (M$^+$); IR (KBr, cm$^{-1}$): 3070, 1684, 1608, 1560, 1406; Melting point: 178.0–179.0° C.; Elemental analysis: C$_{17}$H$_{15}$N$_5$O$_4$; Found (%): C, 57.99, H, 4.40, N, 19.56; Calcd.(%): C, 57.79, H, 4.28, N, 19.82.

EXAMPLE 34

5-Amino-2-(2-furyl)-7-(4-nitrophenoxy)[1,2,4]triazolo[1,5-c]pyrimidine (Compound 34)

Yield: 46% (white solid); $^1$H NMR (δ ppm, CDCl$_3$): 8.30 (dd, J=6.8 Hz, 2.0 Hz, 2H), 7.64 (t, J=1.0 Hz, 1H), 7.29–7.20 (m, 3H), 6.60 (dd, J=3.5 Hz, 1.5 Hz, 1H), 6.55 (s, 1H), 5.92 (brs, 2H); Mass (m/z): 338 (M$^+$); IR (KBr, cm$^{-1}$): 1670, 1616, 1604, 1587, 1490, 1348; Melting point: 274.3–274.7° C.; Elemental analysis: C$_{15}$H$_{16}$N$_6$O$_4$ 0.2H$_2$O; Found (%): C, 52.82, H, 2.98, N, 24.40; Calcd.(%): C, 52.70, H, 3.07, N, 24.58.

EXAMPLE 35

5-Amino-7-(4-chlorophenoxy)-2-(2-furyl)[1,2,4]triazolo[1,5-c]pyrimidine (Compound 35)

Yield: 64% (white solid); $^1$H NMR (δ ppm, DMSO-d$_6$): 8.16 (brs, 2H), 7.92–7.91 (m, 1H), 7.48 (dd, J=6.6 Hz, 2.0 Hz, 2H), 7.23 (dd, J=6.6 Hz, 2.0 Hz, 2H), 7.16–7.15 (m, 1H), 6.71 (dd, J=3.6 Hz, 2.0 Hz, 1H), 6.32 (s, 1H); Mass (m/z): 329, 327 (M$^+$); IR (KBr, cm$^{-1}$): 3320, 3260, 3136, 1662, 1605, 1228; Melting point: 250.0–251.0° C.; Elemental analysis: C$_{15}$H$_{10}$ClN$_5$O$_2$; Found (%): C, 55.03, H, 3.07, N, 21.13; Calcd.(%): C, 54.97, H, 3.08, N, 21.37.

EXAMPLE 36

5-Amino-2-(2-furyl)-7-(4-phenylphenoxy)[1,2,4]triazolo[1,5-c]pyrimidine (Compound 36)

Yield: 61% (white solid); $^1$H NMR (δ ppm, DMSO-d$_6$): 8.19 (brs, 2H), 7.91 (d, J=1.0 Hz, 1H), 7.74–7.66 (m, 5H), 7.48 (t, J=6.9 Hz, 2H), 7.37 (t, J=7.4 Hz, 1H), 7.27 (dd, J=6.9 Hz, 2.0 Hz, 2H), 7.16 (d, J=3.5 Hz, 1H), 6.70 (dd, J=3.5 Hz, 1.5 Hz, 1H), 6.32 (s, 1H); Mass (m/z): 369 (M$^+$); IR (KBr, cm$^{-1}$): 1668, 1606, 1560, 1486, 1226; Melting point: 264.8–267.2° C.; Elemental analysis: C$_{21}$H$_{15}$N$_5$O$_2$; Found (%): C, 68.04, H, 4.02, N, 18.86; Calcd.(%): C, 68.28, H, 4.09, N, 18.96.

EXAMPLE 37

5-Amino-2-(2-furyl)-7-phenylthio[1,2,4]triazolo[1,5-c]pyrimidine (Compound 37)

Compound 37 was obtained using Compound 10 obtained in Example 10 in the same manner as in Example 30.

Yield: 61% (white solid); $^1$H NMR (δ ppm, CDCl$_3$): 7.66–7.46 (m, 6H), 7.15–7.14 (m, 1H), 6.57–6.54 (m, 1H), 6.33 (s, 1H), 6.14 (brs, 2H); Mass (m/z): 309 (M$^+$); IR (KBr, cm$^{-1}$): 1668, 1652, 1596, 1548; Melting point: 241.5–242.5° C.; Elemental analysis: C$_{15}$H$_{11}$N$_5$OS 0.1H$_2$O; Found (%): C, 58.10, H, 3.53, N, 22.58; Calcd.(%): C, 58.09, H, 3.31, N, 22.58.

Examples 38 to 42 were carried out below using Compounds 16 to 20 obtained in Examples 16 to 20 to give Compounds 38 to 42.

EXAMPLE 38

5-Amino-2-(2-furyl)-7-piperidino[1,2,4]triazolo[1,5-c]pyrimidine (Compound 38)

Yield: 49% (brown solid); $^1$H NMR (δ ppm, DMSO-d$_6$): 7.85 (d, J=1.0 Hz, 1H), 7.53 (brs, 2H), 7.05 (d, J=3.5 Hz, 1H), 6.66 (dd, J=3.5 Hz, 2.0 Hz, 1H), 5.98 (s, 1H), 3.55–3.50 (m, 4H), 1.65–1.48 (m, 6H); Mass (m/z): 284 (M$^+$); IR (KBr, cm$^{-1}$): 1577, 1469, 1457, 1378; Melting point: 224.5–225.5° C.

EXAMPLE 39

5-Amino-2-(2-furyl)-7-morpholino[1,2,4]triazolo[1.5-c]pyrimidine (Compound 39)

Yield: 44% (brown solid); $^1$H NMR (δ ppm, DMSO-d$_6$): 7.88 (t, J=1.0 Hz, 1H), 7.66 (brs, 2H), 7.07 (dd, J=3.6 Hz, 1.0 Hz, 1H), 6.67 (dd, J=3.3 Hz, 1.7 Hz, 1H), 6.04 (s, 1H), 3.69 (t, J=4.3 Hz, 4H), 3,47 (t, J=4.3 Hz, 4H); Mass (m/z): 286 (M$^+$); IR (KBr, cm$^{-1}$): 1662, 1619, 1596, 1438; Melting point: 99.5–100.0° C.

EXAMPLE 40

5-Amino-2-(2-furyl)-7-(4-methylpiperazinyl)[1,2,4]triazolo[1,5-c]pyrimidine (Compound 40)

Yield: 53% (white solid); $^1$H NMR (δ ppm, DMSO-d$_6$): 7.58 (d, J=1.0 Hz, 1H), 7.15 (d, J=3.0 Hz, 1H), 6.55 (dd, J=3.5 Hz, 2.0 Hz, 1H), 6.03 (s, 1H), 5.61 (brs, 2H), 3.57 (t, J=5.0 Hz, 4H), 2.50 (t, J=5.0 Hz, 4H), 2.35 (s, 3H); Mass (m/z): 299 (M$^+$); IR (KBr, cm$^{-1}$): 1664, 1600, 1442, 1226; Melting point: 239.5–240.0° C.; Elemental analysis: C$_{14}$H$_{17}$N$_7$O; Found (%): C, 56.17, H, 5.71, N, 32.43; Calcd.(%): C, 56.18, H, 5.72, N, 32.75.

EXAMPLE 41

5-Amino-2-(2-furyl)-7-(4-phenylpiperazinyl)[1,2,4]triazolo[1,5-c]pyrimidine (Compound 41)

Yield: 62% (pale yellow solid); $^1$H NMR (δ ppm, DMSO-d$_6$): 7.87 (t, J=1.0 Hz, 1H), 7.65 (brs, 2H), 7.24 (t, J=6.9 Hz, 2H), 7.07 (d, J=4.0 Hz, 1H), 6.99 (d, J=7.9 Hz, 2H), 6.81 (t, J=6.9 Hz, 1H), 6.67 (dd, J=3.5 Hz, 1.5 Hz, 1H), 6.09 (s, 1H), 3.68 (t, J=4.5 Hz, 4H), 3.23 (t, J=4.5 Hz, 4H); Mass (m/z): 361 (M$^+$); IR (KBr, cm$^{-1}$): 1670, 1652, 1610, 1606, 1444, 1232; Melting point: 261.5–262.0° C.; Elemental analysis: C$_{19}$H$_{19}$N$_7$O; Found (%): C, 63.24, H, 5.37, N, 26.83; Calcd.(%): C, 63.14, H, 5.30, N, 27.13.

EXAMPLE 42

5-Amino-7-(4-benzylpiperazinyl)2-(2-furyl)[1,2,4]triazolo[1,5-c]pyrimidine (Compound 42)

Yield: 40% (white powder); $^1$H NMR (δ ppm, CDCl$_3$): 7.58 (dd, J=1.7 Hz, 0.7 Hz, 1H), 7.26–7.35 (m, 5H), 7.15 (dd, J=3.3. Hz, 0.7 Hz, 1H), 6.55 (dd, J=3.3 Hz, 1.7 Hz, 1H), 6.01 (s, 1H), 5.62 (brs, 2H), 3.56 (s, 2H), 3.55 (t, J=5.0 Hz, 4H), 2.53 (t, J=5.0 Hz, 4H); Mass (m/z): 375 (M$^+$); IR (KBr, cm$^{-1}$): 1653, 1608, 1558, 1442; Melting point: 210–220° C. (decomposed); Elemental analysis: C$_{20}$H$_{21}$N$_7$O 0.6H$_2$O; Found (%): C, 62.10, H, 5.60, N, 25.33; Calcd.(%): C, 62.19, H, 5.79, N, 25.38.

EXAMPLE 43

5-Amino-2-(2-furyl)-7-piperazinyl[1,2,4]triazolo[1,5-c]-pyrimidine hydrochloride (Compound 43)

In 50 ml of chloroform, 6.0 g (15.98 mmol) of Compound 42 obtained in Example 42 was dissolved, and 5.1 g (48.0 mmol) of vinyl chlorocarbonate was added thereto, followed by stirring at 0° C. to room temperature for one hour. After evaporation of the solvent under reduced pressure, 10 ml of methanol and 50 ml of a saturated methanolic hydrogen chloride were added to the residue, followed by refluxing at 80° C. for 2 hours. After evaporation of the solvent under reduced pressure, the residue was recrystallized from ethanol to give 3.58 g (yield: 58%) of Compound 43 as a white solid.

$^1$H NMR (δ ppm, DMSO-d$_6$): 9.74 (brs, 1H), 8.04 (dd, J=1.7 Hz, 0.7 Hz, 1H), 7.46 (dd, J=3.3 Hz, 0.7 Hz, 1H), 6.79 (dd, J=3.3 Hz, 1.7 Hz, 1H), 6,21 (s, 1H), 6.21 (brs, 2H), 3.56 (s, 2H), 3.89 (t, J=5.0 Hz, 4H), 3.17 (t, J=5.0 Hz, 4H); Mass (m/z): 285 (M$^+$); IR (KBr, cm$^{-1}$): 3122, 3093, 2954, 1684, 1646, 1637, 1458; Melting point: 260–280° C. (decomposed); Elemental analysis: C$_{13}$H$_{15}$N$_7$O$_2$ 1.5HCl 2.5H$_2$O; Found (%): C, 40.87, H, 5.53, N, 25.31; Calcd.(%): C, 40.55, H, 5.62, N, 25.46.

EXAMPLE 44

7-(4-Acetylpiperazinyl)-5-amino-2-(2-furyl)[1,2,4]triazolo[1,5-c]pyrimidine (Compound 44)

In 10 ml of pyridine, 400 mg (1.04 mmol) of Compound 43 obtained in Example 43 was dissolved, and 0.13 ml (1.86 mmol) of acetyl chloride was added thereto, followed by stirring at 0° C. to room temperature for 1.5 hours. The reaction mixture was extracted by adding chloroform and water, and the organic phase was dried over anhydrous magnesium sulfate. After evaporation of the solvent under reduced pressure, the residue was purified by silica gel column chromatography [chloroform-methanol (98:2)] and recrystallized from ethanol-isopropyl ether to give 271 mg (yield: 80%) of Compound 44 as white powder.

$^1$H NMR (δ ppm, CDCl$_3$): 7.59 (dd, J=1.65 Hz, 0.7 Hz, 1H), 7.17 (dd, J=3.3 Hz, 0.7 Hz, 1H), 6.56 (dd, J=3.3 Hz, 1.7 Hz, 1H), 6,03 (s, 1H), 5.70 (brs, 2H), 3.74 (t, J=5.0 Hz, 4H), 3.57 (t, J=5.0 Hz, 4H), 2.16 (s, 3H); Mass (m/z): 327 (M$^+$); IR (KBr, cm$^{-1}$): 1648, 1608, 1558, 1436, 1243, 1207; Melting point: 231° C.; Elemental analysis: C$_{15}$H$_{17}$N$_7$O$_2$ 0.6H$_2$O; Found (%): C, 54.82, H, 5.33, N, 29.59; Calcd.(%): C, 55.04, H, 5.23, N, 29.95.

EXAMPLE 45

5-Amino-7-(4-benzoylpiperazinyl)-2-(2-furyl)[1,2,4]triazolo[1,5-c]pyrimidine (Compound 45)

Compound 45 was obtained using Compound 43 obtained in Example 43 and benzoyl chloride in the same manner as in Example 44.

Yield: 80% (light brown powder); $^1$H NMR ($\delta$ ppm, CDCl$_3$): 7.59 (dd, J=1.7 Hz, 0.7 Hz, 1H), 7.41–7.50 (m, 5H), 7.17 (dd, J=3.3 Hz, 0.7 Hz, 1H), 6.56 (dd, J=3.3 Hz, 1.7 Hz, 1H), 6.03 (s, 1H), 5.74 (brs, 2H), 3,42–4.00 (m, 8H); Mass (m/z): 389 (M$^+$); IR (KBr, cm$^{-1}$): 3372, 1660, 1608, 1560, 1516, 1417, 1226, 1203; Melting point: 236–240° C.; Elemental analysis: C$_{20}$H$_{19}$N$_7$O$_2$; Found (%): C, 61.35, H, 5.24, N, 24.20; Calcd.(%): C, 61.69, H, 4.92, N, 25.18.

EXAMPLE 46

5-Amino-2-(2-furyl)-7-[4-(2-phenylethyl)piperazinyl][1,2,4]triazolo[1,5-c]pyrimidine (Compound 46)

In 10 ml of DMF, 400 mg (1.04 mmol) of Compound 43 obtained in Example 43 was dissolved, and 0.51 ml (3.6 mmol) of 2-phenylethyl bromide and 1 ml of triethylamine were added thereto, followed by stirring at 60° C. for 2 hours. The reaction mixture was extracted by adding chloroform and water, and the organic phase was dried over anhydrous magnesium sulfate. After evaporation of the solvent under reduced pressure, the residue was purified by silica gel column chromatography [chloroform-methanol (97:3)] and recrystallized from ethyl. acetate-hexane to give 369 mg (yield: 95%) of Compound 46 as light gray powder.

$^1$H NMR ($\delta$ ppm, CDCl$_3$): 7.59 (dd, J=1.7 Hz, 0.7 Hz, 1H), 7.21–7.33 (m, 5H), 7.16 (dd, J=3.3 Hz, 0.7 Hz, 1H), 6.56 (dd, J=3.3 Hz, 1.7 Hz, 1H), 6.04 (s, 1H), 5.63 (brs, 2H), 3.59 (t, J=5.0 Hz, 4H), 2.82–2.88 (m, 2H), 2.60–2.69 (m, 6H); Mass (m/z): 389 (M$^+$); IR (KBr, cm$^{-1}$): 3106, 1670, 1654, 1606, 1560, 1444, 1417, 1226; Melting point: 225–226° C.; Elemental analysis: C$_{21}$H$_{23}$N$_7$O; Found (%): C, 64.76, H, 5.95, N, 25.18; Calcd.(%): C, 64.47, H, 5.94, N, 25.13.

Examples 47 to 50 were carried out below using Compounds 12 to 15 obtained in Examples 12 to 15 in the same manner as in Example 30 to give Compounds 47 to 50.

EXAMPLE 47

5-Amino-7-phenoxy-2-phenyl[1,2,4]triazolo[1,5-c]pyrimidine (Compound 47)

Yield: 54% (white solid); $^1$H NMR ($\delta$ ppm, CDCl$_3$): 8.25–8.21 (m, 2H), 7.49–7.40 (m, 4H), 7.30–7.24 (m, 1H), 7.18 (dd, J=8.9 Hz, 1.5 Hz, 2H), 6.25 (s, 1H), 5.97 (brs, 2H); Mass (m/z): 303 (M$^+$); IR (KBr, cm$^{-1}$): 1673, 1608, 1589, 1394, 1213; Melting point: 249.5–250.0° C.; Elemental analysis: C$_{17}$H$_{13}$N$_5$O 0.1H$_2$O; Found (%): C, 66.90, H, 4.30, N, 22.61; Calcd.(%): C, 66.92, H, 4.36, N, 22.95.

EXAMPLE 48

5-Amino-2-(3-anisyl)-7-phenoxy[1,2,4]triazolo[1,5-c]pyrimidine (Compound 48)

Yield: 55% (white solid); $^1$H NMR ($\delta$ ppm, CDCl$_3$): 7.83 (d, J=7.9 Hz, 1H), 7.77 (t, J=1.5 Hz, 1H), 7.47–7.25 (m, 3H), 7.18 (dd, J=8.9 Hz, 1.5 Hz, 2H), 7.05–7.00 (m, 1H), 6.24 (s, 1H), 6.10 (brs, 2H), 3.90 (s, 3H); Mass (m/z): 334 (M$^+$); IR (KBr, cm$^{-1}$): 1666, 1606, 1592, 1473, 1216; Melting point: 178.0–178.5° C.; Elemental analysis: C$_{18}$H$_{16}$N$_5$O$_2$; Found (%): C, 64.75, H, 4.49, N, 20.92; Calcd.(%): C, 64.66, H, 4.82, N, 20.95.

EXAMPLE 49

5-Amino-7-phenoxy-2-(3-pyridyl)[1,2,4]triazolo[1,5-c]pyrimidine (Compound 49)

Yield: 30% (white solid); $^1$H NMR ($\delta$ ppm, DMSO-d$_6$): 9.33 (t, J=1.0 Hz, 1H), 8.72 (dd, J=4.9 Hz, 1.5 Hz, 1H), 8.46 (dd, J=7.9 Hz, 1.5 Hz, 1H), 8.20 (brs, 2H), 7.59 (dd, J=7.9 Hz, 4.9 Hz, 1H), 7.45 (t, J=7.9 Hz, 2H), 7.24 (t, J=7.2 Hz, 1H), 7.20 (d, J=7.9 Hz, 2H), 6.30 (s, 1H); Mass (m/z): 304 (M$^+$); IR (KBr, cm$^{-1}$): 1679, 1618, 1571, 1390, 1216; Melting point: 287.5–288.0° C.; Elemental analysis: C$_{16}$H$_{12}$N$_6$O; Found (%): C, 63.11, H, 3.89, N, 27.49; Calcd.(%): C, 63.15, H, 3.97, N, 27.62.

EXAMPLE 50

5-Amino-7-phenoxy-2-(2-thienyl)[1,2,4]triazolo[1,5-c]pyrimidine (Compound 50)

Yield: 55% (white solid); $^1$H NMR ($\delta$ ppm, DMSO-d$_6$): 8.11 (brs, 2H), 7.80–7.73 (m, 2H), 7.47–7.41 (m, 2H), 7.26–7.17 (m, 4H), 6.22 (s, 1H); Mass (m/z): 309 (M$^+$); IR (KBr, cm$^{-1}$): 1668, 1606, 1569, 1417, 1390, 1214; Melting point: 138.5–139.0° C.; Elemental analysis: C$_{15}$H$_{11}$N$_5$OS 0.1H$_2$O; Found (%): C, 57.99, H, 3.54, N, 22.38; Calcd.(%): C, 57.90, H, 3.63, N, 22.51.

Examples 51 to 59 were carried out using Compounds obtained in Examples 8, 11, 21, 9, 22 and 25 to 28 in the same manner as in Example 30 to give Compounds 51 to 59.

EXAMPLE 51

5-Amino-2-(2-furyl)-7-phenoxy-8-phenyl[1,2,4]triazolo[1,5-c]pyrimidine (Compound 51)

Yield: 53% (white solid); $^1$H NMR ($\delta$ ppm, CDCl$_3$): 8.14 (brs, 2H), 7.91 (d, J=1.0 Hz, 1H), 7.78–7.74 (m, 2H), 7.47–7.13 (m, 9H), 6.69 (dd, J=3.5 Hz, 1.5 Hz, 1H); Mass (m/z): 369 (M$^+$); IR (KBr, cm$^{-1}$): 1656, 1650, 1587, 1490, 1216; Melting point: 241.5–242.5° C.; Elemental analysis: C$_{21}$H$_{15}$N$_5$O$_2$; Found (%): C, 68.28, H, 4.06, N, 18.75; Calcd.(%): C, 68.28, H, 4.09, N, 18.96.

EXAMPLE 52

5-Amino-2-(2-furyl)-8-phenyl-7-phenylthio[1,2,4]triazolo[1,5-c]pyrimidine (Compound 52)

Yield: 87% (white solid); $^1$H NMR ($\delta$ ppm, CDCl$_3$): 7.90 (brs, 2H), 7.89 (s, 1H), 7.55–7.32 (m, 1OH), 7.11 (d, J=3.5 Hz, 1H), 6.67 (dd, J=3.5 Hz, 2.0 Hz, 1H); Mass (m/z): 385 (M$^+$); IR (KBr, cm$^{-1}$): 1664, 1648, 1583, 1531; Melting point: 176.4–178.3° C.; Elemental analysis: C$_{21}$H$_{15}$N$_5$OS 0.3H$_2$O; Found (%): C, 64.67, H, 3.92, N, 17.52; Calcd.(%): C, 64.53, H, 4.02, N, 17.91.

EXAMPLE 53

5-Amino-2-(2-furyl)-7-morpholino-8-phenyl[1,2,4]triazolo[1,5-c]pyrimidine (Compound 53)

Yield: 66% (white solid); $^1$H NMR ($\delta$ ppm, DMSO-d$_6$): 7.86 (d, J=1.0 Hz, 1H), 7.81 (brs, 2H), 7.65 (d, J=6.9 Hz, 2H), 7.44 (t, J=7.4 Hz, 2H), 7.28 (d, J=7.4 Hz, 1H), 7.04 (d, J=3.0 Hz, 1H), 6.65 (dd, J=3.0 Hz, 1.5 Hz, 1H), 3.50 (t, J=4.0 Hz, 4H), 3.12 (t, J=4.5 Hz, 4H); Mass (m/z): 362 (M$^+$); IR (KBr, cm$^-$): 1650, 1643, 1592, 1544; Melting point: >300° C.; Elemental analysis: $C_{19}H_{18}N_6O_2$ 0.1$H_2O$; Found (%): C, 62.77, H, 5.05, N, 22.67; Calcd.(%): C, 62.66, H, 5.04, N, 23.08.

EXAMPLE 54

5-Amino-2-(2-furyl)-8-methyl-7-phenoxy[1,2,4]triazolo[1,5-c]pyrimidine (Compound 54)

Yield: 41% (yellow solid); $^1$H NMR (δ ppm, CDCl$_3$): 7.62 (t, J=1.0 Hz, 1H), 7.39 (t, J=7.9 Hz, 2H), 7.26–7.15 (m, 2H), 7.09 (dd, J=8.6 Hz, 1.3 Hz, 2H), 6.59 (dd, J=2.0 Hz, 1.0 Hz, 1H), 5.68 (brs, 2H), 2.45 (s, 3H); Mass (m/z): 307 (M$^+$); IR (KBr, cm$^{-1}$): 1673, 1645, 1616, 1567, 1490; Melting point: 219.5–220.0° C.; Elemental analysis: $C_{16}H_{13}N_5O_2$; Found (%): C, 62.73, H, 4.31, N, 22.53; Calcd.(%): C, 62.53, H, 4.26, N, 22.79.

EXAMPLE 55

5-Amino-8-ethoxycarbonyl-2-(2-furyl)[1,2,4]triazolo[1,5-c]pyrimidine (Compound 55)

Yield: 81% (brown solid); $^1$H NMR (δ ppm, CDCl$_3$): 8.66 (s, 1H), 7.64 (t, J=1.0 Hz, 1H), 7.39 (dd, J=3.6 Hz, 0.7 Hz, 1H), 6.62–6.56 (m, 3H), 4.48 (q, J=7.3 Hz, 2H), 1.45 (t, J=7.3 Hz, 3H); Mass (m/z): 273 (M$^+$); IR (KBr, cm$^{-1}$): 1716, 1695, 1646, 1558, 1421, 1270; Melting point: 230.0–230.5° C.; Elemental analysis: $C_{12}H_{11}N_5O_3$ 0.5$H_2O$; Found (%): C, 52.73, H, 4.96, N, 22.54; Calcd.(%): C, 52.68, H, 5.14, N, 22.58.

EXAMPLE 56

5-Amino-2-(2-furyl)-8-(4-methylpiperazinylmethyl)[1,2,4]triazolo[1,5-c]pyrimidine (Compound 56)

Yield: 83% (white solid); $^1$H NMR (δ ppm, DMSO-d$_6$): 7.93 (t, J=1.0 Hz, 1H), 7.86 (brs, 2H), 7.76 (s, 1H), 7.20 (d, J=3.3 Hz, 1H), 6.73–6.71 (m, 1H), 3.64 (s, 2H), 2.50–2.22 (m, 8H), 2.13 (s, 3H); Mass (m/z): 299 (M$^+$); IR (KBr, cm$^{-1}$): 1672, 1652, 1577, 1421, 1281; Melting point: 265.5–265.9° C.; Elemental analysis: $C_{15}H_{19}N_7O$ 0.3$H_2O$; Found (%): C, 56.68, H, 6.42, N, 30.67; Calcd.(%): C, 56.52, H, 6.20, N, 30.76.

EXAMPLE 57

5-Amino-2-(2-furyl)-8-(4-phenylpiperazinylmethyl)[1,2,4]triazolo[1,5-c]pyrimidine (Compound 57)

Yield: 63% (pale dark brown solid); $^1$H NMR (δ ppm, CDCl$_3$): 7.92 (s, 1H), 7.64 (dd, J=1.7 Hz, 0.7 Hz, 1H), 7.29–7.23 (m, 3H), 6.94–6.82 (m, 3H), 6.59 (dd, J=3.3 Hz, 1.7 Hz, 1H), 5.92 (s, 2H), 3.91 (s, 2H), 3.23 (t, J=5.0 Hz, 4H), 2.76 (t, J=5.0 Hz, 4H); Mass (m/z): 375 (M$^+$); IR (KBr, cm$^{-1}$): 3440, 2816, 1660, 1589, 1235; Melting point: 225.0–226.0° C.; Elemental analysis: $C_{20}H_{21}N_7O$ 0.2EtOH; Found (%): C, 63.89, H, 5.74, N, 25.32; Calcd.(%): C, 63.70, H, 5.82, N, 25.49.

EXAMPLE 58

5-Amino-8-(4-fluoroanilinomethyl)-2-(2-furyl)[1,2,4]triazolo[1,5-c]pyrimidine (Compound 58)

Yield: 64% (pale dark brown solid); $^1$H NMR (δ ppm, CDCl$_3$): 7.84 (s, 1H), 7.65 (d, J=1.7 Hz, 1H), 7.26–7.23 (m, 1H), 6.90–6.84 (m, 2H), 6.66–6.60 (m, 3H), 5.83 (brs, 2H), 4.56 (s, 2H); Mass (m/z): 324 (M$^+$); IR (KBr, cm$^{-1}$): 3230, 1653, 1508, 1209; Melting point: 235.0–236.0° C.; Elemental analysis: $C_{16}H_{13}FN_6O$; Found (%): C, 59.18, H, 4.09, N, 25.61; Calcd.(%): C, 59.26, H, 4.04, N, 25.91.

EXAMPLE 59

5-Amino-2-(2-furyl)-8-morpholinomethyl[1,2,4]triazolo[1,5-c]pyrimidine (Compound 59)

Yield: 51% (pale dark brown solid); $^1$H NMR (δ ppm, CDCl$_3$): 7.89 (s, 1H), 7.64 (t, J=0.7 Hz, 1H), 7.25 (s, 1H), 6.59 (dd, J=3.3 Hz, 1.7 Hz, 1H), 5.86 (s, 2H), 3.83 (s, 2H), 3.74 (t, J=4.6 Hz, 4H), 2.60 (t, J=4.6 Hz, 4H); Mass (m/z): 300 (M$^+$); IR (KBr, cm$^{-1}$): 3336, 3109, 2875, 2800, 1674, 1578; Melting point: >300° C.

EXAMPLE 60

5-Amino-7-(4-ethylpiperazinyl)-2-(2-furyl)[1,2,4]triazolo[1,5-c]pyrimidine (Compound 60)

Compound 60 was obtained using Compound 43 obtained in Example 43 in the same manner as in Example 46.

Yield: 54% (white powder); $^1$H NMR (δ ppm, CDCl$_3$): 7.58 (dd, J=1.7 Hz, 0.7 Hz, 1H), 7.15 (dd, J=3.3 Hz, 0.7 Hz, 1H), 6.56 (dd, J=3.3 Hz, 1.7 Hz, 1H), 6.03 (s, 1H), 5.62 (brs, 2H), 3.58 (t, J=5.0 Hz, 4H), 2.54 (t, J=5.0 Hz, 4H), 2.44 (q, J=7.3 Hz, 2H), 1.13 (t, J=7.3 Hz, 3H); Mass (m/z): 313 (M$^+$); IR (KBr, cm$^{-1}$): 3175, 1662, 1601, 1560, 1442, 1334, 1233, 1224, 1216; Melting point: 213–214° C.; Elemental analysis: $C_{15}H_{19}N_7O$; Found (%): C, 57.49, H, 6.11, N, 31.29; Calcd.(%): C, 57.60, H, 6.33, N, 31.37.

EXAMPLE 61

5-Amino-7-chloro-2-(2-furyl)[1,2,4]triazolo[1,5-c]pyrimidine (Compound 61)

In 100 ml of trifluoroacetic acid, 16.8 g (43.55 mmol) of Compound 29 obtained in Example 29 was dissolved, and 19.23 ml (218 mmol) of trifluoromethanesulfonic acid and 20 ml (175 mmol) of anisole were added thereto, followed by stirring at room temperature for about 2 hours. After completion of the reaction, trifluoroacetic acid was evaporated under reduced pressure, and chloroform was added to the residue, followed by washing with a saturated aqueous sodium bicarbonate solution. The organic layer was dried over magnesiumسulfate, the solvent was evaporated, and the residue was washed with diisopropyl ether to give 7.3 g (yield: 71%) of Compound 61 as a white solid.

$^1$H NMR (δ ppm, CDCl$_3$): 7.64 (dd, J=1.7 Hz, 0.7 Hz, 1H), 7.25 (dd, J=3.3 Hz, 0.7 Hz, 1H), 7.04 (s, 1H), 6.60 (dd, J=3.3 Hz, 1.7 Hz, 1H), 6.30 (brs, 2H); Mass (m/z): 235, 237 (M$^+$); IR (KBr, cm$^{-1}$): 3104, 3070, 1666, 1592, 1552; Melting point: >270° C.;

EXAMPLE 62

5-Amino-2-(2-furyl)-7-[4-(2-hydroxyethyl)piperazinyl][1,2,4]triazolo[1,5-c]pyrimidine (Compound 62)

In 60 ml of DMSO, 3.0 g (12.7 mmol) of Compound 61 obtained in Example 61 was dissolved, and 5 ml (38.2 mmol) of 1-(2-hydroxyethyl)piperazine was added thereto, followed by stirring at 140° C. for about 4 hours. After completion of the reaction, the reaction mixture was extracted by adding chloroform and water, and the organic layer was dried over magnesium sulfate. After evaporation of the solvent, the residue was purified by silica gel column chromatography [chloroform-methanol (97:3–85:15), gradation] and then recrystallized from ethanol to give 1.48 g (yield: 35%) of Compound 62 as a white solid.

$^1$H NMR (δ ppm, DMSO-d$_6$): 7.86 (dd, J=1.7 Hz, 0.7 Hz, 1H), 7.60 (brs, 2H), 7.06 (dd, J=3.3 Hz, 0.7 Hz, 1H), 6.67 (dd, J=3.3 Hz, 1.7 Hz, 1H), 6.00 (s, 1H), 4.44 (t, J=5.3 Hz, 1H), 3,44–3.57 (m, 6H), 2.40–2.47 (m, 6H); Mass (m/z): 329 (M$^+$); IR (KBr, cm$^1$): 3401, 1645, 1608, 1560, 1436, 1245; Melting point: 213° C.; Elemental analysis: C$_{15}$H$_{19}$N$_7$O$_2$; Found (%): C, 54.70, H, 5.81, N, 29.77; Calcd.(%): C, 54.70, H, 6.00, N, 29.49.

Examples 63 to 107 were carried out below using Compound 61 obtained in Example 61 and various piperazine derivatives in the same manner as in Example 62 to give Compounds 63 to 107.

EXAMPLE 63

5-Amino-2-(2-furyl)-7-[4-(3-phenylpropyl)piperazinyl][1,2,4]triazolor[1,5-c]pyrimidine (Compound 63)

Yield: 66% (light brown powder); $^1$H NMR (δ ppm, CDCl$_3$): 7.58 (dd, J=1.7 Hz, 0.7 Hz, 1H), 7.14–7.32 (m, 6H), 6.55 (dd, J=3.3 Hz, 1.7 Hz, 1H), 6.02 (s, 1H), 5.63 (brs, 2H), 3.56 (t, J=5.0 Hz, 4H), 2.67 (t, J=7.8 Hz, 2H), 2.52 (t, J=5.0 Hz, 4H), 2.42 (t, J=7.9 Hz, 2H), 1.87 (m, 2H); Mass (m/z): 403 (M$^+$); IR (KBr, cm$^{-1}$): 3320, 3280, 1668, 1612, 1558, 1438, 1224; Melting point: 172–174° C.; Elemental analysis: C$_{22}$H$_{25}$N$_7$O; Found (%): C, 65.49, H, 6.24, N, 24.30; Calcd.(%): C, 65.39, H, 6.49, N, 24.00.

EXAMPLE 64

5-Amino-2-(2-furyl)-7-[4-(2-pyrimidyl)piperazinyl][1,2,4]triazolo[1,5-c]pyrimidine (Compound 64)

Yield: 39% (light brown powder); $^1$H NMR (δ ppm, CDCl$_3$): 8.34 (d, J=4.6 Hz, 2H), 7.59 (dd, J=1.7 Hz, 0.7 Hz, 1H), 7.17 (dd, J=3.3 Hz, 0.7 Hz, 1H), 6.55 (dd, J=3.3 Hz, 1.7 Hz, 1H), 6.54 (t, J=4.6 Hz, 1H), 6.07 (s, 1H), 5.96 (s, 2H), 5.69 (brs, 2H), 3.96 (t, J=5.0 Hz, 4H), 3.66 (t, J=5.0 Hz, 4H); Mass (m/z): 363 (M$^+$); IR (KBr, cm$^{-1}$): 1660, 1621, 1589, 1556, 1492, 1444, 1288; Melting point: 134–135° C.; Elemental analysis: C$_{17}$H$_{17}$N$_9$O 1.2H$_2$O; Found (%): C, 53.04, H, 5.08, N, 32.74; Calcd.(%): C, 53.24, H, 4.92, N, 32.47.

EXAMPLE 65

5-Amino-2-(2-furyl)-7-[4-(4-methoxyphenyl)piperazinyl][1,2,4]triazolo[1,5-c]pyrimidine (Compound 65)

Yield: 73% (brown powder); $^1$H NMR (δ ppm, CDCl$_3$): 7.59 (dd, J=1.7 Hz, 0.7 Hz, 1H), 7.17 (dd, J=3.3 Hz, 0.7 Hz, 1H), 6.96 (d, J=8.9 Hz, 2H), 6.87 (d, J=8.9 Hz, 2H), 6.56 (dd, J=3.3 Hz, 1.7 Hz, 1H), 6.08 (s, 1H), 5.66 (brs, 2H), 3.78 (s, 3H), 3.72 (t, J=5.0 Hz, 4H), 3.17 (t, J=5.0 Hz, 4H); Mass (m/z): 391 (M$^+$); IR (KBr, cm$^{-1}$): 1653, 1610, 1558, 1512, 1439, 1232, 1026; Melting point: 226–227° C.; Elemental analysis: C$_{20}$H$_{21}$N$_7$O$_2$ 0.1C$_6$H$_5$CH$_3$; Found (%): C, 62.05, H, 5.48, N, 24.47; Calcd.(%): C, 61.92, H, 5.50, N, 24.81.

EXAMPLE 66

5-Amino-2-(2-furyl)-7-(4-piperonylpiperazinyl)[1,2,4]triazolo[1,5-c]pyrimidine (Compound 66)

Yield: 59% (light brown powder); $^1$H NMR (δ ppm, CDCl$_3$): 7.58 (dd, J=1.7 Hz, 0.7 Hz, 1H), 7.15 (dd, J=3.3 Hz, 0.7 Hz, 1H), 6.88 (s, 1H), 6.77 (s, 1H), 6.76 (s, 1H), 6.55 (dd, J=3.3 Hz, 1.7 Hz, 1H), 6.01 (s, 1H), 5.96 (s, 2H), 5.59 (brs, 2H), 3.55 (t, J=5.0 Hz, 4H), 3,46 (s, 2H), 2.52 (t, J=5.0 Hz, 4H); Mass (m/z): 419 (M$^+$); IR (KBr, cm$^{-1}$) 3320, 3150, 2820, 1650, 1603, 1560, 1448; Melting point: 134–137° C.; Elemental analysis: C$_{21}$H$_{21}$N$_7$O$_3$ 0.1C$_6$H$_{12}$; Found (%): C, 60.63, H, 5.23, N, 22.92; Calcd.(%): C, 60.28, H, 5.20, N, 22.43.

EXAMPLE 67

5-Amino-7-[4-(3,4-dimethoxybenzyl)piperazinyl]-2-(2-furyl)[1,2,4]triazolo[1,5-c]pyrimidine (Compound 67)

Yield: 23% (ocher powder); $^1$H NMR (δ ppm, CDCl$_3$): 7.58 (dd, J=1.7 Hz, 0.7 Hz, 1H), 7.15 (dd, J=3.3 Hz, 0.7 Hz, 1H), 6.83–6.92 (m, 3H), 6.55 (dd, J=3.3 Hz, 1.7 Hz, 1H), 6.01 (s, 1H), 5.61 (brs, 2H), 3.90 (s, 3H), 3.88 (s, 3H), 3.55 (t, J=5.0 Hz, 4H), 3,49 (s, 2H), 2.52 (t, J=5.0 Hz, 4H); Mass (m/z): 435 (M$^+$); IR (KBr, cm$^{-1}$): 3420, 3250, 2961, 1650, 1611, 1515, 1444, 1417, 1228; Melting point: 150–152° C.; Elemental analysis: C$_{22}$H$_{25}$N$_7$O$_3$ 0.1H$_2$O; Found (%): C, 60.43, H, 5.81, N, 22.42; Calcd.(%): C, 60.55, H, 5.93, N, 22.02.

EXAMPLE 68

5-Amino-7-[4-(2-chlorobenzyl)piperazinyl]-2-(2-furyl)[1,2,4]triazolo[1,5-c]pyrimidine (Compound 68)

Yield: 51% (brown powder); $^1$H NMR (δ ppm, CDCl$_3$): 7.59 (dd, J=1.7 Hz, 0.7 Hz, 1H), 7.20–7.52 (m, 4H), 7.15 (dd, J=3.3 Hz, 0.7 Hz, 1H), 6.55 (dd, J=3.3 Hz, 1.7 Hz, 1H), 6.02 (s, 1H), 5.59 (brs, 2H), 3.68 (s, 2H), 3.57 (t, J=5.0 Hz, 4H), 2.61 (t, J=5.0 Hz, 4H); Mass (m/z): 409, 411 (M$^+$); IR (KBr, cm$^{-1}$): 3160, 1658, 1606, 1558, 1441, 1226; Melting point: 196° C.; Elemental analysis: C$_{20}$H$_{20}$ClN$_7$O; Found (%): C, 58.61, H, 4.92, N, 23.92; Calcd.(%): C, 58.78, H, 4.97, N, 23.92.

EXAMPLE 69

5-Amino-7-[4-(3-chlorobenzyl)piperazinyl]-2-(2-furyl)[1,2,4]triazolo[1,5-c]pyrimidine (Compound 69)

Yield: 34% (brown powder); $^1$H NMR (δ ppm, CDCl$_3$): 7.59 (dd, J=1.7 Hz, 0.7 Hz, 1H), 7.37 (s, 1H), 7.19–7.26 (m, 3H), 7.15 (dd, J=3.3 Hz, 0.7 Hz, 1H), 6.55 (dd, J=3.3 Hz, 1.7 Hz, 1H), 6.02 (s, 1H), 5.61 (brs, 2H), 3.56 (t, J=5.0 Hz, 4H), 3.52 (s, 2H), 2.53 (t, J=5.0 Hz, 4H); Mass (m/z): 409, 411 (M$^+$); IR (KBr, cm$^{-1}$): 1662, 1654, 1570, 1560, 1436, 1226; Melting point: 199–201° C.; Elemental analysis: C$_{20}$H$_{20}$ClN$_7$O 0.7C$_6$H$_5$CH$_3$; Found (%): C, 60.01, H, 5.08, N, 22.89; Calcd.(%): C, 59.86, H, 5.12, N, 22.65.

EXAMPLE 70

5-Amino-2-(2-furyl)-7-[4-(3-picolyl)piperazinyl][1,2,4]triazolo[1,5-c]pyrimidine (Compound 70)

Yield: 70% (light brown solid); $^1$H NMR ($\delta$ ppm, CDCl$_3$): 8.58 (s, 1H), 8.53 (d, J=4.6 Hz, 1H), 7.71 (d, J=7.6 Hz, 1H), 7.58 (dd, J=1.7 Hz, 0.7 Hz, 1H), 7.28 (dd, J=7.6 Hz, 4.6 Hz, 1H), 7.15 (dd, J=3.3 Hz, 0.7 Hz, 1H), 6.55 (dd, J=3.3 Hz, 1.7 Hz, 1H), 6.02 (s, 1H), 5.68 (brs, 2H), 3.57 (s, 2H), 3.54 (t, J=5.0 Hz, 4H), 2.54 (t, J=5.0 Hz, 4H); Mass (m/z): 376 (M$^+$); IR (KBr, cm$^{-1}$): 1670, 1606, 1552, 1438, 1334, 1244; Melting point: 191–192° C.; Elemental analysis: C$_{19}$H$_{20}$N$_8$O; Found (%): C, 60.62, H, 5.36, N, 29.77; Calcd.(%): C, 60.72, H, 5.47, N, 29.60.

EXAMPLE 71

5-Amino-2-(2-furyl)-7-[4-(4-picolyl)piperazinyl][1,2,4]triazolo[1,5-c]pyrimidine (Compound 71)

Yield: 75% (light brown solid); $^1$H NMR ($\delta$ ppm, CDCl$_3$): 8.56 (dd, J=4.6 Hz, 1.3 Hz, 2H), 7.58 (dd, J=1.7 Hz, 0.7 Hz, 1H), 7.30 (dd, J=4.6 Hz, 1.3 Hz, 2H), 7.15 (dd, J=3.3 Hz, 0.7 Hz, 1H), 6.55 (dd, J=3.3 Hz, 1.7 Hz, 1H), 6.02 (s, 1H), 5.74 (brs, 2H), 3.56 (t, J=5.0 Hz, 4H), 3.56 (s, 2H), 2.54 (t, J=5.0 Hz, 4H); Mass (m/z): 376 (M$^+$); IR (KBr, cm$^{-1}$): 1670, 1606, 1552, 1438, 1334, 1244; Melting point: 226–228° C.; Elemental analysis: C$_{19}$H$_{20}$N$_8$O; Found (%): C, 60.62, H, 5.36, N, 29.77; Calcd.(%): C, 60.50, H, 5.51, N, 29.63.

EXAMPLE 72

5-Amino-7-(4-cyclohexylmethylpiperazinyl)-2-(2-furyl)[1,2,4]triazolo[1,5-c]pyrimidine (Compound 72)

Yield: 68% (light brown solid); $^1$H NMR ($\delta$ ppm, CDCl$_3$): 7.58 (dd, J=1.7 Hz, 0.7 Hz, 1H), 7.15 (dd, J=3.3 Hz, 0.7 Hz, 1H), 6.55 (dd, J=3.3 Hz, 1.7 Hz, 1H), 6.02 (s, 1H), 5.67 (brs, 2H), 3.54 (t, J=5.0 Hz, 4H), 2.47 (t, J=5.0 Hz, 4H), 2.16 (d, J=7.3 Hz, 2H), 1.61–1.89 (m, 6H), 1.47–1,54 (m, 1H), 1.07–1.40 (m, 2H), 0.81–0.97 (m, 2H); Mass (m/z): 381 (M$^+$); IR (KBr, cm$^{-1}$): 3746, 1662, 1654, 1604, 1560, 1508, 1434, 1226; Melting point: 204–207° C.; Elemental analysis: C$_{20}$H$_{27}$N$_7$O; Found (%): C, 62.97, H, 7.13, N, 25.70; Calcd.(%): C, 62.99, H, 7.44, N, 25.63.

EXAMPLE 73

5-Amino-2-(2-furyl)-7-[4-(1-phenylethyl)piperazinyl][1,2,4]triazolo[1,5-c]pyrimidine (Compound 73)

Yield: 60% (white powder); $^1$H NMR ($\delta$ ppm, CDCl$_3$): 7.58 (dd, J=1.7 Hz, 0.7 Hz, 1H), 7.24–7.34 (m, 5H), 7.14 (dd, J=3.3 Hz, 0.7 Hz, 1H), 6.55 (dd, J=3.3 Hz, 1.7 Hz, 1H), 5.99 (s, 1H), 5.61 (brs, 2H), 3.52 (t, J=5.0 Hz, 4H), 3,40 (q, J=6.6 Hz, 1H), 2.54–2.62 (m, 2H), 2.43–2.51 (m, 2H), 1.40 (d, J=6.6 Hz, 3H); Mass (m/z): 389 (M$^+$); IR (KBr, cm$^{-1}$): 1662, 1654, 1558, 1438, 1413, 1201; Melting point: 201–202° C.; Elemental analysis: C$_{21}$H$_{23}$N$_7$O; Found (%): C, 64.76, H, 5.98, N, 25.18; Calcd.(%): C, 64.84, H, 6.03, N, 25.18.

EXAMPLE 74

5-Amino-7-[4-(2-methoxyethyl)piperazinyl]-2-(2-furyl)[1,2,4]triazolo[1,5-c]pyrimidine (Compound 74)

Yield: 67% (white powder); 1H NMR ($\delta$ ppm, CDCl$_3$): 7.58 (dd, J=1.7 Hz, 0.7 Hz, 1H), 7.15 (dd, J=3.3 Hz, 0.7 Hz, 1H), 6.55 (dd, J=3.3 Hz, 1.7 Hz, 1H), 6.02 (s, 1H), 5.63 (brs, 2H), 3.53–3.60 (m, 6H), 3.38 (s, 3H), 2.58–2.65 (m, 6H); Mass (m/z): 343 (M$^+$); IR (KBr, cm$^{-1}$): 1670, 1606, 1560, 1446, 1232; Melting point: 171–174° C.; Elemental analysis: C$_{16}$H$_{21}$N$_7$O$_2$; Found (%): C, 55.95, H, 6.27, N, 28.49; Calcd.(%): C, 55.96, H, 6.16, N, 28.55.

EXAMPLE 75

5-Amino-7-((2,5-dimethoxybenzyl)piperazinyl)-2-(2-furyl)[1,2,4]triazolo[1,5-c]pyrimidine (Compound 75)

Yield: 44% (white powder); $^1$H NMR ($\delta$ ppm, CDCl$_3$): 7.58 (dd, J=0.7 Hz, 1.7 Hz, 1H), 7.14 (dd, J=0.7 Hz, 3.3 Hz, 1H), 7.00 (d, J=2.6 Hz, 1H), 6.77–6.80 (m, 2H), 6.55 (dd, J=1.7 Hz, 3.3 Hz, 1H), 6.01 (s, 1H), 5.60 (brs, 2H), 3.79 (s, 6H), 3.59 (s, 2H), 3.57 (t, J=5.0 Hz, 4H), 2.59 (t, J=5.0 Hz, 4H); Mass (m/z): 435 (M$^+$); IR (KBr, cm$^{-1}$): 1668, 1645, 1610, 1560, 1500, 1446, 1224; Melting point: 188–189° C.l Elemental analysis: C$_{22}$H$_{25}$N$_7$O$_3$ 0.3EtOH; Found (%): C, 60.60, H, 5.93, N, 21.79; Calcd.(%): C, 60.42, H, 6.01, N, 21.82.

EXAMPLE 76

5-Amino-7-(4-(3,5-dimethoxybenzyl)piperazinyl)-2-(2-furyl)[1,2,4]triazolo[1,5-c]pyrimidine (Compound 76)

Yield: 40% (dark brown crystals); $^1$H NMR ($\delta$ ppm, CDCl$_3$): 7.59 (dd, J=0.7 Hz, 1.7 Hz, 1H), 7.16 (dd, J=0.7 Hz, 3.3 Hz, 1H), 6.55–6.57 (m, 3H), 6.39 (s, 1H), 6.02 (s, 1H), 5.60 (brs, 2H), 3.81 (s, 6H), 3,41–3.70 (m, 6H), 2.55 (t, J=5.0 Hz, 4H); Mass (m/z): 435 (M$^+$); IR (KBr, cm$^{-1}$): 3440, 1683, 1635, 1560, 1500, 1456, 1155; Melting point: 198–200° C.

EXAMPLE 77

5-Amino-2-(2-furyl)-7-(4-(3,4,5-trimethoxybenzyl)piperazinyl)[1,2,4]triazolo[1,5-c]pyrimidine (Compound 77)

Yield: 60% (brown powder); $^1$H NMR ($\delta$ ppm, CDCl$_3$): 7.58 (dd, J=0.7 Hz, 1.7 Hz, 1H), 7.16 (dd, J=0.7 Hz, 3.3 Hz, 1H), 6.59 (s, 2H), 6.56 (dd, J=1.7 Hz, 3.3 Hz, 1H), 6.03 (s, 1H), 5.66 (brs, 2H), 3.87 (s, 6H), 3.85 (s, 3H), 3.57 (t, J=5.0 Hz, 4H), 3,49 (s, 2H), 2.54 (t, J=5.0 Hz, 4H); Mass (m/z): 465 (M$^+$); IR (KBr, cm$^{-1}$): 3469, 3332, 2645, 1604, 1546, 1506, 1450, 1333, 1234, 1124; Melting point: 203–204° C. (decomposed); Elemental analysis: C$_{23}$H$_{27}$N$_7$O$_4$ 0.3EtOH; Found (%): C, 59.08, H, 6.08, N, 20.48; Calcd.(%): C, 59.14, H, 6.06, N, 20.45.

EXAMPLE 78

5-Amino-7-(4-(2-fluorobenzyl)piperazinyl)-2-(2-furyl)[1,2,4]triazolo[1,5-c]pyrimidine (Compound 78)

Yield: 35% (white powder); $^1$H NMR ($\delta$ ppm, CDCl$_3$): 7.58 (dd, J=0.7 Hz, 1.7 Hz, 1H), 7.05–7.40 (m, 4H), 7.15 (dd, J=0.7 Hz, 3.3 Hz, 1H), 6.55 (dd, J=1.7 Hz, 3.3 Hz, 1H), 6.01 (s, 1H), 5.58 (brs, 2H), 3.65 (s, 2H), 3.56 (t, J=5.0 Hz, 4H), 2.58 (t, J=5.0 Hz, 4H); Mass (m/z): 465 (M⁺); IR (KBr, cm⁻¹): 1654, 1608, 1558, 1442, 1228; Melting point: 180° C. (decomposed); Elemental analysis: $C_{20}H_{20}N_7OF$; Found (%): C, 61.08, H, 5.17, N, 24.88; Calcd.(%): C, 61.06, H, 5.12, N, 24.92.

EXAMPLE 79

5-Amino-7-(4-(4-chlorobenzyl)piperazinyl)-2-(2-furyl)[1,2,4]triazolo[1,5-c]pyrimidine (Compound 79)

Yield: 56% (light brown powder); ¹H NMR (δ ppm, CDCl₃): 7.58 (dd, J=0.7 Hz, 1.7 Hz, 1H), 7.29 (s, 4H), 7.15 (dd, J=0.7 Hz, 3.3 Hz, 1H), 6.54 (dd, J=1.7 Hz, 3.3 Hz, 1H), 6.01 (s, 1H), 5.58 (brs, 2H), 3.55 (t, J=5.0 Hz, 4H), 3.51 (s, 2H), 2.52 (t, J=5.0 Hz, 4H); Mass (m/z): 409, 411 (M⁺); IR (KBr, cm⁻¹): 3157, 2359, 1662, 1618, 1560, 1508, 1448, 1234; Melting point: 252–253° C.; Elemental analysis: $C_{20}H_{20}N_7OCl$ 0.8EtOH; Found (%): C, 57.71, H, 5.34, N, 22.04; Calcd.(%): C, 58.07, H, 5.59, N, 21.95.

EXAMPLE 80

5-Amino-7-(4-(2,6-dichlorobenzyl)piperazinyl)-2-(2-furyl)[1,2,4]triazolo[1,5-c]pyrimidine hydrochloride (Compound 80)

Yield: 35% (white powder); Mass (m/z): 444 (M⁺); IR (KBr, cm⁻¹): 3141, 2354, 1683, 1652, 1560, 1508, 1438; Melting point: >275° C.; Elemental analysis: $C_{20}H_{19}N_7OCl_2$ 2.0HCl 2.0H₂O; Found (%): C, 43.84, H, 4.52, N, 17.55; Calcd.(%): C, 43.71, H, 4.57, N, 17.84.

EXAMPLE 81

5-Amino-7-(4-(4-biphenylmethyl)piperazinyl)-2-(2-furyl)[1,2,4]triazolo[1,5-c]pyrimidine (Compound 81)

Yield: 60% (light brown powder); ¹H NMR (δ ppm, CDCl₃): 7.58 (dd, J=0.7 Hz, 1.7 Hz, 1H), 7.32–7.62 (m, 9H), 7.16 (dd, J=0.7 Hz, 3.3 Hz, 1H), 6.56 (dd, J=1.7 Hz, 3.3 Hz, 1H), 6.02 (s, 1H), 5.60 (brs, 2H), 3.60 (s, 2H), 3.58 (t, J=5.0 Hz, 4H), 2.58 (t, J=5.0 Hz, 4H); Mass (m/z): 451 (M⁺); IR (KBr, cm⁻¹): 1656, 1610, 1560, 1444, 1252, 1203; Melting point: 207–208° C.; Elemental analysis: $C_{26}H_{25}N_7O$ 0.1$C_6H_5CH_3$; Found (%): C, 69.82, H, 5.96, N, 21.14; Calcd.(%): C, 69.60, H, 5.64, N, 21.28.

EXAMPLE 82

5-Amino-7-(4-diphenylmethylpiperazinyl)-2-(2-furyl)[1,2,4]triazolo[1,5-c]pyrimidine (Compound 82)

Yield: 70% (light brown powder); ¹H NMR (δ ppm, CDCl₃): 7.57 (dd, J=0.7 Hz, 1.7 Hz, 1H), 7.17–7.46 (m, 10H), 7.14 (dd, J=0.7 Hz, 3.3 Hz, 1H), 6.55 (dd, J=1.7 Hz, 3.3 Hz, 1H), 5.99 (s, 1H), 5.61 (brs, 2H), 4.25 (s, 1H), 3.53 (t, J=5.0 Hz, 4H), 2.49 (t, J=5.0 Hz, 4H); Mass (m/z): 451 (M⁺); IR (KBr, cm⁻¹): 1645, 1604, 1556, 1511, 1446, 1332, 1230, 1003, 754, 707; Melting point: 249–251° C. (decomposed); Elemental analysis: $C_{26}H_{25}N_7O$; Found (%): C, 66.84, H, 5.96, N, 20.38; Calcd.(%): C, 67.06, H, 6.04, N, 20.28.

EXAMPLE 83

5-Amino-7-(4-benzylhomopiperazinyl)-2-(2-furyl)[1,2,4]triazolo[1,5-c]pyrimidine (Compound 83)

Yield: 34% (white powder); ¹H NMR (δ ppm, CDCl₃): 7.58 (dd, J=0.7 Hz, 1.7 Hz, 1H), 7.23–7.33 (m, 5H), 7.15 (dd, J=0.7 Hz, 3.3 Hz, 1H), 6.55 (dd, J=1.7 Hz, 3.3 Hz, 1H), 5.88 (s, 1H), 5.58 (brs, 2H), 3.78–3.87 (m, 2H), 3.60–3.65 (m, 2H), 3.63 (s, 2H), 2.73 (t, J=5.0 Hz, 4H), 2.63 (t, J=5.6 Hz, 2H), 1.92–2.00 (m, 2H); Mass (m/z): 389 (M⁺); IR (KBr, cm⁻¹): 1658, 1653, 1606, 1558, 1516, 1450, 1415; Melting point: 166–167° C.; Elemental analysis: $C_{21}H_{23}N_7O$ 0.3H₂O; Found (%): C, 63.93, H, 5.91, N, 24.83; Calcd.(%): C, 63.87, H, 6.02, N, 24.83.

EXAMPLE 84

5-Amino-2-(2-furyl)-7-(4-(2-picolyl)piperazinyl)[1,2,4]triazolo[1,5-c]pyrimidine (Compound 84)

Yield: 84% (dark brown crystals); ¹H NMR (δ ppm, CDCl₃): 8.59 (dd, J=1.7 Hz, 5.0 Hz, 1H), 7.68 (dt, J=1.7 Hz, 7.6 Hz, 1H), 7.58 (dd, J=0.7 Hz, 1.7 Hz, 1H), 7.42 (dd, J=1.7 Hz, 7.6 Hz, 1H), 7.19 (ddd, J=1.7 Hz, 5.0 Hz, 7.6 Hz, 1H), 7.15 (dd, J=0.7 Hz, 3.3 Hz, 1H), 6.55 (dd, J=1.7 Hz, 3.3 Hz, 1H), 6.01 (s, 1H), 5.73 (brs, 2H), 3.72 (s, 2H), 3.58 (t, J=5.0 Hz, 4H), 2.61 (t, J=5.0 Hz, 4H); Mass (m/z): 376 (M⁺); IR (KBr, cm⁻¹): 3232, 3149, 2831, 1652, 1610, 1562, 1446, 1413, 1334, 1226, 1209, 985; Melting point: 183–184° C.; Elemental analysis: $C_{19}H_{20}N_8O$ 0.2EtOH Found (%): C, 60.38, H, 5.58, N, 29.14; Calcd.(%): C, 60.42, H, 5.54, N, 29.06.

EXAMPLE 85

5-Amino-7-(4-(2-(3,4-dimethoxyphenyl)ethyl)piperazinyl)-2-(2-furyl)[1,2,4]triazolo[1,5-c]pyrimidine (Compound 85)

Yield: 68% (brown crystals); ¹H NMR (δ ppm, CDCl₃): 7.58 (dd, J=0.7 Hz, 1.7 Hz, 1H), 7.15 (dd, J=0.7 Hz, 3.3 Hz, 1H), 6.74–6.83 (m, 3H), 6.56 (dd, J=1.7 Hz, 3.3 Hz, 1H), 6.04 (s, 1H), 5.70 (brs, 2H), 3.88 (s, 3H), 3.86 (s, 3H), 3.59 (t, J=5.0 Hz, 4H), 2.77–2.82 (m, 2H), 2.62–2.67 (m, 6H); Mass (m/z): 449 (M⁺); IR (KBr, cm⁻¹): 3097, 2940, 1668, 1606, 1560, 1515, 1463, 1332, 1214, 1145, 1025, 769; Melting point: 187–189° C.; Elemental analysis: $C_{23}H_{27}N_7O_3$; Found (%): C, 61.26, H, 6.19, N, 21.49; Calcd.(%): C, 61.46, H, 6.05, N, 21.81.

EXAMPLE 86

5-Amino-7-(4-(3-(3,4-dimethoxyphenyl)propyl)piperazinyl)-2-(2-furyl)[1,2,4]triazolo[1,5-c]pyrimidine (Compound 86)

Yield: 72% (brown powder); ¹H NMR (δ ppm, CDCl₃): 7.58 (dd, J=0.7 Hz, 1.7 Hz, 1H), 7.15 (dd, J=0.7 Hz, 3.3 Hz, 1H), 6.73–6.82 (m, 3H), 6.55 (dd, J=1.7 Hz, 3.3 Hz, 1H), 6.02 (s, 1H), 5.63 (brs, 2H), 3.88 (s, 3H), 3.86 (s, 3H), 3.56 (t, J=5.0 Hz, 4H), 2.62 (t, J=7.3 Hz, 2H), 2.53 (t, J=5.0 Hz, 4H), 2.41 (J=7.3 Hz, 2H), 1.81–1.89 (m, 2H); Mass (m/z): 463 (M⁻); IR (KBr, cm⁻¹): 2936, 1660, 1654, 1608, 1577, 1510, 1444, 1257, 1232, 1145, 1029; Melting point: 146° C.; Elemental analysis: $C_{24}H_{29}N_7O_3$ 0.3AcOEt; Found (%): C, 61.88, H, 6.63, N, 20.13; Calcd.(%): C, 61.77, H, 6.46, N, 20.01.

EXAMPLE 87

5-Amino-2-(2-furyl)-7-(4-(3-(3-pyridyl)propyl) piperazinyl)[1,2,4]triazolo[1,5-c]pyrimidine hydrochloride (Compound 87)

Yield: 50% (white powder); Mass (m/z): 404 (M$^+$); IR (KBr, cm$^{-1}$): 3087, 2675, 1682, 1630, 1560, 1519, 1498; Melting point: 270° C.; Elemental analysis: $C_{21}H_{24}N_8O$ 3.0HCl 0.2H$_2$O; Found (%): C, 48.89, H, 5.45, N, 21.25; Calcd.(%): C, 48.74, H, 5.33, N, 21.65.

EXAMPLE 88

5-Amino-7-(4-trans-cinnamylpiperazinyl)-2-(2-furyl)[1,2,4]triazolo[1,5-c]pyrimidine (Compound 88)

Yield: 63% (white powder); $^1$H NMR (δ ppm, CDCl$_3$): 7.58 (dd, J=0.7 Hz, 1.7 Hz, 1H), 7.42–7.20 (m, 5H), 7.15 (dd, J=0.7 Hz, 3.3 Hz, 1H), 6.56 (d, J=15.8 Hz, 1H), 6.56 (dd, J=1.7 Hz, 3.3 Hz, 1H), 6.28 (dt, J=15.8 Hz, 6.6 Hz, 1H), 6.03 (s, 1H), 5.63 (brs, 2H), 3.58 (t, J=5.0 Hz, 4H), 3.20 (d, J=6.6 Hz, 2H), 2.59 (t, J=5.0 Hz, 4H); Mass (m/z): 401 (M$^+$); IR (KBr, cm$^{-1}$): 3310, 3180, 2800, 1668, 1651, 1614, 1562, 1558, 1440, 1415, 1230, 1201; Melting point: 199–200° C.; Elemental analysis: $C_{22}H_{23}N_7O$ 0.2H$_2$O; Found (%): C, 65.35, H, 5.82, N, 24.19; Calcd.(%): C, 65.23, H, 5.82, N, 24.20.

EXAMPLE 89

5-Amino-2-(2-furyl)-7-(4-(3-phenylpropargyl) piperazinyl)[1,2,4]triazolo[1,5-c]pyrimidine hydrochloride (Compound 89)

Yield: 49% (white powder); Mass (m/z): 399 (M$^+$); IR (KBr, cm$^{-1}$): 1681, 1633, 1628, 1522, 1497, 1444; Melting point: 207–210° C.; Elemental analysis: $C_{22}H_{21}N_7O$ 2.0HCl 2.0H$_2$O; Found (%): C, 52.21, H, 5.20, N, 18.81; Calcd.(%): C, 51.98, H, 5.35, N, 19.28.

EXAMPLE 90

5-Amino-2-(2-furyl)-7-(4-(2-phenoxyethyl) piperazinyl)[1,2,4]triazolo[1,5-c]pyrimidine hydrochloride (Compound 90)

Yield: 79% (white solid); Mass (m/z): 405 (M$^+$); IR (KBr, cm$^{-1}$): 3112, 2457, 1679, 1629, 1568, 1522, 1492, 1444, 1222; Melting point: 263–265° C. (decomposed); Elemental analysis: $C_{21}H_{23}N_7O_2$ 2.0HCl 0.6EtOH 0.2MeOH 0.7H$_2$O; Found (%): C, 51,53, H, 5.81, N, 18.76; Calcd.(%): C, 51.24, H, 5.91, N, 18.67.

EXAMPLE 91

5-Amino-2-(2-furyl)-7-(4-(2-hydroxy-2-phenylethyl) piperazinyl)[1,2,4]triazolo[1,5-c]pyrimidine (Compound 91)

Yield: 46% (light brown powder); $^1$H NMR (δ ppm, CDCl$_3$): 7.58 (dd, J=0.7 Hz, 1.7 Hz, 1H), 7.41–7.26 (m, 5H), 7.16 (dd, J=0.7 Hz, 3.3 Hz, 1H), 6.56 (dd, J=1.7 Hz, 3.3 Hz, 1H), 6.05 (s, 1H), 5.64 (brs, 2H), 4.80 (t, J=7.3 Hz, 1H), 3.71–3.53 (m, 4H), 2.93–2.80 (m, 2H), 2.80–2.49 (m, 4H); Mass (m/z): 405 (M$^+$); IR (KBr, cm$^{-1}$): 1662, 1610, 1556, 1439, 1417, 1225, 1203; Melting point: 216–217° C.; Elemental analysis: $C_{21}H_{23}N_7O_2$ 0.1C$_6$H$_5$CH$_3$; Found (%): C, 62.77, H, 5.98, N, 23.74; Calcd.(%): C, 62.85, H, 5.78, N, 23.64.

EXAMPLE 92

5-Amino-2-(2-furyl)-7-(4-(4-phenylbutyl) piperazinyl)[1,2,4]triazolo[1,5-c]pyrimidine hydrochloride (Compound 92)

Yield: 23% (light brown powder); Mass (m/z): 417 (M$^+$); IR (KBr, cm$^{-1}$): 3379, 3149, 1681, 1650, 1565, 1506, 1446; Melting point: 206–207° C. (decomposed); Elemental analysis: $C_{23}H_{27}N_7O$ 2.0HCl 0.5H$_2$O; Found (%): C, 55.45, H, 6.41, N, 19.60; Calcd.(%): C, 55.31, H, 6.05, N, 19.63.

EXAMPLE 93

5-Amino-2-(2-furyl)-7-(4-(2-pyridyl)piperazinyl)[1,2,4]triazolo[1,5-c]pyrimidine (Compound 93)

Yield: 58% (brown powder); $^1$H NMR (δ ppm, CDCl$_3$): 8.22 (d, J=4.0 Hz, 1H), 7.59 (dd, J=0.7 Hz, 1.7 Hz, 1H), 7.52 (dd, J=7.3 Hz, 7.3 Hz, 1H), 7.16 (dd, J=0.7 Hz, 3.3 Hz, 1H), 6.64–6.69 (m, 2H), 6.56 (dd, J=1.7 Hz, 3.3 Hz, 1H), 6.07 (s, 1H), 5.66 (brs, 2H), 3.70 (brt, 8H); Mass (m/z): 362 (M$^+$); IR (KBr, cm$^{-1}$): 1674, 1608, 1558, 1485, 1435, 1240; Melting point: 231° C.; Elemental analysis: $C_{18}H_{18}N_8O$; Found (%): C, 59.87, H, 5.21, N, 31.03; Calcd.(%): C, 59.66, H, 5.01, N, 30.92.

EXAMPLE 94

5-Amino-7-(4-(2-benzoxazolyl)piperazinyl)-2-(2-furyl)[1,2,4]triazolo[1,5-c]pyrimidine (Compound 94)

Yield: 24%; $^1$H NMR (δ ppm, CDCl$_3$): 7.59 (dd, J=0.7 Hz, 1.7 Hz, 1H), 7.29 (d, J=7.6 Hz, 1H), 7.23–7.16 (m, 3H), 7.07 (t, J=7.6 Hz, 1H), 6.57 (dd, J=1.7 Hz, 3.3 Hz, 1H), 6.10 (s, 1H), 5.69 (brs, 2H), 3.85–3.70 (m, 8H); Mass (m/z): 402 (M$^+$); IR (KBr, cm$^{-1}$): 1651, 1645, 1604, 1564, 1456, 1234; Melting point: >270° C.; Elemental analysis: $C_{20}H_{18}N_8O_2$; Found (%): C, 59.55, H, 4.39, N, 27.60; Calcd.(%): C, 59.60, H, 4.51, N, 27.85.

EXAMPLE 95

5-Amino-7-(4-(2-benzothiazolyl)piperazinyl)-2-(2-furyl)[1,2,4]triazolo[1,5-c]pyrimidine (Compound 95)

Yield: 30% (light brown cotton wool crystals); $^1$H NMR (δ ppm, CDCl$_3$): 7.65–7.57 (m, 3H), 7.30 (t, J=7.6 Hz, 1H), 7.15 (dd, J=0.7 Hz, 3.3 Hz, 1H), 6.55 (dd, J=1.7 Hz, 3.3 Hz, 1H), 6.02 (s, 1H), 5.66 (brs, 2H), 3.62–3.48 (m, 8H), 2.66–2.59 (m, 6H); Mass (m/z): 418 (M$^+$); IR (KBr, cm$^{-1}$): 1653, 1606, 1558, 1539, 1442, 1227, 1198; Melting point: >270° C.; Elemental analysis: $C_{20}H_{18}N_8OS$; Found (%): C, 57.18, H, 4.23, N, 26.46; Calcd.(%): C, 57.40, H, 4.34, N, 26.78.

EXAMPLE 96

5-Amino-7-(4-(2-ethoxyethyl)piperazinyl)-2-(2-furyl)[1,2,4]triazolo[1,5-c]pyrimidine (Compound 96)

Yield: 61% (white powder); $^1$H NMR (δ ppm, CDCl$_3$): 7.58 (dd, J=0.7 Hz, 1.7 Hz, 1H), 7.15 (dd, J=0.7 Hz, 3.3 Hz, 1H), 6.55 (dd, J=1.7 Hz, 3.3 Hz, 1H), 6.02 (s, 1H), 5.66 (brs, 2H), 3.48–3.62 (m, 8H), 2.59–2.66 (m, 6H), 1.22 (t, J=6.9 Hz, 3H); Mass (m/z): 357 (M$^+$); IR (KBr, cm$^{-1}$): 1653, 1610, 1558, 1446, 1236, 769; Melting point: 164–165° C.; Elemental analysis: $C_{17}H_{23}N_7O_2$ 0.2H$_2$O; Found (%): C, 56.48, H, 6.60, N, 27.14; Calcd.(%): C, 56.56, H, 6.53, N, 27.16.

EXAMPLE 97

5-Amino-7-(4-(2-benzyloxyethyl)piperazinyl)-2-(2-furyl)[1,2,4]triazolo[1,5-c]pyrimidine hydrochloride (Compound 97)

Yield: 54% (white powder); Mass (m/z): 419 (M$^+$); IR (KBr, cm$^{-1}$): 1684, 1635; Melting point: 227–228° C.; Elemental analysis: $C_{22}H_{25}N_7O_2$ 2.0HCl 0.3AcOEt; Found (%): C, 53.22, H, 5.83, N, 18.85; Calcd.(%): C, 53.34, H, 5.75, N, 18.77.

EXAMPLE 98

5-Amino-2-(2-furyl)-7-(4-(3-hydroxypropyl)piperazinyl)[1,2,4]triazolo[1,5-c]pyrimidine hydrochloride (Compound 98)

Yield: 57% (light yellow powder); Mass (m/z): 343 (M$^+$); IR (KBr, cm$^{-1}$): 3300, 2597, 1687, 1651, 1645, 1531, 1504; Melting point: >270° C.; Elemental analysis: $C_{16}H_{23}N_7O_2$ 2.0HCl 0.6H$_2$O; Found (%): C, 45.09, H, 5.72, N, 22.87; Calcd.(%): C, 44.99, H, 5.71, N, 22.96.

EXAMPLE 99

5-Amino-2(2-furyl)-7-(4-(3-methoxypropyl)piperazinyl)[1,2,4]triazolo[1,5-c]pyrimidine (Compound 99)

Yield: 21% (light yellow plate crystals); $^1$H NMR (δ ppm, CDCl$_3$): 7.58 (dd, J=0.7 Hz, 1.7 Hz, 1H), 7.15 (dd, J=0.7 Hz, 3.3 Hz, 1H), 6.56 (dd, J=1.7 Hz, 3.3 Hz, 1H), 6.02 (s, 1H), 5.60 (brs 2H), 3.56 (t, J=5.0 Hz, 4H), 3,4 5 (t, J=6.6 Hz, 2H), 3.35 (s, 3H), 2.54 (t, J=5.0 Hz, 4H), 2.47 (t, J=7.6 Hz, 2H), 1.76–1.86 (m, 2H); Mass (m/z): 357 (M$^+$); IR (KBr, cm$^{-1}$): 1660, 1614, 1568, 1444, 1222, 1209; Melting point: 144–145° C.; Elemental analysis: $C_{17}H_{23}N_7O_2$; Found (%): C, 57.00, H, 6.54, N, 27.56; Calcd.(%): C, 57.13, H, 6.49, N, 27.43.

EXAMPLE 100

5-Amino-7-(4-(3-ethoxypropyl)piperazinyl)-2-(2-furyl)[1,2,4]triazolo[1,5-c]pyrimidine (Compound 100)

Yield: 54% (brown plate crystals); $^1$H NMR (δ ppm, CDCl$_3$): 7.58 (dd, J=0.7 Hz, 1.7 Hz, 1H), 7.15 (dd, J=0.7 Hz, 3.3 Hz, 1H), 6.56 (dd, J=1.7 Hz, 3.3 Hz, 1H), 6.02 (s, 1H), 5.65 (brs, 2H), 3.56 (t, J=5.0 Hz, 4H), 3.50 (t, J=6.6 Hz, 2H), 3,48 (q, J=6.9 Hz, 2H), 2.54 (t, J=5.0 Hz, 4H), 2.47 (t, J=7.3 Hz, 2H), 1.78 (tt, J=6.6 Hz, 7.3 Hz, 2H), 1.21 (t, J=6.9 Hz, 3H); Mass (m/z): 371 (M$^+$); IR (KBr, cm$^{-1}$): 1660, 1614, 1568, 1558, 1443, 1435, 1416, 1235; Melting point: 143–144° C.; Elemental analysis: $C_{18}H_{25}N_7O_2$; Found (%): C, 58.25, H, 6.88, N, 26.38; Calcd.(%): C, 58.21, H, 6.78, N, 26.40.

EXAMPLE 101

5-Amino-2-(2-furyl)-7-(4-(3-isopropoxypropyl)piperazinyl)[1,2,4]triazolo[1,5-c]pyrimidine (Compound 101)

Yield: 44% (white powder); $^1$H NMR (δ ppm, CDCl$_3$): 7.58 (dd, J=0.7 Hz, 1.7 Hz, 1H), 7.15 (dd, J=0.7 Hz, 3.3 Hz, 1H), 6.55 (dd, J=1.7 Hz, 3.3 Hz, 1H), 6.02 (s, 1H), 5.71 (brs, 2H), 3.60–3,45 (m, 7H), 2.57–2.46 (m, 6H), 1.84–1.76 (m, 2H), 1.15 (d, J=6.3 Hz, 6H); Mass (m/z): 385 (M$^+$); IR (KBr, cm$^{-1}$): 1653, 1608, 1558, 1444; Melting point: 150° C.; Elemental analysis: $C_{19}H_{27}N_7O_2$ 0.7H$_2$O; Found (%): C, 57.31, H, 7.45, N, 24.90; Calcd.(%): C, 57.33, H, 7.19, N, 24.63.

EXAMPLE 102

5-Amino-7-(4-(3-benzyloxypropyl)piperazinyl)-2-(2-furyl)[1,2,4]triazolo[1,5-c]pyrimidine hydrochloride (Compound 102)

Yield: 22% (white powder); Mass (m/z): 433 (M$^+$); IR (KBr, cm$^{-1}$): 1684, 1628, 1559, 1522, 1498; Melting point: 211–215° C. Elemental analysis: $C_{23}H_{27}N_7O_2$ 2.0HCl 1.0H$_2$O; Found (%): C, 52.68, H, 6.04, N, 19.00; Calcd.(%): C, 52.67, H, 5.96, N, 18.69.

EXAMPLE 103

5-Amino-2-(2-furyl)-7-(4-(2-(2-hydroxyethoxy)ethyl)piperazinyl)[1,2,4]triazolo[1,5-c]pyrimidine (Compound 103)

Yield: 54% (light brown powder); $^1$H NMR (δ ppm, CDCl$_3$): 7.58 (dd, J=0.7 Hz, 1.7 Hz, 1H), 7.16 (dd, J=0.7 Hz, 3.3 Hz, 1H), 6.56 (dd, J=1.7 Hz, 3.3 Hz, 1H), 6.03 (s, 1H), 5.65 (brs, 2H), 3.55–3.77 (m, 10H), 2.60–2.72 (m, 6H), 1.69 (brs, 1H); Mass (m/z): 373 (M$^+$); IR (KBr, cm$^{-1}$): 3340, 1662, 1610, 1560, 1438, 1230; Melting point: 163–164° C.; Elemental analysis: $C_{17}H_{23}N_7O_3$; Found (%): C, 54.52, H, 6.32, N, 25.94; Calcd.(%): C, 54.68, H, 6.21, N, 26.26.

EXAMPLE 104

5-Amino-2-(2-furyl)-7-(4-(2-(2-methoxyethoxy)ethyl)piperazinyl)[1,2,4]triazolo[1,5-c]pyrimidine (Compound 104)

Yield: 23% (light brown plate crystals); $^1$H NMR (δ ppm, CDCl$_3$): 7.58 (dd, J=0.7 Hz, 1.7 Hz, 1H), 7.15 (dd, J=0.7 Hz, 3.3 Hz, 1H), 6.56 (dd, J=1.7 Hz, 3.3 Hz, 1H), 6.03 (s, 1H), 5.63 (brs, 2H), 3.51–3.73 (m, 10H), 3,40 (s, 3H), 2.52–2.70 (m, 6H); Mass (m/z): 387 (M$^+$); IR (KBr, cm$^{-1}$): 1658, 1653, 1562, 1558, 1232, 1097; Melting point: 134° C.; Elemental analysis: $C_{18}H_{25}N_7O_3$; Found (%): C, 55.85, H, 6.86, N, 25.53; Calcd.(%): C, 55,80, H, 6.50, N, 25.31.

EXAMPLE 105

(±)-5-Amino-2-(2-furyl)-7-(4-(2-hydroxypropyl)piperazinyl)[1,2,4]triazolo[1,5-c]pyrimidine (Compound 105)

Yield: 37% (light brown powder); $^1$H NMR (δ ppm, CDCl$_3$): 7.58 (dd, J=0.7 Hz, 1.7 Hz, 1H), 7.15 (dd, J=0.7 Hz, 3.3 Hz, 1H), 6.55 (dd, J=1.7 Hz, 3.3 Hz, 1H), 6.03 (s, 1H), 5.62 (brs, 2H), 3.83–3.98 (m, 1H), 3,47–3.68 (m, 4H), 2.69–2.83 (m, 2H), 1.16 (d, J=6.3 Hz, 3H); Mass (m/z): 343 (M$^+$); IR (KBr, cm$^{-1}$): 3340, 1676, 1653, 1608, 1560, 1442, 1230; Melting point: 192–193° C.; Elemental analysis: $C_{16}H_{21}N_7O_2$; Found (%): C, 55.91, H, 6.24, N, 28.55; Calcd.(%): C, 55.96, H, 6.16, N, 28.55.

EXAMPLE 106

(±)-5-Amino-2-(2-furyl)-7-(4-(2-methoxypropyl)piperazinyl)[1,2,4]triazolo[1,5-c]pyrimidine (Compound 106)

Yield: 41% (brown particle crystals); $^1$H NMR (δ ppm, CDCl$_3$): 7.58 (dd, J=0.7 Hz, 1.7 Hz, 1H), 7.16 (dd, J=0.7 Hz, 3.3 Hz, 1H), 6.55 (dd, J=1.7 Hz, 3.3 Hz, 1H), 6.02 (s, 1H), 5.70 (brs, 2H), 3.56 (t, J=5.0 Hz, 4H), 3.56 (m, 1H), 3.37 (s, 3H), 2.51–2.60 (m, 6H), 1.17 (d, J=6.3 Hz, 3H); Mass (m/z): 357 (M$^+$); IR (KBr, cm$^{-1}$): 1653, 1608, 1446, 1238; Melting point: 181–182° C.; Elemental analysis: $C_{17}H_{23}N_7O_2$; Found (%): C, 57.32, H, 6.62, N, 27.74; Calcd.(%): C, 57.13, H, 6.49, N, 27.43.

EXAMPLE 107

5-Amino-7-(4-(ethoxycarbonylmethyl)piperazinyl)-2-(2-furyl)[1,2,4]triazolo[1,5-c]pyrimidine (Compound 107)

Yield: 73% (light brown powder); $^1$H NMR (δ ppm, CDCl$_3$): 7.59 (dd, J=0.7 Hz, 1.7 Hz, 1H), 7.15 (dd, J=0.7 Hz, 3.3 Hz, 1H), 6.56 (dd, J=1.7 Hz, 3.3 Hz, 1H), 6.03 (s, 1H), 5.60 (brs, 2H), 4.20 (q, J=7.3 Hz, 2H), 3.62 (t, J=5.0 Hz, 4H), 3.27 (s, 2H), 2.68 (t, J=5.0 Hz, 4H), 1.29 (t, J=7.3 Hz, 3H); Mass (m/z): 371 (M$^+$); IR (KBr, cm$^{-1}$): 3382, 3157, 2840, 1706, 1652, 1608, 1560, 1456, 1409, 1223, 770; Melting point: 172° C.; Elemental analysis: C$_{17}$H$_{21}$N$_7$O$_3$; Found (%): C, 54.95, H, 5.82, N, 26.05; Calcd.(%): C, 54.98, H, 5.70, N, 26.40.

EXAMPLE 108

5-Amino-2-(2-furyl)-7-(4-carboxymethylpiperazinyl)[1,2,4]triazolo[1,5-c]pyrimidine (Compound 108)

In 100 ml of methanol and 50 ml of a 2 N aqueous sodium hydroxide solution, 790 mg (2.12 mmol) of Compound 107 obtained in Example 107 was dissolved, followed by stirring at room temperature for 2 hours. After evaporation of the solvent under reduced pressure, the residue was purified by preparative HPLC (column: YMC-Pack ODS SH-365–10 500×30 φmm; elution solvent: acetonitrile-water (20:80), 10 mM ammonium acetate addition; flow rate: 40 ml/minute; UV 254 nm) to give 300 mg (yield: 36%) of Compound 108 as white powder.

$^1$H NMR (δ ppm, CDCl$_3$): 7.86 (dd, J=0.7 Hz, 1.7 Hz, 1H), 7.61 (brs, 2H), 7.05 (dd, J=0.7 Hz, 3.3 Hz, 1H), 6.66 (dd, J=1.7 Hz, 3.3 Hz, 1H), 6.03 (s, 1H), 3.53 (brt, 4H), 3.19 (s, 2H), 2.63 (brt, 4H); Mass (m/z): 343 (M$^+$); IR (KBr, cm$^{-1}$): 1655, 1610, 1560, 1448, 1417, 1392, 1236; Melting point: >270° C.; Elemental analysis: C$_{15}$H$_{17}$N$_7$O$_3$; Found (%): C, 46.61, H, 5.66, N, 25.43; Calcd.(%): C, 46.39, H, 5.71, N, 25.24.

EXAMPLE 109

(±)-5-Amino-7-(4-(1-ethoxycarbonylethyl)piperazinyl)-2-(2-furyl)[1,2,4]triazolo[1,5-c]pyrimidine hydrochloride (Compound 109)

Compound 109 was obtained using Compound 61 obtained in Example 61 and (1-ethoxycarbonylethyl)piperazine in the same manner as in Example 62.

Yield: 62% (white powder); Mass (m/z): 385 (M$^+$); IR (KBr, cm$^{-1}$): 1740, 1680, 1628, 1568, 1491, 1444; Melting point: 220–224° C.; Elemental analysis: C$_{24}$H$_{29}$N$_7$O$_2$ 2.0HCl; Found (%): C, 47.26, H, 5.54, N, 21.25; Calcd.(%): C, 47.16, H, 5.49, N, 21.39.

EXAMPLE 110

(±)-5-Amino-2-(2-furyl)-7-(4-(1-carboxyethyl)piperazinyl)[1,2,4]triazolo[1,5-c]pyrimidine (Compound 110)

Compound 110 was obtained using Compound 109 obtained in Example 109 in the same manner as in Example 108.

Yield: 38% (ocher powder); $^1$H NMR (δ ppm, CDCl$_3$): 7.58 (dd, J=0.7 Hz, 1.7 Hz, 1H), 7.62 (brs, 2H), 7.06 (dd, J=0.7 Hz, 3.3 Hz, 1H), 6.67 (dd, J=1.7 Hz, 3.3 Hz, 1H), 6.02 (s, 1H), 3.53 (brt, 4H), 3.28 (q, J=6.9 Hz, 1H), 2.57–2.73 (m, 4H), 1.21 (d, J=6.9 Hz, 3H); Mass (m/z): 357 (M$^+$); IR (KBr, cm$^{-1}$): 1649, 1614, 1560, 1444, 1390, 1240; Melting point: 229–230° C.; Elemental analysis: C$_{16}$H$_{19}$N$_7$O$_3$ 0.4MeOH 0.6H$_2$O; Found (%): C, 51.43, H, 6.09, N, 25.88; Calcd.(%): C, 51.70, H, 5.76, N, 25.73.

EXAMPLE 111

(±)-5-Amino-2-(2-furyl)-7-(4-((2-hydroxy-1-methyl)ethyl)piperazinyl)[1,2,4]triazolo[1,5-c]pyrimidine (Compound 111)

In 50 ml of THF, 1.86 g (4.83 mmol) of Compound 109 obtained in Example 109 was dissolved, and 370 mg (9.66 mmol) of lithium aluminum hydride was added thereto under ice-cooling, followed by stirring at 0° C. for 1 hour. After completion of the reaction, 50 ml of diethyl ether and a saturated aqueous sodium sulfate solution were added to the reaction solution until foaming ended, followed by stirring at room temperature for 1 hour and further drying over anhydrous magnesium sulfate. After evaporation of the solvent under reduced pressure, the resulting residue was purified by silica gel column chromatography [chloroform-methanol (97:3–90:10), gradation] and then recrystallized from ethyl acetate-hexane to give 360 mg (yield: 22%) of Compound 111 as light yellow powder.

$^1$H NMR (δ ppm, CDCl$_3$): 7.59 (dd, J=0.7 Hz, 1.7 Hz, 1H), 7.16 (dd, J=0.7 Hz, 3.3 Hz, 1H), 6.56 (dd, J=1.7 Hz, 3.3 Hz, 1H), 6.04 (s, 1H), 5.62 (brs, 2H), 3.32–3.71 (m, 6H), 2.84–3.30 (m, 1H), 2.71–2.84 (m, 2H), 2.45–2.63 (m, 2H), 0.94 (d, J=6.9 Hz, 3H); Mass (m/z): 343 (M$^+$); IR (KBr, cm$^{-1}$): 1674, 1655, 1606, 1560, 1444, 1228; Melting point: 203° C.; Elemental analysis: C$_{16}$H$_{21}$N$_7$O$_2$; Found (%): C, 55.98, H, 6.22, N, 28.68; Calcd.(%): C, 55.96, H, 6.16, N, 28.55.

Examples 112 to 119 were carried out below using Compound 61 obtained in Example 61 and various piperazine derivatives in the same manner as in Example 62 to give Compounds 112 to 119.

EXAMPLE 112

5-Amino-7-(4-(tert-butoxycarbonyl)piperazinyl)-2-(2-furyl)[1,2,4]triazolo[1,5-c]pyrimidine (Compound 112)

Yield: 85% (white powder); $^1$H NMR (δ ppm, CDCl$_3$): 7.58 (dd, J=0.7 Hz, 1.7 Hz, 1H), 7.16 (dd, J=0.7 Hz, 3.3 Hz, 1H), 6.56 (dd, J=1.7 Hz, 3.3 Hz, 1H), 6.03 (s, 1H), 5.64 (brs, 2H), 3.55 (s, 8H), 1.49 (s, 9H); Mass (m/z): 385 (M$^+$); IR (KBr, cm$^{-1}$): 1699, 1652, 1608, 1556, 1446, 1417, 1228, 1172; Melting point: 188–189° C.; Elemental analysis: C$_{18}$H$_{23}$N$_7$O$_3$ 0.5C$_6$H$_5$CH$_3$ 0.4H$_2$O; Found (%): C, 58.84, H, 6.33, N, 22.34; Calcd.(%): C, 58.86, H, 6.39, N, 22.35.

EXAMPLE 113

5-Amino-7-(4-formylpiperazinyl)-2-(2-furyl)[1,2,4]triazolo[1,5-c]pyrimidine (Compound 113)

Yield: 12% (white powder); $^1$H NMR (δ ppm, CDCl$_3$): 8.14 (s, 1H), 7.60 (dd, J=0.7 Hz, 1.7 Hz, 1H), 7.16 (dd, J=0.7 Hz, 3.3 Hz, 1H), 6.57 (dd, J=1.7 Hz, 3.3 Hz, 1H), 6.07 (s, 1H), 5.67 (brs, 2H), 3.47–3.72 (m, 8H); Mass (m/z): 313 (M$^+$); IR (KBr, cm$^{-1}$): 1653, 1649, 1610, 1558, 1439; Melting point: >270° C.

EXAMPLE 114

5-Amino-7-(cis-3,5-dimethylpiperazinyl)-2-(2-furyl)[1,2,4]triazolo[1,5-c]pyrimidine (Compound 114)

Yield: 73% (light brown powder); $^1$H NMR (δ ppm, CDCl$_3$): 7.58 (dd, J=0.7 Hz, 1.7 Hz, 1H), 7.15 (dd, J=0.7 Hz, 3.3 Hz, 1H), 6.56 (dd, J=1.7 Hz, 3.3 Hz, 1H), 6.01 (s, 1H), 5.61 (brs, 2H), 4.12 (d, J=12.2 Hz, 2H), 2.86–3.00 (m, 2H), 2.43 (dd, J=10.6 Hz, 12.2 Hz, 2H), 1.15 (d, J=6.3 Hz, 6H); Mass (m/z): 313 (M$^+$); IR (KBr, cm$^{-1}$): 1687, 1653, 1633, 1558, 1506; Melting point: 212° C. (decomposed).

EXAMPLE 115

5-Amino-7-(cis-3,5-dimethyl-4-methylpiperazinyl)-2-(2-furyl)[1,2,4]triazolo[1,5-c]pyrimidine hydrochloride (Compound 115)

Yield: 14% (white powder); Mass (m/z): 327 (M$^+$); IR (KBr, cm$^{-1}$): 1684, 1650, 1646, 1636, 1504; Melting point: 253° C. (decomposed); Elemental analysis: C$_{15}$H$_{19}$N$_7$O$_2$ 1,5HCl 2.0H$_2$O; Found (%): C, 46.03, H, 6.39, N, 23.32; Calcd.(%): C, 45.96, H, 6.39, N, 23,45.

EXAMPLE 116

5-Amino-7-(4-benzyl-cis-3,5-dimethylpiperazinyl)-2-(2-furyl)[1,2,4]triazolo[1,5-c]pyrimidine (Compound 116)

Yield: 29% (white powder); $^1$H NMR (δ ppm, CDCl$_3$): 7.58 (dd, J=0.7 Hz, 1.7 Hz, 1H), 7.22–7.41 (m, 5H), 7.15 (dd, J=0.7 Hz, 3.3 Hz, 1H), 6.56 (dd, J=1.7 Hz, 3.3 Hz, 1H), 5.99 (s, 1H), 5.56 (brs, 2H), 4.01 (d, J=12.2 Hz, 2H), 3.85 (s, 2H), 2.63–2.89 (m, 4H), 1.12 (d, J=5.6 Hz, 6H); Mass (m/z): 403 (M$^+$); IR (KBr, cm$^{-1}$): 1668, 1652, 1646, 1606, 1558; Melting point: 195–196° C.

EXAMPLE 117

5-Amino-7-(cis-3,5-dimethyl-4-(2-methoxyethyl)piperazinyl)-2-(2-furyl)[1,2,4]triazolo[1,5-c]pyrimidine (Compound 117)

Yield: 65% (white powder); $^1$H NMR (δ ppm, CDCl$_3$): 7.58 (dd, J=0.7 Hz, 1.7 Hz, 1H), 7.14 (dd, J=0.7 Hz, 3.3 Hz, 1H), 6.55 (dd, J=1.7 Hz, 3.3 Hz, 1H), 5.99 (s, 1H), 5.61 (brs, 2H), 4.00 (d, J=10.6 Hz, 2H), 3,44 (t, J=6.6 Hz, 2H), 3.34 (s, 3H), 2.92 (t, J=6.6 Hz, 2H), 2.62–2.74 (m, 4H), 1.17 (d, J=5.9 Hz, 6H); Mass (m/z): 371 (M$^+$); IR (KBr, cm$^{-1}$): 1654, 1612, 1557, 1448; Melting point: 179–180° C.; Elemental analysis: C$_{18}$H$_{25}$N$_7$O$_2$; Found (%): C, 58.06, H, 6.98, N, 26.42; Calcd.(%): C, 58.21, H, 6.78, N, 26.40.

EXAMPLE 118

5-Amino-7-(4-(2-benzyloxyethyl)-cis-3,5-dimethylpiperazinyl)-2-(2-furyl)[1,2,4]triazolo[1,5-c]pyrimidine (Compound 118)

Yield: 24% (white powder); $^1$H NMR (δ ppm, CDCl$_3$): 7.58 (dd, J=0.7 Hz, 1.7 Hz, 1H), 7.28–7.34 (m, 5H), 7.15 (dd, J=0.7 Hz, 3.3 Hz, 1H), 6.55 (dd, J=1.7 Hz, 3.3 Hz, 1H), 5.98 (s, 1H), 5.59 (brs, 2H), 4.51 (s, 2H), 3.99 (d, J=11.5 Hz, 2H), 3.54 (t, J=6.6 Hz, 2H), 2.99 (t, J=6.6 Hz, 2H), 2.61–2.72 (m, 4H), 1.16 (d, J=5.9 Hz, 6H); Mass (m/z): 447 (M$^+$); IR (KBr, cm$^-$): 1653, 1606, 1556; Melting point: 135° C.; Elemental analysis: C$_{24}$H$_{29}$N$_7$O$_2$; Found (%): C, 64.61, H, 6.76, N, 21.99; Calcd.(%): C, 64.41, H, 6.53, N, 21.91.

EXAMPLE 119

5-Amino-7-(cis-3,5-dimethyl-4-(3-phenylpropyl)piperazinyl)-2-(2-furyl)[1,2,4]triazolo[1,5-c]pyrimidine (Compound 119)

Yield: 57% (ocher powder); $^1$H NMR (δ ppm, CDCl$_3$): 7.57 (dd, J=0.7 Hz, 1.7 Hz, 1H), 7.31–7.14 (m, 6H), 6.54 (dd, J=0.7 Hz, 3.3 Hz, 1H), 5.97 (s, 1H), 5.72 (brs, 2H), 3.99 (d, J=8.6 Hz, 2H), 2.81 (d, J=8.6 Hz, 2H), 2.71–2.61 (m, 4H), 2.55 (t, J=7.9 Hz, 2H), 1.65–1.79 (m, 2H), 1.07 (d, J=5.3 Hz, 6H); Mass (m/z): 431 (M$^+$); IR (KBr, cm$^{-1}$): 1668, 1653, 1603, 1558; Melting point: 154–155° C.; Elemental analysis: C$_{24}$H$_{29}$N$_7$O 0.1C$_6$H$_{12}$; Found (%): C, 66.98, H, 7.12, N, 22.33; Calcd.(%): C, 67.16, H, 6.92, N, 22.29.

EXAMPLE 120

5-Amino-7-(cis-3,5-dimethyl-4-(2-hydroxyethyl)piperazinyl)-2-(2-furyl)[1,2,4]triazolo[1,5-c]pyrimidine (Compound 120)

In 6 ml of methylene chloride, 1.29 g (2.88 mmol) of Compound 118 obtained in Example 118 was dissolved, and 6 ml of dimethyl sulfide and 4 ml (28.8 mmol) of a borone trifluoride ether complex were added thereto, followed by stirring at room temperature for 42 hours. After completion of the reaction, the reaction solution was extracted by adding chloroform and saturated aqueous sodium bicarbonate, and the organic layer was dried over anhydrous magnesium sulfate. After evaporation of the solvent under reduced pressure, the resulting residue was recrystallized from ethanol to give 602 mg (yield: 59%) of Compound 120 as white powder.

$^1$H NMR (δ ppm, CDCl$_3$): 7.58 (dd, J=0.7 Hz, 1.7 Hz, 1H), 7.15 (dd, J=0.7 Hz, 3.3 Hz, 1H), 6.55 (dd, J=1.7 Hz, 3.3 Hz, 1H), 5.99 (s, 1H), 5.66 (brs, 2H), 3.96 (d, J=10.9 Hz, 2H), 3.61 (dt (broad), 2H), 2.67–2.82 (m, 6H), 2.46 (brt, 1H), 1.16 (d, J=5.9 Hz, 6H); Mass (m/z): 357 (M$^+$); IR (KBr, cm$^{-1}$): 3418, 1647, 1616, 1562, 1516, 1485, 1444, 1217; Melting point: 207–209° C.; Elemental analysis: C$_{17}$H$_{23}$N$_7$O$_2$; Found (%): C, 57.30, H, 6.58, N, 27.55; Calcd.(%): C, 57.13, H, 6.49, N, 27.43.

EXAMPLE 121

5-Amino-2-(2-furyl)-7-thiomorpholino[1,2,4]triazolo[1,5-c]pyrimidine (Compound 121)

Example 121 was carried out using Compound 61 obtained in Example 61 and thiomorpholine in the same manner as in Example 62 to give Compound 121.

Yield: 34% (white powder); $^1$H NMR (δ ppm, CDCl$_3$): 7.59 (dd, J=0.7 Hz, 1.7 Hz, 1H), 7.15 (dd, J=0.7 Hz, 3.3 Hz, 1H), 6.56 (dd, J=1.7 Hz, 3.3 Hz, 1H), 6.01 (s, 1H), 5.62 (brs, 2H), 3.95 (t, J=5.0 Hz, 4H), 2.67 (t, J=5.0 Hz, 4H); Mass (m/z): 302 (M$^+$); IR (KBr, cm$^{-1}$): 1658, 1647, 1608, 1508, 1442, 1415, 1223, 1207; Melting point: 253–255° C.; Elemental analysis: C$_{13}$H$_{14}$N$_6$OS; Found (%): C, 49.87, H, 4.54, N, 26.24; Calcd.(%): C, 49.57, H, 4.93, N, 26.68.

EXAMPLE 122

5-Amino-2-(2-furyl)-7-(4-hydroxypiperidinyl)[1,2,4]triazolo[1,5-c]pyrimidine (Compound 122)

Example 122 was carried out using Compound 61 obtained in Example 61 and 4-hydroxypiperidine in the same manner as in Example 62 to give Compound 122.

Yield: 44% (light brown needle crystals); $^1$H NMR ($\delta$ ppm, CDCl$_3$): 7.58 (dd, J=0.7 Hz, 1.7 Hz, 1H), 7.16 (dd, J=0.7 Hz, 3.3 Hz, 1H), 6.56 (dd, J=1.7 Hz, 3.3 Hz, 1H), 6.06 (s, 1H), 5.60 (brs, 2H), 3.90–4.09 (m, 3H), 3.15–3.29 (m, 2H), 1.91–2.05 (m, 2H), 1.51–1.66 (m, 3H); Mass (m/z): 300 (M$^+$); IR (KBr, cm$^{-1}$): 1653, 1612, 1558, 1444, 1219; Melting point: 207–208° C.; Elemental analysis: C$_{14}$H$_{16}$N$_6$O$_2$ 0.7C$_6$H$_5$CH$_3$ 0.1AcOEt; Found (%): C, 59.88, H, 5.84, N, 24.22; Calcd.(%): C, 59.71, H, 5.83, N, 24.29.

Examples 123 to 132 were carried out below using Compound 43 obtained in Example 43 and various alkyl halides or trifluoromethanesulfonates in the same manner as in Example 46 to give Compounds 123 to 132.

EXAMPLE 123

5-Amino-2-(2-furyl)-7-(4-propylpiperazinyl)[1,2,4]triazolo[1,5-c]pyrimidine (Compound 123)

Yield: 53% (ocher powder); $^1$H NMR ($\delta$ ppm, CDCl$_3$): 7.58 (dd, J=0.7 Hz, 1.7 Hz, 1H), 7.15 (dd, J=0.7 Hz, 3.3 Hz, 1H), 6.55 (dd, J=1.7 Hz, 3.3 Hz, 1H), 6.02 (s, 1H), 5.67 (brs, 2H), 3.56 (t, J=5.0 Hz, 4H), 2.53 (t, J=5.0 Hz, 4H), 2.35 (t, J=7.6 Hz, 2H), 1.51–1,59 (m, 2H), 0.93 (t, J=7.6 Hz, 3H); Mass (m/z): 327 (M$^+$); IR (KBr, cm$^{-1}$): 1660, 1606, 1568, 1440, 1417, 1223; Melting point: 191–192° C.; Elemental analysis: C$_{16}$H$_{21}$N$_7$O; Found (%): C, 58.29, H, 6.63, N, 30.07; Calcd.(%): C, 58.70, H, 6.47, N, 29.95.

EXAMPLE 124

5-Amino-7-(4-allylpiperazinyl)-2-(2-furyl)[1,2,4]triazolo[1,5-c]pyrimidine (Compound 124)

Yield: 60% (white powder); $^1$H NMR ($\delta$ ppm, CDCl$_3$): 7.58 (dd, J=0.7 Hz, 1.7 Hz, 1H), 7.15 (dd, J=0.7 Hz, 3.3 Hz, 1H), 6.55 (dd, J=1.7 Hz, 3.3 Hz, 1H), 6.03 (s, 1H), 5.89 (ddd, J=6.6 Hz, 10.2 Hz, 17.2 Hz, 1H), 5.77 (brs, 2H), 5.23 (dd, J=1.7 Hz, 17.2 Hz, 1H), 5.20 (dd, J=1.7 Hz, 10.2 Hz, 1H), 3.57 (t, J=5.0 Hz, 4H), 3.05 (d, J=6.6 Hz, 2H), 2.54 (t, J=5.0 Hz, 4H); Mass (m/z): 325 (M$^+$); IR (KBr, cm$^{-1}$): 1666, 1653, 1606, 1553, 1444, 1226; Melting point: 210–211° C.; Elemental analysis: C$_{16}$H$_{19}$N$_7$O 0.2H$_2$O; Found (%): C, 58.83, H, 5.85, N, 30.15; Calcd.(%): C, 59.06, H, 5.89, N, 30.14.

EXAMPLE 125

5-Amino-2-(2-furyl)-7-(4-homoallylpiperazinyl)[1,2,4]triazolo[1,5-c]pyrimidine (Compound 125)

Yield: 51% (white powder); $^1$H NMR ($\delta$ ppm, CDCl$_3$): 7.58 (dd, J=0.7 Hz, 1.7 Hz, 1H), 7.15 (dd, J=0.7 Hz, 3.3 Hz, 1H), 6.55 (dd, J=1.7 Hz, 3.3 Hz, 1H), 6.03 (s, 1H), 5.83 (ddd, J=6.6 Hz, 10.2 Hz, 17.2 Hz, 1H), 5.69 (brs, 2H), 5.09 (dd, J=1.7 Hz, 17.2 Hz, 1H), 5.03 (dd, J=1.7 Hz, 10.2 Hz, 1H), 3.58 (t, J=5.0 Hz, 4H), 2.57 (t, J=5.0 Hz, 4H), 2.53–2.45 (m, 2H), 2.34–2.04 (m, 2H); Mass (m/z): 339 (M$^+$); IR (KBr, cm$^{-1}$): 1670, 1655, 1651, 1606, 1556, 1443, 1417, 1242, 1225; Melting point: 185° C.; Elemental analysis: C$_{17}$H$_{21}$N$_7$O 0.2H$_2$O; Found (%): C, 59.52, H, 6.27, N, 28.72; Calcd.(%): C, 59.53, H, 6.29, N, 28.58.

EXAMPLE 126

5-Amino-7-(4-(2-fluoroethyl)piperazinyl)-2-(2-furyl)[1,2,4]triazolo[1,5-c]pyrimidine (Compound 126)

Yield: 54% (white powder); $^1$H NMR ($\delta$ ppm, CDCl$_3$): 7.58 (dd, J=0.7 Hz, 1.7 Hz, 1H), 7.15 (dd, J=0.7 Hz, 3.3 Hz, 1H), 6.55 (dd, J=1.7 Hz, 3.3 Hz, 1H), 6.03 (s, 1H), 5.66 (brs, 2H), 4.61 (dt, J=47.5 Hz, 5.0 Hz, 2H), 3.59 (t, J=5.0 Hz, 4H), 2.75 (dt, J=28.4 Hz, 5.0 Hz, 2H), 2.64 (t, J=5.0 Hz, 4H); Mass (m/z): 331 (M$^+$); IR (KBr, cm$^{-1}$): 1653, 1608, 1558, 1446; Melting point: 219° C.; Elemental analysis: C$_{15}$H$_{18}$N$_7$OF; Found (%): C, 53,40, H, 5.44, N, 29.04; Calcd.(%): C, 53.50, H, 5.57, N, 29.11.

EXAMPLE 127

5-Amino-7-(4-(3-fluoropropyl)piperazinyl)-2-(2-furyl)[1,2,4]triazolo[1,5-c]pyrimidine (Compound 127)

Yield: 62% (white powder); $^1$H NMR ($\delta$ ppm, CDCl$_3$): 7.58 (dd, J=0.7 Hz, 1.7 Hz, 1H), 7.16 (dd, J=0.7 Hz, 3.3 Hz, 1H), 6.55 (dd, J=1.7 Hz, 3.3 Hz, 1H), 6.03 (s, 1H), 5.74 (brs, 2H), 4.53 (dt, J=47.2 Hz, 5.9 Hz, 2H), 3.55 (t, J=5.0 Hz, 4H), 2.53 (t, J=5.0 Hz, 4H), 2.52 (t, J=7.6 Hz, 2H), 1.91 (dtt, J=25.4 Hz, 5.9 Hz, 7.6 Hz, 2H); Mass (m/z): 345 (M$^+$); IR (KBr, cm$^{-1}$): 1659, 1614, 1558, 1442, 1417, 1223; Melting point: 201–202° C.; Elemental analysis: C$_{16}$H$_{20}$N$_7$OF; Found (%): C, 54.37, H, 5.84, N, 27.62; Calcd.(%): C, 54.22, H, 5.97, N, 27.67.

EXAMPLE 128

5-Amino-7-(4-(4-fluorobutyl)piperazinyl)-2-(2-furyl)[1,2,4]triazolo[1,5-c]pyrimidine (Compound 128)

Yield: 40% (ocher powder); $^1$H NMR ($\delta$ ppm, CDCl$_3$): 7.58 (dd, J=0.7 Hz, 1.7 Hz, 1H), 7.15 (dd, J=0.7 Hz, 3.3 Hz, 1H), 6.55 (dd, J=1.7 Hz, 3.3 Hz, 1H), 6.03 (s, 1H), 5.62 (brs, 2H), 4.48 (dt, J=47.5 Hz, 5.9 Hz, 2H), 3.56 (t, J=5.0 Hz, 4H), 2.53 (t, J=5.0 Hz, 4H), 2.43 (t, J=7.3 Hz, 2H), 1.62–1.81 (m, 4H); Mass (m/z): 359 (M$^+$); IR (KBr, cm$^{-1}$): 1658, 1655, 1564, 1560, 1442, 1227; Melting point: 120–123° C.; Elemental analysis: C$_{17}$H$_{22}$N$_7$OF 0.2H$_2$O; Found (%): C, 55.99, H, 6.25, N, 27.25; Calcd.(%): C, 56.25, H, 6.22, N, 27.01.

EXAMPLE 129

5-Amino-2-(2-furyl)-7-(4-(2,2,2-trifluoroethyl)piperazinyl)[1,2,4]triazolo[1,5-c]pyrimidine (Compound 129)

Yield: 50% (white plate crystals); $^1$H NMR ($\delta$ ppm, CDCl$_3$): 7.59 (dd, J=0.7 Hz, 1.7 Hz, 1H), 7.16 (dd, J=0.7 Hz, 3.3 Hz, 1H), 6.56 (dd, J=1.7 Hz, 3.3 Hz, 1H), 6.03 (s, 1H), 5.62 (brs, 2H), 3.58 (t, J=5.0 Hz, 4H), 3.03 (q, J=9.6 Hz, 2H), 2.77 (t, J=5.0 Hz, 4H); Mass (m/z): 367 (M$^+$); IR (KBr, cm$^{-1}$): 1678, 1657, 1610, 1558, 1271, 1153; Melting point: 249–251° C.; Elemental analysis: C$_{15}$H$_{16}$N$_7$OF$_3$; Found (%): C, 49.19, H, 4.36, N, 27.04; Calcd.(%): C, 49.05, H, 4.34, N, 26.69.

EXAMPLE 130

5-Amino-7-(4-(3-cyclohexylpropyl)piperazinyl)-2-(2-furyl)[1,2,4]triazolo[1,5-c]pyrimidine (Compound 130)

Yield: 70% (light yellow needle crystals); $^1$H NMR ($\delta$ ppm, CDCl$_3$): 7.58 (dd, J=0.7 Hz, 1.7 Hz, 1H), 7.14 (dd, J=0.7 Hz, 3.3 Hz, 1H), 6.55 (dd, J=1.7 Hz, 3.3 Hz, 1H), 6.02 (s, 1H), 5.62 (brs, 2H), 3.56 (t, J=5.0 Hz, 4H), 2.52 (t, J=5.0 Hz, 4H), 2,35 (t, J=7.6 Hz, 2H), 1.45–1.86 (m, 7H), 1.09–1.35 (m, 6H), 0.80–1.04 (m, 2H); Mass (m/z): 409 (M$^+$); IR (KBr, cm$^{-1}$): 1652, 1610, 1552, 1444, 1240; Melting point: 189° C.; Elemental analysis: $C_{22}H_{31}N_7O$; Found (%): C, 64.81, H, 7.88, N, 24.50; Calcd.(%): C, 64.52, H, 7.63, N, 23.94.

EXAMPLE 131

7-(4-Acetonylpiperazinyl)-5-amino-2-(2-furyl)[1,2,4]triazolo[1,5-c]pyrimidine (Compound 131)

Yield: 35% (white powder); $^1$H NMR (δ ppm, CDCl$_3$): 7.59 (dd, J=0.7 Hz, 1.7 Hz, 1H), 7.16 (dd, J=0.7 Hz, 3.3 Hz, 1H), 6.56 (dd, J=1.7 Hz, 3.3 Hz, 1H), 6.03 (s, 1H), 5.61 (brs, 2H), 3.61 (t, J=5.0 Hz, 4H), 3.27 (s, 2H), 2.59 (t, J=5.0 Hz, 4H), 2.19 (s, 3H); Mass (m/z): 341 (M$^+$); IR (KBr, cm$^{-1}$): 1653, 1610, 1558, 1417, 1230; Melting point: 167° C.;

EXAMPLE 132

5-Amino-2-(2-furyl)-7-(4-(3-oxo-3-phenylpropyl)piperazinyl)[1,2,4]triazolo[1,5-c]pyrimidine (Compound 132)

Yield: 31% (light yellow powder); $^1$H NMR (δ ppm, CDCl$_3$): 7.98 (d, J=6.9 Hz, 2H), 7.58 (dd, J=0.7 Hz, 1.7 Hz, 1H), 7.57 (d, J=7.3 Hz, 1H), 7.48 (dd, J=6.9 Hz, 7.3 Hz, 2H), 7.15 (dd, J=0.7 Hz, 3.3 Hz, 1H), 6.56 (dd, J=1.7 Hz, 3.3 Hz, 1H), 6.03 (s, 1H), 5.63 (brs, 2H), 3.57 (t, J=5.0 Hz, 4H), 3.24 (t, J=7.3 Hz, 2H), 2.90 (t, J=7.3 Hz, 2H), 2.61 (t, J=5.0 Hz, 4H); Mass (m/z): 417 (M$^+$); IR (KBr, cm$^{-1}$): 1670, 1653, 1606, 1560, 1446, 1417, 1226; Melting point: 181–183° C.; Elemental analysis: $C_{22}H_{23}N_7O_2$ 0.1$C_6H_5CH_3$; Found (%): C, 63.67, H, 5.73, N, 23.16; Calcd.(%): C, 63.90, H, 5.62, N, 22.98.

EXAMPLE 133

(±)-5-Amino-2-(2-furyl)-7-(4-(3-hydroxy-3-phenylpropyl)piperazinyl)[1,2,4]triazolo[1,5-c]pyrimidine (Compound 133)

Compound 133 was obtained using Compound 132 obtained in Example 132 in the same manner as in Example 111.

Yield: 39% (white powder); $^1$H NMR (δ ppm, CDCl$_3$): 7.59 (dd, J=0.7 Hz, 1.7 Hz, 1H), 7.26–7.39 (m, 5H), 7.16 (dd, J=0.7 Hz, 3.3 Hz, 1H), 6.56 (dd, J=1.7 Hz, 3.3 Hz, 1H), 6.05 (s, 1H), 5.60 (s(br), 2H), 4.98 (t, J=6.8 Hz, 1H), 3.63 (t, J=5.0 Hz, 4H), 2.55–2.88 (m, 6H), 1.88–2.01 (m, 2H) Mass (m/z): 419 (M$^+$); IR (KBr, cm$^{-1}$): 1653, 1612, 1558, 1442, 1417, 1224; Melting point: 159–160° C.; Elemental analysis: $C_{22}H_{25}N_7O_2$ 0.3$H_2O$; Found (%): C, 62.15, H, 6.04, N, 22.92; Calcd.(%): C, 62.19, H, 6.07, N, 23.08.

EXAMPLE 134

5-Amino-2-(2-furyl)-7-(4-(1-oxo-3-phenylpropyl)piperazinyl)[1,2,4]triazolo[1,5-c]pyrimidine (Compound 134)

Compound 134 was obtained using Compound 43 obtained in Example 43 in the same manner as in Example 44.

Yield: 27% (white powder); $^1$H NMR (δ ppm, CDCl$_3$): 7.59 (dd, J=0.7 Hz, 1.7 Hz, 1H), 7.18–7.33 (m, 5H), 7.16 (dd, J=0.7 Hz, 3.3 Hz, 1H), 6.56 (dd, J=1.7 Hz, 3.3 Hz, 1H), 5.99 (s, 1H), 5.66 (brs, 2H), 3.75 (t, J=5.0 Hz, 2H), 3.51 (t, J=5.0 Hz, 2H), 3,44–3.53 (m, 4H), 3.01 (t, J=7.75 Hz, 2H), 2.67 (t, J=7.75 Hz, 2H); Mass (m/z): 417 (M$^+$); IR (KBr, cm$^{-1}$): 1653, 1645, 1610, 1558, 1446, 1437; Melting point: 178° C.; Elemental analysis: $C_{22}H_{23}N_7O_2$; Found (%): C, 63.31, H, 5.67, N, 23.30; Calcd.(%): C, 63.30, H, 5.55, N, 23,49.

EXAMPLE 135

5-Amino-7-(4-butylpiperazinyl)-2-(2-furyl)[1,2,4]triazolo[1,5-c]pyrimidine (Compound 135)

In 10 ml of methylene chloride and 1 ml of acetic acid, 500 mg (1.75 mmol) of Compound 43 obtained in Example 43 was dissolved, and 1.6 ml (17.5 mmol) of n-butyraldehyde and 740 mg (3.5 mmol) of sodium triacetate borohydride were added thereto, followed by stirring at room temperature for 22 hours. After completion of the reaction, the reaction solution was extracted by adding chloroform and a 2 N aqueous sodium hydroxide solution, and the organic layer was dried over anhydrous magnesium sulfate. After evaporation of the solvent under reduced pressure, the resulting residue was purified by silica gel column chromatography [chloroform-methanol (99:1–95:5), gradation], and recrystallized from ethyl acetate-hexane to give 270 mg (yield: 45%) of Compound 135 as white powder.

$^1$H NMR (δ ppm, CDCl$_3$): 7.58 (dd, J=0.7 Hz, 1.7 Hz, 1H), 7.14 (dd, J=0.7 Hz, 3.3 Hz, 1H), 6.55 (dd, J=1.7 Hz, 3.3 Hz, 1H), 6.03 (s, 1H), 5.60 (brs, 2H), 3.57 (t, J=5.0 Hz, 4H), 2.53 (t, J=5.0 Hz, 4H), 2.38 (t, J=7.6 Hz, 2H), 1.28–1.70 (m, 4H), 0.94 (t, J=7.26 Hz, 3H); Mass (m/z): 341 (M$^+$); IR (KBr, cm$^{-1}$): 1655, 1608, 1560, 1439, 1225; Melting point: 217–223° C.; Elemental analysis: $C_{17}H_{23}N_7O$; Found (%): C, 59.71, H, 6.87, N, 28.72; Calcd.(%): C, 59.81, H, 6.79, N, 28.71.

Examples 136 to 141 were carried out below using Compound 43 obtained in Example 43 and various carbonyl compounds in the same manner as in Example 135 to give Compound 136 to 141.

EXAMPLE 136

5-Amino-2-(2-furyl)-7-(4-(2-methylpropyl)piperazinyl)[1,2,4]triazolo[1,5-c]pyrimidine (Compound 136)

Yield: 50% (light brown needle crystals); $^1$H NMR (δ ppm, CDCl$_3$): 7.58 (dd, J=0.7 Hz, 1.7 Hz, 1H), 7.15 (dd, J=0.7 Hz, 3.3 Hz, 1H), 6.55 (dd, J=1.7 Hz, 3.3 Hz, 1H), 6.02 (s, 1H), 5.67 (brs, 2H), 3.54 (t, J=5.0 Hz, 4H), 2.47 (t, J=5.0 Hz, 4H), 2.13 (d, J=7.3 Hz, 2H), 1.76–1.91 (m, 1H), 0.92 (d, J=6.6 Hz, 6H); Mass (m/z): 341 (M$^+$); IR (KBr, cm$^{-1}$): 1662, 1608, 1557, 1439, 1416, 1234, 1205; Melting point: 204° C.; Elemental analysis: $C_{17}H_{23}N_7O$ Found (%): C, 59.80, H, 6.90, N, 28.98; Calcd.(%): C, 59.81, H, 6.79, N, 28.72.

EXAMPLE 137

5-Amino-7-(4-(cyclopropylmethyl)piperazinyl)-2-(2-furyl)[1,2,4]triazolo[1,5-c]pyrimidine (Compound 137)

Yield: 46% (white powder); $^1$H NMR (δ ppm, CDCl$_3$): 7.58 (dd, J=0.7 Hz, 1.7 Hz, 1H), 7.15 (dd, J=0.7 Hz, 3.3 Hz, 1H), 6.55 (dd, J=1.7 Hz, 3.3 Hz, 1H), 6.03 (s, 1H), 5.61 (brs, 2H), 3.59 (t, J=5.0 Hz, 4H), 2.62 (t, J=5.0 Hz, 4H), 2.31 (d, J=6.6 Hz, 2H), 0.83–1.00 (m, 1H), 0.50–0.68 (m, 2H), 0.10–0.21 (m, 2H); Mass (m/z): 339 (M$^+$); IR (KBr, cm$^{-1}$):

1670, 1608, 1559, 1444, 1242; Melting point: 207–208° C.; Elemental analysis: $C_{17}H_{21}N_7O$; Found (%): C, 60.03, H, 6.35, N, 29.08; Calcd.(%): C, 60.16, H, 6.24, N, 28.89.

EXAMPLE 138

5-Amino-2-(2-furyl)-7-(4-(4-trifluoromethoxybenzyl)piperazinyl)[1,2,4]triazolo[1,5-c]pyrimidine (Compound 138)

Yield: 41% (white powder); $^1$H NMR ($\delta$ ppm, CDCl$_3$): 7.58 (dd, J=0.7 Hz, 1.7 Hz, 1H), 7.39 (d, J=8.6 Hz, 2H), 7.18 (d, J=8.6 Hz, 2H), 7.16 (dd, J=0.7 Hz, 3.3 Hz, 1H), 6.56 (dd, J=1.7 Hz, 3.3 Hz, 1H), 6.02 (s, 1H), 5.65 (s(br), 2H), 3.56 (t(br), 6H), 2.54 (brt, 4H); Mass (m/z): 459 (M$^+$); IR (KBr, cm$^{-1}$): 1674,1657, 1651, 1606, 1558, 1444, 1273, 1224, 1170; Melting point: 216° C.; Elemental analysis: $C_{21}H_{20}N_7O_2F_3$; Found (%): C, 54.81, H, 4.25, N, 21.18; Calcd.(%): C, 54.90, H, 4.39, N, 21.34.

EXAMPLE 139

5-Amino-2-(2-furyl)-7-(4-isopropylpiperazinyl)[1,2,4]triazolo[1,5-c]pyrimidine (Compound 139)

Yield: 65% (white powder); $^1$H NMR ($\delta$ ppm, CDCl$_3$): 7.58 (dd, J=0.7 Hz, 1.7 Hz, 1H), 7.15 (dd, J=0.7 Hz, 3.3 Hz, 1H), 6.55 (dd, J=1.7 Hz, 3.3 Hz, 1H), 6.02 (s, 1H), 5.64 (brs, 2H), 3.56 (t, J=5.0 Hz, 4H), 2.71 (q, J=6.6 Hz, 1H), 2.61 (t, J=5.0 Hz, 4H), 1.07 (d, J=6.6 Hz, 6H); Mass (m/z): 327 (M$^+$) IR (KBr, cm$^{-1}$): 1668, 1647, 1614, 1603, 1444, 1233, 1205; Melting point: 221–222° C.; Elemental analysis: $C_{16}H_{21}N_7O$; Found (%): C, 58.60, H, 6.60, N, 30.34; Calcd.(%): C, 58.70, H, 6.47, N, 29.95.

EXAMPLE 140

($\pm$)-5-Amino-2-(2-furyl)-7-(4-(1-methylpropyl)piperazinyl)[1,2,4]triazolo[1,5-c]pyrimidine (Compound 140)

Yield: 33% (white powder); $^1$H NMR ($\delta$ ppm, CDCl$_3$): 7.58 (dd, J=0.7 Hz, 1.7 Hz, 1H), 7.15 (dd, J=0.7 Hz, 3.3 Hz, 1H), 6.55 (dd, J=1.7 Hz, 3.3 Hz, 1H), 6.02 (s, 1H), 5.63 (brs, 2H), 3.54 (t, J=5.0 Hz, 4H), 2.46–2.67 (m, 5H), 1.54–1.64 (m, 1H), 1.26–1.37 (m, 1H), 0.99 (d, J=6.6 Hz, 3H), 0.92 (t, J=7.6 Hz, 3H); Mass (m/z): 341 (M$^+$); IR (KBr, cm$^{-1}$): 1653, 1606, 1562, 1558, 1444, 1205; Melting point: 197–198° C.; Elemental analysis: $C_{17}H_{23}N_7O$; Found (%): C, 59.78, H, 6.90, N, 29.22; Calcd.(%): C, 59.81, H, 6.79, N, 28.72.

EXAMPLE 141

($\pm$)-5-Amino-2-(2-furyl)-7-(4-((2-methoxy-1-methyl)ethyl)piperazinyl)[1,2,4]triazolo[1,5-c]pyrimidine (Compound 141)

Yield: 44% (white powder); $^1$H NMR ($\delta$ ppm, CDCl$_3$): 7.58 (dd, J=0.7 Hz, 1.7 Hz, 1H), 7.16 (dd, J=0.7 Hz, 3.3 Hz, 1H), 6.55 (dd, J=1.7 Hz, 3.3 Hz, 1H), 6.02 (s, 1H), 5.74 (s(br), 2H), 3.55 (t, J=5.0 Hz, 4H), 3,46 (d, J=5.9 Hz, 2H), 3.35 (s, 3H), 2.84 (dq, J=5.9, 6.6 Hz, 1H), 2.67 (t, J=5.0 Hz, 4H), 1.06 (d, 6.6 Hz, 3H); Mass (m/z): 357 (M$^+$); IR (KBr, cm$^{-1}$): 3128, 1668, 1606, 1552, 1446, 1417, 1230, 769; Melting point: 186–187° C.; Elemental analysis: $C_{17}H_{23}N_7O_2$; Found (%): C, 57.18, H, 6.40, N, 27.53; Calcd.(%): C, 57.13, H, 6.49, N, 27.43.

Examples 142 to 144 were carried out below using Compound 61 and various piperazine derivatives in the same manner as in Example 62 to give Compounds 142 to 144.

EXAMPLE 142

5-Amino-2-(2-furyl)-7-(4-(2-methylthiazol-4-ylmethyl)piperazinyl)[1,2,4]triazolo[1,5-c]pyrimidine (Compound 142)

Yield: 24% (light brown solid); $^1$H NMR ($\delta$ ppm, CDCl$_3$): 7.63 (d, J=1.0 Hz, 1H), 7.20 (d, J=3.3 Hz, 1H), 7.02 (brs, 1H), 6.60 (dd, J=3.4 Hz, 1.8 Hz, 1H), 6.06 (brs, 1H), 5.69 (brs, 2H), 3.72 (s, 2H), 3.64 (t, J=5.1 Hz, 4H), 2.77 (s, 3H), 2.65 (t, J=5.1 Hz, 4H); Mass (m/z): 396 (M$^+$); IR (KBr, cm$^{-1}$): 1654, 1608, 1558, 1220; Melting point: 197–198° C.; Elemental analysis: $Cl_8H_{20}N_8OS$; Found (%): C, 54.27, H, 5.10, N, 28.46; Calcd.(%): C, 54.53, H, 5.08, N, 28.26.

EXAMPLE 143

5-Amino-2-(2-furyl)-7-(4-(1,2,3-thiadiazol-4-ylmethyl)piperazinyl)-2-(2-furyl)[1,2,4]triazolo[1,5-c]pyrimidine (Compound 143)

Yield: 38% (light brown solid); $^1$H NMR ($\delta$ ppm, DMSO-d$_6$): 9.15 (s, 1H), 7.86 (dd, J=1.7 Hz, 0.7 Hz, 1H), 7.60 (brs, 2H), 7.06 (dd, J=3.3 Hz, 0.7 Hz, 1H), 6.66 (dd, J=3.5 Hz, 1.8 Hz, 1H), 6.02 (s, 1H), 4.16 (s, 2H), 3.53 (t, J=4.6 Hz, 4H), 2.54 (t, J=5.2 Hz, 4H); Mass (m/z): 383 (M$^+$); IR (KBr, cm$^{-1}$): 1668, 1606, 1567, 1443; Melting point: 210–212° C.; Elemental analysis: $C_{16}H_{17}N_9OS$ 0.4H$_2$O; Found (%): C, 49.43, H, 4.67, N, 31.84; Calcd.(%): C, 49.20, H, 4.59, N, 32.27.

EXAMPLE 144

5-Amino-2-(2-furyl)-7-(4-(1,2,3-thiadiazol-5-ylmethyl)piperazinyl)[1,2,4]triazolo[1,5-c]pyrimidine (Compound 144)

Yield: 30% (light brown solid); $^1$H NMR ($\delta$ ppm, DMSO-d$_6$): 8.90 (s, 1H), 7.86 (dd, J=1.7 Hz, 0.7 Hz, 1H), 7.60 (brs, 2H), 7.06 (dd, J=3.3 Hz, 0.7 Hz, 1H), 6.66 (dd, J=3.5 Hz, 1.8 Hz, 1H), 6.02 (s, 1H), 4.06 (s, 2H), 3.53 (t, J=4.6 Hz, 4H), 2.54 (t, J=5.2 Hz, 4H); Mass (m/z): 383 (M$^+$); IR (KBr, cm$^{-1}$): 1653, 1610, 1513, 1223; Melting point: 216–218° C.;

Compound 145 was obtained using Compound 43 and 2-methylthiazol-5-ylmethanol methanesulfonate in the same manner as in Example 46.

EXAMPLE 145

5-Amino-2-(2-furyl)-7-(4-(2-methylthiazol-5-ylmethyl)piperazinyl)[1,2,4]triazolo[1,5-c]pyrimidine (Compound 145)

Yield: 49% (light brown solid); $^1$H NMR ($\delta$ ppm, CDCl$_3$): 7.58 (d, J=1.0 Hz, 1H), 7.42 (s, 1H), 7.15 (d, J=2.6 Hz, 1H), 6.55 (dd, J=3.5 Hz, 1.8 Hz, 1H), 6.02 (brs, 1H), 5.65 (brs, 2H), 3.72 (s, 2H), 3.56 (t, J=4.9 Hz, 4H), 2.77 (s, 3H), 2.56 (t, J=5.1 Hz, 4H); FAB-Mass (m/z): 397 ((M+1)$^+$); IR (KBr, cm$^{-1}$): 1653, 1608, 1562, 1225; Melting point: 95–97° C.

Examples 146 to 150 were carried out below using Compound 43 obtained in Example 43 and various carbonyl compounds in the same manner as in Example 135 to give Compounds 146 to 150.

EXAMPLE 146

5-Amino-2-(2-furyl)-7-(4-(3-thienyl)piperazinyl)[1,2,4]triazolo[1,5-c]pyrimidine (Compound 146)

Yield: 61% (white solid); $^1$H NMR (δ ppm, DMSO-d$_6$): 7.86 (d, J=1.0 Hz, 1H), 7.59 (brs, 2H), 7.50 (dd, J=5.0 Hz, 3.0 Hz, 1H), 7.34 (s, 1H), 7.07 (d, J=3.3 Hz, 1H), 7.06 (d, J=3.6 Hz, 1H), 6.67 (dd, J=3.3 Hz, 1.6 Hz, 1H), 6.00 (s, 1H), 3.53 (t, J=4.6 Hz, 4H), 3.52 (s, 2H), 2.50 (t, J=5.2 Hz, 4H); FAB-Mass (m/z): 382 ((M+1)$^+$); IR (KBr, cm$^{-1}$): 1650, 1608, 1556, 1236; Melting point: 231–232° C.; Elemental analysis: $C_{18}H_{19}N_7OS$ 0.2H$_2$O; Found (%): C, 56.08, H, 5.09, N, 25.52; Calcd.(%): C, 56.15, H, 5.08, N, 25.46.

EXAMPLE 147

5-Amino-2-(2-furyl)-7-(4-(pyrrol-2-ylmethyl)piperazinyl)[1,2,4]triazolo[1,5-c]pyrimidine (Compound 147)

Yield: 41% (light brown solid); $^1$H NMR (δ ppm, DMSO-d$_6$): 10.69 (brs, 1H), 7.86 (d, J=1.0 Hz, 1H), 7.60 (brs, 2H), 7.06 (dd, J=2.6 Hz, 1.0 Hz, 1H), 6.67 (d, J=2.0 Hz, 1H), 6.66 (d, J=2.0 Hz, 1H), 6.00 (s, 1H), 5.94 (d, J=2.6 Hz, 1H), 5.90 (s, 1H), 3.53 (t, J=4.6 Hz, 4H), 3.52 (s, 2H), 2.50 (t, J=5.2 Hz, 4H); FAB-Mass (m/z): 365 ((M+1)$^+$); IR (KBr, cm$^{-1}$): 1651, 1610, 1562, 1234; Melting point: 228–230° C.; Elemental analysis: $C_{18}H_{19}N_8O$ 0.5H$_2$O; Found (%): C, 58.26, H, 5.62, N, 29.80; Calcd.(%): C, 58.05, H, 5.41, N, 30.09.

EXAMPLE 148

5-Amino-2-(2-furyl)-7-(4-(1-methylimidazol-2-ylmethyl)piperazinyl)[1,2,4]triazolo[1,5-c]pyrimidine (Compound 148)

Yield: 44% (light brown solid); $^1$H NMR (δ ppm, CDCl$_3$): 7.86 (d, J=1.0 Hz, 1H), 7.60 (brs, 2H), 7.10 (s, 1H), 7.06 (d, J=3.3 Hz, 1H), 6.77 (d, J=1.3 Hz, 1H), 6.67 (dd, J=3.3 Hz, 1.6 Hz, 1H), 6.01 (s, 1H), 3.68 (s, 3H), 3.57 (s, 2H), 3,49 (t, J=4.0 Hz, 4H), 2.45 (t, J=5.2 Hz, 4H); FAB-Mass (m/z): 380 ((M+1)$^+$); IR (KBr, cm$^{-1}$): 1653, 1608, 1560, 1446; Melting point: 126–127° C.

EXAMPLE 149

5-Amino-2-(2-furyl)-7-(4-(pyrazol-3-ylmethyl)piperazinyl)[1,2,4]triazolo[1,5-c]pyrimidine (Compound 149)

Yield: 38% (white solid); $^1$H NMR (δ ppm, CDCl$_3$): 7 65 (d, J=1.3 Hz, 1H), 7.58 (d, J=1.0 Hz, 1H), 7.13 (d, J=3.3 Hz, 1H), 6.55 (dd, J=3.5 Hz, 1.8 Hz, 1H), 6.46 (s, 1H), 6.29 (s, 1H), 5.97 (s, 1H), 5.58 (brs, 2H), 3.67 (s, 2H), 3.58 (t, J=4.9 Hz, 4H), 2.60 (t, J=5.1 Hz, 4H); FAB-Mass (m/z): 366 ((M+1)$^+$); IR (KBr, cm$^{-1}$): 1651, 1614, 1565, 1228; Melting point: 228–230° C.

EXAMPLE 150

5-Amino-2-(2-furyl)-7-(4-(thiazol-2-ylmethyl)piperazinyl)[1,2,4]triazolo[1,5-c]pyrimidine (Compound 150)

Yield: 48% (light brown solid); $^1$H NMR (δ ppm, CDCl$_3$): 7.74 (d, J=3.3 Hz, 1H), 7.58 (d, J=0.8 Hz, 1H), 7.32 (d, J=3.3 Hz, 1H), 7.15 (d, J=2.6 Hz, 1H), 6.56 (dd, J=3.6 Hz, 2.0 Hz, 1H), 6.03 (s, 1H), 5.67 (brs, 2H), 3.94 (s, 2H), 3.60 (t, J=4.9 Hz, 4H), 2.69 (t, J=5.1 Hz, 4H); FAB-Mass (m/z): 383 ((M+1)$^+$); IR (KBr, cm$^{-1}$): 1653, 1608, 1556, 1227; Melting point: 80–82° C.

EXAMPLE 151

5-(3,4-Dimethoxybenzylamino)-2-(2-furyl)-8-(1-hydroxy-2-methylpropyl)[1,2,4]triazolo[1,5-c]pyrimidine (Compound 151)

In 10 ml of tetrahydrofuran, 1.5 g (3.95 mmol) of Compound 24 obtained in Example 24 was dissolved, and 17.2 ml (11.86 mmol) of a 0.69 M isopropylmagnesium bromide tetrahydrofuran solution was added dropwise thereto, followed by stirring at room temperature for 4 hours. The reaction solution was poured into an aqueous ammonium chloride solution under ice-cooling and then extracted with ethyl acetate. The organic phase was washed with an aqueous ammonium chloride solution, water and then a saturated brine and dried over anhydrous magnesium sulfate, the solvent was evaporated under reduced pressure, and a main product was isolated by silica gel column chromatography (elution solvent: chloroform) and then recrystallized from ethanol to give 0.92 g (yield: 55%) of Compound 151 as a white solid.

$^1$H NMR (δ ppm, CDCl$_3$): 7.84 (s, 1H), 7.60 (dd, J=1.7 Hz, 0.7 Hz, 1H), 7.21 (dd, J=3.3 Hz, 0.7 Hz, 1H), 6.99–6.95 (m, 2H), 6.85 (d, J=7.9 Hz, 1H), 6.57 (dd, J=3.3 Hz, 1.7 Hz, 1H), 6.42 (t, J=5.6 Hz, 1H), 4.76 (d, J=5.6 Hz, 2H), 4.55 (t, J=8.2 Hz, 1H), 3.89 (s, 3H), 3.88 (s, 3H), 3.12 (d, J=8.2 Hz, 1H), 2.38–2.31 (m, 1H), 1.12 (d, J=6.6 Hz, 3H), 0.89 (d, J=6.6 Hz, 3H); IR (KBr, cm$^{-1}$): 3323, 2962, 1626, 1238, 1026; Melting point: 136.0–137.4° C.

EXAMPLE 152

5-(3,4-Dimethoxybenzylamino)-2-(2-furyl)-8-(1-oxo-2-methylpropyl)[1,2,4]triazolo[1,5-c]pyrimidine (Compound 152)

In 20 ml of methylene chloride, 2.12 g (9.84 mmol) of pyridinium chlorochromate and 100 mg of silica gel were suspended, and 833 mg (1.97 mmol) of Compound 151 obtained in Example 151 which had been dissolved in 4 ml of methylene chloride was added dropwise thereto, followed by stirring at room temperature for 4 hours. Ether and anhydrous magnesium sulfate were added to the reaction mixture, followed by stirring at room temperature for 10 minutes, and the insoluble materials were removed by filtration. After evaporation of the filtrate under reduced pressure, the residue was purified by silica gel column chromatography (elution solvent: hexane-chloroform (1:4)) to give 551 mg (yield: 67%) of Compound 152 as a white solid.

1H NMR (δ ppm, CDCl$_3$): 8.75 (s, 1H), 7.62 (s, 1H), 7.29 (d, J=3.3 Hz, 1H), 6.99–6.84 (m, 4H), 6.60 (dd, J=3.3 Hz, 1.7 Hz, 1H), 4.84 (d, J=5.6 Hz, 2H), 4.21 (q, J=6.6 Hz, 1H), 1.25 (d, J=6.6 Hz, 6H); Mass (m/z): 421 (M$^+$); IR (KBr, cm$^{-1}$): 3354, 2970, 1632, 1518, 1234; Melting point: 154.8–155.2° C.

EXAMPLE 153

5-Amino-8-(1-oxo-2-methylpropyl)-2-(2-furyl)[1,2,4]triazolo[1,5-c]pyrimidine (Compound 153)

In 12 ml of trifluoroacetic acid, 794 mg (1.88 mmol) of Compound 152 obtained in Example 152 was dissolved, and 1.36 ml (15.37 mmol) of trifluoromethane-sulfonic acid was added thereto, followed by stirring at room temperature for 19 hours and then at 50° C. for 1.5 hours. The reaction mixture was cooled to room temperature, water and 4 N sodium hydroxide were added thereto, and the reaction mixture was extracted with chloroform. The organic phase was washed with a saturated brine and dried over anhydrous magnesium sulfate, the solvent was evaporated, and the residue was recrystallized from ethyl acetate-hexane to give 256 mg (yield: 50%) of Compound 153 as a white solid.

$^1$H NMR (δ ppm, DMSO-d$_6$): 9.09–8.90 (brs, 2H), 8.50 (s, 1H), 7.98 (d, J=0.7 Hz, 1H), 7.26 (d, J=3.3 Hz, 1H), 6.75 (dd, J=3.3 Hz, 1.7 Hz, 1H), 4.18 (septet, J=6.6 Hz, 1H), 1.14 (d, J=6.6 Hz, 6H); Mass (m/z): 271 (M$^+$); IR (KBr, cm$^{-1}$): 3490, 2831, 1657, 1512, 1230; Melting point: 255.7–258.0° C.; Elemental analysis: C$_{13}$H$_{13}$N$_5$O$_2$ 0.1EtOH; Found (%): C, 57.66, H, 5.01, N, 25.18; Calcd.(%): C, 57.47, H, 4.97, N, 25.35.

EXAMPLE 154

5-(3,4-Dimethoxybenzylamino)-2-(2-furyl)-8-(α-hydroxybenzyl)[1,2,4]triazolo[1,5-c]pyrimidine (Compound 154)

Compound 154 (1.35 g, yield: 75%) was obtained as a white solid using 1.5 g (3.95 mmol) of Compound 24 obtained in Example 24 by carrying out a procedure similar to that in Example 151.

$^1$H NMR (δ ppm, CDCl$_3$): 7.63–7.60 (m, 2H), 7.56–7.53 (m, 2H), 7.41–7.28 (m, 2H), 7.23 (d, J=3.3 Hz, 1H), 6.95–6.90 (m, 2H), 6.83 (d, J=7.9 Hz, 1H), 6.58 (dd, J=3.3 Hz, 1.7 Hz, 1H), 6.45 (t, J=5.6 Hz, 1H), 6.22 (d, J=5.0 Hz, 1H), 4.72 (d, J=5.6 Hz, 2H); Mass (m/z): 457 (M$^+$); IR (KBr, cm$^{-1}$): 3412, 1628, 1595, 1518, 1269; Melting point: 127.8–132.4° C.

EXAMPLE 155

8-Benzoyl-5-(3,4-dimethoxybenzylamino)-2-(2-furyl)[1,2,4]triazolo[1,5-c]pyrimidine (Compound 155)

Compound 155 (790 mg, yield: 66%) was obtained as a white solid using 1.21 g (2.65 mmol) of Compound 154 obtained in Example 154 by carrying out a procedure similar to that in Example 152.

$^1$H NMR (δ ppm, CDCl$_3$): 8.41 (s, 1H), 7.87–7.84 (m, 2H), 7.61–7.52 (m, 2H), 7.49–7.47 (m, 2H), 7.30 (d, J=3.3 Hz, 1H), 7.00–6.94 (m, 3H), 6.87 (d, J=7.9 Hz, 1H), 6.62 (dd, J=3.3 Hz, 1.7 Hz, 1H), 4.85 (d, J=5.6 Hz, 2H), 3.89 (s, 6H); Mass (m/z): 455 (M$^+$); IR (KBr, cm$^{-1}$): 3647, 3566, 3415, 1624, 1579, 1508, 1265; Melting point: 168.2–168.9° C.

EXAMPLE 156

5-Amino-8-benzoyl-2-(2-furyl)[1,2,4]triazolo[1,5-c]pyrimidine (Compound 156)

Compound 156 (271 mg, yield: 39%) was obtained as a pale yellow solid using 1.05 g (2.30 mmol) of Compound 155 obtained in Example 155 by carrying out a procedure similar to that in Example 153.

$^1$H NMR (δ ppm, DMSO-d$_6$): 8.21 (s, 1H), 7.95 (t, J=0.7 Hz, 1H), 7.81 (d, J=7.6 Hz, 2H), 7.66–7.64 (m, 1H), 7.56–7.51 (m, 2H), 7.13 (d, J=3.3 Hz, 1H), 6.72 (dd, J=3.3 Hz, 1.7 Hz, 1H); Mass (m/z): 305 (M$^+$); IR (KBr, cm$^{-1}$): 3423, 3235, 1660, 1591, 1510, 1323; Melting point: 254.5–260.5° C.; Elemental analysis: C$_{16}$H$_{11}$N$_5$O$_2$ 0.1EtOH; Found (%): C, 63.06, H, 3.85, N, 22.35; Calcd. (%): C, 62.79, H, 3.77, N, 22.60.

EXAMPLE 157

5-(3,4-Dimethoxybenzylamino)-2-(2-furyl)-8-propionyl[1,2,4]triazolo[1,5-c]pyrimidine (Compound 157)

In 1 ml of tetrahydrofuran, 100 mg (0.236 mmol) of Compound 22 obtained in Example 22 and 46 mg (0.472 mmol) of N,O-dimethylhydroxylamine hydrochloride were suspended, and 1.31 ml of a 0.90 M ethylmagnesium bromide tetrahydrofuran solution was added dropwise thereto at −10° C. The reaction solution was stirred at −5 to −2° C. for 1 hour, then at room temperature for 3.5 hours, and then at 60° C. for 30 minutes. After cooling the reaction solution to room temperature once, 0.52 ml of a 0.90 M ethylmagnesium bromide tetrahydrofuran solution was added thereto, followed by stirring at 60° C. for 8 hours. The reaction solution was poured into 1 N hydrochloric acid, followed by stirring at 60° C. for 1.5 hours. The reaction mixture was cooled to room temperature, the solvent was evaporated under reduced pressure, and the residue was extracted by adding water and chloroform. The organic phase was washed with 2 N NaOH and a saturated brine and dried over anhydrous magnesium sulfate, the solvent was evaporated under reduced pressure, and the residue was separated and purified by silica gel thin layer chromatography to give 18 mg (yield: 19%) of Compound 157 as a dark brown solid.

$^1$H NMR (δ ppm, DMSO-d$_6$): 8.55 (s, 1H), 7.98 (d, J=1.7 Hz, 1H), 7.27 (d, J=3.3 Hz, 1H), 7.07 (brs, 1H), 6.94–6.85 (m, 2H), 6.75 (dd, J=3.3 Hz, 1.7 Hz, 1H), 4.71 (s, 2H), 3.73 (s, 3H), 3.71 (s, 3H), 3.32–3.21 (m, 2H), 1.12 (t, J=6.9 Hz, 3H); Mass (m/z): 407 (M$^+$); IR (KBr, cm$^{-1}$): 3903, 3840, 3749, 3527, 1628, 1581; Melting point: 197.4–198.0° C.

EXAMPLE 158

5-Amino-2-(2-furyl)-8-propionyl[1,2,4]triazolo[1,5-c]pyrimidine (Compound 158)

Compound 158 (338 mg, yield: 69%) was obtained as a white solid using 780 mg (1.91 mmol) of Compound 157 obtained in Example 157 by carrying out a procedure similar to that in Example 153. $^1$H NMR (δ ppm, DMSO-d$_6$): 8.50 (s, 1H), 7.98 (dd, J=1.7 Hz, 0.7 Hz, 1H), 7.26 (d, J=3.3 Hz, 1H), 6.76–6.74 (m, 1H), 3.34–3.28 (m, 2H), 1.12 (t, J=6.9 Hz, 3H); Mass (m/z): 257 (M$^+$); IR (KBr, cm$^{-1}$): 3440, 3017, 1641, 1531, 1412, 1227; Melting point: 279.5–283.0° C.; Elemental analysis: C$_{12}$H$_{11}$N$_5$O$_2$ 0.2EtOH; Found (%): C, 55.83, H, 4.40, N, 26.24; Calcd.(%): C, 55.89, H, 4.61, N, 26.28.

EXAMPLE 159

8-Carboxy-5-(3,4-dimethoxybenzylamino)-2-(2-furyl)[1,2,4]triazolo[1,5-c]pyrimidine (Compound 159)

In 300 ml of ethanol, 19.92 g (47.04 mmol) of Compound 22 obtained in Example 22 was dissolved, 19.74 g (470.4 mmol) of lithium hydroxide monohydrate and 7.5 ml of water were added thereto, followed by refluxing for 3 hours. The reaction mixture was cooled to 0° C., 100 ml of water was added thereto, and the pH was adjusted to 3.5 using concentrated hydrochloric acid. The precipitated crystals were collected by filtration to give 14.55 g (yield: 78%) of Compound 159 as a white solid.

$^1$H NMR (δ ppm, DMSO-d$_6$): 12.80 (brs, 1H), 9.44 (t, J=5.6 Hz, 1H), 8.53 (s, 1H), 7.98 (s, 1H), 7.32 (dd, J=3.3 Hz, 0.7 Hz, 1H), 7.12 (brs, 1H), 6.98–6.80 (m, 2H), 6.68 (m, 1H), 4.72–4.68 (m, 2H), 3.72 (s, 3H), 3.67 (s, 3H); IR (KBr, cm$^{-1}$): 3661, 1701, 1638, 1616, 1265; Melting point: 178.5–190.0° C.

EXAMPLE 160

5-(3,4-Dimethoxybenzylamino)-8-(N,O-dimethylhydroxylcarbamoyl)-2-(2-furyl)[1,2,4]triazolo[1,5-c]pyrimidine (Compound 160)

In 50 ml of dimethylformamide, 5 g (12.65 mmol) of Compound 159 obtained in Example 159 was dissolved, and 5.2 g (27.24 mmol) of 1-ethyl-3-(3-dimethylaminopropyl)carbodiimide hydrochloride and 4.17 g (27.24 mmol) of 1-hydroxybenzotriazole were added thereto, followed by stirring at room temperature for 15 minutes. Next, 1.95 g (19.98 mmol) of N,O-dimethylhydroxylamine hydrochloride was added thereto, followed by stirring at room temperature for 70 hours and then at 50° C. for 1.5 hours. The reaction mixture was cooled to room temperature, water and aqueous sodium bicarbonate were added thereto, and the reaction mixture was extracted with ethyl acetate. The organic phase was washed with a saturated brine and dried over anhydrous magnesium sulfate, the solvent was evaporated under reduced pressure, and the residue was purified by silica gel column chromatography (elution solvent: 1.5% methanol-chloroform) to give 1.35 g (yield: 24%) of Compound 160 as a white solid.

$^1$H NMR (δ ppm, CDCl$_3$): 8.30 (s, 1H), 7.61 (dd, J=1.7 Hz, 0.7 Hz, 1H), 7.28 (dd, J=3.3 Hz, 0.7 Hz, 1H), 6.98–6.92 (m, 2H), 7.83 (d, J=7.9 Hz, 1H), 6.72 (t, J=5.6 Hz, 1H), 6.58 (dd, J=3.3 Hz, 1.7 Hz, 1H), 4.80 (d, J=5.6 Hz, 2H), 3.88 (s, 6H), 3.73 (s, 3H), 3,41 (s, 3H); Mass (m/z): 438 (M$^+$); IR (KBr, cm$^{-1}$): 3363, 2980, 1579, 1508, 1448, 1267; Melting point: 144.0–148.3° C.

EXAMPLE 161

8-Acetyl-5-(3,4-dimethoxybenzylamino)-2-(2-furyl)[1,2,4]triazolo[1,5-c]pyrimidine (Compound 161)

In 8 ml of tetrahydrofuran, 1 g (2.28 mmol) of Compound 160 obtained in Example 160 was dissolved, and 13.3 ml of a 0.86 M methylmagnesium bromide tetrahydrofuran solution was added thereto, followed by stirring at room temperature for 1.5 hours. The reaction solution was poured into an aqueous ammonium chloride solution under ice-cooling and extracted with ethyl acetate. The organic phase was washed with an aqueous ammonium chloride solution, water and then a saturated brine and dried over anhydrous magnesium sulfate, the solvent was evaporated under reduced pressure, and the residue was purified by silica gel column chromatography (elution solvent: chloroform) to give 681 mg (yield: 76%) of Compound 161 as a pale yellow solid.

$^1$H NMR (δ ppm, CDCl$_3$): 8.74 (s, 1H), 7.63 (dd, 3 1.7 Hz, 0.7 Hz, 1H), 7.29 (d, J=3.3 Hz, 1H), 6.98–6.84 (m, 4H), 6.60 (dd, J=3.3 Hz, 1.7 Hz, 1H), 4.85 (d, J=5.6 Hz, 2H), 3.89 (s, 6H), 2.92 (s, 3H); Mass (m/z): 393 (M$^+$); IR (KBr, cm$^{-1}$): 3263, 3230, 1619, 1508, 1267; Melting point: 198.7–203.2° C.

EXAMPLE 162

8-Acetyl-5-amino-2-(2-furyl)[1,2,4]triazolo[1,5-c]pyrimidine (Compound 162)

Compound 162 (264 mg, yield: 63%) was obtained as a white solid using 681 mg (1.73 mmol) of Compound 161 obtained in Example 161 by carrying out a procedure similar to that in Example 153.

$^1$H NMR (δ ppm, DMSO-d$_6$): 8.50 (d, J=1.7 Hz, 1H), 7.98 (d, J=0.7 Hz, 1H), 7.27 (d, J=2.6 Hz, 1H), 6.76 (dd, J=3.3 Hz, 1.7 Hz, 1H), 2.77 (d, J=1.7 Hz, 3H); Mass (m/z): 243 (M$^+$); IR (KBr, cm$^{-1}$): 3420, 3045, 1651, 1556, 1319, 1211; Melting point: >300° C.

EXAMPLE 163

5-Amino-8-formyl-2-(2-furyl)[1,2,4]triazolo[1,5-c]pyrimidine (Compound 163)

Compound 163 (336 mg, yield: 28%) was obtained as a pale yellow solid from 2.0 g (5.27 mmol) of Compound 24 obtained in Example 24 in the same manner as in Example 153.

$^1$H NMR (δ ppm, DMSO-d$_6$): 10.02 (s, 1H), 9.28–9.11 (brs, 1H), 8.92–8.80 (m, 1H), 8.52 (s, 1H), 7.98 (s, 1H), 7.28 (d, J=3.3 Hz, 1H), 6.75 (dd, J=3.3 Hz, 1.7 Hz, 1H); Mass (m/z): 229 (M$^+$); IR (KBr, cm$^{-1}$): 3320, 3140, 1637, 1558, 1508, 1421, 1323; Melting point: 255° C. (decomposed); Elemental analysis: C$_{10}$H$_7$N$_5$O$_2$ 0.3H$_2$O 0.2EtOH; Found (%): C, 51.29, H, 3.28, N, 29.01; Calcd.(%): C, 51.23, H, 3.64, N, 28.72.

EXAMPLE 164

5-(3,4-Dimethoxybenzylamino)-2-(2-furyl)-8-isopropylcarbamoyl[1,2,4]triazolo[1,5-c]pyrimidine (Compound 164)

In 8 ml of pyridine, 400 mg (1.01 mmol) of Compound 159 obtained in Example 159 was dissolved, and 1.32 ml (15.18 mmol) of thionyl chloride and 1.29 ml (15.18 mmol) of isopropylamine were added thereto at 0° C., followed by stirring at room temperature for 1 hour. After addition of water, the solvent was evaporated under reduced pressure, water and aqueous sodium bicarbonate were added thereto, and the reaction mixture was extracted with chloroform. The organic phase was washed with diluted hydrochloric acid and a saturated brine and dried over anhydrous magnesium sulfate, the solvent was evaporated under reduced pressure, and the residue was purified by silica gel column chromatography (elution solvent: chloroform) to give 271 mg (yield: 61%) of Compound 164 as a white solid.

$^1$H NMR (δ ppm, CDCl$_3$): 8.84 (s, 1H), 8.58 (d, J=6.6 Hz, 1H), 7.63 (s, 1H), 7.23 (dd, J=3.3 Hz, 0.7 Hz, 1H), 6.99–6.94 (m, 2H), 6.86 (d, J=7.9 Hz, 1H), 6.73 (t, J=5.6 Hz, 1H), 6.61 (dd, J=3.3 Hz, 1.7 Hz, 1H), 4.82 (d, J=5.6 Hz, 2H), 4.34 (Q, J=6.6 Hz, 1H), 3.89 (s, 3H), 3.87 (s, 3H), 1.35 (d, J=6.6 Hz, 6H); Mass (m/z): 436 (M$^+$); IR (KBr, cm$^{-1}$): 3853, 3278, 1653, 1589, 1254; Melting point: 168.5–171.2° C.

EXAMPLE 165

5-Amino-2-(2-furyl)-8-isopropylcarbamoyl[1,2,4]triazolo[1,5-c]pyrimidine (Compound 165)

Compound 165 (102 mg, yield: 28%) was obtained as a white solid using 554 mg (1.27 mmol) of Compound 164 obtained in Example 164 by carrying out a procedure similar to that in Example 153.

$^1$H NMR (δ ppm, DMSO-d$_6$): 8.52 (d, J=6.6 Hz, 1H), 8.45 (s, 1H), 8.00 (s, 1H), 7.31 (d, J=3.3 Hz, 1H), 6.76 (dd, J=3.3 Hz, 1.7 Hz, 1H), 4.18 (q, J=6.6 Hz, 1H), 1.26 (d, J=6.6 Hz, 6H); Mass (m/z): 286 (M$^+$); IR (KBr, cm$^{-1}$): 3317, 2970, 1680, 1556, 1433, 1261; Melting point: 228.4–229.3° C.; Elemental analysis: C$_{13}$H$_{14}$N$_6$O$_2$ 0.1EtOH; Found (%): C, 54.47, H, 4.92, N, 28.69; Calcd.(%): C, 54.50, H, 5.06, N, 28.89.

EXAMPLE 166

5-(3,4-Dimethoxybenzylamino)-2-(2-furyl)-8-methylcarbamoyl[1,2,4]triazolo[1,5-c]pyrimidine (Compound 166)

Compound 166 (159 mg, yield: 31%) was obtained as a white solid using 400 mg (1.01 mmol) of Compound 159 obtained in Example 159 and methylamine by carrying out a procedure similar to that in Example 164.

$^1$H NMR (δ ppm, CDCl$_3$): 8.87 (s, 1H), 8.59–8.55 (m, 1H), 7.62 (dd, J=1.7 Hz, 0.7 Hz, 1H), 7.27 (dd, J=3.3 Hz, 0.7 Hz, 1H), 6.99–6.94 (m, 2H), 6.86 (d, J=7.9 Hz, 1H), 6.74 (t, J=5.6 Hz, 1H), 6.60 (dd, J=3.3 Hz, 1.7 Hz, 1H), 4.84 (d, J=5.6 Hz, 2H), 3.89 (s, 6H), 3.12 (d, J=5.0 Hz, 3H); Mass (m/z): 408 (M$^+$); IR (KBr, cm$^{-1}$): 3244, 1626, 1570, 1317, 1269; Melting point: 214.0–215.3° C.

EXAMPLE 167

5-Amino-2-(2-furyl)-8-methylcarbamoyl[1,2,4]triazolo[1,5-c]pyrimidine (Compound 167)

Compound 167 (303 mg, yield: 87%) was obtained as a pale dark brown solid using 551 mg (13,48 mmol) of Compound 166 obtained in Example 166 by carrying out a procedure similar to that in Example 153.

$^1$H NMR (δ ppm, DMSO-d$_6$): 8.50 (d, J=5.0 Hz, 1H), 8.46 (s, 1H), 7.99 (dd, J=1.7 Hz, 0.7 Hz, 1H), 7.39 (dd, J=3.3 Hz, 0.7 Hz, 1H), 6.77 (dd, J=3.3 Hz, 1.7 Hz, 1H), 2.94 (d, J=5.0 Hz, 3H); Mass (m/z): 258 (M$^+$); IR (KBr, cm$^{-1}$): 3471, 3390, 1659, 1558; Melting point: 249.5–255.0° C.

EXAMPLE 168

5-(3,4-Dimethoxybenzylamino)-8-ethylcarbamoyl-2-(2-furyl)[1,2,4]triazolo[1,5-c]pyrimidine (Compound 168)

Compound 168 (153 mg, yield: 36%) was obtained as a white solid using 400 mg (1.01 mmol) of Compound 159 obtained in Example 159 and ethylamine by carrying out a procedure similar to that in Example 164.

$^1$H NMR (δ ppm, CDCl$_3$): 8.88 (s, 1H), 8.63 (m, 1H), 7.63 (dd, J=1.7 Hz, 0.7 Hz, 1H), 7.25 (dd, J=3.3 Hz, 0.7 Hz, 1H), 6.98–6.93 (m, 2H), 6.85 (d, J=7.9 Hz, 1H), 6.74 (t, J=5.6 Hz, 1H), 6.61 (dd, J=3.3 Hz, 1.7 Hz, 1H), 4.82 (d, J=5.6 Hz, 2H), 3.90 (s, 3H), 3.87 (s, 3H), 3.60 (m, 2H), 1.33 (t, J=7.3 Hz, 3H); Mass (m/z): 422 (M$^+$); IR (KBr, cm$^{-1}$): 3293, 2970, 1616, 1510, 1416, 1269; Melting point: 207.4–208.0° C.

EXAMPLE 169

5-Amino-8-ethylcarbamoyl-2-(2-furyl)[1,2,4]triazolo[1,5-c]pyrimidine (Compound 169)

Compound 169 (170 mg, yield: 40%) was obtained as a white solid using 663 mg (1,57 mmol) of Compound 168 obtained in Example 168 by carrying out a procedure similar to that in Example 30.

$^1$H NMR (δ ppm, CDCl$_3$): 8.78 (s, 1H), 8.64 (brs, 1H), 7.67 (t, J=0.7 Hz, 1H), 7.29 (dd, J=3.3 Hz, 0.7 Hz, 1H), 6.63 (dd, J=3.3 Hz, 1.7 Hz, 1H), 6.49 (brs, 2H), 3.65–3.55 (m, 2H), 1.34 (t, J=7.3 Hz, 3H); Mass (m/z): 272 (M$^+$); IR (KBr, cm$^{-1}$): 3320, 1647, 1560, 1421, 1261; Melting point: 192.0–200.0° C.; Elemental analysis: C$_{12}$H$_{12}$N$_6$O$_2$ 0.5EtOH; Found (%): C, 52.66, H, 4.70, N, 28.45; Calcd. (%): C, 52.88, H, 5.12, N, 28.46.

EXAMPLE 170

8-(N,N-Diethylcarbamoyl)-5-(3,4-dimethoxybenzylamino)-2-(2-furyl)[1,2,4]triazolo[1,5-c]pyrimidine (Compound 170)

In 8 ml of tetrahydrofuran, 1.2 g (2.83 mmol) of Compound 22 obtained in Example 22 was suspended, and 0.82 ml of diethylamine was added thereto. A 2 M isopropylmagnesium chloride tetrahydrofuran solution (0.82 ml) was added dropwise thereto at −5° C., followed by stirring for 30 minutes, and the temperature was raised up to 4° C., followed by stirring for 7.5 hours. The reaction solution was poured into an aqueous ammonium chloride solution under ice-cooling and the mixture was extracted with ethyl acetate. The organic phase was washed with an aqueous ammonium chloride solution, water and then a saturated brine and dried over anhydrous magnesium sulfate, the solvent was evaporated under reduced pressure, and the residue was purified by silica gel column chromatography (elution solvent: chloroform) to give 990 mg (yield: 77%) of Compound 170 as a yellow solid.

$^1$H NMR (δ ppm, CDCl$_3$): 8.50 (s, 1H), 7.59 (dd, J=1.7 Hz, 0.7 Hz, 1H), 7.25 (dd, J=3.3 Hz, 0.7 Hz, 1H), 6.97–6.92 (m, 2H), 6.85 (d, J=7.9 Hz, 1H), 6.60 (t, J=5.6 Hz, 1H), 6.55 (dd, J=3.3 Hz, 1.7 Hz, 1H), 4.80 (d, J=5.6 Hz, 2H), 3.89 (s, 6H), 3.63 (brs, 2H), 3,42 (brs, 2H), 1.25 (brs, 6H); Mass (m/z): 450 (M$^+$); IR (KBr, cm$^{-1}$): 3232, 2968, 1626, 1510, 1429, 1267; Melting point: 67.4–73.8° C.

EXAMPLE 171

5-Amino-8-(N,N-diethylcarbamoyl)-2-(2-furyl)[1,2,4]triazolo[1,5-c]pyrimidine (Compound 171)

Compound 171 (60 mg, yield: 90%) was obtained as a white solid using 100 mg (0.22 mmol) of Compound 170 obtained in Example 170 by carrying out a procedure similar to that in Example 30.

$^1$H NMR (δ ppm, DMSO-d$_6$): 8.20 (brs, 2H), 7.94 (s, 1H), 7.89 (s, 1H), 7.20 (d, J=3.3 Hz, 1H), 6.72 (t, J=3.3 Hz, 1.7 Hz, 1H), 3.46–3.42 (m, 4H), 1.21–1.12 (m, 6H); Mass (m/z): 300 (M$^+$); IR (KBr, cm$^{-1}$): 3740, 3617, 3439, 1655, 1560, 1508, 1443; Melting point: 92.4–95.7° C.; Elemental analysis: C$_{14}$H$_{16}$N$_6$O$_2$ 0.3H$_2$O 0.2EtOH; Found (%): C, 54.68, H, 5.69, N, 26.55; Calcd.(%): C, 54.92, H, 5.70, N, 26.68.

EXAMPLE 172

5-(3,4-Dimethoxybenzylamino)-8-(N,N-dimethylcarbamoyl)-2-(2-furyl)[1,2,4]triazolo[1,5-c]pyrimidine (Compound 172)

Compound 172 (780 mg, yield: 60%) was obtained as a white solid using 1.3 g (3.07 mmol) of Compound 22 obtained in Example 22 and 4.27 ml (8.54 mmol) of a 2 M dimethylamine tetrahydrofuran solution by carrying out a procedure similar to that in Example 170.

$^1$H NMR (δ ppm, CDCl$_3$): 8.21 (s, 1H), 7.61 (d, J=1.7 Hz, 1H), 7.25 (s, 1H), 6.98–6.94 (m, 2H), 6.86 (d, J=7.9 Hz, 1H), 6.64 (t, J=5.6 Hz, 1H), 6.58 (dd, J=3.3 Hz, 1.7 Hz, 1H), 4.80 (d, J=5.6 Hz, 2H), 3.89 (s, 6H), 3.19 (brs, 3H), 3.09 (brs, 3H); Mass (m/z): 422 (M$^+$); IR (KBr, cm$^{-1}$): 3415, 3210, 1628, 1574, 1429, 1248; Melting point: 191.3–194.5° C.

EXAMPLE 173

5-Amino-8-(N,N-dimethylcarbamoyl)-2-(2-furyl)[1,2,4]triazolo[1,5-c]pyrimidine (Compound 173)

Compound 173 (312 mg, yield: 66%) was obtained as a white solid using 740 mg (1.75 mmol) of Compound 172 obtained in Example 172 by carrying out a procedure similar to that in Example 30.

$^1$H NMR ($\delta$ ppm, DMSO-$d_6$): 8.29 (brs, 2H), 7.95 (s, 1H), 7.94 (s, 1H), 7.23 (d, J=3.3 Hz, 1H), 6.72 (dd, J=3.3 Hz, 1.7 Hz, 1H), 3.30 (brs, 6H); Mass (m/z): 272 (M$^+$); IR (KBr, cm$^{-1}$): 3720, 3430, 1647, 1560, 1508, 1421, 1327; Melting point: 241.5–242.0° C.; Elemental analysis: $C_{21}H_{22}N_6O_4$ 0.4H$_2$O 0.3EtOH; Found (%): C, 51.65, H, 4.93, N, 28.51; Calcd.(%): C, 51.66, H, 5.03, N, 28.65.

EXAMPLE 174

5-(3,4-Dimethoxybenzylamino)-2-(2-furyl)-8-piperidinocarbamoyl[1,2,4]triazolo[1,5-c]pyrimidine (Compound 174)

Compound 174 (1.09 g, yield: 77%) was obtained as a white solid using 1.3 g (3.07 mmol) of Compound 22 obtained in Example 22 and 0.61 ml (6.17 mmol) of piperidine by carrying out a procedure similar to that in Example 170.

$^1$H NMR ($\delta$ ppm, CDCl$_3$): 8.18 (s, 1H), 7.60 (dd, J=1.7 Hz, 0.7 Hz, 1H), 7.25 (dd, J=3.3 Hz, 0.7 Hz, 1H), 6.98–6.94 (m, 2H), 6.85 (d, J=7.9 Hz, 1H), 6.64 (t, J=5.6 Hz, 1H), 6.57 (dd, J=3.3 Hz, 1.7 Hz, 1H), 4.79 (d, J=5.6 Hz, 2H), 3.89 (s, 6H), 3.74 (brs, 2H), 3,44 (brs, 2H), 1.69 (brs, 6H); Mass (m/z): 462 (M$^+$); IR (KBr, cm$^{-1}$): 3360, 2945, 1616, 1581, 1321, 1261; Melting point: 154.0–155.5° C.

EXAMPLE 175

5-Amino-2-(2-furyl)-8-piperidinocarbamoyl[1,2,4]triazolo[1,5-c]pyrimidine (Compound 175)

Compound 175 (250 mg, yield: 36%) was obtained as a white solid using 1.02g (2.21 mmol) of Compound 174 obtained in Example 174 in the same manner as in Example 30.

$^1$H NMR ($\delta$ ppm, DMSO-$d_6$): 8.26 (brs, 2H), 7.95 (dd, J=1.7 Hz, 0.7 Hz, 1H), 7.94 (s, 1H), 7.21 (dd, J=3.3 Hz, 0.7 Hz, 1H), 6.73 (dd, J=3.3 Hz, 1.7 Hz, 1H), 3.58 (brs, 4H), 1.59 (brs, 6H); Mass (m/z): 312 (M$^+$); IR (KBr, cm$^{-1}$): 3417, 2920, 1618, 1508, 1325, 1203; Melting point: 119.8–123.0° C.; Elemental analysis: $C_{15}H_{16}N_6O_2$ 0.2H$_2$O 0.7EtOH; Found (%): C, 56.43, H, 5.75, N, 24.12; Calcd.(%): C, 56.57, H, 5.96, N, 24.14.

EXAMPLE 176

5-(3,4-Dimethoxybenzylamino)-2-(2-furyl)-8-morpholinocarbamoyl[1,2,4]triazolo[1,5-c]pyrimidine (Compound 176)

Compound 176 (1.12g, yield: 78%) was obtained as a white solid using 1.3 g (3.07 mmol) of Compound 22 obtained in Example 22 and 0.54 ml (6.14 mmol) of morpholine by carrying out a procedure similar to that in Example 170.

$^1$H NMR ($\delta$ ppm, CDCl$_3$): 8.28 (s, 1H), 7.61 (dd, J=1.7 Hz, 0.7 Hz, 1H), 7.24 (dd, J=3.3 Hz, 0.7 Hz, 1H), 6.98–6.93 (m, 2H), 6.86 (d, J=7.9 Hz, 1H), 6.69 (t, J=5.6 Hz, 1H), 6.59 (dd, J=3.3 Hz, 1.7 Hz, 1H), 4.80 (d, J=5.6 Hz, 2H), 3.89 (s, 6H), 3.82 (brs, 4H), 3.55 (brs, 4H); Mass (m/z): 464 (M$^+$); IR (KBr, cm$^{-1}$): 3853, 3370, 3140, 1601, 1513, 1268; Melting point: 199.8–200.3° C.

EXAMPLE 177

5-Amino-2-(2-furyl)-8-morpholinocarbamoyl[1,2,4]triazolo[1,5-c]pyrimidine (Compound 177)

Compound 177 (620 mg, yield: 92%) was obtained as a white solid using 1 g (2.15 mmol) of Compound 176 obtained in Example 176 by carrying out a procedure similar to that in Example 30.

$^1$H NMR ($\delta$ ppm, DMSO-$d_6$): 8.32 (brs, 1H), 8.01 (s, 1H), 7.95 (d, J=1.7 Hz, 1H), 7.23 (d, J=3.3 Hz, 1H), 6.73 (dd, J=3.3 Hz, 1.7 Hz, 1H), 3.65 (brs, 4H), 3.38 (brs, 4H); Mass (m/z): 314 (M$^+$); IR (KBr, cm$^{-1}$): 3460, 3107, 1643, 1560, 1444, 1327, 1205; Melting point: 258.0–259.8° C.; Elemental analysis: $C_{14}H_{14}N_6O_3$ 0.2EtOH; Found (%): C, 53.46, H, 4.50, N, 26.09; Calcd.(%): C, 53.46, H, 4.74, N, 25.98.

EXAMPLE 178

5-Amino-7-(4-bromobenzylthio)-2-(2-furyl)[1,2,4]triazolo[1,5-c]pyrimidine (Compound 178)

In dimethylformamide (2 ml), 200 mg (0.84 mmol) of Compound 61 obtained in Example 61 was dissolved, and 141 mg (2.52 mmol) of sodium hydrosulfide was added thereto, followed by stirring at 120° C. for 2 hours. Then, the reaction solution was cooled to room temperature, and water (0.2 ml) was added thereto, followed by stirring for 10 minutes. When 314 mg (1.26 mmol) of p-bromobenzyl bromide was added thereto, followed by stirring at room temperature for 30 minutes and then water was poured, a white solid was precipitated. The precipitate was collected by filtration and recrystallized from ethanol to give 150 mg (yield: 45%) of Compound 178 as a white solid.

$^1$H NMR ($\delta$ ppm, DMSO-$d_6$): 8.11 (brs, 2H), 7.91 (d, J=1.9 Hz, 1H), 7.52 (d, J=8.6 Hz, 2H), 7.44 (d, J=8.6 Hz, 2H), 7.15 (d, J=3.3 Hz, 1H), 6.80 (s, 1H), 6.70 (dd, J=1.9 Hz, 3.3 Hz, 1H), 4.38 (s, 2H); Mass (m/z): 404 ((M+3)$^+$), 403 ((M+2)$^+$), 402 ((M+1)$^+$), 401 (M$^+$); IR (KBr, cm$^{-1}$): 3141, 1670, 1598, 1560, 1178, 740; Melting point: 200–201° C.

EXAMPLE 179

5-Amino-2-(2-furyl)-7-(4-methoxybenzylthio)[1,2,4]triazolo[1,5-c]pyrimidine (Compound 179)

Compound 179 was obtained as a white solid using p-methoxybenzyl bromide in the same manner as in Example 178.

Yield: 38%; $^1$H NMR ($\delta$ ppm, DMSO-$d_6$): 8.10 (brs, 2H), 7.91 (d, J=1.9 Hz, 1H), 7.39 (d, J=8.8 Hz, 2H), 7.15 (d, J=3.3 Hz, 1H), 6.88 (d, J=8.8 Hz, 2H), 6.79 (s, 1H), 6.70 (dd, J=1.9 Hz, 3.3 Hz, 1H), 4.33 (s, 2H), 3.73 (s, 3H); Mass (m/z): 355 (M$^+$+2), 354 (M$^+$+1), 353 (M$^+$); IR (KBr, cm$^{-1}$): 3172, 1664, 1585, 1511, 1174, 750; Melting point: 210–211° C.; Elemental analysis: $C_{17}H_{15}N_5O_2S$; Found (%): C, 57.75, H, 4.24, N, 19.61; Calcd.(%): C, 57.78, H, 4.28, N, 19.82.

EXAMPLE 180

5-Amino-2-(2-furyl)-7-(4-trifluoromethoxybenzylthio)[1,2,4]triazolo[1,5-c]pyrimidine (Compound 180)

Compound 180 was obtained as a white solid using p-trifluoromethoxybenzyl bromide in the same manner as in Example 178.

Yield: 79%; $^1$H NMR ($\delta$ ppm, DMSO-d$_6$): 8.14 (brs, 2H), 7.92 (d, J=1.9 Hz, 1H), 7.62 (d, J=8.5 Hz, 2H), 7.32 (d, J=8.5 Hz, 2H), 7.16 (d, J=2.6 Hz, 1H), 6.83 (s, 1H), 6.70 (dd, J=1.9 Hz, 2.6 Hz, 1H), 4.44 (s, 2H); Mass (m/z): 409 ((M+2)$^+$), 408 ((M+1)$^+$), 407 (M$^+$); IR (KBr, cm$^{-1}$): 3129, 1668, 1591, 1550, 1508, 1309, 1151, 759; Melting point: 225–226° C.; Elemental analysis: C$_{17}$H$_{12}$F$_3$N$_5$O$_2$S; Found (%): C, 50.26, H, 2.89, N, 17.00; Calcd.(%): C, 50.12, H, 2.97, N, 17.19.

EXAMPLE 181

5-Amino-2-(2-furyl)-7-(4-picolylthio)[1,2,4]triazolo[1,5-c]pyrimidine (Compound 181)

Compound 181 was obtained as a white solid using 4-picolyl chloride hydrochloride in the same manner as in Example 178.

Yield: 37%; $^1$H NMR ($\delta$ ppm, DMSO-d$_6$): 8.51 (d, J=5.9 Hz, 2H), 8.15 (brs, 2H), 7.91 (d, J=1.6 Hz, 1H), 7.49 (d, J=5.9 Hz, 2H), 7.14 (d, J=3.3 Hz, 1H), 6.81 (s, 1H), 6.71 (dd, J=1.6 Hz, 3.3 Hz, 1H), 4.42 (s, 2H); Mass (m/z): 326 ((M+2)$^+$), 325 ((M+1)$^+$), 324 (M$^+$); IR (KBr, cm$^{-1}$): 3153, 1660, 1597, 1560, 1221; Melting point: 208–209° C.; Elemental analysis: C$_{15}$H$_{12}$N$_6$OS 0.1EtOH 0.7H$_2$O; Found (%): C, 53.54, H, 3.89, N, 24.63; Calcd.(%): C, 53.45, H, 4.13, N, 24.60.

EXAMPLE 182

5-Amino-2-(2-furyl)-7-(2-picolylthio)[1,2,4]triazolo[1,5-c]pyrimidine (Compound 182)

Compound 182 was obtained as a white solid using 2-picolyl chloride hydrochloride in the same manner as in Example 178.

Yield: 29%; $^1$H NMR ($\delta$ ppm, DMSO-d$_6$): 8.52 (d, J=5.0 Hz, 1H), 8.10 (brs, 2H), 7.91 (d, J=1.6 Hz, 1H), 7.77 (dd, J=5.9 Hz, 7.6 Hz, 1H), 7.57 (d, J=7.6 Hz, 1H), 7.28 (dd, J=5.0 Hz, 5.9 Hz, 1H), 7.15 (d, J=3.3 Hz, 1H), 6.89 (s, 1H), 6.71 (dd, J=1.6 Hz, 3.3 Hz, 1H), 4.48 (s, 2H) Mass (m/z): 326 ((M+2)$^+$), 325 ((M+1)$^+$), 324 (M$^+$); IR (KBr, cm$^{-1}$): 3104, 1655, 1585, 1544, 748; Melting point: 187–188° C.

EXAMPLE 183

5-Amino-7-benzylthio-2-(2-furyl)[1,2,4]triazolo[1,5-c]pyrimidine (Compound 183)

Compound 183 was obtained as a white solid using benzyl bromide in the same manner as in Example 178.

Yield: 33%; $^1$H NMR ($\delta$ ppm, DMSO-d$_6$): 8.10 (brs, 2H), 7.92 (d, J=1.7 Hz, 1H), 7.48 (d, J=7.0 Hz, 2H), 7.20–7.40 (m, 3H), 7.16 (d, J=2.6 Hz, 1H), 6.81 (s, 1H), 6.70 (dd, J=1.7 Hz, 2.6 Hz, 1H), 4.40 (s, 2H); Mass (m/z): 325 ((M+2)$^+$), 324 ((M+1)$^+$), 323 (M$^+$); IR (KBr, cm$^{-1}$): 3122, 1662, 1585, 1544, 1174, 752, 705; Melting point: 200–201° C.; Elemental analysis: C$_{16}$H$_{13}$N$_5$OS 0.1H$_2$O; Found (%): C, 59.09, H, 4.21, N, 21.80; Calcd.(%): C, 59.10, H, 4.09, N, 21.54.

EXAMPLE 184

5-Amino-7-(4-cyanobenzylthio)-2-(2-furyl)[1,2,4]triazolo[1,5-c]pyrimidine (Compound 184)

Compound 184 was obtained as a white solid using p-cyanobenzyl bromide in the same manner as in Example 178.

Yield: 42%; $^1$H NMR ($\delta$ ppm, DMSO-d$_6$): 8.15 (brs, 2H), 7.91 (d, J=1.6 Hz, 1H), 7.79 (d, J=8.2 Hz, 2H), 7.68 (d, J=8.2 Hz, 2H), 7.15 (d, J=3.3 Hz, 1H), 6.82 (s, 1H), 6.70 (dd, J=1.6 Hz, 3.3 Hz, 1H), 4.49 (s, 2H); Mass (m/z): 350 ((M+2)$^+$), 349 ((M+1)$^+$), 348 (M$^+$); IR (KBr, cm$^{-1}$): 3151, 2226, 1668, 1598, 1178, 933; Melting point: 258–259° C.

EXAMPLE 185

5-Amino-2-(2-furyl)-7-(4-nitrobenzylthio)[1,2,4]triazolo[1,5-c]pyrimidine (Compound 185)

Compound 185 was obtained as a white solid using p-nitrobenzyl bromide in the same manner as in Example 178.

Yield: 42%; $^1$H NMR ($\delta$ ppm, DMSO-d$_6$): 8.19 (brs, 2H), 8.18 (d, J=8.9 Hz, 2H), 7.91 (d, J=1.7 Hz, 1H), 7.77 (d, J=8.9 Hz, 2H), 7.14 (d, J=3.3 Hz, 1H), 6.83 (s, 1H), 6.70 (dd, J=1.7 Hz, 3.3 Hz, 1H), 4.54 (s, 2H); Mass (m/z): 370 ((M+2)$^+$), 369 ((M+1)$^+$), 368 (M$^+$); IR (KBr, cm$^{-1}$): 1664, 1652, 1542, 1508, 1351; Melting point: 135–136° C.

EXAMPLE 186

5-Amino-2-(2-furyl)-7-(4-methylbenzylthio)[1,2,4]triazolo[1,5-c]pyrimidine (Compound 186)

Compound 186 was obtained as a white solid using p-methylbenzyl bromide in the same manner as in Example 178.

Yield: 50%; $^1$H NMR ($\delta$ ppm, DMSO-d$_6$): 8.10 (brs, 2H), 7.92 (d, J=1.6 Hz, 1H), 7.35 (d, J=8.0 Hz, 2H), 7.15 (d, J=3.3 Hz, 1H), 7.12 (d, J=8.0 Hz, 2H), 6.79 (s, 1H), 6.71 (dd, J=1.6 Hz, 3.3 Hz, 1H), 4.34 (s, 2H), 2.27 (s, 3H); Mass (m/z): 339 ((M+2)$^+$), 338 ((M+1)$^+$), 337 (M$^+$); IR (KBr, cm$^{-1}$): 3122, 1670, 1587, 1508, 1217, 929, 756; Melting point: 185–186° C.

EXAMPLE 187

5-Amino-7-(4-(tert-butyl)benzylthio)-2-(2-furyl)[1,2,4]triazolo[1,5-c]pyrimidine (Compound 187)

Compound 187 was obtained as a white solid using p-tert-butylbenzyl bromide in the same manner as in Example 178.

Yield: 50%; $^1$H NMR ($\delta$ ppm, DMSO-d$_6$): 8.08 (brs, 2H), 7.91 (d, J=2.0 Hz, 1H), 7.38 (d, J=8.6 Hz, 2H), 7.33 (d, J=8.6 Hz, 2H), 7.14 (d, J=3.6 Hz, 1H), 6.81 (s, 1H), 6.70 (dd, J=2.0 Hz, 3.6 Hz, 1H), 4.35 (s, 2H), 1.26 (s, 9H); Mass (m/z): 381 ((M+2)$^+$), 380 ((M+1)$^+$), 379 (M$^+$); IR (KBr, cm$^{-1}$): 3110, 2960, 1647, 1596, 1548, 1508, 1216, 929, 756; Melting point: 192–193° C.

EXAMPLE 188

5-Amino-7-(2-cyanobenzylthio)-2-(2-furyl)[1,2,4]triazolo[1,5-c]pyrimidine (Compound 188)

Compound 188 was obtained as a white solid using o-cyanobenzyl bromide in the same manner as in Example 178.

Yield: 43%; $^1$H NMR (δ ppm, DMSO-$d_6$): 8.18 (brs, 2H), 7.92 (d, J=2.0 Hz, 1H), 7.84 (d, J=7.5 Hz, 1H), 7.80 (d, J=7.9 Hz, 1H), 7.67 (dd, J=7.5 Hz, 8.8 Hz, 1H), 7.47 (dd, J=7.9 Hz, 8.8 Hz, 1H), 7.17 (d, J=3.6 Hz, 1H), 6.90 (s, 1H), 6.71 (dd, J=2.0 Hz, 3.6 Hz, 1H), 4.58 (s, 2H); Mass (m/z): 350 ((M+2)$^+$), 349 ((M+1)$^+$), 348 (M$^+$); IR (KBr, cm$^{-1}$): 3110, 2223, 1652, 1589, 1540, 1216, 779, 756; Melting point: 200–201° C.

EXAMPLE 189

5-Amino-7-(4-fluorobenzylthio)-2-(2-furyl)[1,2,4]triazolo[1,5-c]pyrimidine (Compound 189)

Compound 189 was obtained as a white solid using p-fluorobenzyl bromide in the same manner as in Example 178.

Yield: 56%; $^1$H NMR (δ ppm, DMSO-$d_6$): 8.12 (brs, 2H), 7.91 (d, J=2.0 Hz, 1H), 7.53 (dd, J=5.3 Hz, 8.6 Hz, 2H), 7.16 (dd, J=8.6 Hz, 8.6 Hz, 2H), 7.15 (d, J=3.6 Hz, 1H), 6.81 (s, 1H), 6.70 (dd, J=2.0 Hz, 3.6 Hz, 1H), 4.39 (s, 2H); Mass (m/z): 343 ((M+2)$^+$), 342 ((M+1)$^+$), 341 (M$^+$); IR (KBr, cm$^{-1}$): 3128, 1668, 1589, 1176, 779; Melting point: 201–202° C.

EXAMPLE 190

5-Amino-2-(2-furyl)-7-(4-methoxycarbonylbenzylthio)[1,2,4]triazolo[1,5-c]pyrimidine (Compound 190)

Compound 190 was obtained as a white solid using methyl α-bromo-p-toluate in the same manner as in Example 178.

Yield: 56%; $^1$H NMR (δ ppm, DMSO-$d_6$): 8.12 (brs, 2H), 7.92 (d, J=8.2 Hz, 2H), 7.91 (d, J=1.6 Hz, 1H), 7.63 (d, J=8.2 Hz, 2H), 7.15 (d, J=3.3 Hz, 1H), 6.81 (s, 1H), 6.70 (dd, J=1.6 Hz, 3.3 Hz, 1H), 4.48 (s, 2H), 3.84 (s, 3H) Mass (m/z): 383 ((M+2)$^+$), 382 ((M+1)$^+$), 380 (M$^+$); IR (KBr, cm$^{-1}$): 3168, 1726, 1662, 1598, 1508, 1282, 754; Melting point: 226–227° C.

EXAMPLE 191

5-Amino-2-(2-furyl)-7-(3-iodobenzylthio)[1,2,4]triazolo[1,5-c]pyrimidine (Compound 191)

Compound 191 was obtained as a white solid using m-iodobenzyl bromide in the same manner as in Example 178.

Yield: 47%; $^1$H NMR (δ ppm, DMSO-$d_6$): 8.13 (brs, 2H), 7.91 (d, J=1.6 Hz, 1H), 7.86 (s, 1H), 7.61 (d, J=7.9 Hz, 1H), 7.50 (d, J=7.9 Hz, 1H), 7.16 (d, J=3.3 Hz, 1H), 7.15 (dd, J=7.9 Hz, 7.9 Hz, 1H), 6.81 (s, 1H), 6.70 (dd, J=1.6 Hz, 3.3 Hz, 1H), 4.37 (s, 2H); Mass (m/z): 451 ((M+2)$^+$), 450 ((M+1)$^+$), 449 (M$^+$); IR (KBr, cm$^{-1}$): 3128, 1666, 1591, 1548, 1218, 1179, 937, 757; Melting point: 169–170° C.

EXAMPLE 192

5-Amino-2-(2-furyl)-7-(3-nitrobenzylthio)[1,2,4]triazolo[1,5-c]pyrimidine (Compound 192)

Compound 192 was obtained as a white solid using m-nitrobenzyl chloride in the same manner as in Example 178.

Yield: 52%; $^1$H NMR (δ ppm, DMSO-$d_6$): 8.37 (s, 1H), 8.17 (brs, 2H), 8.12 (d, J=8.3 Hz, 1H), 7.97 (d, J=7.9 Hz, 1H), 7.92 (d, J=1.0 Hz, 1H), 7.63 (dd, J=7.9 Hz, 8.3 Hz, 1H), 7.15 (d, J=3.3 Hz, 1H), 6.86 (s, 1H), 6.71 (dd, J=1.0 Hz, 3.3 Hz, 1H), 4.56 (s, 2H); Mass (m/z): 370 ((M+2)$^+$), 369 ((M+1)$^+$), 368 (M$^+$); IR (KBr, cm$^{-1}$): 3085, 1672, 1654, 1588, 1508, 1359, 781, 746; Melting point: 191–192° C.

EXAMPLE 193

5-Amino-7-(3-cyanobenzylthio)-2-(2-furyl)[1,2,4]triazolo[1,5-c]pyrimidine (Compound 193)

Compound 193 was obtained as a white solid using m-cyanobenzyl bromide in the same manner as in Example 178.

Yield: 51%; $^1$H NMR (δ ppm, DMSO-$d_6$): 8.17 (brs, 2H), 7.98 (s, 1H), 7.92 (d, J=1.6 Hz, 1H), 7.84 (d, J=8.2 Hz, 1H), 7.71 (d, J=8.0 Hz, 1H), 7.54 (dd, J=8.0 Hz, 8.2 Hz, 1H), 7.15 (d, J=3.3 Hz, 1H), 6.83 (s, 1H), 6.71 (dd, J=1.6 Hz, 3.3 Hz, 1H), 4.45 (s, 2H); Mass (m/z): 350 ((M+2)$^+$), 349 ((M+1)$^+$), 348 (M$^+$); IR (KBr, cm$^{-1}$): 3166, 2223, 1646, 1635, 1598, 1375, 1215, 926, 742; Melting point: 201–202° C.

EXAMPLE 194

5-Amino-2-(2-furyl)-7-(2-nitrobenzylthio)[1,2,4]triazolo[1,5-c]pyrimidine (Compound 194)

Compound 194 was obtained as a white solid using o-nitrobenzyl bromide in the same manner as in Example 178.

Yield: 58%; $^1$H NMR (δ ppm, DMSO-$d_6$): 8.19 (brs, 2H), 8.06 (d, J=7.9 Hz, 1H), 7.92 (d, J=1.6 Hz, 1H), 7.90 (d, J=7.4 Hz, 1H), 7.70 (dd, J=7.4 Hz, 7.6 Hz, 1H), 7.54 (dd, J=7.6 Hz, 7.9 Hz, 1H), 7.15 (d, J=3.3 Hz, 1H), 6.86 (s, 1H), 6.71 (dd, J=1.6 Hz, 3.3 Hz, 1H), 4.72 (s, 2H); Mass (m/z): 370 ((M+2)$^+$), 369 ((M+1)$^+$), 368 (M$^+$); IR (KBr, cm$^{-1}$): 3120, 1654, 1594, 1558, 1332, 750; Melting point: 186–187° C.

EXAMPLE 195

5-Amino-2-(2-furyl)-7-(2-phenylbenzylthio)[1,2,4]triazolo[1,5-c]pyrimidine (Compound 195)

Compound 195 was obtained as a white solid using o-phenylbenzyl bromide in the same manner as in Example 178.

Yield: 42%; $^1$H NMR (δ ppm, DMSO-$d_6$): 8.08 (brs, 2H), 7.91 (d, J=1.6 Hz, 1H), 7.61 (m, 1H), 7.30–7.60 (m, 7H), 7.26 (m, 1H), 7.15 (d, J=3.3 Hz, 1H), 6.71 (dd, J=1.6 Hz, 3.3 Hz, 1H), 6.69 (s, 1H), 4.32 (s, 2H); Mass (m/z): 401 ((M+2)$^+$), 400 ((M+1)$^+$), 399 (M$^+$); IR (KBr, cm$^{-1}$): 3120, 1654, 1595, 1355, 777; Melting point: 188–190° C.

EXAMPLE 196

5-Amino-7-(4-carboxy-2-nitrobenzylthio)-2-(2-furyl)[1,2,4]triazolo[1,5-c]pyrimidine (Compound 196)

Compound 196 was obtained as a white solid using α-bromo-m-nitro-p-toluic acid in the same manner as in Example 178.

Yield: 29%; $^1$H NMR (δ ppm, DMSO-$d_6$): 13.61 (brs, 1H), 8.47 (s, 1H), 8.18 (brs, 2H), 8.16 (d, J=8.2 Hz, 1H), 8.04 (d, J=8.2 Hz, 1H), 7.91 (d, J=1.6 Hz, 1H), 7.15 (d, J=3.3 Hz, 1H), 6.87 (s, 1H), 6.71 (dd, J=1.6 Hz, 3.3 Hz, 1H), 4.77 (s, 2H); Mass (m/z): 431 (M$^+$+H$_2$O); IR (KBr, cm$^{-1}$): 1700, 1637, 1591, 1537, 1359, 1213, 754; Melting point: 298–300° C. (decomposed).

EXAMPLE 197

5-Amino-7-(4-carboxybenzylthio)-2-(2-furyl)[1,2,4]triazolo[1,5-c]pyrimidine (Compound 197)

Compound 197 was obtained as a white solid using α-chloro-p-toluic acid in the same manner as in Example 178.

Yield: 42%; $^1$H NMR (δ ppm, DMSO-$d_6$): 12.88 (brs, 1H), 8.12 (brs, 2H), 7.91 (d, J=2.0 Hz, 1H), 7.89 (d, J=8.6 Hz, 2H), 7.60 (d, J=8.6 Hz, 2H), 7.15 (d, J=3.3 Hz, 1H), 6.81 (s, 1H), 6.70 (dd, J=2.0 Hz, 3.3 Hz, 1H), 4.47 (s, 2H); Mass (m/z): 369 ((M+2)$^+$), 368 ((M+1)$^+$), 367 (M$^+$); IR (KBr, cm$^{-1}$): 1697, 1629, 1589, 1539, 1271, 756; Melting point: 283–284° C.

EXAMPLE 198

5-Amino-7-(4-chlorobenzylthio)-2-(2-furyl)[1,2,4]triazolo[1,5-c]pyrimidine (Compound 198)

Compound 198 was obtained as a white solid using p-chlorobenzyl chloride in the same manner as in Example 178.

Yield: 52%; $^1$H NMR (δ ppm, DMSO-$d_6$): 8.12 (brs, 2H), 7.91 (d, J=1.6 Hz, 1H), 7.51 (d, J=8.6 Hz, 2H), 7.38 (d, J=8.6 Hz, 2H), 7.15 (d, J=3.3 Hz, 1H), 6.81 (s, 1H), 6.71 (dd, J=1.6 Hz, 3.3 Hz, 1H), 4.40 (s, 2H) Mass (m/z): 359 ((M+2)$^+$), 358 ((M+1)$^+$), 357 (M$^+$); IR (KBr, cm$^{-1}$): 3110, 1662, 1541, 771, 738; Melting point: 197–198° C.

EXAMPLE 199

5-Amino-2-(2-furyl)-7-(3-trifluoromethylbenzylthio)[1,2,4]triazolo[1,5-c]pyrimidine (Compound 199)

Compound 199 was obtained as a white solid using m-trifluoromethylbenzyl bromide in the same manner as in Example 178.

Yield: 52%; $^1$H NMR (δ ppm, DMSO-$d_6$): 8.15 (brs, 2H), 7.91 (d, J=1.6 Hz, 1H), 7.86 (s 1H), 7.82 (d, J=7.2 Hz, 1H), 7.53–7.54 (m, 2H), 7.15 (d, J=3.3 Hz, 1H), 6.84 (s, 1H), 6.71 (dd, J=1.6 Hz, 3.3 Hz, 1H), 4.51 (s, 2H); Mass (m/z): 393 ((M+2)$^+$), 392 ((M+1)$^+$), 391 (M$^+$); IR (KBr, cm$^{-1}$): 3058, 1675, 1587, 1328, 1116, 781; Melting point: 156–157° C.

EXAMPLE 200

5-Amino-7-(2-chlorobenzylthio)-2-(2-furyl)[1,2,4]triazolo[1,5-c]pyrimidine (Compound 200)

Compound 200 was obtained as a white solid using o-chlorobenzyl chloride in the same manner as in Example 178.

Yield: 48%; $^1$H NMR (δ ppm, DMSO-$d_6$): 8.17 (brs, 2H), 7.92 (d, J=1.7 Hz, 1H), 7.68 (dd, J=3.7 Hz, 5.6 Hz, 1H), 7.49 (dd, J=3.3 Hz, 5.6 Hz, 1H), 7.29–7.33 (m, 2H), 7.16 (d, J=3.3 Hz, 1H), 6.86 (s, 1H), 6.71 (dd, J=1.7 Hz, 3.3 Hz, 1H), 4.50 (s, 2H); Mass (m/z): 359 ((M+2)$^+$), 358 ((M+1)$^+$), 357 (M$^+$); IR (KBr, cm$^{-1}$): 3120, 1662, 1587, 1546, 1222, 748; Melting point: 169–170° C.

EXAMPLE 201

5-Amino-7-(2-fluorobenzylthio)-2-(2-furyl)[1,2,4]triazolo[1,5-c]pyrimidine (Compound 201)

Compound 201 was obtained as a white solid using o-fluorobenzyl bromide in the same manner as in Example 1.

Yield: 44%; $^1$H NMR (δ ppm, DMSO-$d_6$): 8.14 (brs, 2H), 7.92 (d, J=1.7 Hz, 1H), 7.60 (ddd, J=1.6 Hz, 7.9 Hz, 7.9 Hz, 1H), 7.35 (m, 1H), 7.13–7.25 (m, 3H), 6.85 (s, 1H), 6.71 (dd, J=1.7 Hz, 3.3 Hz, 1H), 4.42 (s, 2H); Mass (m/z): 343 ((M+2)$^+$), 342 ((M+1)$^+$), 341 (M$^+$); IR (KBr, cm$^{-1}$): 3172, 1646, 1591, 1540, 1355, 746; Melting point: 178–179° C.

EXAMPLE 202

5-Amino-2-(2-furyl)-7-(3-methylbenzylthio)[1,2,4]triazolo[1,5-c]pyrimidine (Compound 202)

Compound 202 was obtained as a white solid using m-methylbenzyl bromide in the same manner as in Example 1.

Yield: 49%; $^1$H NMR (δ ppm, DMSO-$d_6$): 8.11 (brs, 2H), 7.92 (d, J=1.6 Hz, 1H), 7.28 (s, 1H), 7.18–7.25 (m, 2H), 7.15 (d, J=3.3 Hz, 1H), 7.06 (d, J=7.3 Hz, 1H), 6.80 (s, 1H), 6.71 (dd, J=1.6 Hz, 3.3 Hz, 1H), 4.35 (s, 2H), 2.29 (s, 3H); Mass (m/z): 339 ((M+2)$^+$), 338 ((M+1)$^+$), 337 (M$^+$); IR (KBr, cm$^{-1}$): 3124, 1664, 1587, 1351, 752; Melting point: 182–183° C.

EXAMPLE 203

5-Amino-7-(2,6-dichlorobenzylthio)-2-(2-furyl)[1,2,4]triazolo[1,5-c]pyrimidine (Compound 203)

Compound 203 was obtained as a white solid using 2,6-dichlorobenzyl bromide in the same manner as in Example 178.

Yield: 41%; $^1$H NMR (δ ppm, DMSO-$d_6$): 8.17 (brs, 2H), 7.95 (d, J=1.7 Hz, 1H), 7.53 (d, J=7.3 Hz, 2H), 7.38 (t, J=7.3 Hz, 1H), 7.17 (d, J=3.3 Hz, 1H), 6.96 (s, 1H), 6.71 (dd, J=1.7 Hz, 3.3 Hz, 1H), 4.66 (s, 2H); Mass (m/z): 395 ((M+4)$^+$), 394 ((M+3)$^+$), 393 ((M+2)$^+$), 392 ((M+1)$^+$), 391 (M$^+$); IR (KBr, cm$^{-1}$): 1645, 1608, 1327, 995, 785; Melting point: 195–196° C.

EXAMPLE 204

5-Amino-7-(2,6-difluorobenzylthio)-2-(2-furyl)[1,2,4]triazolo[1,5-c]pyrimidine (Compound 204)

Compound 204 was obtained using 2,6-difluorobenzyl bromide in the same manner as in Example 178.

Yield: 42%; $^1$H NMR (δ ppm, DMSO-$d_6$): 8.12 (brs, 2H), 7.92 (d, J=1.6 Hz, 1H), 7.43 (tt, J=7.8 Hz, 7.9 Hz, 1H), 7.18 (d, J=3.3 Hz, 1H), 7.17 (m, 2H), 6.92 (s, 1H), 6.71 (dd, J=1.6 Hz, 3.3 Hz, 1H), 4.45 (s, 2H); Mass (m/z): 361 ((M+2)$^+$), 360 ((M+1)$^+$), 359 (M$^+$); IR (KBr, cm$^{-1}$): 1645, 1623, 1356, 1327, 996, 785; Melting point: 168–169° C.

EXAMPLE 205

5-Amino-7-(2-anthrylmethylbenzylthio)-2-(2-furyl)[1,2,4]triazolo[1,5-c]pyrimidine (Compound 205)

Compound 205 was obtained as a yellow solid using 9-anthrylmethyl chloride in the same manner as in Example 178.

Yield: 45%; $^1$H NMR (δ ppm, DMSO-$d_6$): 8.64 (s, 1H), 8.43 (d, J=8.9 Hz, 2H), 8.23 (brs, 2H), 8.13 (d, J=8.6 Hz, 2H), 7.94 (d, J=2.0 Hz, 1H), 7.60 (dd, J=6.6 Hz, 8.9 Hz, 2H), 7.55 (dd, J=6.6 Hz, 8.6 Hz, 2H), 7.20 (d, J=3.7 Hz, 1H), 7.09 (s, 1H), 6.73 (dd, J=2.0 Hz, 3.7 Hz, 1H), 5.47 (s, 2H); Mass (m/z): 425 ((M+2)$^+$), 424 ((M+1)$^+$), 423 (M$^+$); IR (KBr, cm$^{-1}$): 3047, 1670, 1646, 1589, 1147, 790, 750; Melting point: 195–196° C.

EXAMPLE 206

5-Amino-2-(2-furyl)-7-(4-trifluoromethylbenzylthio)[1,2,4]triazolo[1,5-c]pyrimidine (Compound 206)

Compound 206 was obtained as a white solid using p-trifluoromethylbenzyl bromide in the same manner as in Example 178.

Yield: 48%; $^1$H NMR (δ ppm, DMSO-$d_6$): 8.15 (brs, 2H), 7.92 (d, J=1.6 Hz, 1H), 7.73 (d, J=8.6 Hz, 2H), 7.69 (d, J=8.6 Hz, 2H), 7.15 (d, J=3.3 Hz, 1H), 6.83 (s, 1H), 6.71 (dd, J=1.6 Hz, 3.3 Hz, 1H), 4.50 (s, 2H); Mass (m/z): 393 ((M+2)$^+$), 392 ((M+1)$^+$), 391 (M$^+$), 359, 357; IR (KBr, cm$^{-1}$): 3112, 1668, 1592, 1550, 1335, 1109, 1070; Melting point: 236–237° C.

EXAMPLE 207

5-Amino-7-(4-benzyloxybenzylthio)-2-(2-furyl)[1,2,4]triazolo[1,5-c]pyrimidine (Compound 207)

Compound 207 was obtained as a white solid using p-benzyloxybenzyl bromide in the same manner as in Example 178.

Yield: 62%; $^1$H NMR (δ ppm, DMSO-$d_6$): 8.10 (brs, 2H), 7.91 (d, J=2.0 Hz, 1H), 7.31–7.45 (m, 7H), 7.15 (d, J=3.6 Hz, 1H), 6.96 (d, J=8.5 Hz, 2H), 6.80 (s, 1H), 6.71 (dd, J=2.0 Hz, 3.6 Hz, 1H), 5.08 (s, 2H), 4.33 (s, 2H); Mass (m/z): 429 (M$^+$), 396; IR (KBr, cm$^{-1}$): 3101, 1651, 1602, 1540, 1508, 1248, 737; Melting point: 183–184° C.

EXAMPLE 208

5-Amino-2-(2-furyl)-7-(4-isopropylbenzylthio)[1,2,4]triazolo[1,5-c]pyrimidine (Compound 208)

Compound 208 was obtained as a white solid using p-isopropylbenzyl bromide in the same manner as in Example 178.

Yield: 54%; $^1$H NMR (δ ppm, DMSO-$d_6$): 8.10 (brs, 2H), 7.91 (d, J=1.6 Hz, 1H), 7.38 (d, J=8.0 Hz, 2H), 7.20 (d, J=8.0 Hz, 2H), 7.15 (d, J=3.3 Hz, 1H), 6.81 (s, 1H), 6.71 (dd, J=1.6 Hz, 3.3 Hz, 1H), 4.35 (s, 2H), 2.85 (sep, J=6.6 Hz, 1H), 1.17 (d, J=6.6 Hz, 6H); Mass (m/z): 367 ((M+2)$^+$), 366 ((M+1)$^+$), 365 (M$^+$), 333, 332; IR (KBr, cm$^{-1}$): 3174, 1659, 1600, 1535, 1217, 931, 748; Melting point: 201–202° C.

EXAMPLE 209

5-Amino-7-(4-ethylbenzylthio)-2-(2-furyl)[1,2,4]triazolo[1,5-c]pyrimidine (Compound 209)

Compound 209 was obtained as a white solid using p-ethylbenzyl bromide in the same manner as in Example 178.

Yield: 39%; $^1$H NMR (δ ppm, DMSO-$d_6$): 8.10 (brs, 2H), 7.91 (d, J=1.6 Hz, 1H), 7.38 (d, J=8.3 Hz, 2H), 7.16 (d, J=8.3 Hz, 2H), 7.15 (d, J=3.3 Hz, 1H), 6.80 (s, 1H), 6.71 (dd, J=1.6 Hz, 3.3 Hz, 1H), 4.35 (s, 2H), 2.58 (sep, J=7.6 Hz, 2H), 1.15 (t, J=6.6 Hz, 3H); Mass (m/z): 353 ((M+2)$^+$), 352 ((M+1)$^+$), 351 (M$^+$), 319, 318; IR (KBr, cm$^{-1}$): 3172, 1660, 1603, 1550, 1215, 748; Melting point: 221–222° C.

EXAMPLE 210

5-Amino-2-(2-furyl)-7-(4-phenylbenzylthio)[1,2,4]triazolo[1,5-c]pyrimidine (Compound 210)

Compound 210 was obtained as a white solid using p-phenylbenzyl bromide in the same manner as in Example 178.

Yield: 46%; $^1$H NMR (δ ppm, DMSO-$d_6$): 8.13 (brs, 2H), 7.91 (d, J=2.0 Hz, 1H), 7.55–7.66 (m, 2H), 7.45 (dd, J=6.9 Hz, 7.9 Hz, 2H), 7.35 (t, J=6.9 Hz, 1H), 7.15 (d, J=3.6 Hz, 1H), 6.85 (s, 1H), 6.71 (dd, J=2.0 Hz, 3.6 Hz, 1H), 4.45 (s, 2H); Mass (m/z): 399 (M$^+$), 366; IR (KBr, cm$^{-1}$): 3168, 1666, 1600, 1639, 1599, 1570, 1550, 1356, 1325, 750; Melting point: 235–236° C.

EXAMPLE 211

5-Amino-7-(4-formylbenzylthio)-2-(2-furyl)[1,2,4]triazolo[1,5-c]pyrimidine (Compound 211)

Compound 211 was obtained as a white solid using p-formylbenzyl bromide in the same manner as in Example 178.

Yield: 65%; $^1$H NMR (δ ppm, DMSO-$d_6$): 9.97 (s, 1H), 8.16 (brs, 2H), 7.92 (d, J=1.6 Hz, 1H), 7.86 (d, J=8.0 Hz, 2H), 7.72 (d, J=8.0 Hz, 2H), 7.15 (d, J=3.3 Hz, 1H), 6.83 (s, 1H), 6.71 (dd, J=1.6 Hz, 3.3 Hz, 1H), 4.50 (s, 2H); Mass (m/z): 353 ((M+2)$^+$), 352 ((M+1)$^+$), 351 (M$^+$); IR (KBr, cm$^{-1}$): 3122, 1686, 1654, 1594, 1558, 781; Melting point: 142–144° C.

EXAMPLE 212

5-Amino-7-(3-formylbenzylthio)-2-(2-furyl)[1,2,4]triazolo[1,5-c]pyrimidine (Compound 212)

Compound 212 was obtained as a white solid using m-formylbenzyl bromide in the same manner as in Example 178.

Yield: 36%; $^1$H NMR (δ ppm, DMSO-$d_6$): 10.00 (s, 1H), 8.13 (brs, 2H), 8.02 (s, 1H), 7.91 (d, J=1.6 Hz, 1H), 7.84 (d, J=8.9 Hz, 1H), 7.80 (d, J=8.1 Hz, 1H), 7.57 (dd, J=8.1 Hz, 8.9 Hz, 1H), 7.15 (d, J=3.3 Hz, 1H), 6.83 (s, 1H), 6.70 (dd, J=1.6 Hz, 3.3 Hz, 1H), 4.51 (s, 2H); Mass (m/z): 353 ((M+2)$^+$), 352 ((M+1)$^+$), 351 (M$^+$); IR (KBr, cm$^{-1}$): 3122, 1685, 1672, 1587, 1535, 1353, 1222, 781, 752; Melting point: 142–144° C.

EXAMPLE 213

5-Amino-7-(2-formylbenzylthio)-2-(2-furyl)[1,2,4]triazolo[1,5-c]pyrimidine (Compound 213)

Compound 213 was obtained as a white solid using o-formylbenzyl bromide in the same manner as in Example 178.

Yield: 40%; $^1$H NMR (δ ppm, DMSO-d$_6$): 10.30 (s, 1H), 8.16 (brs, 2H), 7.91 (d, J=1.7 Hz, 1H), 7.89 (d, J=6.6 Hz, 1H), 7.73 (d, J=7.6 Hz, 1H), 7.62 (dd, J=7.3 Hz, 7.6 Hz, 1H), 7.52 (dd, J=6.6 Hz, 7.3 Hz, 1H), 7.15 (d, J=3.3 Hz, 1H), 6.84 (s, 1H), 6.71 (dd, J=1.7 Hz, 3.3 Hz, 1H), 4.81 (s, 2H); Mass (m/z): 352 ((M+1)$^+$), 351 (M$^+$); IR (KBr, cm$^{-1}$): 3155, 1695, 1647, 1592, 1356, 928, 736; Melting point: 196–197° C.

EXAMPLE 214

5-Amino-2-(2-furyl)-7-(β-phenethylthio)[1,2,4]triazolo[1,5-c]pyrimidine (Compound 214)

Compound 214 was obtained as a white solid using β-phenethyl bromide in the same manner as in Example 178.

Yield: 94%; $^1$H NMR (δ ppm, DMSO-d$_6$): 8.08 (brs, 2H), 7.92 (d, J=2.0 Hz, 1H), 7.19–7.33 (m, 5H), 7.17 (d, J=3.3 Hz, 1H), 6.83 (s, 1H), 6.71 (dd, J=2.0 Hz, 3.3 Hz, 1H), 3.36 (t, J=7.3 Hz, 2H), 2.97 (t, J=7.3 Hz, 2H); Mass (m/z): 338 ((M+1)$^+$), 337 (M$^+$); IR (KBr, cm$^{-1}$): 3112, 1670, 1585, 1548, 935, 734; Melting point: 174–175° C.

EXAMPLE 215

5-Amino-2-(2-furyl)-7-(α-methylbenzylthio)[1,2,4]triazolo[1,5-c]pyrimidine (Compound 215)

Compound 215 was obtained as a white solid using α-methylbenzyl bromide in the same manner as in Example 178.

Yield: 71%; $^1$H NMR (δ ppm, DMSO-d$_6$): 8.08 (brs, 2H), 7.91 (d, J=1.7 Hz, 1H), 7.52 (d, J=7.2 Hz, 2H), 7.35 (dd, J=7.2 Hz, 7.2 Hz, 2H), 7.24 (t, J=7.2 Hz, 1H), 7.15 (d, J=3.3 Hz, 1H), 6.75 (s, 1H), 6.70 (dd, J=1.7 Hz, 3.3 Hz, 1H), 4.98 (q, J=7.3 Hz, 1H), 1.66 (d, J=7.3 Hz, 3H); Mass (m/z): 339 ((M+2)$^+$), 338 ((M+1)$^+$), 337 (M$^+$); IR (KBr, cm$^{-1}$): 3122, 1646, 1542; Melting point: 192–193° C.

EXAMPLE 216

7-Chloro-5-(3,4-dimethoxybenzylamino)-2-(2-furyl)-8-methyl[1,2,4]triazolo[1,5-c]pyrimidine (Compound 216)

Compound 216 (yield: 41%) was obtained as a white solid using 4,6-dichloro-5-methyl-2-methylthiopyrimidine in the same manner as in Reference Example 19 and then Example 29.

$^1$H NMR (δ ppm, CDCl$_3$): 6.60 (t, J=1.0 Hz, 1H), 7.21 (d, J=3.6 Hz, 1H), 7.17–6.83 (m, 3H), 6.57 (dd, J=3.3 Hz, 1.7 Hz, 1H), 6.40–6.30 (m, 1H), 4.71 (d, J=5.9 Hz, 2H), 3.90 (s, 3H), 3.88 (s, 3H), 2.51 (s, 3H); Mass (m/z): 399 (M$^+$); IR (KBr, cm$^{-1}$): 1629, 1614, 1575, 1506; Melting point: 163.5–164.0° C.

EXAMPLE 217

5-Amino-7-chloro-2-(2-furyl)-8-methyl[1,2,4]triazolo[1,5-c]pyrimidine (Compound 217)

Compound 217 (2.76 g, yield: 89%) was obtained as a yellow solid using 5.0 g (12.5 mmol) of Compound 216 obtained in Example 216 in the same manner as in Example 30.

$^1$H NMR (δ ppm, CDCl$_3$): 6.63 (t, J=1.0 Hz, 1H), 7.24 (d, J=0.7 Hz, 1H), 6.60 (dd, J=3.3 Hz, 1.7 Hz, 1H), 6.06 (brs, 2H), 2.17 (s, 3H); Mass (m/z): 249 (M$^+$); IR (KBr, cm$^{-1}$): 1677, 1668, 1591, 1581; Melting point: 124.5–126.0° C.

The following compounds were synthesized using Compound 217 obtained in Example 217 in the same manner as in Example 62.

EXAMPLE 218

5-Amino-2-(2-furyl)-8-methyl-7-(4-methylpiperazinyl)[1,2,4]triazolo[1,5-c]pyrimidine (Compound 218)

Yield: 70% (brown solid); $^1$H NMR (δ ppm, DMSO-d$_6$): 7.88 (d, J=1.5 Hz, 1H), 7.53 (brs, 2H), 7.13 (d, J=3.0 Hz, 1H), 6.68 (dd, J=3.5 Hz, 2.0 Hz, 1H), 3.21–3.16 (m, 4H), 2.46–2.43 (m, 4H), 2.22 (s, 3H), 2.09 (s, 3H); Mass (m/z): 313 (M$^+$); IR (KBr, cm$^{-1}$) 1731, 1646, 1591, 1556, 1322; Melting point: 192.5–193.0° C.; Elemental analysis: C$_{15}$H$_{19}$N$_7$O 0.1i-PrOH 0.8EtOH 0.2H$_2$O; Found (%): C, 56.87, H, 6.67, N, 26.80; Calcd.(%): C, 56.75, H, 7.09, N, 26.93.

EXAMPLE 219

5-Amino-2-(2-furyl)-8-methyl-7-(4-phenylpiperazinyl)[1,2,4]triazolo[1,2,4]pyrimidine (Compound 219)

Yield: 39% (white solid); $^1$H NMR (δ ppm, DMSO-d$_6$): 7.89 (t, J=1.0 Hz, 1H), 7.57 (brs, 2H), 7.24 (t, J=8.6 Hz, 2H), 7.14 (d, J=3.3 Hz, 1H), 6.99 (d, J=8.3 Hz, 2H), 6.81 (t, J=7.3 Hz, 1H), 6.68 (dd, J=3.3 Hz, 2.0 Hz, 1H), 3.38–3.25 (m, 8H), 2.78 (s, 3H); Mass (m/z): 375 (M$^+$); IR (KBr, cm$^{-1}$): 1662, 1608, 1552, 1409; Melting point: 269.5–270.0° C.; Elemental analysis: C$_{20}$H$_{21}$N$_7$O 0.3H$_2$O; Found (%): C, 63.11, H, 5.70, N, 25.79; Calcd.(%): C, 63.08, H, 5.72, N, 25.75.

EXAMPLE 220

5-Amino-7-(4-benzylpiperazinyl)-2-(2-furyl)-8-methyl[1,2,4]triazolo[1,5-c]pyrimidine (Compound 220)

Yield: 80% (pale brown solid); $^1$H NMR (δ ppm, DMSO-d$_6$): 7.88 (t, J=1.0 Hz, 1H), 7.50 (brs, 2H), 7.35–7.25 (m, 5H), 7.11 (d, J=3.3 Hz, 1H), 6.68 (dd, J=3.3 Hz, 1.6 Hz, 1H), 3.54 (s, 2H), 3.25–3.19 (m, 4H), 2.56–2.49 (m, 4H), 2.21 (s, 3H); Mass (m/z): 389 (M$^+$); IR (KBr, cm$^1$): 1652, 1648, 1600, 1558; Melting point: 217.5–219.0° C.; Elemental analysis: C$_{21}$H$_{23}$N$_7$O 0.1EtOH 1.6H$_2$O; Found (%): C, 60.14, H, 6.04, N, 22.99; Calcd.(%): C, 60.21, H, 6.39, N, 23.18.

EXAMPLE 221

5-Amino-7-(4-(t-butoxycarbonyl)piperazinyl)-2-(2-furyl)-8-methyl[1,2,4]triazolo[1,5-c]pyrimidine (Compound 221)

Yield: 53% (yellow solid); $^1$H NMR (δ ppm, DMSO-d$_6$): 7.88 (d, J=0.7 Hz, 1H), 7.56 (brs, 2H), 7.14 (d, J=3.6 Hz, 1H), 3.51–3.40 (m, 4H), 3.18–3.08 (m, 4H), 2.23 (s, 3H), 1.43 (s, 9H); Mass (m/z): 399 (M$^+$); IR (KBr, cm$^{-1}$): 1700, 1654, 1594, 1558; Melting point: 223.5–224.0° C.; Elemental analysis: C$_{19}$H$_{25}$N$_7$O$_3$; Found (%): C, 57.15, H, 6.54, N, 24.80; Calcd.(%): C, 57.13, H, 6.31, N, 24.54.

EXAMPLE 222

5-Amino-2-(2-furyl)-7-(4-(2-hydroxyethyl)piperazinyl)-8-methyl[1,2,4]triazolo[1,5-c]pyrimidine (Compound 222)

Yield: 48% (pale yellow solid); $^1$H NMR (δ ppm, DMSO-d$_6$): 7.87 (t, J=1.0 Hz, 1H), 7.49 (brs, 2H), 7.12 (d, J=3.3 Hz, 1H), 6.68 (dd, J=3.6 Hz, 2.0 Hz, 1H), 4.41–4.33 (m, 1H), 3.55–3.46 (m, 2H), 3.25–3.12 (m, 4H), 2.61–2.40 (m, 6H), 2.22 (s, 3H); Mass (m/z): 343 (M$^+$); IR (KBr, cm$^{-1}$): 1660, 1652, 1646, 1560; Melting point: 209.5–210.0° C.; Elemental analysis: $C_{16}H_{21}N_7O_2$ 0.3EtOH 1.0H$_2$O; Found (%): C, 53.24, H, 6.38, N, 26.14; Calcd.(%): C, 53.14, H, 6.66, N, 26.13.

EXAMPLE 223

5-Amino-2-(2-furyl)-7-(4-(2-methoxyethyl)piperazinyl)-8-methyl[1,2,4]triazolo[1,5-c]pyrimidine (Compound 223)

Yield: 51% (white solid); $^1$H NMR (δ ppm, DMSO-d$_6$): 7.88 (t, J=1.0 Hz, 1H), 7.51 (brs, 2H), 7.12 (d, J=3.3 Hz, 1H), 6.68 (dd, J=3.3 Hz, 2.0 Hz, 1H), 3.47 (t, J=5.6 Hz, 2H), 3.25 (s, 3H), 3.21–3.17 (m, 4H), 2.56–2.48 (m, 6H), 2.22 (s, 3H); Mass (m/z): 357 (M$^+$); IR (KBr, cm$^{-1}$): 1654, 1600, 1560, 1405; Melting point: 218.5–219.0° C.

EXAMPLE 224

5-Amino-2-(2-furyl)-8-methyl-7-piperazinyl[1,2,4]triazolo[1,5-c]pyrimidine hydrochloride (Compound 224)

To 1.45 g (13.63 mmol) of Compound 221 obtained in Example 221, 40 ml of 4 M hydrochloric acid-ethyl acetate was added, followed by stirring at room temperature for 2 hours. To the reaction mixture, 100 ml of ether was added, and the precipitated solid was collected by filtration. The collected solid was washed with diisopropyl ether and dried to give 1.25 g (yield: quantitative) of Compound 224 as a brown solid. $^1$H NMR (δ ppm, DMSO-d$_6$): 9.60 (brs, 2H), 7.97 (brs, 1H), 7.41 (brd, J=3.3 Hz, 1H), 6.76–6.74 (m, 1H), 3.58–3.42 (m, 4H), 3.23–3.15 (m, 4H), 2.27 (s, 3H); Mass (m/z): 299 (M$^+$); IR (KBr, cm$^{-1}$): 1672, 1629, 1619, 1564; Melting point: 232.0–234.0° C.

EXAMPLE 225

5-Amino-7-butylthio-2-(2-furyl)[1,2,4]triazolo[1,5-c]pyrimidine (Compound 225)

In 10 ml of DMF, 700 mg (1.82 mmol) of Compound 29 obtained in Example 29 was dissolved, and 440 mg (5.45 mmol) of sodium hydrosulfide was added thereto, followed by stirring at 140° C. for 3 hours. The reaction mixture was cooled to room temperature, 0.1 ml of water was added thereto, and then 2.07 ml (18.2 mmol) of n-butyl iodide was added thereto, followed by stirring for 1 hour. The reaction mixture was extracted by adding water and chloroform. The organic phase was dried over anhydrous magnesium sulfate, and was purified by silica gel column chromatography (elution solvent: chloroform) to give a main product. Using the obtained main product, 260 mg (yield: 49%) of Compound 225 was obtained as a pale brown solid by carrying out a procedure similar to that in Example 30. $^1$H NMR (δ ppm, DMSO-d$_6$): 8.02 (brs, 2H), 7.91 (d, J=1.0 Hz, 1H), 7.15 (d, J=3.3 Hz, 1H), 6.77 (s, 1H), 6.71 (dd, J=3.0 Hz, 1.0 Hz, 1H), 3.08 (t, J=6.9 Hz, 2H), 1.63 (q, J=7.3 Hz, 2H), 1.44 (q, J=7.5 Hz, 2H), 0.92 (t, J=7.3 Hz, 3H); Mass (m/z): 289 (M$^+$); IR (KBr, cm$^{-1}$): 1656, 1646, 1594, 1589, 1421; Melting point: 130.5–131.0° C.; Elemental analysis: $C_{13}H_{15}N_5OS$ 0.3EtOH; Found (%): C, 54.20, H, 5.48, N, 23.03; Calcd.(%): C, 53.87, H, 5.59, N, 23.10.

The following compounds were synthesized using 4,6-dichloro-2-methylthiopyrimidine and corresponding 4-bromophenol or 4-iodophenol in the same manner as in Example 1.

EXAMPLE 226

7-(4-Bromophenoxy)-5-(3,4-dimethoxybenzylamino)-2-(2-furyl)-8-methyl[1,2,4]triazolo[1,5-c]pyrimidine (Compound 226)

Yield: 29% (4 steps) (white solid); $^1$H NMR (δ ppm, DMSO-d$_6$): 9.12 (t, J=5.9 Hz, 1H), 7.93 (t, J=1.0 Hz, 1H), 7.61 (d, J=8.6 Hz, 2H), 7.18–7.14 (m, 3H), 6.90 (s, 1H), 6.79 (d, J=8.3 Hz, 1H), 6.72 (dd, J=3.3 Hz, 1.0 Hz, 1H), 6.56 (d, J=7.9 Hz, 1H), 6.36 (s, 1H), 4.35 (d, J=5.6 Hz, 2H), 3.72 (s, 3H), 3.67 (s, 3H); Mass (m/z): 521 (M$^+$); IR (KBr, cm$^{-1}$): 1635, 1585, 1413; Melting point: 138.5–139.0° C.

EXAMPLE 227

5-(3,4-Dimethoxybenzylamino)-2-(2-furyl)-7-(4-iodophenoxy)-8-methyl[1,2,4]triazolo[1,5-c]pyrimidine (Compound 227)

Yield: 29% (4 steps) (pale yellow solid); $^1$H NMR (δ ppm, CDCl$_3$): 7.71 (dd, J=6.9 Hz, 2.3 Hz, 2H), 7.58 (t, J=1.0 Hz, 1H), 7.17 (d, J=3.0 Hz, 1H), 6.94 (dd, J=6.9 Hz, 2.3 Hz, 2H), 6.84–6.80 (m, 3H), 6.56 (dd, J=3.3 Hz, 1.7 Hz, 1H), 6.26 (s, 3H), 4.58 (d, J=5.9 Hz, 2H), 3.89 (s, 3H), 3.86 (s, 3H); Mass (m/z): 569 (M$^+$); IR (KBr, cm$^{-1}$): 1608, 1596, 1513, 1411; Melting point: 74.5–80.0° C.

The following compounds were synthesized using the compounds obtained in Examples 226 and 227 in the same manner as in Example 30.

EXAMPLE 228

5-Amino-7-(4-bromophenoxy)-2-(2-furyl)-8-methyl[1,2,4]triazolo[1,5-c]pyrimidine (Compound 228)

Yield: 95% (white solid); $^1$H NMR (δ ppm, DMSO-d$_6$): 8.19 (brs, 2H), 7.92 (s, 1H), 7.61 (dd, J=8.9 Hz, 1.0 Hz, 2H), 7.18 (dd, J=6.9 Hz, 1.0 Hz, 2H), 7.16 (s, 1H), 6.70–6.73 (m, 1H), 6.34 (s, 1H); Mass (m/z): 371 (M$^+$); IR (KBr, cm$^{-1}$): 1660, 1600, 1564, 1560, 1483; Melting point: 234.0–235.0° C.; Elemental analysis: $C_{15}H_{10}BrN_5O_2$; Found (%): C, 48.55, H, 2.64, N, 18.57; Calcd.(%): C, 48.41, H, 2.71, N, 18.82.

EXAMPLE 229

5-Amino-2-(2-furyl)-7-(4-iodophenoxy)[1,2,4]triazolo[1,5-c]pyrimidine (Compound 229)

Yield: quantitative (white solid); $^1$H NMR (δ ppm, DMSO-d$_6$): 8.17 (brs, 2H), 7.92 (t, J=0.7 Hz, 1H), 7.75 (dd, J=6.6 Hz, 2.0 Hz, 2H), 7.16 (t, J=1.0 Hz, 1H), 7.03 (dd, J=6.9 Hz, 2.0 Hz, 2H), 6.71 (dd, J=3.6 Hz, 2.0 Hz, 1H), 6.34 (s, 1H); Mass (m/z): 418 (M$^+$); IR (KBr, cm$^{-1}$): 1672, 1602, 1565, 1226; Melting point: 234.5–236.0° C.

EXAMPLE 230

5-Amino-2-(2-furyl)-7-(4-(2-pyridyl)phenoxy)[1,2,4]triazolo[1,5-c]pyrimidine (Compound 230)

In 10 ml of DMF, 500 mg (0.96 mmol) of Compound 228 obtained in Example 228 was dissolved, and 222 mg (0.96 mmol) of silver oxide and 56 mg of tetrakis (triphenylphosphine)palladium (0) were added thereto, followed by stirring at 100° C. for 5 minutes. Next, 600 mg (1.63 mmol) of 2-pyridyltributyltin was added thereto, followed by further stirring at 100° C. for 12 hours. The reaction mixture was cooled to room temperature, an aqueous ammonium fluoride solution was added thereto, followed by stirring for 1 hour, and the precipitated solid was removed by filtration using celite. The filtrate was extracted by adding chloroform and water. The organic phase was dried over anhydrous magnesium sulfate, and purified by silica gel column chromatography (elution solvent: 2% methanol-chloroform), followed by recrystallization from ethanol to give 360 mg (yield: 74%) of Compound 230 as a white solid.

$^1$H NMR (δ ppm, CDCl$_3$): 8.72–8.70 (m, 1H), 8.06 (dd, J=6.6 Hz, 2.0 Hz, 2H), 7.79–7.75 (m, 2H), 7.62 (t, J=1.0 Hz, 1H), 7.29–7.24 (m, 3H), 7.19 (d, J=3.3 Hz, 1H), 6.58 (dd, J=3.3 Hz, 1.7 Hz, 1H), 6.35 (s, 1H), 6.16 (brs, 2H); Mass (m/z): 370 (M$^+$); IR (KBr, cm$^{-1}$): 1652, 1600, 1560, 1402; Melting point: 204.5–205.0° C.; Elemental analysis: C$_{20}$H$_{14}$N$_6$O$_2$ 0.2H$_2$O 0.3EtOH; Found (%): C, 63.75, H, 3.97, N, 21.49; Calcd.(%): C, 63.80, H, 4.21, N, 21.67.

EXAMPLE 231

5-Amino-2-(2-furyl)-7-(4-(2-thiazolyl)phenoxy)[1,2,4]triazolo[1,5-c]pyrimidine (Compound 231)

Compound 231 was obtained using 2-thiazolotributyltin in the same manner as in Example 230.

Yield: 25% (white solid); $^1$H NMR (δ ppm, DMSO-d$_6$): 9.14 (s, 1H), 8.23 (s, 1H), 8.17 (brs, 2H), 7.92 (t, J=1.0 Hz, 1H), 7.60 (dd, J=6.6 Hz, 2.0 Hz, 2H), 7.18 (dd, J=6.6 Hz, 2.0 Hz, 2H), 7.16 (s, 1H), 6.71 (dd, J=3.6 Hz, 2.0 Hz, 1H), 6.34 (s, 1H); Mass (m/z): 376 (M$^+$); IR (KBr, cm$^{-1}$): 1662, 1604, 1398, 1224; Melting point: 200.5–203.0° C.

FORMULATION EXAMPLE 1

Tablets

Tablets having the following composition are prepared in the usual way.

| | |
|---|---|
| Compound 63 | 10 mg |
| Lactose | 30 mg |
| Potato starch | 15 mg |
| Polyvinyl alcohol | 1.5 mg |
| Magnesium stearate | 0.5 mg |

FORMULATION EXAMPLE 2

Capsules

Capsules having the following composition are prepared in the usual way.

| | |
|---|---|
| Compound 63 | 10 mg |
| Lactose | 100 mg |
| Magnesium stearate | 2.5 mg |

These components are mixed and packed in gelatin capsules.

FORMULATION EXAMPLE 3

Injections

Injections having the following composition are prepared in the usual way.

| | |
|---|---|
| Compound 63 | 2 mg |
| Purified soybean oil | 200 mg |
| Purified egg yolk lecithin | 24 mg |
| Glycerol for injection | 50 mg |
| Distilled water for injection | 1.72 ml |

INDUSTRIAL APPLICABILITY

The present invention provides novel triazolopyrimidine derivatives and pharmaceutically acceptable salts thereof, which have adenosine A$_{2A}$ receptor antagonism and are useful for the treatment or prevention of various diseases caused by hyperactivity of adenosine A$_{2A}$ receptors (for example, Parkinson's disease, senile dementia or depression).

While the invention has been described in detail and with reference to specific embodiments thereof, it will be apparent to one skilled in the art that various changes and modifications can be made therein without departing from the spirit and scope thereof.

This application is based on Japanese application No. Hei 9-69566 filed on Mar. 24, 1997 and International application No. PCT/JP98/01266 filed on Mar. 24, 1998, the entire contents of which are incorporated hereinto by reference.

What is claimed is:

1. A [1,2,4]triazolo[1,5-c]pyrimidine derivative represented by formula (I):

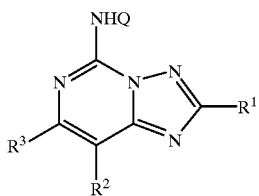

I

{wherein

R$^1$ represents substituted or unsubstituted aryl, or a substituted or unsubstituted aromatic heterocyclic ring;

R$^2$ represents
1) hydrogen,
2) halogen,
3) lower alkyl,
4) lower alkanoyl,
5) aroyl,
6) substituted or unsubstituted aryl,
7) a substituted or unsubstituted aromatic heterocyclic ring,
8) CHR$^{4A}$R$^{4B}$ (wherein R$^{4A}$ represents hydrogen, hydroxy, or aryl; R$^{4B}$ represents hydroxy, substituted or unsubstituted aryloxy, lower alkyl, lower alkoxy, formyl, lower alkanoyl, halogen, lower alkylthio, formula (A¹):

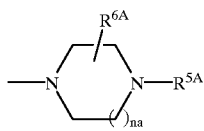

(wherein na represents an integer of 0 to 3; $R^{5A}$ represents hydrogen, substituted or unsubstituted lower alkyl, substituted or unsubstituted aryl, a substituted or unsubstituted aromatic heterocyclic ring, lower alkoxycarbonyl, formyl, lower alkanoyl, aroyl, or substituted or unsubstituted aralkyl; and $R^{6A}$ represents hydrogen, lower alkyl, halogen, or hydroxy, and $R^{6A}$ represents 1 to 3 substituents which are the same or different), formula (B¹):

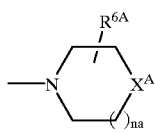

(wherein $X^A$ represents methylene, oxygen, sulfur, sulfinyl, or sulfonyl), or $NR^{7A}R^{8A}$ (wherein $R^{7A}$ and $R^{8A}$ independently represent hydrogen, lower alkyl, lower cycloalkyl, substituted or unsubstituted aryl, a substituted or unsubstituted aromatic heterocyclic ring, substituted or unsubstituted aralkyl, aroyl, formyl, or lower alkanoyl)),
9) formyl,
10) carboxyl,
11) lower alkoxycarbonyl,
12) $CONR^{9A}R^{9B}$ (wherein $R^{9A}$ represents hydrogen or lower alkyl; and $R^{9B}$ represents hydrogen, substituted or unsubstituted aryl, a substituted or unsubstituted aromatic heterocyclic ring, substituted or unsubstituted aralkyl, lower cycloalkyl, lower alkoxy, or lower alkyl),
13) $COA^3$ (wherein $A^3$ represents formula (A³):

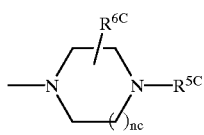

in which nc $R^{5C}$, and $R^{6C}$ have the same meanings as na, $R^{5A}$, and $R^{6A}$, respectively), or
14) $COB^3$ (wherein $B^3$ represents:

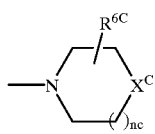

in which nc, $R^{6C}$, and $X^C$ have the same meanings as na, $R^{5A}$, and $X^A$, respectively);
$R^3$ represents
1) hydrogen,
2) halogen,
3) $XR^{10}$ (wherein X represents O or S; and $R^{10}$ represents substituted or unsubstituted aryl, a substituted or unsubstituted aromatic heterocyclic ring, substituted or unsubstituted aralkyl, aromatic heterocyclic ring substituted lower alkyl, lower alkyl, or hydroxy-substituted lower alkyl),
4) formula (A²):

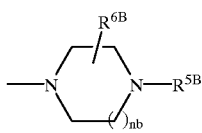

(in which nb, $R^{5B}$, and $R^{6B}$ have the same meanings as na, $R^{5A}$, and $R^{6A}$, respectively),
5) formula (B²):

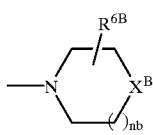

(in which nb, $R^{6B}$, and $X^B$ have the same meanings as na, $R^{5A}$, and $X^A$, respectively), or
6) $NR^{7B}R^{8B}$ (wherein $R^{7B}$ and $R^{8B}$ have the same meanings as $R^{7A}$ and $R^{8A}$, respectively), wherein $R^2$ and $R^3$ are not both hydrogen simultaneously and Q represents hydrogen or 3,4-dimethoxybenzyl,
wherein the substituents on said substituted aryl and substituted aromatic heterocyclic ring are 1 to 3 substituents independently selected from the group consisting of lower alkyl, hydroxy, hydroxy-substituted lower alkyl, halogeno lower alkyl, lower alkoxy, lower alkoxycarbonyl, lower alkylthio, lower alkylsulfinyl, lower alkylsulfonyl, aryl, aryloxy, aralkyl, aralkyloxy, an aromatic heterocyclic ring, halogenoaryloxy, halogenoaralkyloxy, carboxy, carbamoyl, formyl, lower alkanoyl, aroyl, halogen, nitro, amino, cyano, trifluoromethyl, trifluoromethoxy, methylenedioxy, and ethylenedioxy}, or a pharmaceutically acceptable salt thereof.

2. The [1,2,4]triazolo[1,5-c]pyrimidine derivative according to claim 1, wherein Q is hydrogen, or a pharmaceutically acceptable salt thereof.

3. The [1,2,4]triazolo[1,5-c]pyrimidine derivative according to claim 2, wherein $R^2$ is $CH_2R^{4B}$, or a pharmaceutically acceptable salt thereof.

4. The [1,2,4]triazolo[1,5-c]pyrimidine derivative according to claim 2, wherein $R^1$ is a substituted or unsubstituted aromatic heterocyclic ring, or a pharmaceutically acceptable salt thereof.

5. The [1,2,4]triazolo[1,5-c]pyrimidine derivative according to claim 2, wherein $R^1$ is furyl, or a pharmaceutically acceptable salt thereof.

6. The [1,2,4]triazolo[1,5-c]pyrimidine derivative according to claim 4 or 5, wherein $R^2$ is hydrogen, or a pharmaceutically acceptable salt thereof.

7. The [1,2,4]triazolo[1,5-c]pyrimidine derivative according to claim 6, wherein $R^3$ is $A^2$, or a pharmaceutically acceptable salt thereof.

8. The [1,2,4]triazolo[1,5-c]pyrimidine derivative according to claim 7, wherein nb is 1 and $R^{6B}$ is hydrogen, or a pharmaceutically acceptable salt thereof.

9. The [1,2,4]triazolo[1,5-c]pyrimidine derivative according to claim 8, wherein $R^{5B}$ is hydroxy-substituted lower alkyl, lower alkoxy-substituted lower alkyl, a substituted or unsubstituted aromatic heterocyclic ring, or substituted or unsubstituted aralkyl, or a pharmaceutically acceptable salt thereof.

10. The [1,2,4]triazolo[1,5-c]pyrimidine derivative according to claim 4 or 5, wherein $R^3$ is hydrogen, or a pharmaceutically acceptable salt thereof.

11. The [1,2,4]triazolo[1,5-c]pyrimidine derivative according to claim 10, wherein $R^2$ is lower alkanoyl, aroyl, $CONR^{9A}R^{9B}$, or $COA^3$, or a pharmaceutically acceptable salt thereof.

12. A [1,2,4]triazolo[1,5-c]pyrimidine derivative represented by formula (I):

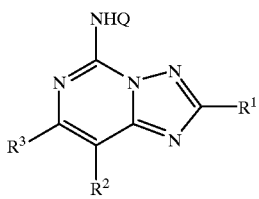

{wherein $R^1$ represents substituted or unsubstituted phenyl, or substituted or unsubstituted aromatic heterocyclic ring selected from the group consisting of furyl, thienyl, and pyridyl;

$R^2$ represents
1) hydrogen,
2) halogen,
3) lower alkyl,
4) lower alkanoyl,
5) aroyl,
6) substituted or unsubstituted aryl,
7) a substituted or unsubstituted aromatic heterocyclic ring,
8) $CHR^{4A}R^{4B}$ (wherein $R^{4A}$ represents hydrogen, hydroxy, or aryl; and $R^{4B}$ represents hydroxy, substituted or unsubstituted aryloxy, lower alkyl, lower alkoxy, formyl, lower alkanoyl, halogen, lower alkylthio, formula $(A^1)$:

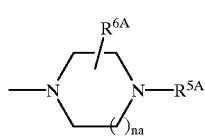

(in which na represents an integer of 0 to 3; $R^{5A}$ represents hydrogen, substituted or unsubstituted lower alkyl, substituted or unsubstituted aryl, a substituted or unsubstituted aromatic heterocyclic ring, lower alkoxycarbonyl, formyl, lower alkanoyl, aroyl, or substituted or unsubstituted aralkyl; and $R^{6A}$ represents hydrogen, lower alkyl, halogen, or hydroxy, and $R^{6A}$ represents 1 to 3 substituents which are the same or different), formula $(B^1)$:

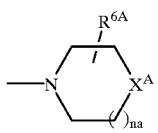

(wherein $X^A$ represents methylene, oxygen, sulfur, sulfinyl, or sulfonyl), or $NR^{7A}R^{8A}$ (wherein $R^{7A}$ and $R^{8A}$ independently represent hydrogen, lower alkyl, lower cycloalkyl, substituted or unsubstituted aryl, a substituted or unsubstituted aromatic heterocyclic ring, substituted or unsubstituted aralkyl, aroyl, formyl, or lower alkanoyl)), 9) formyl,
10) carboxyl,
11) lower alkoxycarbonyl,
12) $CONR^{9A}R^{9B}$ (wherein $R^{9A}$ represents hydrogen or lower alkyl; and $R^{9B}$ represents hydrogen, substituted or unsubstituted aryl, a substituted or unsubstituted aromatic heterocyclic ring, substituted or unsubstituted aralkyl, lower cycloalkyl, lower alkoxy, or lower alkyl),
13) $COA^3$ (wherein $A^3$ represents:

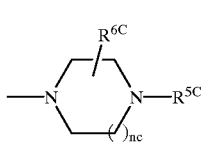

in which nc, $R^{5C}$, and $R^{6C}$ have the same meanings as na, $R^{5A}$, and $R^{6A}$, respectively), or
14) $COB^3$ (wherein $B^3$ represents:

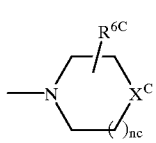

in which nc, $R^{6C}$, and $X^C$ have the same meanings as na, $R^{5A}$, and $X^A$, respectively);

$R^3$ represents
1) hydrogen,
2) halogen,
3) $XR^{10}$ (wherein X represents O or S; and $R^{10}$ represents substituted or unsubstituted aryl, a substituted or unsubstituted aromatic heterocyclic ring, substituted or unsubstituted aralkyl, aromatic heterocyclic ring substituted lower alkyl, lower alkyl, or hydroxy-substituted lower alkyl), 4) formula (A²):

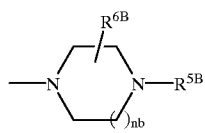

(wherein nb, $R^{5B}$, and $R^{6B}$ have the same meanings as na, $R^{5A}$, and $R^{6A}$, respectively), 5) formula (B²):

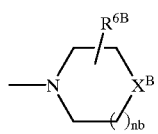

(wherein nb, $R^{6B}$, and $X^B$ have the same meanings as na, $R^{5A}$, and $X^A$, respectively), or 6) $NR^{7B}R^{8B}$ (wherein $R^{7B}$ and $R^{8B}$, have the same meanings as $R^{7A}$ and $R^{8A}$, respectively), wherein $R^2$ and $R^3$ are not both hydrogen simultaneously and Q represents hydrogen or 3,4-dimethoxybenzyl, wherein the substituents on said substituted phenyl and substituted aromatic heterocyclic ring are 1 to 3 substituents independently selected from the group consisting of lower alkyl, hydroxy, hydroxy-substituted lower alkyl, halogeno lower alkyl, lower alkoxy, lower alkoxycarbonyl, lower alkylthio, lower alkylsulfinyl, lower alkylsulfonyl, aryl, aryloxy, aralkyl, aralkyloxy, an aromatic heterocyclic ring, halogenoaryloxy, halogenoaralkyloxy, carboxy, carbamoyl, formyl, lower alkanoyl, aroyl, halogen, nitro, amino, cyano, trifluoromethyl, trifluoromethoxy, methylenedioxy, and ethylenedioxy}, or a pharmaceutically acceptable salt thereof.

13. The [1,2,4]triazolo[1,5-c]pyrimidine derivative according to claim 12, wherein Q is hydrogen, or a pharmaceutically acceptable salt thereof.

14. The [1,2,4]triazolo[1,5-c]pyrimidine derivative according to claim 13, wherein $R^2$ is $CH_2R^{4B}$, or a pharmaceutically acceptable salt thereof.

15. The [1,2,4]triazolo[1,5-c]pyrimidine derivative according to claim 13, wherein $R^1$ is a substituted or unsubstituted aromatic heterocyclic ring, or a pharmaceutically acceptable salt thereof.

16. The [1,2,4]triazolo[1,5-c]pyrimidine derivative according to claim 13, wherein $R^1$ is furyl, or a pharmaceutically acceptable salt thereof.

17. The [1,2,4]triazolo[1,5-c]pyrimidine derivative according to claim 15 or 16, wherein $R^2$ is hydrogen, or a pharmaceutically acceptable salt thereof.

18. The [1,2,4]triazolo[1,5-c]pyrimidine derivative according to claim 17, wherein $R^3$ is $A^2$, or a pharmaceutically acceptable salt thereof.

19. The [1,2,4]triazolo[1,5-c]pyrimidine derivative according to claim 18, wherein nb is 1 and $R^{6B}$ is hydrogen, or a pharmaceutically acceptable salt thereof.

20. The [1,2,4]triazolo[1,5-c]pyrimidine derivative according to claim 19, wherein $R^{5B}$ is hydroxy-substituted lower alkyl, lower alkoxy-substituted lower alkyl, a substi-tuted or unsubstituted aromatic heterocyclic ring, or substituted or unsubstituted aralkyl, or a pharmaceutically acceptable salt thereof.

21. The [1,2,4]triazolo[1,5-c]pyrimidine derivative according to claim 15 or 16, wherein $R^3$ is hydrogen, or a pharmaceutically acceptable salt thereof.

22. The [1,2,4]triazolo[1,5-c]pyrimidine derivative according to claim 21, wherein $R^2$ is lower alkanoyl, aroyl, $CONR^{9A}R^{9B}$, or $COA^3$, or a pharmaceutically acceptable salt thereof.

23. A [1,2,4]triazolo[1,5-c]pyrimidine derivative represented by formula (I):

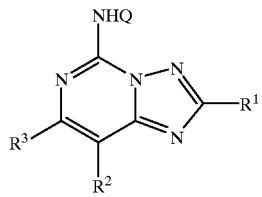

{wherein $R^1$ represents substituted or unsubstituted phenyl, or substituted or unsubstituted aromatic heterocyclic ring selected from the group consisting of furyl, and thienyl);

$R^2$ represents
1) hydrogen,
2) halogen,
3) lower alkyl,
4) lower alkanoyl,
5) aroyl,
6) substituted or unsubstituted aryl,
7) a substituted or unsubstituted aromatic heterocyclic ring,
8) $CHR^{4A}R^{4B}$ (wherein $R^{4A}$ represents hydrogen, hydroxy, or aryl; and $R^{4B}$ represents hydroxy, substituted or unsubstituted aryloxy, lower alkyl, lower alkoxy, formyl, lower alkanoyl, halogen, lower alkylthio, formula ($A^1$):

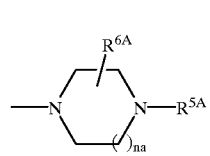

(wherein na represents an integer of 0 to 3; $R^{5A}$ represents hydrogen, substituted or unsubstituted lower alkyl, substituted or unsubstituted aryl, a substituted or unsubstituted aromatic heterocyclic ring, lower alkoxycarbonyl, formyl, lower alkanoyl, aroyl, or substituted or unsubstituted aralkyl; and $R^{6A}$ represents hydrogen, lower alkyl, halogen, or hydroxy, and $R^{6A}$ represents 1 to 3 substituents which are the same or different), formula ($B^1$):

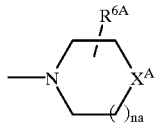

$B^1$ (wherein $X^A$ represents methylene, oxygen, sulfur, sulfinyl, or sulfonyl), or $NR^{7B}R^{8A}$ (wherein $R^{7B}$ and $R^{8A}$ independently represent hydrogen, lower alkyl, lower cycloalkyl, substituted or unsubstituted aryl, a substituted or unsubstituted aromatic heterocyclic ring, substituted or unsubstituted aralkyl, aroyl, formyl, or lower alkanoyl)), 9) formyl,
10) carboxyl,
11) lower alkoxycarbonyl,
12) $CONR^{9A}R^{9B}$ (wherein $R^{9A}$ represents hydrogen or lower alkyl; and $R^{9B}$ represents hydrogen, substituted or unsubstituted aryl, a substituted or unsubstituted aromatic heterocyclic ring, substituted or unsubstituted aralkyl, lower cycloalkyl, lower alkoxy, or lower alkyl),
13) $COA^3$ (wherein $A^3$ represents:

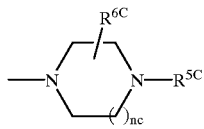

$A^3$ in which nc, $R^{5C}$, and $R^{6C}$ have the same meanings as na, $R^{5A}$, and $R^{6A}$, respectively), or
14) $COB^3$ (wherein $B^3$ represents:

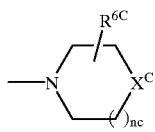

$B^3$ in which nc, $R^{6C}$, and $X^C$ have the same meanings as na, $R^{5A}$, and $X^A$, respectively);

$R^3$ represents
1) hydrogen,
2) halogen,
3) $XR^{10}$ (wherein X represents O or S; and $R^{10}$ represents substituted or unsubstituted aryl, a substituted or unsubstituted aromatic heterocyclic ring, substituted or unsubstituted aralkyl, aromatic heterocyclic ring substituted lower alkyl, lower alkyl, or hydroxy-substituted lower alkyl), 4) formula ($A^2$):

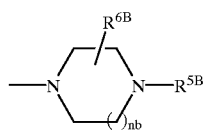

$A^2$ (wherein nb, $R^{5B}$, and $R^{6B}$ have the same meanings as na, $R^{5A}$, and $R^{6A}$, respectively),
5) formula ($B^2$):

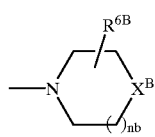

$B^2$ (wherein nb, $R^{6B}$, and $X^B$ have the same meanings as na, $R^{5A}$, and $X^A$, respectively), or
6) $NR^{7B}R^{8B}$ (wherein $R^{7B}$ and $R^{8B}$ have the same meanings as $R^{7A}$ and $R^{8A}$, respectively),
wherein $R^2$ and $R^3$ cannot both be hydrogen simultaneously and
Q represents hydrogen or 3,4-dimethoxybenzyl,
wherein the substituents on said substituted phenyl and substituted aromatic heterocyclic ring are 1 to 3 substituents independently selected from the group consisting of lower alkyl, hydroxy, hydroxy-substituted lower alkyl, halogeno lower alkyl, lower alkoxy, lower alkoxycarbonyl, lower alkylthio, lower alkylsulfinyl, lower alkylsulfonyl, aryl, aryloxy, aralkyl, aralkyloxy, an aromatic heterocyclic ring, halogenoaryloxy, halogenoaralkyloxy, carboxy, carbamoyl, formyl, lower alkanoyl, aroyl, halogen, nitro, amino, cyano, trifluoromethyl, trifluoromethoxy, methylenedioxy, and ethylenedioxy}, or
a pharmaceutically acceptable salt thereof.

24. The [1,2,4]triazolo[1,5-c]pyrimidine derivative according to claim 23, wherein Q is hydrogen, or a pharmaceutically acceptable salt thereof.

25. The [1,2,4]triazolo[1,5-c]pyrimidine derivative according to claim 24, wherein $R^2$ is $CH_2R^{4B}$, or a pharmaceutically acceptable salt thereof.

26. The [1,2,4]triazolo[1,5-c]pyrimidine derivative according to claim 24, wherein $R^1$ is a substituted or unsubstituted aromatic heterocyclic ring, or a pharmaceutically acceptable salt thereof.

27. The [1,2,4]triazolo[1,5-c]pyrimidine derivative according to claim 24, wherein $R^1$ is furyl, or a pharmaceutically acceptable salt thereof.

28. The [1,2,4]triazolo[1,5-c]pyrimidine derivative according to claim 26 or 27, wherein $R^2$ is hydrogen, or a pharmaceutically acceptable salt thereof.

29. The [1,2,4]triazolo[1,5-c]pyrimidine derivative according to claim 28, wherein $R^3$ is $A^2$, or a pharmaceutically acceptable salt thereof.

30. The [1,2,4]triazolo[1,5-c]pyrimidine derivative according to claim 29, wherein nb is 1 and $R^{6B}$ is hydrogen, or a pharmaceutically acceptable salt thereof.

31. The [1,2,4]triazolo[1,5-c]pyrimidine derivative according to claim 30, wherein $R^{5B}$ is hydroxy-substituted lower alkyl, lower alkoxy-substituted lower alkyl, a substituted or unsubstituted aromatic heterocyclic ring, or substituted or unsubstituted aralkyl, or a pharmaceutically acceptable salt thereof.

32. The [1,2,4]triazolo[1,5-c]pyrimidine derivative according to claim 26 or 27, wherein $R^3$ is hydrogen, or a pharmaceutically acceptable salt thereof.

33. The [1,2,4]triazolo[1,5-c]pyrimidine derivative according to claim 32, wherein $R^2$ is lower alkanoyl, aroyl, $CONR^{9A}R^{9B}$, or $COA^3$, or a pharmaceutically acceptable salt thereof.

34. A [1,2,4]triazolo[1,5-c]pyrimidine derivative represented by formula (I):

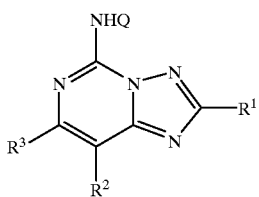

I

{wherein
$R^1$ represents substituted or unsubstituted aryl, or a substituted or unsubstituted aromatic heterocyclic ring;
$R^2$ represents hydrogen;
$R^3$ represents hydrogen; and
Q represents 3,4-dimethoxybenzyl,
wherein the substituents on said substituted aryl and substituted aromatic heterocyclic ring are 1 to 3 substituents independently selected from the group consisting of lower alkyl, hydroxy, hydroxy-substituted lower alkyl, halogeno lower alkyl, lower alkoxy, lower alkoxycarbonyl, lower alkylthio, lower alkylsulfinyl, lower alkylsulfonyl, aryl, aryloxy, aralkyl, aralkyloxy, an aromatic heterocyclic ring, halogenoaryloxy, halogenoaralkyloxy, carboxy, carbamoyl, formyl, lower alkanoyl, aroyl, halogen, nitro, amino, cyano, trifluoromethyl, trifluoromethoxy, methylenedioxy, and ethylenedioxy}, or
a pharmaceutically acceptable salt thereof.

35. A [1,2,4]triazolo[1,5-c]pyrimidine derivative represented by formula (I):

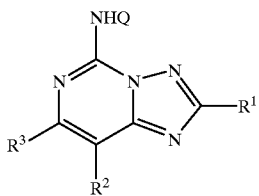

I

{wherein
$R^1$ represents substituted or unsubstituted phenyl, or substituted or unsubstituted aromatic heterocyclic ring selected from the group consisting of furyl, thienyl, and pyridyl;
$R^2$ represents hydrogen;
$R^3$ represents hydrogen; and
Q represents 3,4-dimethoxybenzyl,
wherein the substituents on said substituted phenyl and substituted aromatic heterocyclic ring are 1 to 3 substituents independently selected from the group consisting of lower alkyl, hydroxy, hydroxy-substituted lower alkyl, halogeno lower alkyl, lower alkoxy, lower alkoxycarbonyl, lower alkylthio, lower alkylsulfinyl, lower alkylsulfonyl, aryl, aryloxy, aralkyl, aralkyloxy, an aromatic heterocyclic ring, halogenoaryloxy, halogenoaralkyloxy, carboxy, carbamoyl, formyl, lower alkanoyl, aroyl, halogen, nitro, amino, cyano, trifluoromethyl, trifluoromethoxy, methylenedioxy, and ethylenedioxy}, or
a pharmaceutically acceptable salt thereof.

36. A [1,2,4]triazolo[1,5-c]pyrimidine derivative represented by formula (I):

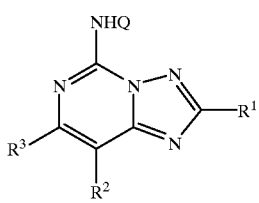

I

{wherein
$R^1$ represents substituted or unsubstituted phenyl, or substituted or unsubstituted aromatic heterocyclic ring selected from the group consisting of furyl, and thienyl);
$R^2$ represents hydrogen;
$R^3$ represents hydrogen; and
Q represents 3,4-dimethoxybenzyl,
wherein the substituents on said substituted phenyl and substituted aromatic heterocyclic ring are 1 to 3 substituents independently selected from the group consisting of lower alkyl, hydroxy, hydroxy-substituted lower alkyl, halogeno lower alkyl, lower alkoxy, lower alkoxycarbonyl, lower alkylthio, lower alkylsulfinyl, lower alkylsulfonyl, aryl, aryloxy, aralkyl, aralkyloxy, an aromatic heterocyclic ring, halogenoaryloxy, halogenoaralkyloxy, carboxy, carbamoyl, formyl, lower alkanoyl, aroyl, halogen, nitro, amino, cyano, trifluoromethyl, trifluoromethoxy, methylenedioxy, and ethylenedioxy}, or
a pharmaceutically acceptable salt thereof.

* * * * *